US011014989B2

(12) United States Patent
Smith et al.

(10) Patent No.: US 11,014,989 B2
(45) Date of Patent: May 25, 2021

(54) ANTI-CLL1 SPECIFIC SINGLE-CHAIN CHIMERIC ANTIGEN RECEPTORS (SCCARS) FOR CANCER IMMUNOTHERAPY

(71) Applicant: Cellectis, Paris (FR)

(72) Inventors: Julianne Smith, New York, NY (US); Julien Valton, New York, NY (US); Alexandre Juillerat, New York, NY (US); Philippe Duchateau, Draveil (FR); Barbra Johnson Sasu, San Francisco, CA (US); Arvind Rajpal, San Francisco, CA (US)

(73) Assignee: Cellectis, Paris (FR)

( * ) Notice: Subject to any disclaimer, the term of this patent is extended or adjusted under 35 U.S.C. 154(b) by 161 days.

(21) Appl. No.: 15/546,633

(22) PCT Filed: Jan. 25, 2016

(86) PCT No.: PCT/EP2016/051469
§ 371 (c)(1),
(2) Date: Jul. 26, 2017

(87) PCT Pub. No.: WO2016/120218
PCT Pub. Date: Aug. 4, 2016

(65) Prior Publication Data
US 2018/0009895 A1    Jan. 11, 2018

(30) Foreign Application Priority Data
Jan. 26, 2015  (DK) .............................. PA201570044

(51) Int. Cl.
| | | |
|---|---|---|
| *A61K 35/17* | (2015.01) | |
| *C07K 16/28* | (2006.01) | |
| *C07K 14/725* | (2006.01) | |
| *C07K 16/30* | (2006.01) | |
| *C12N 5/00* | (2006.01) | |
| *C12N 5/0783* | (2010.01) | |
| *A61K 39/00* | (2006.01) | |
| *A61K 39/395* | (2006.01) | |
| *C07K 14/705* | (2006.01) | |
| *C07K 14/735* | (2006.01) | |
| *G01N 15/10* | (2006.01) | |
| *G01N 15/14* | (2006.01) | |
| *G01N 15/00* | (2006.01) | |

(52) U.S. Cl.
CPC .......... *C07K 16/2866* (2013.01); *A61K 35/17* (2013.01); *A61K 39/0011* (2013.01); *A61K 39/001176* (2018.08); *A61K 39/39558* (2013.01); *C07K 14/7051* (2013.01); *C07K 14/70517* (2013.01); *C07K 14/70535* (2013.01); *C07K 14/70578* (2013.01); *C07K 16/2803* (2013.01); *C07K 16/2887* (2013.01); *C07K 16/3061* (2013.01); *C12N 5/0093* (2013.01); *C12N 5/0636* (2013.01); *C12N 5/0638* (2013.01); *G01N 15/1031* (2013.01); *G01N 15/14* (2013.01); *A61K 2039/505* (2013.01); *A61K 2039/5156* (2013.01); *A61K 2039/5158* (2013.01); *A61K 2039/6056* (2013.01); *A61K 2039/64* (2013.01); *C07K 2317/24* (2013.01); *C07K 2317/53* (2013.01); *C07K 2317/56* (2013.01); *C07K 2317/622* (2013.01); *C07K 2319/00* (2013.01); *C07K 2319/02* (2013.01); *C07K 2319/03* (2013.01); *C12N 2510/00* (2013.01); *G01N 2015/008* (2013.01); *G01N 2015/1006* (2013.01); *G01N 2015/1081* (2013.01); *G01N 2015/149* (2013.01)

(58) Field of Classification Search
CPC .................................................... A61K 35/17
See application file for complete search history.

(56) References Cited

U.S. PATENT DOCUMENTS

| | | | |
|---|---|---|---|
| 4,683,195 A | 7/1987 | Mullis et al. | |
| 5,037,743 A | 8/1991 | Welch et al. | |
| 5,143,830 A | 9/1992 | Holland et al. | |
| 5,225,539 A | 7/1993 | Winter | |
| 5,530,101 A | 6/1996 | Queen et al. | |
| 5,565,332 A | 10/1996 | Hendricus et al. | |
| 5,585,089 A | 12/1996 | Queen et al. | |
| 5,766,886 A | 6/1998 | Studnicka et al. | |
| 5,858,358 A | 1/1999 | June et al. | |
| 5,883,223 A | 3/1999 | Gray et al. | |
| 6,010,613 A | 1/2000 | Walters | |

(Continued)

FOREIGN PATENT DOCUMENTS

| | | | |
|---|---|---|---|
| CA | 2869562 A1 | † | 10/2013 |
| EP | 239400 | | 9/1987 |

(Continued)

OTHER PUBLICATIONS

Bridgeman et al. (J. Immunol. Jun. 15, 2010; 184 (12): 6938-49).*

(Continued)

*Primary Examiner* — Stephen L Rawlings

(74) *Attorney, Agent, or Firm* — Casimir Jones, S.C.; Peter J. Schlueter

(57) ABSTRACT

The present invention relates to Chimeric Antigen Receptors (CAR) that are recombinant chimeric proteins able to redirect immune cell specificity and reactivity toward CLL1 positive cells. The engineered immune cells endowed with such CARs are particularly suited for immunotherapy for treating cancer, in particular leukemia.

24 Claims, 4 Drawing Sheets

Specification includes a Sequence Listing.

(56) References Cited

U.S. PATENT DOCUMENTS

| | | |
|---|---|---|
| 6,352,694 B1 | 3/2002 | June et al. |
| 6,407,213 B1 | 6/2002 | Carter et al. |
| 6,534,055 B1 | 3/2003 | June et al. |
| 6,642,043 B1 | 11/2003 | Bertino et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,446,179 B2 | 11/2008 | Jensen et al. |
| 7,446,190 B2 | 11/2008 | Sadelain et al. |
| 7,514,537 B2 | 4/2009 | Jensen |
| 8,324,353 B2 | 12/2012 | Jensen |
| 8,399,645 B2 | 3/2013 | Campana et al. |
| 9,765,342 B2 | 9/2017 | Kochenderfer et al. |
| 2004/0058414 A1 | 3/2004 | Queen et al. |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0121005 A1 | 6/2006 | Berenson et al. |
| 2007/0014794 A1 | 1/2007 | Carter et al. |
| 2013/0266551 A1 | 10/2013 | Campana et al. |
| 2013/0295118 A1 | 11/2013 | Jiang et al. |
| 2013/0309223 A1 | 11/2013 | Sutherland et al. |
| 2014/0022163 A1 | 1/2014 | Milone et al. |
| 2014/0023674 A1 | 1/2014 | Tuomanen et al. |
| 2014/0024809 A1 | 1/2014 | Cheung et al. |
| 2014/0134142 A1 | 5/2014 | Smith et al. |
| 2014/0322183 A1 | 10/2014 | Milone et al. |
| 2016/0046724 A1 | 2/2016 | Brogdon et al. |
| 2016/0184362 A1 | 6/2016 | Duchateau et al. |
| 2016/0237139 A1 | 8/2016 | Pule et al. |
| 2016/0297884 A1 | 10/2016 | Kuo et al. |
| 2017/0073423 A1 | 3/2017 | Juillerat et al. |
| 2017/0105161 A1 | 4/2017 | Axmon et al. |

FOREIGN PATENT DOCUMENTS

| | | |
|---|---|---|
| EP | 519596 | 12/1992 |
| EP | 592106 | 4/1994 |
| EP | 2332994 A1 | 6/2011 |
| EP | 2765193 A1 | 8/2014 |
| WO | WO 91/09967 | 11/1991 |
| WO | WO 93/17105 | 9/1993 |
| WO | WO 94/24277 | 10/1994 |
| WO | WO 2004/043344 A2 | 5/2004 |
| WO | WO 2004/083379 | 9/2004 |
| WO | WO 2005/000894 A2 | 1/2005 |
| WO | WO2005000894 A2 † | 1/2005 |
| WO | WO 2006/020258 | 2/2006 |
| WO | WO 2007/024715 | 3/2007 |
| WO | WO 2008/121420 | 10/2008 |
| WO | WO 2009/051974 A1 | 4/2009 |
| WO | WO2009051974 A1 † | 4/2009 |
| WO | WO 2009/091826 A3 | 7/2009 |
| WO | WO 2010/025177 | 3/2010 |
| WO | WO 2011/036183 A2 | 3/2011 |
| WO | WO 2012/031744 | 3/2012 |
| WO | WO 2012/050374 A2 | 4/2012 |
| WO | WO 2012/058458 A2 | 5/2012 |
| WO | WO 2012/079000 | 6/2012 |
| WO | WO 2012/099973 | 7/2012 |
| WO | WO 2012/136231 A1 | 10/2012 |
| WO | WO 2012/138475 A1 | 10/2012 |
| WO | WO 2012/138927 | 10/2012 |
| WO | WO 2013/123061 A1 | 2/2013 |
| WO | WO 2013/040557 | 3/2013 |
| WO | WO 2013/059593 | 4/2013 |
| WO | WO 2013/067492 | 5/2013 |
| WO | WO 2013/070468 | 5/2013 |
| WO | WO 2013/074916 | 5/2013 |
| WO | WO 2013/126712 | 8/2013 |
| WO | WO 2013/126726 | 8/2013 |
| WO | WO 2013/126729 | 8/2013 |
| WO | WO 2013/126733 | 8/2013 |
| WO | WO 2013/153391 | 10/2013 |
| WO | WO 2013/154760 | 10/2013 |
| WO | WO 2013/169625 | 11/2013 |
| WO | WO 2013/176915 | 11/2013 |
| WO | WO 2013/176916 | 11/2013 |
| WO | WO2013169625 A1 † | 11/2013 |
| WO | WO 2014/011987 A1 | 1/2014 |
| WO | WO 2014/011988 | 1/2014 |
| WO | WO 2014/039523 | 3/2014 |
| WO | WO 2014/144622 | 3/2014 |
| WO | WO 2014/100385 A1 | 6/2014 |
| WO | WO 2014/130635 A1 | 8/2014 |
| WO | WO2014130635 A1 † | 8/2014 |
| WO | WO 2014/145252 A2 | 9/2014 |
| WO | WO 2014/152177 A1 | 9/2014 |
| WO | WO 2014/153270 A1 | 9/2014 |
| WO | WO 2014/191128 A1 | 9/2014 |
| WO | WO 2014/184143 | 11/2014 |
| WO | WO 2014/184744 | 11/2014 |
| WO | WO 2015/075195 A1 | 5/2015 |
| WO | WO 2015/075468 A1 | 5/2015 |
| WO | WO 2015/121454 A1 | 8/2015 |
| WO | WO 2015/123527 A1 | 8/2015 |
| WO | WO 2015/136001 A1 | 9/2015 |
| WO | WO 2015/140268 A1 | 9/2015 |
| WO | WO 2015/142675 A2 | 9/2015 |
| WO | WO 2016/14535 A1 | 1/2016 |
| WO | WO 2016/090369 A1 | 6/2016 |

OTHER PUBLICATIONS

Winkler et al. (J. Immunol. Oct. 15, 2000; 165 (8): 4505-4514).*
Hudecek et al. (Clin. Cancer Res. Jun. 15, 2013; 19 (12): 3153-64).*
Marshall et al. (J. Biol. Chem. Apr. 9, 2004; 279 (15): 14792-802).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Cartellieri Marc et al., "A Novel Ex Vivo Isolation and Expansion Procedure for Chimeric Antigen Receptor Engrafted Human T Cells" Plos One, vol. 9, No. 4, Apr. 3, 2014; p. e93745.
International Search Report issued in International Application No. DK201570748 dated Dec. 18, 2015.
International Search Report issued in International Application No. PCT/EP2016/051469 dated Apr. 19, 2016.
Lu Hua et al.; "Targeting Human C-Type Lectin-like Molecule-1 (CLL1) with a Bispecific Antibody for Immunotherapy of Acute Myeloid Leukemia"; Angewandte Chemie International ED.; Sep. 8, 2014; vol. 53; pp. 9841-9845.
Noorduis Paul et al., "Targeting of CLEC12A in Acute Myeloid Leukemia by Antibody-Drug-Conjugates and Bispecific CLL-1xCD3 BiTE Antibody"; blood; American Society of Hematology, Nov. 1, 2010; pp. 1-2.

(56) References Cited

OTHER PUBLICATIONS

Sadelain Michel et al., "The Basic Principles of Chimeric Antigen Receptor Design" Cancer Discovery, vol. 3, No. 4, Apr. 1, 2013, pp. 388-398.
Zhao Xiaoxian et al.; "Targeting C-type lectin-like molecule-1 for antibody-mediated immunotherapy in acute myeloid leukemia"; Haematologica, vol. 95, No. 1, Jul. 31, 2009; pp. 71-78.
Zhuang Xiaodong et al.; "Abstract LB-256: Immunotherapy using genetically modified T lymphocytes to target CLEC14A on the tumor vasculature" Proceedings: AACR Annual Meeting 2014; Oct. 1, 2014, doi: 10,1158/1538-7445.AM2014-LB-256.
"Treatment of Relapsed and/or Chemotherapy Refractory CD33 Positive Acute Myeloid Leukemia by CART-33 (CART33)," Feb. 1, 2015 [Online], May 20, 2013.
Arbiza, et al., "Characterization of two antigenic sites recognized by neutralizing monoclonal antibodies directed against the fusion glycoprotein of human respiratory syncytial virus." J Gen Viro. 1992; 73(9):2225-34).
Arimondo et al. "Exploring the cellular activity of camptothecin-triple-helix-forming oligonucleotide conjugates." Mol Cell Bioi 2006; 26(1): 324-33.
Atkins et al., "A case for "StopGo": Reprogramming translation to augment codon meaning of GGN by promoting unconventional termination (Stop) after addition of glycine and then allowing continued translation (Go)," RNA, 2007; 3: 803-810.
Ausubel et al., "Current Protocols in Molecular Biology," 2000, Wiley and Son Inc, Library of Congress, USA.
Baca, et al., "Antibody humanization using monovalent phage display." J Biol Chem. Apr. 18, 1997; 272(16):10678-84.
Bai, et al., "Involvement of miR-21 in resistance to daunorubicin by regulating PTEN expression in the leukaemia K562 cell line." FEBS Lett. Jan. 21, 2011; 585(2):402-8.
Bakker, et al., "C-type lectin-like molecule-1: a novel myeloid cell surface marker associated with acute myeloid leukemia", Cancer Res. 2004; 64(22):8443-50).
Bardenheuer, et al., "Resistance to cytarabine and gemcitabine and in vitro selection of transduced cells after retroviral expression of cytidine deaminase in human hematopoietic progenitor cells." Leukemia. Dec. 2005; 19(12):2281-8.
Barrow & Trowsdale, "You say ITAM and I say ITIM, let's call the whole thing off: the ambiguity of immunoreceptor signalling." Eur J Immunol. Jul. 2006; 36(7):1646-53.
Bauer; et al., "Activation of NK cells and T cells by NKG2D, a receptor for stress-inducible MICA." Science. Jul. 30, 1999; 285(5428):727-9.
Beckman, et al., "Antibody constructs in cancer therapy: protein engineering strategies to improve exposure in solid tumors." Cancer. Jan. 15, 2007; 109(2):170-9.
Behringer, et al., "Manipulating the Mouse Embryo", Cold Spring Harbor Laboratory Press, Cold Spring Harbor, N.Y., 1986.
Betts, et al. "Sensitive and viable identification of antigenspecific CD8+ T cells by a flow cytometric assay for degranulation." J Immunol Methods 2003, 281(1-2): 65-78.
Bierer, et al., "Cyclosporin A and FK506: molecular mechanisms of immunosuppression and probes for transplantation biology," Curr Opin Immunol. 1993; 5(5):763-73.
Boch, et al., "Breaking the code of DNA binding specificity of TAL-type III effectors." Science 326(5959): 1509-12.
Brewin; et al. "Generation of EBV-specific cytotoxic T cells that are resistant to calcineurin inhibitors for the treatment of posttransplantation lymphoproliferative disease." Blood 114(23): 4792-803.
Byrd, et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)." Blood. Dec. 15, 2002; 100(13):4325-36.
Carpenter, et al., "B-cell maturation antigen is a promising target for adoptive T-cell therapy of multiple myeloma." Clin Cancer Res. Apr. 15, 2013; 19(8):2048-60.

Cartellieri, et al., "A novel ex vivo isolation and expansion procedure for chimeric antigen receptor engrafted human T cells." PLoS One. Apr. 3, 2014; 9(4):e93745.
Cespedes, "Mouse models in oncogenesis and cancer therapy." Clin Transl Oncol. May 2006; 8(5):318-29.
Chen et al., "Molecular mechanisms of T cell co-stimulation and co-inhibition." Nat Rev Immunol. Apr. 2013; 13(4):227-42.
Chicaybam et al., "Abstract 2797: Construction and validation of an activating and inhibitory chimeric antigen receptor (CAR) system" Cancer Research 2014, 4 pages.
Choulika, et al., "Induction of homologous recombination in mammalian chromosomes by using the 1-Scel system of *Saccharomyces cerevisiae*." Mol Cell Bio. 1995; 15(4): 1968-73.
Christian, et al. "Targeting DNA double-strand breaks with TAL effector nucleases." Genetics 2010; 186(2): 757-61.
Coles, et al., "Increased CD200 expression in acute myeloid leukemia is linked with an increased frequency of FoxP3+ regulatory T cells." Leukemia. Sep. 2012; 26(9):2146-8.
Cong, et al., "Multiplex genome engineering using CRISPR/Cas systems." Science 2013; 339(6121): 819-23.
Couto, et al., "Anti-BA46 monoclonal antibody Mc3: humanization using a novel positional consensus and in vivo and in vitro characterization." Cancer Res. Apr. 15, 1995; 55(8):1717-22.
Couto, et al., "Designing human consensus antibodies with minimal positional templates." Cancer Res. Dec. 1, 1995;55(23 Suppl):5973s-5977s.
Dasgupta, et al., "Engineered drug-resistant immunocompetent cells enhance tumor cell killing during a chemotherapy challenge." Biochem Biophys Res Commun 2011; 391(1): 170-5.
Daugaard, "The heat shock protein 70 family: Highly homologous proteins with overlapping and distinct functions" FEBS Letters vol. 581, Issue 19, Jul. 31, 2007, pp. 3702-3710.
Deltcheva et al., "CRISPR RNA maturation by trans-encoded small RNA and host factor RNase III." Nature 471 2011; (7340): 602-7.
Deng, et al., "Structural basis for sequence-specific recognition of DNA by TAL effectors." Science 2012; 335(6069): 720-3.
Dennis, "Cancer: off by a whisker." Nature. Aug. 17, 2006; 442(7104):739-41.
Dixon, "Evaluation of the CASP2 docking section." Proteins. 1997; Suppl 1:198-204.
Domb, et al., "Focal Controlled Drug Delivery". Advances in Delivery Science and Technology. 2014.
Donnelly, et al., "Analysis of the aphthovirus 2A/2B polyprotein 'cleavage' mechanism indicates not a proteolytic eaction, but a novel translational effect: a putative ribosomal 'skip'," J. of General Virology, 2001; 82: 1013-1025.
Donnelly, et al., "Nuclear localization and shuttling of herpes simplex virus tegument protein VP13/14." J Viral 2001; 75(6): 2566-74.
Donnelly, et al., "The cleavage activities of aphthovirus and cardiovirus 2A proteins.," J. of Gen. Virology, 1997; 78:13-21.
Doronina, et al., "Site-specific release of nascent chains from ribosomes at a sense codon." Mol Cell Bio 2008; 28(13}: 4227-39.
Dutour, et al., "In Vitro and In Vivo Antitumor Effect of Anti-CD33 Chimeric Receptor-Expressing EBV-CTL against CD33 Acute Myeloid Leukemia." Adv Hematol. 2012.
Eisenschmidt, et al., "Developing a programmed restriction endonuclease for highly specific DNA cleavage." Nucleic Acids Res 2005; 33(22): 7039-47.
Fedorov et al., "PD-1- and CTLA-4-based inhibitory chimeric antigen receptors (iCARs) divert off-target immunotherapy responses." Sci Transl Med. Dec. 11, 2013; 5(215):215ra172.
Finney, et al., "Activation of resting human primary T cells with chimeric receptors: costimulation from CD28, inducible costimulator, CD134, and CD137 in series with signals from the TCR zeta chain." J Immunol. Jan. 1, 2004; 172(1):104-13.
Freshney, et al, "Culture of Animal Cells," 1987, Wiley and Son Inc.
Fujimori, et al., "A modeling analysis of monoclonal antibody percolation through tumors: a binding-site barrier." J Nucl Med. Jul. 1990; 31(7):1191-8.
Gait, "Oligonucleotide Synthesis," 1984, IRL Press.
Garfall, et al., "Immunotherapy with chimeric antigen receptors for multiple myeloma." Discov Med. Jan. 2014; 17(91):37-46.

(56) References Cited

OTHER PUBLICATIONS

Garneau, et al., "The CRISPR/Cas bacterial immune system cleaves bacteriophage and plasmid DNA." Nature 2010; 468(7320): 67-71.
Gasiunas, et al., "Cas9-crRNA ribonucleoprotein complex mediates specific DNA cleavage for adaptive immunity in bacteria." Proc Natl Acad Sci U S A 2012; 109(39): E2579-86.
Gaudin, et al., "A hsp70-2 mutation recognized by CTL on a human renal cell carcinoma." J Immunol. 1999; 162(3):1730-8.
Geissler, et al., "Transcriptional activators of human genes with programmable DNA-specificity." PLoS One 2011; 6(5): e19509.
Gorczynski, "CD200 and its receptors as targets for immunoregulation." Curr Opin Investig Drugs. May 2005; 6(5):483-8.
Hacke, et al., "Genetic modification of mouse bone marrow by lentiviral vector-mediated delivery of hypoxanthine-Guanine phosphoribosyltransferase short hairpin RNA confers chemoprotection against 6-thioguanine cytotoxicity." Transplant Proc 45(5): 2040-4.
Hames, et al., "Transcription and Translation" 1984, IRL Press.
Han, et al., "Chimeric antigen receptor-engineered T cells for cancer immunotherapy: progress and challenges." J Hematol Oncol. Jul. 8, 2013; 6:47.
Hanly, et al., "Review of Polyclonal Antibody Production Procedures in Mammals and Poultry." ILAR J. 1995; 37(3):93-118.
Hantschel, et al., "Hsp70 plasma membrane expression on primary tumor biopsy material and bone marrow of leukemic patients." Cell Stress Chaperones. 2000; 5(5):438-42).
Hau, et al., "Production of polyclonal antibodies: New technologies." ILAR J 2005; 46:294-299.
Heck, et al., "HSP70 expression: does it a novel fatigue signalling factor from immune system to the brain?" Cell Biochem Funct. 2011; 29(3):215-26.
Hellwig, et al., "TRAIL Signaling and Synergy Mechanisms Used in TRAIL-Based Combination Therapies", Mol Cancer Ther. 2012; 11(1):3-13.
Henderson, et al., "Comparison of the effects of FK-506, cyclosporin A and rapamycin on IL-2 production." Immunology 1991; 73(3): 316-21.
Holliger, et al., ""Diabodies": small bivalent and bispecific antibody fragments." 1993 Proc Natl Acad. Sci. U.S.A. 90:6444-6448.
Hromadnikova, et al., "Expression of heat shock protein 70 and NKG2D ligands in acute myeloid leukemia cell lines." J Recept Signal Transduct Res. Jun. 2010; 30(3):161-9.
Huang, et al., "Recombinant immunotherapeutics: current state and perspectives regarding the feasibility and market." Appl Microbiol Biotechnol. Jun. 2010; 87(2):401-10.
Huston, et al., "Protein engineering of antibody binding sites: recovery of specific activity in an anti-digoxin single-chain Fv analogue produced in Escherichia coli." Proc Natl Acad Sci U S A. Aug. 1988; 85(16):5879-83.
Jakobsson, et al., "Identification and characterization of a novel human methyltransferase modulating Hsp70 function through lysine methylation."J. Bioi. Chem. 2013; 288:27752-27763.
Jena, et al., "Redirecting T-cell specificity by introducing a tumor-specific chimeric antigen receptor," Blood, 2010; 116 (7): 1035-1044.
Jensen, et al., "Design and implementation of adoptive therapy with chimeric antigen receptor-modified T cells." Immunol Rev. Jan. 2014; 257(1): 127-144.
Jinek, et al., "A programmable dual-RNA-guided DNA endonuclease in adaptive bacterial immunity." Science 2012; 337(6096): 816-21.
Jonnalagadda, et al., "Engineering human T cells for resistance to methotrexate and mycophenolate mofetil as an in vivo cell selection strategy." PLoS One 2013; 8(6): e65519.
Juillerat, et al., "An oxygen sensitive self-decision making engineered CAR T-cell." Sci Rep. Jan. 20, 2017; 7:39833.
Juillerat, et al., "Design of chimeric antigen receptors with integrated controllable transient functions." Sci Rep. Jan. 11, 2016; 6:18950.
Jushman, "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1", Carcinogenesis vol. 28 No. 1 pp. 207-214, 2007.
Kabani, et al., "Multiple Hsp70 Isoforms in the Eukaryotic Cytosol: Mere Redundancy or Functional Specificity?" Curr Genomics. 2008; 9(5): 338-248.
Kobayashi et al., "A chimeric antigen receptor for TRAIL-receptor 1 induces apoptosis in various types of tumor cells." Biochem Biophys Res Commun. Oct. 31, 2014;453(4):798-803.
Krause, et al., "The Chaperone Balance Hypothesis: The Importance of the Extracellular to Intracellular HSP70 Ratio to Inflammation-Driven Type 2 Diabetes, the Effect of Exercise, and the Implications for Clinical Management", Mediators of Inflammation 2015, vol. 2015, Article ID 249205, 12 pages.
Kushman, et al., "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1." Carcinogenesis 2007; 28(1): 207-14.
Larsen, et al., "Expression of the hMICL in acute myeloid leukemia—a highly reliable disease marker at diagnosis and during follow-up". Cytometry B Clin Cytom. 2012; 82(1):3-8).
Lensink, "Docking and scoring protein complexes: CAPRI 3rd Edition." Proteins. Dec. 1, 2007; 69(4):704-18.
Lewandoski, "Conditional control of gene expression in the mouse." Nat Rev Genet. Oct. 2001; 2(10):743-55.
Li, et al., "Modularly assembled designer TAL effector nucleases for targeted gene knockout and gene replacement in eukaryotes." Nucleic Acids Res 2011; 39(14): 25 6315-25.
Li, et al., "Rapid and highly efficient construction of Tale-based transcriptional regulators and nucleases for genome modification." Plant Mol Bioi 2012; 78(4-5): 20 407-16.
Li, et al., "TAL nucleases (TALNs): hybrid proteins composed of TAL effectors and FokI DNA-cleavage domain." Nucleic Acids Res 2011; 39(1): 359-72.
Liu, et al., "Calcineurin is a common target of cyclophilin-cyclosporin A and FKBP-FK506 complexes," Cell, 1991;66:807-815.
Liu, et al., "Inhibition of T cell signaling by immunophilin-ligand complexes correlates with loss of calcineurin phosphatase activity." Biochemistry 1992; 31(16): 3896-901.
Ma, et al., "Yeast Mre11 and Rad1 proteins define a Ku-independent mechanism to repair double-strand breaks lacking overlapping end sequences." Mol Cell Bioi 2003; 23(23): 8820-8.
Mahfouz, et al., "Targeted transcriptional repression using a chimeric TALE-SRDX repressor protein." Plant Mol Biol 2012; 78(3): 311-21.
Mak, et al., "The crystal structure of TAL effector PthXo1 bound to its DNA target." Science 2012; 335(6069): 716-9.
Mali, et al., "RNA-guided human genome engineering via Cas9." Science 2013; 339(6121): 823-6.
Malin, et al., "Enhanced metastasis suppression by targeting TRAIL receptor 2 in a murine model of triple-negative breast cancer." Clin Cancer Res. 2013; 17(15):5005-15.
Mardiros, et al., "T cells expressing CD123-specific chimeric antigen receptors exhibit specific cytolytic effector functions and antitumor effects against human acute myeloid leukemia," Blood, 2013; 122(18):3138-48.
Marin, et al., "Cytokine-induced killer cells for cell therapy of acute myeloid leukemia: improvement of their immune activity by expression of CD33-specific chimeric receptors." Haematologica. Dec. 2010;95(12):2144-52.
Maus, et al., "Zoom Zoom: racing CARs for multiple myeloma." Clin Cancer Res. Apr. 15, 2013; 19(8):1917-9.
Mayer, et al., "Immunochemical Methods in Cell and Molecular Biology" 1987, Academic Press.
McGrath, "The tumor necrosis factor-related apoptosis-inducing ligand and lung cancer: still following the right TRAIL?" J Thorac Oncol. Jun. 2011;6(6):983-7.
Miller, et al., "A TALE nuclease architecture for efficient genome editing." Nat Biotechnol 2011; 29(2): 143-8.

(56) References Cited

OTHER PUBLICATIONS

Miller, et al., "Gene Transfer Vectors for Mammalian Cells" 1987, Cold Spring Harbor Laboratory.
Milone, et al., "Chimeric receptors containing CD137 signal transduction domains mediate enhanced survival of T cells and increased antileukemic efficacy in vivo." Mol Ther. Aug. 2009; 17(8):1453-64.
Morbitzer; et al., "Regulation of selected genome loci using de novoengineered transcription activator-like effector (TALE)-type transcription factors." Proc Natl Acad Sci USA 2011; 107(50): 21617-22.
Morrow, et al., "Multidrug resistance protein 1 (MRP1, ABCC1) mediates resistance to mitoxantrone via glutathione-dependent drug efflux." Mol Pharmacol. Apr. 2006; 69(4):1499-505.
Moscou, et al., "A simple cipher governs DNA recognition by TAL effectors." Science 2009; 326(5959): 1501.
Multhoff & Hightower, "Distinguishing integral and receptor-bound heat shock protein 70 (Hsp70) on the cell surface by Hsp70-specific antibodies." Cell Stress Chaperones. May 2011; 16(3):251-5.
Multhoff, "Heat shock protein 70 (Hsp70): membrane location, export and immunological relevance". Methods 2007; 43:229-237.
Mussolino, et al., "A novel TALE nuclease scaffold enables high genome editing activity in combination with low toxicity." Nucleic Acids Res 2011; 39(21): 9283-93.
Ormhoj, et al., "CARs in the Lead Against Multiple Myeloma." Curr Hematol Malig Rep. Apr. 2017; 12(2):119-125.
Paques, et al., "Meganucleases and DNA double-strand break-induced recombination: perspectives for gene therapy." Curr Gene Ther 2007; 7(1): 49-66.
Park, et al., "Treating Cancer with Genetically Engineered T Cells," Trends Biotechnol., 2011; 29(11): 550-557.
Perbai "A Practical Guide to Molecular Cloning," 1984, Wiley & Sons.
Perrin, et al., "Asymmetrical recognition and activity of the 1-SceI endonuclease on its site and on intron-exon junctions." Embo J 1993; 12(7): 2939-47.
Pingoud, et al. "Precision genome surgery." Nat Biotechnol 2007; 25(7): 743-4.
Pitti, et al., "Induction of apoptosis by Apo-2 ligand, a new member of the tumor necrosis factor cytokine family". J Bioi Chem 1996; 271:12687-90.
Pizzitola et al., "Chimeric antigen receptors against CD33/CD123 antigens efficiently target primary acute myeloid eukemia cells in vivo," Leukemia, 2014; 28(8):1596-605.
Pockley, et al., "Detection of heat shock protein 70 (Hsp70) and anti-Hsp70 antibodies in the serum of normal individuals." Immunol. Invest. 1998; 27 367-377.
Poirot, et al., "Multiplex Genome-Edited T-cell Manufacturing Platform for "Off-the-Shelf" Adoptive T-cell Immunotherapies." Cancer Res. Sep. 15, 2015; 75(18):3853-64.
Porter, et al., "Chimeric Antigen Receptor-Modified T Cells in Chronic Lymphoid Leukemia," N. Engl. J. Med., 2011; 365:725-733.
Porteus, et al., "Gene targeting using zinc finger nucleases." Nat Biotechnol 2005; 23(8): 967-73.
Quintarelli, "Co-expression of cytokine and suicide genes to enhance the activity and safety of tumor-specific cytotoxic T lymphocytes." Blood. Oct. 15, 2007; 110(8):2793-802.
Ravetch, et al., "Alternative membrane forms of Fe gamma RIii(CD16) on human natural killer cells and neutrophils. Cell type-specific expression of two genes that differ in single nucleotide substitutions". J. Exp. Med. 1989; 170:481-497.
Riechmann, et al., "Reshaping human antibodies for therapy." Nature. Mar. 24, 1988; 332(6162):323-7.
Riemer, et al., Vaccination with cetuximab mimotopes and biological properties of induced anti-epidermal growth factor receptor antibodies, J Natl Cancer Inst. 2005; 97(22):1663-70.
Roguska, et al., "A comparison of two murine monoclonal antibodies humanized by CDR-grafting and variable domain resurfacing." Protein Eng. Oct. 1996; 9(10):895-904.
Roguska, et al., "Humanization of murine monoclonal antibodies through variable domain resurfacing." Proc Natl Acad Sci U S A. Feb. 1, 1994;91(3):969-73.
Rouet, et al., "Introduction of double-strand breaks into the genome of mouse cells by expression of a rare-cutting endonuclease." Mol Cell Bio 1994; 14(12):8096-106.
Rudikoff, et al., "Single amino acid substitution altering antigen-binding specificity", Proc. Nat. Acad. Sci. USA. Immunology, 1982, 79: abstract on p. 1979.
Rudnick, et al., "Affinity and avidity in antibody-based tumor targeting." Cancer Biother Radiopharm. Apr. 2009; 24(2):155-61.
Sadelain, et al., "The promise and potential pitfalls of chimeric antigen receptors," Curr Opin Immunol, 2009; 21(2):215-23.
Sander, et al., "Targeted gene disruption in somatic zebrafish cells using engineered TALENs." Nat Biotechnol 2011; 29(8): 697-8.
Sambrook, et al., "Molecular Cloning: A Laboratory Manual, Third Edition," 2001, Cold Spring Harbor, New York: Cold Spring Harbor Laboratory Press.
Sangiolo, et al., "Lentiviral vector conferring resistance to mycophenolate mofetil and sensitivity to ganciclovir for in vivo T-cell selection." Gene Ther 2007; 14(21): 1549-54.
Scharfenberger, et al., "Transgenic mouse technology in skin biology: generation of complete or tissue-specific knockout mice." J Invest Dermatol. Jan. 2014; 134(1):1-5.
Schweitzer, et al., "Dihydrofolate reductase as a therapeutic target." Faseb J 1990; 4(8): 2441-52.
Schwenk, et al., "Temporally and spatially regulated somatic mutagenesis in mice." Nucleic Acids Res. Mar. 15, 1998; 26(6):1427-32.
Smyth, et al., 2001, "Tumor necrosis factor-related apoptosis-inducing ligand (TRAIL) contributes to interferon gamma-dependent natural killer cell protection from tumor metastasis." J Exp Med;193:661-70.
Sorek, et al., "CRISPR-mediated Adaptive Immune Systems in Bacteria and Archaea." Annu Rev Biochem. 2013.
Stangl, et al., "Targeting membrane heat-shock protein 70 (Hsp70) on tumors by cmHsp70.1 antibody." Proc Natl Acad Sci U S A. Jan. 11, 2011;108(2):733-8.
Steiner, et al., "High HSP70-membrane expression on leukemic cells from patients with acute myeloid leukemia is associated with a worse prognosis." Leukemia. Nov. 2006; 20(11):2076-9.
Stoddard, "Homing endonuclease structure and function." Q Rev Biophys 2005; 38(1): 49-95.
Takebe, et al., "Generation of dual resistance to 4-hydroperoxycyclophosphamide and methotrexate by retroviral transfer of the human aldehyde dehydrogenase class 1 gene and a mutated dihydrofolate reductase gene." Mol Ther 2001; 3(1): 88-96.
Talmadge, et al., "Murine models to evaluate novel and conventional therapeutic strategies for cancer." Am J Pathol. Mar. 2007; 170(3):793-804.
Tame, et al., "Scoring functions: a view from the bench." J Comput Aided Mol Des. Mar. 1999; 13(2):99-108.
Tan, et al., ""Superhumanized" antibodies: reduction of immunogenic potential by complementarity-determining region grafting with human germline sequences: application to an anti-CD28."J Immunol. Jul. 15, 2002; 169(2):1119-25.
Tesson, et al. "Knockout rats generated by embryo microinjection of TALENs." Nat Biotechnol 2011; 29(8): 695-6.
Thaventhiran, "T cell co-inhibitory receptors-functions and signalling mechanisms." J. Clinical & Cellular Immunology 2012, 12 pages.
Thurber, et al., "Antibody tumor penetration: transport opposed by systemic and antigen-mediated clearance." Adv Drug Deliv Rev. Sep. 2008; 60(12):1421-34.
Valton, et al., "A Multidrug-resistant Engineered CAR T Cell for Allogeneic Combination Immunotherapy." Mol Ther. Sep. 2015;23(9):1507-18.
Van Rhenen; et al., "The novel AML stem cell associated antigen CLL-1 aids in discrimination between normal and leukemic stem cells." Blood 2007; 110(7):2659-66.
Voskoglou-Nomikos, et al., "Clinical predictive value of the in vitro cell line, human xenograft, and mouse allograft preclinical cancer models." Clin Cancer Res. Sep. 15, 2003; 9(11):4227-39.

(56) References Cited

OTHER PUBLICATIONS

Wang, et al., "Treatment of CD33-directed chimeric antigen receptor-modified T cells in one patient with relapsed and refractory acute myeloid leukemia." Mol Ther. Jan. 2015; 23(1):184-91.

Weber, et al., "Assembly of designer TAL effectors by Golden Gate cloning." PLoS One 2011; 6(5): e19722.

Weir, et al., "Handbook of Experimental Immunology, vols. I-IV," 1986 Blackwell Scientific Publications.

White, "Membrane Protein Insertion: The Biology-Physics Nexus", J Gen Physiol. 2007; 129(5): 363-369.

Wiley; et al. "Identification and characterization of a new member of the TN F family that induces apoptosis." Immunity 1995;3:673-82.

Woodward, "Immobilized Cells and Enzymes," 1986, IRL Press.

Wright; et al., "Characterization of the CD200 receptor family in mice and humans and their interactions with CD200." J Immunol. 2003; 171(6):3034-46.

Wu, et al., "An activating immunoreceptor complex formed by NKG2D and DAP10." Science. Jul. 30, 1999; 285(5428):730-2.

Wu, et al., "Methods in Enzymology vol. 154. Recombinant DNA, Part E", 1987 Academic Press.

Wu, et al., "Methods in Enzymology vol. 155. Recombinant DNA, Part F" 1987 Academic Press.

Yam, et al., "Ex vivo selection and expansion of cells based on expression of a mutated inosine monophosphate dehydrogenase 2 after HIV vector transduction: effects on lymphocytes, monocytes, and CD34+ stem cells." Mol Ther 2006; 14(2): 15 236-44.

Yarilin, A.A. "Osnovy immunologii", M: Medizina, 1999, p. 172-174.

Zettlitz, et al., "Humanization of a mouse monoclonal antibody directed against a cell surface-exposed epitope of membrane-associated heat shock protein 70 (Hsp70)." REMol Biotechnol. 2010; 46(3):265-78).

Zhang, et al., "Characterization of high-affinity peptides and their feasibility for use in nanotherapeutics targeting leukemia stem cells" Nanomedicine 2011; 8(7): 1116-1124.

Zhang, et al., "Efficient construction of sequence-specific TAL effectors for modulating mammalian transcription." Nat Biotechnol 2011; 29(2): 149-53.

Zhang, et al., "Plasma levels of Hsp70 and anti-Hsp70 antibody predict risk of acute coronary syndrome" Cell Stress Chaperones. 2010; 15(5): 675-686.

Zhao, et al., "Targeting C-type lectin-like molecule-1 for antibody-mediated immunotherapy in acute myeloid leukemia." Haematologica. Jan. 2010; 95(1):71-8.

Zielske, et al., "In vivo selection of MGMT(P140K) lentivirustransduced human NOD/SCID repopulating cells without pretransplant irradiation conditioning. "J Clin Invest 2003; 112(10)1561-70.

Philip et al., "A highly compact epitope-based marker/suicide gene for easier and safer T-Cell Therapy." Blood, Aug. 21, 2014, 124(8): 1277-1287.

Yarilin A.A., "Molecular and cellular basis of adaptive immunity." Immunology Basics: Manual.—M.: Medicina, 1999, pp. 169-174.

Chien et al., "Significant structural and functional change of an antigen-binding site by a distant amino acid substitution: Proposal of a structural mechanism", Proc. Natl. Acad. Sci. USA 1989, 86:5532-5536.

Chu et al. "Genetic Modification of T Cells Redirected towards CS1 Enhances Eradication of Myeloma Cells", Clin. Cancer Res. Aug. 1, 2014; 20(15):3989-4000.

Lamers et al., "Immune responses to transgene and retroviral vector in patients treated with ex vivo-engineered T cells", Blood, Jan. 6, 2011; 117(1):72-82.

Ohno et al., "Antigen binding specificities of antibodies are primarily determined by seven residues of VH", Proc. Natl. Acad. Sci. USA, 1985, 82(9): 2945-2949.

Singer & Berg P., "Molecules of the Genetic Apparatus." Genes and Genomes, 1998, vol. 1, p. 63.

Kevin J. Curran et al., Chimeric Antigen Receptors Fort Cell Immunotherapy: Current Understanding and Future Directions, pp. 405-415; 2012; John Wiley & Sons, Ltd, J Gene Med.†

Sadelain et al., The Basic Principles of Chimeric Antigen Receptor Design, pp. 388-398; 2013; Cancer Discovery; American Association for Cancer Research.†

Hua Lu et al., Targeting Human C-Type Lectin-Like Molecule-1 (CLL1) With a Bispecific Antibody for Immunotherapy of Acute Myeloid Leukemia, 9841-9845; 2014; Angew. Chem. Int. Ed., Wiley-VCH Verlag GMBH & Co. KGAA, Weinheim.†

Michael C. Jensen, et al., Design and Implementation of Adoptive Therapy With Chimeric Antigen Receptor-Modified T Cells, pp. 127-144, 2014, John Wiley & Sons Ltd., Immunol Rev.†

David C. Taussig, et al., Hematopoietic Stem Cells Express Multiple Myeloid Markers: Implications for the Origin and Targeted Therapy of Acute Myeloid Leukemia.†

\* cited by examiner
† cited by third party

ANTI-CLL1 SPECIFIC SINGLE-CHAIN CHIMERIC ANTIGEN RECEPTORS (SCCARS) FOR CANCER IMMUNOTHERAPY

CROSS-REFERENCE TO RELATED APPLICATION

This application is a 35 U.S.C. 371 National Phase of PCT Application No. PCT/EP2016/051469 filed Jan. 25, 2016 which claims priority to DK Application No. PA201570044 filed Jan. 26, 2015. The disclosure of these prior applications are hereby incorporated by reference herein.

FIELD OF THE INVENTION

C-type lectin-like molecule-1 (CLL1) has been identified as being frequently over-expressed on most acute myeloid leukemia (AML) stem cells (LSC), compared to normal hematopoietic stem cells or other cell types. The present invention relates to methods to target CLL1 positive malignant cells using Chimeric Antigen Receptors (anti CLL1-CAR), which are recombinant chimeric proteins able to redirect immune cell specificity and reactivity toward selected membrane antigen CLL1. These anti-CLL1 CAR more particularly comprise an extracellular ligand binding comprising a scFV derived from some specific anti-CLL1 monoclonal antibodies. The engineered immune cells endowed with such CARs confer adoptive immunity against CLL1 positive cell as part as various cell therapies for treating cancer, in particular hematologic cancers, with higher efficiency.

BACKGROUND OF THE INVENTION

Adoptive immunotherapy, which involves the transfer of antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (scCARs) (Jena, Dotti et al. 2010). scCARs are synthetic receptors consisting of a targeting moiety that is associated with one or more signaling domains in a single fusion molecule. In general, the binding moiety of a scCAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation scCARs are derived from the cytoplasmic region of the CD3zeta or the Fc receptor gamma chains. First generation scCARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of scCAR modified T cells. scCARs have successfully allowed T cells to be redirected against antigens expressed at the surface of tumor cells from various malignancies including lymphomas and solid tumors (Jena, Dotti et al. 2010).

Meanwhile, induction treatments for acute myeloid leukemia (AML) have remained largely unchanged for nearly 50 years and AML remains a disease of poor prognosis. AML is a disease characterized by the rapid proliferation of immature myeloid cells in the bone marrow resulting in dysfunctional hematopoiesis. Although standard induction chemotherapy can induce complete remissions, many patients eventually relapse and succumb to the disease, calling for the development of novel therapeutics for AML. Recent advances in the immunophenotyping of AML cells have revealed several AML associated cell surface antigens that may act as targets for future therapies.

Among others, CLL1 (C-Type Lectin-Like Molecule-1) appears to be an interesting tumoral antigen target as it is expressed by leukemic blasts at diagnosis from 85-92% of AML patients analysed It is a 75 kDa member of the group V C-type lectin-like receptor family of molecules. Group V molecules have a lectin-like domain that binds to non-sugar ligands. CLL1 is a 265 amino acid type II transmembrane glycoprotein (Uniprot database: Q5QGZ9 for human protein encoded by gene no 160364 in "Entrez Gene" database) that contains a 200 AA extracellular domain. CLL1 is also referred to in the literature and databases as MICL, CLEC12 and KLRL1.

Bakker et al, 2004 has shown that the CLL1 antigen is associated with AML stem cells. Like some other antigens (such as CD33), CLL1 is a cell surface protein that is specifically expressed on most malignant lymphoid stem cells (AML LSC), while not being expressed on normal HSC (Van Rhenen et al, 2007). Meanwhile, CLL1 was revealed to be a diagnostic marker in AML (Larsen et al, 2012). Anti-CLL-1 antibodies enable both AML-specific stem-cell detection and possibly antigen-targeting as distinguishing malignant cells from normal stem cells both at diagnosis and in remission (van Rhenen et al, 2007). However, none of these antibodies have been reported to date as being tested in clinical trials as therapeutic antibodies.

Monoclonal antibodies have often been used to treat lymphomas, but their use in leukemias has been more limited. Gemtuzumab ozogamicin (Mylotarg®) is a monoclonal antibody with a cell poison attached to it. Previously approved to treat AML in older patients, it was withdrawn from the market after studies found some toxicity associated with the product (press release of Dec. 10, 2010 in PMLIVE "ASH: Pfizer eyes re-launch of Mylotarg"). Other monoclonal therapeutic antibodies have shown adverse effects over the last decade (Klastersky, J. (2006) "Adverse effects of the humanized antibodies used as cancer therapeutics" Current Opinion in Oncology. 18(4):316-320)

In the publication of Zhang et al (2011), micellar nanoparticles covalently decorated with CLL1-targeting peptides have been described for targeted drug delivery (daunorubicin); these "targeting nanomicelles" transport the drug load to the interior of cells expressing CLL1 and to LSCs isolated from clinical specimens in vitro. It was showed that CLL1-targeting nanomicelles had the potential to be used for targeted drug delivery to leukemia stem cells. However, no therapeutic effects could be attributed to the CCL-1 targeting peptide per se.

In view of the above, the inventors have pursued a new approach to target CLL1 using immune cells endowed with specific chimeric antigen receptors based on anti-CLL1 monoclonal antibodies, which redirect immune cell specificity towards CLL1 positive cell.

The engineered immune cells that they obtained using this approach have proven efficacy to eliminate CLL1 positive malignant cells. In particular, they have appeared to be particularly useful in the context of the production of allogeneic TCR negative engineered immune cells, allowing a reduction of side effects, such as GvHD.

Thus, the present invention opens the way to treating patients affected with a condition characterized by an overabundance of CLL1-expressing cells using adoptive immunotherapy. Even more, the present invention provides with engineered allogeneic immune cells that may be used as "off-the-shelf" allogeneic therapeutic products. As a further advantage of the invention, the CAR positive engineered cells can be made compatible (i.e. resistant) with chemotherapy or immunodepleting treatments, thereby enabling synergistic effects between chemotherapy and immunotherapy.

SUMMARY OF THE INVENTION

The inventors have generated CLL1 specific single-chain scCAR having different design and comprising different scFV derived from anti-CLL1 specific antibodies.

In particular, The Inventors have developed anti-CLL1 specific single-chain CAR (scCAR) comprising VL and VL chains derived from SC02-357, SC02-378, SCO2-161, M26, M31, G4, M22, M29, M2, M5, G12, 21.26 and 1075.7 antibodies, with different architectures and identified highly specific and very selective scCARs constructions that bind to CLL1 expressing cells and selectively destroy CLL1 expressing cancer cells.

Following non-specific activation in vitro (e.g. with anti CD3/CD28 coated beads and recombinant IL2), primary T-cells from donors have been transformed with polynucleotides expressing these scCARs using viral transduction. In certain instances, the T-cells were further engineered to create less or non-alloreactive T-cells, more especially by disruption of a component of TCR ($\alpha\beta$-T-Cell receptors) to prevent Graft versus host reaction.

T-cells were further engineered to create T cells resistant to anti-cancer drugs, to be used in combination with said classical anti-cancer drugs.

The resulting engineered T-cells displayed reactivity in-vitro against CLL1 positive cells to various extend, showing that the scCARs of the present invention contribute to antigen dependent activation, and also proliferation, of the T-cells, making them useful for immunotherapy.

The resulting engineered T-cells displayed reactivity in-vivo against CLL1 positive cells and significantly reduce the number of cancer cells in vivo.

The engineered T-cells of the invention are designed to display in-vivo reactivity against CLL1 positive cells, can be used in concomitance with anti-cancer drugs, are well tolerated. In a particular embodiment, the engineered T-cells of the invention remain efficient even after several administrations, making them useful for immunotherapy as a first treatment (induction), as a consolidation treatment, as a treatment in combination with classical anticancer chemotherapy. The polypeptides and polynucleotide sequences encoding the CARs of the present invention are detailed in the present specification.

The engineered immune cells of the present invention are particularly useful for therapeutic applications such as acute myeloma leukemia (AML) treatments.

Figure 1:
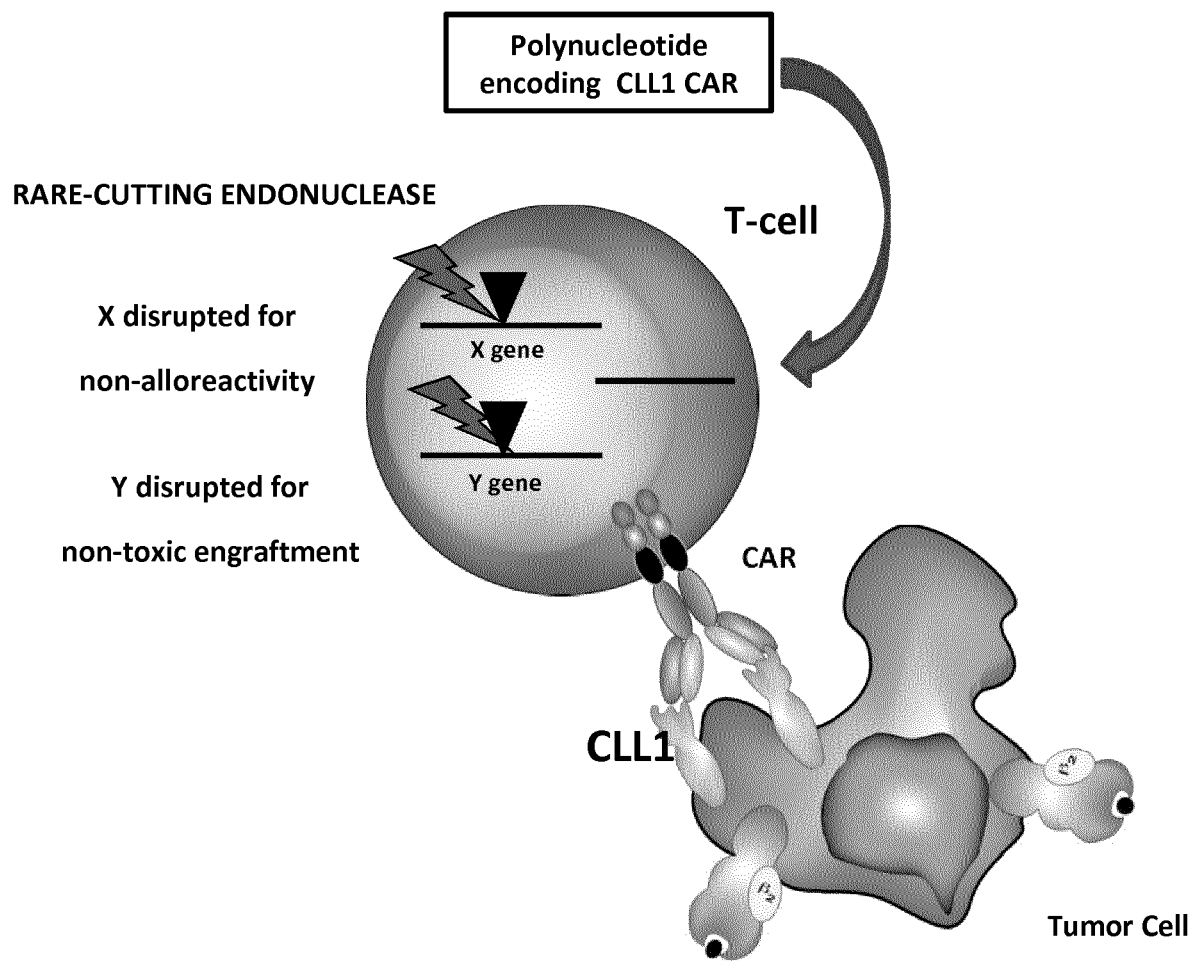
FIG. 1: Schematic representation of an engineered immune cell according to the invention. The engineered immune cell presented in this figure is a T-cell transduced with a retroviral vector encoding CLL1-scCAR. This T-cell was further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or HPRT (with respect to 6-Thioguanine).

(A) CLL1 specific CAR prototype according to the present invention not involving an epitope tagging sequence for sorting or depleting cells: $V_1$ and v2 represents either VH or VL chain respectively of an antibody binding CLL1, TM: transmembrane domain, L: linker, TM: Transmembrane domain (preferably CD8$\alpha$ transmembrane domain), 4-1BB: intracellular co-stimulatory domain, CD3 ITAM: activation domain.

(B) CLL1 specific CAR architectures according to the invention further including at least one epitope inserted in the extracellular ligand binding domain of the CAR, wherein said epitope is inserted between the VH and VL chains; said epitope being bordered by different linkers.;

(C): CLL1 specific CAR architectures according to the invention, where two epitopes are inserted in the extracellular ligand binding domain of the CAR, one is inserted between the N-terminal end of the CAR and the VH chain, said epitope being bordered by at least one or two linkers; the second epitope is inserted between the VH and VL chains, said $2^{nd}$ epitope being also bordered by 2 at least one or two linkers. The architectures illustrated herein differ by the linkers used bordering the $2^{nd}$ epitope.

(D): CLL1 specific CAR architectures according to the invention, where two epitopes are inserted in the extracellular ligand binding domain of the CAR, one is inserted between the VH and VL chains; the other epitope is inserted between the VL chain and the hinge, each said epitope being also bordered by at least one or two linkers. The architectures illustrated herein differ by the linkers used bordering the $1^{st}$ epitope.

(E): CLL1 specific CAR architecture according to the invention, where two epitopes are inserted in the extracellular domain of the CAR, one is inserted between the N-terminal end of the CAR and the VH chain, said epitope being bordered by at least one or two linkers; the second epitope is inserted between the VL chain and the hinge, said $2^{nd}$ epitope being also bordered by such linkers.

(F): CLL1 specific CAR architectures according to the invention, where three epitopes are inserted in the extracellular domain of the CAR, one is inserted between the N-terminal end of the CAR and the VH chain, said epitope being bordered by at least one or two linkers; the second epitope is inserted between the VH and VL chains, said epitope being also bordered by such linkers, and the third epitope being inserted between the VL chain et the hinge. These two architectures differ by the linkers used bordering the 2$^{nd}$ epitope.

(G): CLL1 specific CAR architectures according to the invention, where at least two epitopes (preferably CD20 epitopes) are inserted in the extracellular ligand binding domain between the hinge and the anti CLL1 VH and VL chains. In the third exemplary architecture, one CD34 epitope is included between two CD20 epitopes. Further architectures may be considered where CD34 replaces any other previous CD20 epitopes.

(H): CLL1 specific CAR architectures according to the invention, where at least two epitopes are inserted at the extremity of the extracellular ligand binding domain.

TABLE 1

Sequence of the different scCAR components excepted the scFvs

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| FcεRIIIα hinge | SEQ ID NO. 3 | GLAVSTISSFFPPGYQ |
| CD8α hinge | SEQ ID NO. 4 | TTTPAPRPPTPAPTIASQPLSLR PEACRPAAGGAVHTRGLDFACD |
| IgG1 hinge | SEQ ID NO. 5 | EPKSPDKTHTCPPCPAPPVAGPS VFLFPPKPKDTLMIARTPEVTCV VVDVSHEDPEVKFNWYVDGVEVH NAKTKPREEQYNSTYRVVSVLTV LHQDWLNGKEYKCKVSNKALPAP IEKTISKAKGQPREPQVYTLPPS RDELTKNQVSLTCLVKGFYPSDI AVEWESNGQPENNYKTTPPVLDS DGSFFLYSKLTVDKSRWQQGNVF SCSVMHEALHNHYTQKSLSLSPG K |
| CD8α transmembrane domain | SEQ ID NO. 6 | IYIWAPLAGTCGVLLLSLVITLY C |
| 41BB transmembrane domain | SEQ ID NO. 7 | IISFFLALTSTALLFLLFFLTLR FSVV |
| 41BB intracellular domain | SEQ ID NO. 8 | KRGRKKLLYIFKQPFMRPVQTTQ EEDGCSCRFPEEEEGGCEL |
| CD3ζ intracellular domain | SEQ ID NO. 9 | RVKFSRSADAPAYQQGQNQLYNE LNLGRREEYDVLDKRRGRDPEMG GKPRRKNPQEGLYNELQKDKMAE AYSEIGMKGERRRGKGHDGLYQG LSTATKDTYDALHMQALPPR |
| Linker | SEQ ID NO. 10 | GGGGSGGGGSGGGGS |

TABLE 2

Sequence of variable regions of exemplary anti-CLL1 VH and VL chains and their respective CDRs

| ScFv sequences | SEQ ID # | Raw amino acid sequence |
|---|---|---|
| SC02-357 heavy chain variable region | SEQ ID NO. 11 | QVQLQESGPGLVKPSETLSLTCVVSGGSISSSNWWSWVRQPPGKGLE WIGEIYHSGSPNYNPSLKSRVTISVDKSKNQFSLKLSSVTAADTAVYYSSS GGFFDYWGQGTLVTVSS |
| CDR1 | SEQ ID NO. 119 | GSISSSNWWS |
| CDR2 | SEQ ID NO. 120 | WIGEIYHSGSPDY |
| CDR3 | SEQ ID NO. 121 | KVSTGGFFDY |
| SC02-378 heavy chain variable region | SEQ ID NO. 12 | QVQLQESGPGLVKPSETLSLTCVVSGGSISSSNWWSWVRQPPGKGLE WIGEIYHSGSPNYNPSLKSRVTISVDKSKNQFSLKLSSVTAADTAVYYCAR SSSGGFFDYWGQGTLVTVSS |
| CDR1 | SEQ ID NO. 122 | GSISSSNWWS |
| CDR2 | SEQ ID NO. 123 | WIGEIYHSGSPNY |
| CDR3 | SEQ ID NO. 124 | RSSSGGFFDY |
| SC02-161 heavy chain variable region | SEQ ID NO. 13 | QVQLQESGPGLVKPSETLSLTCVVSGGSISSSNWWSWVRQPPGKGLE WIGEIYHSGSPNYNPSLKSRVTISVDKSKNQFSLKLSSVTAADTAVYYCAR QTTAGSFDYWGQGTLVTVSS |
| CDR1 | SEQ ID NO. 125 | GSISSSNWWS |
| CDR2 | SEQ ID NO. 126 | WIGEIYHSGSPNY |
| CDR3 | SEQ ID NO. 127 | RQTTAGSFDY |
| SC02-357 & SC02-378 & SC02-161 light chain variable region | SEQ ID NO. 14 | DIQMTQSPSSLSASVGDRVTITCRASQSISSYLNWYQQKPGKAPKLLIYA ASSLQSGVPSRFSGSGSGTDFTLTISSLQPEDFATYYCQQSYSTPPTFGQG TKVEIK |

TABLE 2 -continued

Sequence of variable regions of exemplary anti-CLL1 VH and VL chains and their respective CDRs

| ScFv sequences | SEQ ID # | Raw amino acid sequence |
|---|---|---|
| CDR1 | SEQ ID NO. 128 | QSISSYLN |
| CDR2 | SEQ ID NO. 129 | LLIYAASSLQS |
| CDR3 | SEQ ID NO. 130 | QQSYSTPP |
| M26 heavy chain variable region | SEQ ID NO. 15 | EVQLQQSGPELVKPGASVKMSCKASGYTFTSYFIHWVKQKPGQGLEWI GFINPYNDGSKYNEKFKGKATLTSDKSSSTAYMELSSLTSEDSAVYYCTRD DGYYGYAMDYWGQGTSVTVSS |
| CDR1 | SEQ ID NO. 131 | GYTFTSYFIH |
| CDR2 | SEQ ID NO. 132 | WIGFINPYNDGSKY |
| CDR3 | SEQ ID NO. 133 | TRDDGYYGYAMDY |
| M26 light chain variable region | SEQ ID NO. 16 | DIQMTQSPSSLSASLGERVSLTCRATQELSGYLSWLQQKPDGTIKRLIYA ASTLDSGVPKRFSGNRSGSDYSLTISSLESEDFADYYCLQYAIYPYTFGGG TKLEIKR |
| CDR1 | SEQ ID NO. 134 | QELSGYLS |
| CDR2 | SEQ ID NO. 135 | RLIYAASTLDS |
| CDR3 | SEQ ID NO. 136 | LQYAIYPY |
| M31 heavy chain variable region | SEQ ID NO. 17 | EVQLQQSGPELVKPGASVKMSCKASGYTFTSYVMHWVKQKPGQGLE WIGYINPYNDGTKYNEKFKGKATLTSDTSSSTAYMELNSLTSEDSAVYFC ARPIYFDNDYFDYWGQGTTLKVSS |
| CDR1 | SEQ ID NO. 137 | GYTFTSYVMH |
| CDR2 | SEQ ID NO. 138 | WIGYINPYNDGTKY |
| CDR3 | SEQ ID NO. 139 | ARPIYFDNDY |
| M31 light chain variable region | SEQ ID NO. 18 | TIVLTQSPASLAVSLGQRATISCRASESVDSYGNSFMHWYQQKPGQPPK LLIYLASNLESGVPARFSGSGSRTDFTLTIDPVEADDAATYYCQQNNYDP WTFGGGTKLEIK |
| CDR1 | SEQ ID NO. 140 | ESVDSYGNSFMH |
| CDR2 | SEQ ID NO. 141 | LLIYLASNLES |
| CDR3 | SEQ ID NO. 142 | QQNNYDPW |
| G4 heavy chain variable region | SEQ ID NO. 19 | EVQLQQSGPELVKPGASMKISCKASGYSFTGYTMNWVKQSHEKNLEWI GPINPYNDGTIYNPNFKGKATLTVDKASSTAYMELLSLTSDDPAVYYCAR TDDYDDYTMDYWGQGTSVTVSS |
| CDR1 | SEQ ID NO. 143 | QQNNYDPW |
| CDR2 | SEQ ID NO. 144 | WIGPINPYNDGTIY |
| CDR3 | SEQ ID NO. 145 | ARTDDYDDYTMDY |
| G4 light chain variable region | SEQ ID NO. 20 | EIQMTQTPSSLSASLGDRVTISCRASHDISNYLNWYQQKPDGTLKLLIYYT SRLHSGVPSRFSGSGSGTDYSLTISNLEQEDIATYFCQQGKTLLWTFGGG TKLEIK |
| CDR1 | SEQ ID NO. 146 | HDISNYLN |
| CDR2 | SEQ ID NO. 147 | LLIYYTSRLHS |
| CDR3 | SEQ ID NO. 148 | QQGKTLLW |
| M22 heavy chain variable region | SEQ ID NO. 21 | QVQLQQPGAELVKPGASVKLSCKASGYTFTRYWMHWVKQRPGQGLE WIGNIDPSDTETHYNQQFKDKATLTVDKSSSTAYMQLSSLTSEDSAVYY CAIYYGNPSYYAMDYWGQGTSVTVSS |
| CDR1 | SEQ ID NO. 149 | GYTFTRYWMH |
| CDR2 | SEQ ID NO. 150 | WIGNIDPSDTETHY |
| CDR3 | SEQ ID NO. 151 | AIYYGNPSYYAMDY |

TABLE 2 -continued

Sequence of variable regions of exemplary anti-CLL1 VH and VL chains and their respective CDRs

| ScFv sequences | SEQ ID # | Raw amino acid sequence |
|---|---|---|
| M22 light chain variable region | SEQ ID NO. 22 | DIVMTQSPSSLIVTAGEKVTMSCKSSQNLLNSGNQKKYLNWYQQKPG QPPKLLIYWASTRESGVPDRFTGSGSGTDFTLTISSVQAEDLAVYFCQND YSYPFTFGAGTKLELK |
| CDR1 | SEQ ID NO. 152 | QNLLNSGNQKKYLN |
| CDR2 | SEQ ID NO. 153 | LLIYWASTRES |
| CDR3 | SEQ ID NO. 154 | QNDYSYPF |
| M29 heavy chain variable region | SEQ ID NO. 23 | EVQLQQSGPELVKPGASVKMSCKASGYIFTSYVMYWVKQKPGQGLEW IGYINPYNDGTKYNEKFKGKATLTSDKSSSTAYMELSSLTSEDSAVYYCAR YYDYDYYFDYWGQGTTLTVSS |
| CDR1 | SEQ ID NO. 155 | GYIFTSYVMY |
| CDR2 | SEQ ID NO. 156 | WIGYINPY |
| CDR3 | SEQ ID NO. 157 | ARYYDYDYYFDY |
| M29 light chain variable region | SEQ ID NO. 24 | DIQMTQSPSSLSASLGGKVTITCKASQDINKYIAWYQHKPGKGPRLLIHY TSTLQPGIPSRFSGSGSGRDYSFSISNLEPEDIATYYCLQYDYLWTFGGGT KLEIK |
| CDR1 | SEQ ID NO. 158 | QDINKYIA |
| CDR2 | SEQ ID NO. 159 | LLIHYTSTLQP |
| CDR3 | SEQ ID NO. 160 | LQYDYLW |
| M2 heavy chain variable region | SEQ ID NO. 25 | EVQLRQSGPELVKPGASVKMSCKASGYTFTSYFMHWVKQKPGQGLEW IGFINPYNDGTKYNEKFKGKATLTSDKSSSTAYMELNSLTSEDSAVYYCTR DDGYYDYAMDYWGQGTSVTVSS |
| CDR1 | SEQ ID NO. 161 | GYTFTSYFMH |
| CDR2 | SEQ ID NO. 162 | WIGFINPYNDGTKY |
| CDR3 | SEQ ID NO. 163 | TRDDGYYDYAMDY |
| M2 light chain variable region | SEQ ID NO. 26 | DIQMTQSPSSLSASLGERVSLTCRASQEISVYLSWLQQKPDGTIKRLIYAA STLDSGVPERFSGSRSGSDYSLTISSLESEDFADYYCLQYASYPY-TFGGGTK LEIKR |
| CDR1 | SEQ ID NO. 164 | QEISVYLS |
| CDR2 | SEQ ID NO. 165 | RLIYAASTLDS |
| CDR3 | SEQ ID NO. 166 | LQYASYPY |
| M5 heavy chain variable region | SEQ ID NO. 27 | EVQLQQSGAELVRPGASVKLSCTASGFNIKDDYIHWVKQRPEQGLEWI GWIDPEKGDTAYASKFQDKATITSDTSSNTAYLQLSSLTSEDTAVYYCTLT GRFDYWGQGTTLTVSS |
| CDR1 | SEQ ID NO. 167 | GFNIKDDYIH |
| CDR2 | SEQ ID NO. 168 | WIGWIDPEKGDTAYAS |
| CDR3 | SEQ ID NO. 169 | TLTGRFDY |
| M5 light chain variable region | SEQ ID NO. 28 | DIVMSQSPSSLAVSVGEKVTMSCKSSQSLLYSSNQKNNLAWYQQKPGQ SPKLLIYWASTRESGVPDRFTGSGSGTDFTLTISSVQAEDLAVYYCQQYYS YRTFGGGTKLEIK |
| CDR1 | SEQ ID NO. 170 | QSLLYSSNQKNNLA |
| CDR2 | SEQ ID NO. 171 | LLIYWASTRES |
| CDR3 | SEQ ID NO. 172 | QQYYSYR |
| G12 heavy chain variable region | SEQ ID NO. 29 | QVQLQQPGAELVKPGASMKMSCKASGYTFPSSNIHWLKQTPGQGLE WIGVIYPGNGDTSYNQKFKDKATLTTDKSSSTAYMQLSSLTSEDSAIYFC ARVYNWHFDVWGAGTTVTVSS |

TABLE 2 -continued

Sequence of variable regions of exemplary anti-CLL1 VH and VL chains and their respective CDRs

| ScFv sequences | SEQ ID # | Raw amino acid sequence |
|---|---|---|
| CDR1 | SEQ ID NO. 173 | GYTFPSSNIH |
| CDR2 | SEQ ID NO. 174 | WIGVIYPGNGDTSY |
| CDR3 | SEQ ID NO. 175 | AIYFVYNWHFDV |
| G12 light chain variable region | SEQ ID NO. 30 | NIVLTQSPASLAVSLGQRATISCRASESVDGYGDIFMLWYQQKPGQPPK LLIYFASNLESGVPARFSGSGSRTDFTLTIDPVEADDAATYYCQQNNEDP YTFGGGTKLEIKR |
| CDR1 | SEQ ID NO. 176 | ESVDGYGDIFML |
| CDR2 | SEQ ID NO. 177 | LLIYFASNLES |
| CDR3 | SEQ ID NO. 178 | QQNNEDPY |
| 21.26 heavy chain variable region | SEQ ID NO. 31 | QVQLQQPGAELVKPGTSVKLSCKASGYTFTRYWMHWVKQRPGQGLE WIGMIHPSSGSTSYNEKVKNKATLTVDRSSTTAYMQLSSLTSEDSAVYYC ARDGDYYYGTGDYWGQGTTLTVSS |
| CDR1 | SEQ ID NO. 179 | GYTFTRYWMH |
| CDR2 | SEQ ID NO. 180 | MIHPSSGSTSYNEKVK |
| CDR3 | SEQ ID NO. 181 | RDGDYYYGTGDY |
| 21.26 light chain variable region | SEQ ID NO. 32 | QIVLSQSPAILSASPGEKVTMTCRASSSINYMHWYQQKPGSSPKPWIFA TSNLASGVPSRFSGSGSGTSYSLTISRVEAEDAATYYCQQWRSDRALTFG AGTKLEL |
| CDR1 | SEQ ID NO. 182 | RASSSINYMH |
| CDR2 | SEQ ID NO. 183 | PWIFATSNLAS |
| CDR3 | SEQ ID NO. 184 | QQWRSDRALT |
| 1075.7 heavy chain variable region | SEQ ID NO. 33 | DIQLQESGPGLVKPSQSLSLTCSVTGYSITSAYYWNWIRQFPGNKLEWM GYISYDGRNNYNPSLKNRISITRDTSKNQFFLKLNSVTTEDTATYYCAKEG DYDVGNYYAMDYWGQGTSVTVSS |
| CDR1 | SEQ ID NO. 185 | GYSITSAYYWN |
| CDR2 | SEQ ID NO. 186 | YISYDGRNNYNPSLKN |
| CDR3 | SEQ ID NO. 187 | AKEGDYDVGNYYAMDY |
| 1075.7 light chain variable region | SEQ ID NO. 34 | ENVLTQSPAIMSASPGEKVTMTCRASSNVISSYVHWYQQRSGASPKLW IYSTSNLASGVPARFSGSGSGTSYSLTISSVEAEDAATYYCQQYSGYPLTF GAGTKLEL |
| CDR1 | SEQ ID NO. 188 | RASSNVISSYVH |
| CDR2 | SEQ ID NO. 189 | LWIYSTSNLAS |
| CDR3 | SEQ ID NO. 190 | QQYSGYPLT |

TABLE 3 scCAR of structure V-1

| scCAR Designation V-1 | scCAR Structure | | | | | | |
|---|---|---|---|---|---|---|---|
| | signal peptide | VH | VL | FcεRIIIα hinge | CD8α TM | 41BB-IC | CD3ζ CD |
| V1-SCO2-357 scCAR (SEQ ID NO. 35) | SEQ ID NO. 1 | SEQ ID NO. 11 | SEQ ID NO. 14 | SEQ ID NO. 3 | SEQ ID NO. 6 | SEQ ID NO. 8 | SEQ ID NO. 9 |
| V1-SCO2-378 scCAR (SEQ ID NO. 41) | SEQ ID NO. 1 | SEQ ID NO. 12 | SEQ ID NO. 14 | SEQ ID NO. 3 | SEQ ID NO. 6 | SEQ ID NO. 8 | SEQ ID NO. 9 |

TABLE 3-continued scCAR of structure V-1

| scCAR Designation V-1 | scCAR Structure | | | | | | |
|---|---|---|---|---|---|---|---|
| | signal peptide | VH | VL | FcεRIIIα hinge | CD8α TM | 41BB-IC | CD3ζ CD |
| V1-SCO2-161 scCAR (SEQ ID NO. 47) | SEQ ID NO. 1 | SEQ ID NO. 13 | SEQ ID NO. 14 | SEQ ID NO. 3 | SEQ ID NO. 6 | SEQ ID NO. 8 | SEQ ID NO. 9 |
| V1-M26 scCAR (SEQ ID NO. 53) | SEQ ID NO. 1 | SEQ ID NO. 15 | SEQ ID NO. 16 | SEQ ID NO. 3 | SEQ ID NO. 6 | SEQ ID NO. 8 | SEQ ID NO. 9 |
| V1-M31 scCAR (SEQ ID NO. 59) | SEQ ID NO. 1 | SEQ ID NO. 17 | SEQ ID NO. 18 | SEQ ID NO. 3 | SEQ ID NO. 6 | SEQ ID NO. 8 | SEQ ID NO. 9 |
| V1-G4 scCAR (SEQ ID NO. 65) | SEQ ID NO. 1 | SEQ ID NO. 19 | SEQ ID NO. 20 | SEQ ID NO. 3 | SEQ ID NO. 6 | SEQ ID NO. 8 | SEQ ID NO. 9 |
| V1-M22 scCAR (SEQ ID NO. 71) | SEQ ID NO. 1 | SEQ ID NO. 21 | SEQ ID NO. 22 | SEQ ID NO. 3 | SEQ ID NO. 6 | SEQ ID NO. 8 | SEQ ID NO. 9 |
| V1-M29 scCAR (SEQ ID NO. 77) | SEQ ID NO. 1 | SEQ ID NO. 23 | SEQ ID NO. 24 | SEQ ID NO. 3 | SEQ ID NO. 6 | SEQ ID NO. 8 | SEQ ID NO. 9 |
| V1-M2 scCAR (SEQ ID NO. 83) | SEQ ID NO. 1 | SEQ ID NO. 25 | SEQ ID NO. 26 | SEQ ID NO. 3 | SEQ ID NO. 6 | SEQ ID NO. 8 | SEQ ID NO. 9 |
| V1-M5 scCAR (SEQ ID NO. 89) | SEQ ID NO. 1 | SEQ ID NO. 27 | SEQ ID NO. 28 | SEQ ID NO. 3 | SEQ ID NO. 6 | SEQ ID NO. 8 | SEQ ID NO. 9 |
| V1-G12 scCAR (SEQ ID NO. 95) | SEQ ID NO. 1 | SEQ ID NO. 29 | SEQ ID NO. 30 | SEQ ID NO. 3 | SEQ ID NO. 6 | SEQ ID NO. 8 | SEQ ID NO. 9 |
| V1-21.26 scCAR (SEQ ID. NO. 101) | SEQ ID NO. 1 | SEQ ID NO. 31 | SEQ ID NO. 32 | SEQ ID NO. 3 | SEQ ID NO. 6 | SEQ ID NO. 8 | SEQ ID NO. 9 |
| V1-1075.7 scCAR (SEQ ID NO. 107) | SEQ ID NO. 1 | SEQ ID NO. 33 | SEQ ID NO. 34 | SEQ ID NO. 3 | SEQ ID NO. 6 | SEQ ID NO. 8 | SEQ ID NO. 9 |

TABLE 4 scCAR of structure V-2

| scCAR Designation V-2 | scCAR Structure | | | | | | |
|---|---|---|---|---|---|---|---|
| | signal peptide | VH | VL | FcεRIIIα hinge | 41BB-TM | 41BB-IC | CD3ζ CD |
| V2-SCO2-357 scCAR (SEQ ID NO. 36) | SEQ ID NO. 1 | SEQ ID NO. 11 | SEQ ID NO. 14 | SEQ ID NO. 3 | SEQ ID NO. 7 | SEQ ID NO. 8 | SEQ ID NO. 9 |
| V2-SCO2-378 scCAR (SEQ ID NO. 42) | SEQ ID NO. 1 | SEQ ID NO. 12 | SEQ ID NO. 14 | SEQ ID NO. 3 | SEQ ID NO. 7 | SEQ ID NO. 8 | SEQ ID NO. 9 |
| V2-SCO2-161 scCAR (SEQ ID NO. 48) | SEQ ID NO. 1 | SEQ ID NO. 13 | SEQ ID NO. 14 | SEQ ID NO. 3 | SEQ ID NO. 7 | SEQ ID NO. 8 | SEQ ID NO. 9 |
| V2-M26 scCAR (SEQ ID NO. 54) | SEQ ID NO. 1 | SEQ ID NO. 15 | SEQ ID NO. 16 | SEQ ID NO. 3 | SEQ ID NO. 7 | SEQ ID NO. 8 | SEQ ID NO. 9 |
| V2-M31 scCAR (SEQ ID NO. 60) | SEQ ID NO. 1 | SEQ ID NO. 17 | SEQ ID NO. 18 | SEQ ID NO. 3 | SEQ ID NO. 7 | SEQ ID NO. 8 | SEQ ID NO. 9 |
| V2-G4 scCAR (SEQ ID NO. 66) | SEQ ID NO. 1 | SEQ ID NO. 19 | SEQ ID NO. 20 | SEQ ID NO. 3 | SEQ ID NO. 7 | SEQ ID NO. 8 | SEQ ID NO. 9 |
| V2-M22 scCAR (SEQ ID NO. 72) | SEQ ID NO. 1 | SEQ ID NO. 21 | SEQ ID NO. 22 | SEQ ID NO. 3 | SEQ ID NO. 7 | SEQ ID NO. 8 | SEQ ID NO. 9 |
| V2-M29 scCAR (SEQ ID NO. 78) | SEQ ID NO. 1 | SEQ ID NO. 23 | SEQ ID NO. 24 | SEQ ID NO. 3 | SEQ ID NO. 7 | SEQ ID NO. 8 | SEQ ID NO. 9 |
| V2-M2 scCAR (SEQ ID NO. 84) | SEQ ID NO. 1 | SEQ ID NO. 25 | SEQ ID NO. 26 | SEQ ID NO. 3 | SEQ ID NO. 7 | SEQ ID NO. 8 | SEQ ID NO. 9 |
| V2-M5 scCAR (SEQ ID NO. 90) | SEQ ID NO. 1 | SEQ ID NO. 27 | SEQ ID NO. 28 | SEQ ID NO. 3 | SEQ ID NO. 7 | SEQ ID NO. 8 | SEQ ID NO. 9 |
| V2-G12 scCAR (SEQ ID NO. 96) | SEQ ID NO. 1 | SEQ ID NO. 29 | SEQ ID NO. 30 | SEQ ID NO. 3 | SEQ ID NO. 7 | SEQ ID NO. 8 | SEQ ID NO. 9 |
| V2-21.26 scCAR (SEQ ID NO. 102) | SEQ ID NO. 1 | SEQ ID NO. 31 | SEQ ID NO. 32 | SEQ ID NO. 3 | SEQ ID NO. 7 | SEQ ID NO. 8 | SEQ ID NO. 9 |
| V2-1075.7 scCAR (SEQ ID NO. 108) | SEQ ID NO. 1 | SEQ ID NO. 33 | SEQ ID NO. 34 | SEQ ID NO. 3 | SEQ ID NO. 7 | SEQ ID NO. 8 | SEQ ID NO. 9 |

TABLE 5 scCAR of structure V-3

| scCAR Designation V-3 | signal peptide | VH | VL | CD8α hinge | CD8α TM | 41BB-IC | CD3ζ CD |
|---|---|---|---|---|---|---|---|
| V3-SCO2-357 scCAR (SEQ ID NO. 37) | SEQ ID NO. 1 | SEQ ID NO. 11 | SEQ ID NO. 14 | SEQ ID NO. 4 | SEQ ID NO. 6 | SEQ ID NO. 8 | SEQ ID NO. 9 |
| V3-SCO2-378 scCAR (SEQ ID NO. 43) | SEQ ID NO. 1 | SEQ ID NO. 12 | SEQ ID NO. 14 | SEQ ID NO. 4 | SEQ ID NO. 6 | SEQ ID NO. 8 | SEQ ID NO. 9 |
| V3-SCO2-161 scCAR (SEQ ID NO. 49) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| V3-M26 scCAR (SEQ ID NO. 55) | SEQ ID NO. 1 | SEQ ID NO. 15 | SEQ ID NO. 16 | SEQ ID NO. 4 | SEQ ID NO. 6 | SEQ ID NO. 8 | SEQ ID NO. 9 |
| V3-M31 scCAR (SEQ ID NO. 61) | SEQ ID NO. 1 | SEQ ID NO. 17 | SEQ ID NO. 18 | SEQ ID NO. 4 | SEQ ID NO. 6 | SEQ ID NO. 8 | SEQ ID NO. 9 |
| V3-G4 scCAR (SEQ ID NO. 67) | SEQ ID NO. 1 | SEQ ID NO. 19 | SEQ ID NO. 20 | SEQ ID NO. 4 | SEQ ID NO. 6 | SEQ ID NO. 8 | SEQ ID NO. 9 |
| V3-M22 scCAR (SEQ ID NO. 73) | SEQ ID NO. 1 | SEQ ID NO. 21 | SEQ ID NO. 22 | SEQ ID NO. 4 | SEQ ID NO. 6 | SEQ ID NO. 8 | SEQ ID NO. 9 |
| V3-M29 scCAR (SEQ ID NO. 79) | SEQ ID NO. 1 | SEQ ID NO. 23 | SEQ ID NO. 24 | SEQ ID NO. 4 | SEQ ID NO. 6 | SEQ ID NO. 8 | SEQ ID NO. 9 |
| V3-M2 scCAR (SEQ ID NO. 85) | SEQ ID NO. 1 | SEQ ID NO. 25 | SEQ ID NO. 26 | SEQ ID NO. 4 | SEQ ID NO. 6 | SEQ ID NO. 8 | SEQ ID NO. 9 |
| V3-M5 scCAR (SEQ ID NO. 91) | SEQ ID NO. 1 | SEQ ID NO. 27 | SEQ ID NO. 28 | SEQ ID NO. 4 | SEQ ID NO. 6 | SEQ ID NO. 8 | SEQ ID NO. 9 |
| V3-G12 scCAR (SEQ ID NO. 97) | SEQ ID NO. 1 | SEQ ID NO. 29 | SEQ ID NO. 30 | SEQ ID NO. 4 | SEQ ID NO. 6 | SEQ ID NO. 8 | SEQ ID NO. 9 |
| V3-21.26 scCAR (SEQ ID NO. 103) | SEQ ID NO. 1 | SEQ ID NO. 31 | SEQ ID NO. 32 | SEQ ID NO. 4 | SEQ ID NO. 6 | SEQ ID NO. 8 | SEQ ID NO. 9 |
| V3-1075.7 scCAR (SEQ ID NO. 109) | SEQ ID NO. 1 | SEQ ID NO. 33 | SEQ ID NO. 34 | SEQ ID NO. 4 | SEQ ID NO. 6 | SEQ ID NO. 8 | SEQ ID NO. 9 |

TABLE 6 scCAR of structure V-4

| scCAR Designation V-4 | signal peptide | VH | VL | CD8α hinge | 41BB-TM | 41BB-IC | CD3ζCD |
|---|---|---|---|---|---|---|---|
| V4-SCO2-357 scCAR (SEQ ID NO. 38) | SEQ ID NO. 1 | SEQ ID NO. 11 | SEQ ID NO. 14 | SEQ ID NO. 4 | SEQ ID NO. 6 | SEQ ID NO. 8 | SEQ ID NO. 9 |
| V4-SCO2-378 scCAR (SEQ ID NO. 44) | SEQ ID NO. 1 | SEQ ID NO. 12 | SEQ ID NO. 14 | SEQ ID NO. 4 | SEQ ID NO. 6 | SEQ ID NO. 8 | SEQ ID NO. 9 |
| V4-SCO2-161 scCAR (SEQ ID NO. 50) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| V4-M26 scCAR (SEQ ID NO. 56) | SEQ ID NO. 1 | SEQ ID NO. 16 | SEQ ID NO. 14 | SEQ ID NO. 4 | SEQ ID NO. 6 | SEQ ID NO. 8 | SEQ ID NO. 9 |
| V4-M31 scCAR (SEQ ID NO. 62) | SEQ ID NO. 1 | SEQ ID NO. 17 | SEQ ID NO. 18 | SEQ ID NO. 4 | SEQ ID NO. 7 | SEQ ID NO. 8 | SEQ ID NO. 9 |
| V4-G4 scCAR (SEQ ID NO. 68) | SEQ ID NO. 1 | SEQ ID NO. 19 | SEQ ID NO. 20 | SEQ ID NO. 4 | SEQ ID NO. 7 | SEQ ID NO. 8 | SEQ ID NO. 9 |
| V4-M22 scCAR (SEQ ID NO. 74) | SEQ ID NO. 1 | SEQ ID NO. 21 | SEQ ID NO. 22 | SEQ ID NO. 4 | SEQ ID NO. 7 | SEQ ID NO. 8 | SEQ ID NO. 9 |
| V4-M29 scCAR (SEQ ID NO. 80) | SEQ ID NO. 1 | SEQ ID NO. 23 | SEQ ID NO. 24 | SEQ ID NO. 4 | SEQ ID NO. 7 | SEQ ID NO. 8 | SEQ ID NO. 9 |
| V4-M2 scCAR (SEQ ID NO. 86) | SEQ ID NO. 1 | SEQ ID NO. 25 | SEQ ID NO. 26 | SEQ ID NO. 4 | SEQ ID NO. 7 | SEQ ID NO. 8 | SEQ ID NO. 9 |
| V4-M5 scCAR (SEQ ID NO. 92) | SEQ ID NO. 1 | SEQ ID NO. 27 | SEQ ID NO. 28 | SEQ ID NO. 4 | SEQ ID NO. 7 | SEQ ID NO. 8 | SEQ ID NO. 9 |
| V4-G12 scCAR (SEQ ID NO. 98) | SEQ ID NO. 1 | SEQ ID NO. 29 | SEQ ID NO. 30 | SEQ ID NO. 4 | SEQ ID NO. 7 | SEQ ID NO. 8 | SEQ ID NO. 9 |
| V4-21.26 scCAR (SEQ ID NO. 104) | SEQ ID NO. 1 | SEQ ID NO. 31 | SEQ ID NO. 32 | SEQ ID NO. 4 | SEQ ID NO. 7 | SEQ ID NO. 8 | SEQ ID NO. 9 |

TABLE 6-continued scCAR of structure V-4

| scCAR Designation V-4 | scCAR Structure | | | | | | |
|---|---|---|---|---|---|---|---|
| | signal peptide | VH | VL | CD8α hinge | 41BB-TM | 41BB-IC | CD3ζCD |
| V4-1075.7 scCAR (SEQ ID NO. 110) | SEQ ID NO. 1 | SEQ ID NO. 33 | SEQ ID NO. 34 | SEQ ID NO. 4 | SEQ ID NO. 7 | SEQ ID NO. 8 | SEQ ID NO. 9 |

TABLE 7 scCAR of structure V-5

| scCAR Designation V-5 | scCAR Structure | | | | | | |
|---|---|---|---|---|---|---|---|
| | signal peptide | VH | VL | IgG1 hinge | CD8α TM | 41BB-IC | CD3ζCD |
| V5-SCO2-357 scCAR (SEQ ID NO. 39) | SEQ ID NO. 1 | SEQ ID NO. 11 | SEQ ID NO. 14 | SEQ ID NO. 5 | SEQ ID NO. 6 | SEQ ID NO. 8 | SEQ ID NO. 9 |
| V5-SCO2-378 scCAR (SEQ ID NO. 45) | SEQ ID NO. 1 | SEQ ID NO. 12 | SEQ ID NO. 14 | SEQ ID NO. 5 | SEQ ID NO. 6 | SEQ ID NO. 8 | SEQ ID NO. 9 |
| V5-SCO2-161 scCAR (SEQ ID NO. 51) | SEQ ID NO. 1 | SEQ ID NO. 13 | SEQ ID NO. 14 | SEQ ID NO. 5 | SEQ ID NO. 6 | SEQ ID NO. 8 | SEQ ID NO. 9 |
| V5-M26 scCAR (SEQ ID NO. 57) | SEQ ID NO. 1 | SEQ ID NO. 15 | SEQ ID NO. 16 | SEQ ID NO. 5 | SEQ ID NO. 6 | SEQ ID NO. 8 | SEQ ID NO. 9 |
| V5-M31 scCAR (SEQ ID NO. 63) | SEQ ID NO. 1 | SEQ ID NO. 17 | SEQ ID NO. 18 | SEQ ID NO. 5 | SEQ ID NO. 6 | SEQ ID NO. 8 | SEQ ID NO. 9 |
| V5-G4 scCAR (SEQ ID NO. 69) | SEQ ID NO. 1 | SEQ ID NO. 19 | SEQ ID NO. 20 | SEQ ID NO. 5 | SEQ ID NO. 6 | SEQ ID NO. 8 | SEQ ID NO. 9 |
| V5-M22 scCAR (SEQ ID NO. 75) | SEQ ID NO. 1 | SEQ ID NO. 21 | SEQ ID NO. 22 | SEQ ID NO. 5 | SEQ ID NO. 6 | SEQ ID NO. 8 | SEQ ID NO. 9 |
| V5-M29 scCAR (SEQ ID NO. 81) | SEQ ID NO. 1 | SEQ ID NO. 23 | SEQ ID NO. 24 | SEQ ID NO. 5 | SEQ ID NO. 6 | SEQ ID NO. 8 | SEQ ID NO. 9 |
| V5-M2 scCAR (SEQ ID NO. 87) | SEQ ID NO. 1 | SEQ ID NO. 25 | SEQ ID NO. 26 | SEQ ID NO. 5 | SEQ ID NO. 6 | SEQ ID NO. 8 | SEQ ID NO. 9 |
| V5-M5 scCAR (SEQ ID NO. 93) | SEQ ID NO. 1 | SEQ ID NO. 27 | SEQ ID NO. 28 | SEQ ID NO. 5 | SEQ ID NO. 6 | SEQ ID NO. 8 | SEQ ID NO. 9 |
| V5-G12 scCAR (SEQ ID NO. 99) | SEQ ID NO. 1 | SEQ ID NO. 29 | SEQ ID NO. 30 | SEQ ID NO. 5 | SEQ ID NO. 6 | SEQ ID NO. 8 | SEQ ID NO. 9 |
| V5-21.26 scCAR (SEQ ID NO. 105) | SEQ ID NO. 1 | SEQ ID NO. 31 | SEQ ID NO. 32 | SEQ ID NO. 5 | SEQ ID NO. 6 | SEQ ID NO. 8 | SEQ ID NO. 9 |
| V5-1075.7 scCAR (SEQ ID NO. 111) | SEQ ID NO. 1 | SEQ ID NO. 33 | SEQ ID NO. 34 | SEQ ID NO. 5 | SEQ ID NO. 6 | SEQ ID NO. 8 | SEQ ID NO. 9 |

TABLE 8 scCAR of structure V-6

| scCAR Designation V-6 | scCAR Structure | | | | | | |
|---|---|---|---|---|---|---|---|
| | signal peptide | VH | VL | IgG1 hinge | 41BB-TM | 41BB-IC | CD3ζ CD |
| V6-SCO2-357 scCAR (SEQ ID NO. 40) | SEQ ID NO. 1 | SEQ ID NO. 11 | SEQ ID NO. 14 | SEQ ID NO. 5 | SEQ ID NO. 7 | SEQ ID NO. 8 | SEQ ID NO. 9 |
| V6-SCO2-378 scCAR (SEQ ID NO. 46) | SEQ ID NO. 1 | SEQ ID NO. 12 | SEQ ID NO. 14 | SEQ ID NO. 5 | SEQ ID NO. 7 | SEQ ID NO. 8 | SEQ ID NO. 9 |
| V6-SCO2-161 scCAR (SEQ ID NO. 52) | SEQ ID NO. 1 | SEQ ID NO. 13 | SEQ ID NO. 14 | SEQ ID NO. 5 | SEQ ID NO. 7 | SEQ ID NO. 8 | SEQ ID NO. 9 |

TABLE 8-continued scCAR of structure V-6

| scCAR Designation V-6 | scCAR Structure | | | | | | |
|---|---|---|---|---|---|---|---|
| | signal peptide | VH | VL | IgG1 hinge | 41BB-TM | 41BB-IC | CD3ζ CD |
| V6-M26 scCAR (SEQ ID NO. 58) | SEQ ID NO. 1 | SEQ ID NO. 15 | SEQ ID NO. 16 | SEQ ID NO. 5 | SEQ ID NO. 7 | SEQ ID NO. 8 | SEQ ID NO. 9 |
| V6-M31 scCAR (SEQ ID NO. 64) | SEQ ID NO. 1 | SEQ ID NO. 17 | SEQ ID NO. 18 | SEQ ID NO. 5 | SEQ ID NO. 7 | SEQ ID NO. 8 | SEQ ID NO. 9 |
| V6-G4 scCAR (SEQ ID NO. 70) | SEQ ID NO. 1 | SEQ ID NO. 19 | SEQ ID NO. 20 | SEQ ID NO. 5 | SEQ ID NO. 7 | SEQ ID NO. 8 | SEQ ID NO. 9 |
| V6-M22 scCAR (SEQ ID NO. 76) | SEQ ID NO. 1 | SEQ ID NO. 21 | SEQ ID NO. 22 | SEQ ID NO. 5 | SEQ ID NO. 7 | SEQ ID NO. 8 | SEQ ID NO. 9 |
| V6-M29 scCAR (SEQ ID NO. 82) | SEQ ID NO. 1 | SEQ ID NO. 23 | SEQ ID NO. 24 | SEQ ID NO. 5 | SEQ ID NO. 7 | SEQ ID NO. 8 | SEQ ID NO. 9 |
| V6-M2 scCAR (SEQ ID NO. 88) | SEQ ID NO. 1 | SEQ ID NO. 25 | SEQ ID NO. 26 | SEQ ID NO. 5 | SEQ ID NO. 7 | SEQ ID NO. 8 | SEQ ID NO. 9 |
| V6-M5 scCAR (SEQ ID NO. 94) | SEQ ID NO. 1 | SEQ ID NO. 27 | SEQ ID NO. 28 | SEQ ID NO. 5 | SEQ ID NO. 7 | SEQ ID NO. 8 | SEQ ID NO. 9 |
| V6-G12 scCAR (SEQ ID NO. 100) | SEQ ID NO. 1 | SEQ ID NO. 29 | SEQ ID NO. 30 | SEQ ID NO. 5 | SEQ ID NO. 7 | SEQ ID NO. 8 | SEQ ID NO. 9 |
| V6-21.26 scCAR (SEQ ID NO. 106) | SEQ ID NO. 1 | SEQ ID NO. 31 | SEQ ID NO. 32 | SEQ ID NO. 5 | SEQ ID NO. 7 | SEQ ID NO. 8 | SEQ ID NO. 9 |
| V6-1075.7 scCAR (SEQ ID NO. 112) | SEQ ID NO. 1 | SEQ ID NO. 33 | SEQ ID NO. 34 | SEQ ID NO. 5 | SEQ ID NO. 7 | SEQ ID NO. 8 | SEQ ID NO. 9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention provides:
1. A CLL1 specific chimeric antigen receptor (anti-CLL1 CAR) comprising at least:
   an extra cellular ligand binding-domain anti-CLL1,
   a transmembrane domain, and
   a cytoplasmic signaling domain.
2. A CLL1 specific chimeric antigen receptor according to embodiment 1, further comprising a co-stimulatory domain.
3. A CLL1 specific chimeric antigen receptor according to embodiment 1, further comprising a CD28 or a 4-1BB co-stimulatory domain.
4. A CLL1 specific chimeric antigen receptor according to any one of embodiments 1 to 3, wherein said transmembrane domain is a Cd8α transmembrane domain.
5. A CLL1 specific chimeric antigen receptor according to any one of embodiments 1 to 4, further comprising a hinge.
6. A CLL1 specific chimeric antigen receptor according to any one of embodiments 1 to 5, wherein said cytoplasmic signaling domain is a T-cell activating domain.
7. A CLL1 specific chimeric antigen receptor according to any one of embodiments 1 to 6, wherein said chimeric antigen receptor is expressed under the form of a single polypeptide.
8. A CLL1 specific chimeric antigen receptor according to any one of embodiments 1 to 7, wherein said extra cellular ligand binding-domain is from a monoclonal anti-CLL1 antibody.
9. A CLL1 specific chimeric antigen receptor according to embodiment 8, wherein extra cellular ligand binding-domain comprises CDRs from VH and VL domains of monoclonal anti-CLL1 antibody(ies).

Figure 2:
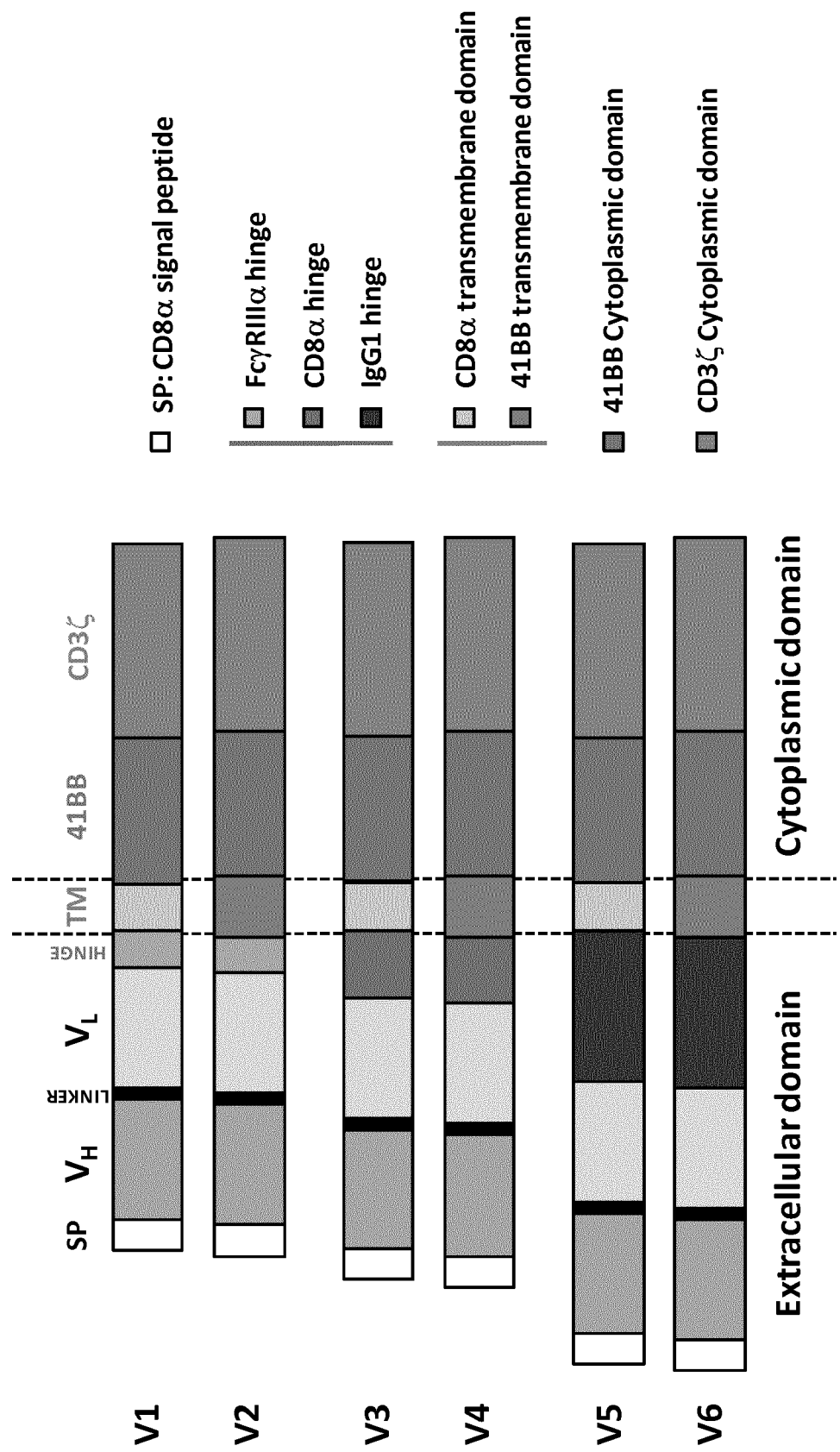
FIG. 2: Schematic representation of the different scCAR Architecture ($V_1$ to V6) of the invention (anti-CLL1 scCAR) with the components presented in the following Table 1.

10. A CLL1 specific chimeric antigen receptor according to embodiment 9, wherein said CDRs are selected from SEQ ID NO. 109 to 190.
11. A CLL1 specific scCAR according to any one of embodiments 1 to 10 having one of the polypeptide structure selected from $V_1$, V3 or V5, as illustrated in FIG. 2, said structure comprising an extra cellular ligand binding-domain comprising VH and VL from a monoclonal anti-CLL1 antibody, a hinge, a CD8α transmembrane domain, a cytoplasmic domain including a CD3 zeta signaling domain and a 4-1BB co-stimulatory domain.
12. A CLL1 specific scCAR according to any one of embodiments 1 to 11, wherein said structure $V_1$ comprises a FcγRIIIα hinge and Cd8α transmembrane domain.
13. A CLL1 specific scCAR according to any one of embodiments 1 to 11, wherein said structure V3 comprises a Cd8α hinge and a Cd8α transmembrane domain.
14. A CLL1 specific scCAR according any one of embodiments 1 to 11, wherein said structure V5 comprises an IgG1 hinge and a Cd8α transmembrane domain.
15. A CLL1 specific scCAR according to any one of embodiments 1 to 14, wherein said VH and VL have at least 80% identity with a polypeptide sequence selected from SEQ ID NO. 11 to 34.
16. A CLL1 specific scCAR according to any one of embodiments 1 to 15, wherein co-stimulatory domain from 4-1BB has at least 80% identity with SEQ ID NO.8.
17. A CLL1 specific scCAR according to any one of embodiments 1 to 16, wherein said CD3 zeta signaling domain has at least 80% identity with SEQ ID NO. 9.
18. A CLL1 specific scCAR according to any one of embodiments 1 to 12 or 15 to 17, wherein said FcγRIIIα hinge has at least 80% identity with SEQ ID NO.3.
19. A CLL1 specific scCAR according to any one of embodiments 1 to 11, 13 or 15 to 17, wherein said Cd8α hinge has at least 80% identity with SEQ ID NO.4.
20. A CLL1 specific scCAR according to any one of embodiments 1 to 11 or 14 to 19, wherein said IgG1 hinge has at least 80% identity with SEQ ID NO.5.
21. A CLL1 specific scCAR according to any one of embodiments 1 to 20, wherein said CD8α transmembrane domain has at least 80% identity with SEQ ID NO.6.
22. A CLL1 specific scCAR according to any one of embodiments 1 to 21 further comprising another extracellular ligand binding domain which is not specific for CLL1.
23. A CLL1 specific scCAR of structure $V_1$ according to any one of embodiments 1 to 12, 15 to 17 or 21 to 22, which comprises a polypeptide sequence having at least 80% identity with SEQ ID NO. 35, 41, 47, 53, 59, 65, 71, 77, 83, 89, 95, 101 or 107.
24. A CLL1 specific scCAR of structure V3 according to any one of embodiments 1 to 11, 13, 15 to 17 or 21 to 22, which comprises a polypeptide sequence having at least 80% identity with SEQ ID NO. 37, 43, 49, 55, 61, 67, 73, 79, 85, 91, 97, 103 or 109.
25. A CLL1 specific scCAR of structure V5 according to any one of embodiments 1 to 11, 14 to 19 or 21 to 22 which comprises a polypeptide sequence having at least 80% identity with SEQ ID NO.39, 45, 51, 57, 63, 69, 75, 81, 87, 93, 99, 105 or 111.
26. A CLL1 specific scCAR according to any one of embodiments 1 to 25 further comprising a signal peptide.
27. A CLL1 specific scCAR according to embodiment 26, wherein said signal peptide has at least 80% sequence identity with SEQ ID NO.1 or SEQ ID NO.2.
28. The polypeptide according to any one of embodiments 1 to 27, wherein the extracellular binding domain comprises 1, 2, 3, 4, 5, 6, 7, 8, 9 or 10 mAb-specific epitopes.
29. The polypeptide according to any one of embodiments 1 to 28, wherein the extracellular binding domain comprises 1, 2, 3 or, 4 mAb-specific epitopes.
30. The polypeptide according to any one of embodiments 1 to 29, wherein the extracellular binding domain comprises 2, 3 or, 4 mAb-specific epitopes
31. The polypeptide according to any one of embodiments 1 to 30, wherein the extracellular binding domain comprises the following sequence $V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;
wherein,
$V_1$ is $V_L$ and $V_2$ is $V_H$ or $V_1$ is $V_H$ and $V_2$ is $V_L$;
$L_1$ is a linker suitable to link the $V_H$ chain to the $V_L$ chain;
L is a linker comprising glycine and serine residues, and each occurrence of L in the extracellular binding domain can be identical or different to other occurrence of L in the same extracellular binding domain, and,
x is 0 or 1 and each occurrence of x is selected independently from the others; and,
Epitope 1, Epitope 2 and Epitope 3 are mAb-specific epitopes and can be identical or differents.
32. The polypeptide according to any one of embodiment 31, wherein the extracellular binding domain comprises the following sequence
$V_1$-$L_1$-$V_2$-L-Epitope1; $V_1$-$L_1$-$V_2$-L-Epitope1-L; $V_1$-$L_1$-$V_2$-L-Epitope1-L-Epitope2; $V_1$-$L_1$-$V_2$-L-Epitope1-L-Epitope2-L; $V_1$-$L_1$-$V_2$-L-Epitope1-L-Epitope2-L-Epitope3; $V_1$-$L_1$-$V_2$-L-Epitope1-L-Epitope2-L-Epitope3-L; $V_1$-$L_1$-$V_2$-Epitope1; $V_1$-$L_1$-$V_2$-Epitope1-L; $V_1$-$L_1$-$V_2$-Epitope1-L-Epitope2; $V_1$-$L_1$-$V_2$-Epitope1-L-Epitope2-L; $V_1$-$L_1$-$V_2$-Epitope1-L-

Epitope2-L-Epitope3; V$_1$-L$_1$-V$_2$-Epitope1-L-Epitope2-L-Epitope3-L; Epitope1-V$_1$-L$_1$-V$_2$; Epitope1-L-V$_1$-L$_1$-V$_2$; L-Epitope1-V$_1$-L$_1$-V$_2$; L-Epitope1-L-V$_1$-L$_1$-V$_2$; Epitope1-L-Epitope2-V$_1$-L$_1$-V$_2$; Epitope1-L-Epitope2-L-V$_1$-L$_1$-V$_2$; L-Epitope1-L-Epitope2-V$_1$-L$_1$-V$_2$; L-Epitope1-L-Epitope2-L-V$_1$-L$_1$-V$_2$; Epitope1-L-Epitope2-L-Epitope3-V$_1$-L$_1$-V$_2$; Epitope1-L-Epitope2-L-Epitope3-L-V$_1$-L$_1$-V$_2$; L-Epitope1-L-Epitope2-L-Epitope3-V$_1$-L$_1$-V$_2$; L-Epitope1-L-Epitope2-L-Epitope3-L-V$_1$-L$_1$-V$_2$; V$_1$-L-Epitope1-L-V$_2$; Epitope1-L-V$_1$-L-Epitope2-L-V$_2$; V$_1$-L-Epitope1-L-V$_2$-L-Epitope2-L; V$_1$-L-Epitope1-L-V$_2$-L-Epitope2-L-Epitope3; V$_1$-L-Epitope1-L-V$_2$-L-Epitope2-Epitope3; V$_1$-L-Epitope1-L-V$_2$-L-Epitope2-L-Epitope3-Epitope4; L-Epitope1-L-V$_1$-L-Epitope2-L-V$_2$-L-Epitope3-L; Epitope1-L-V$_1$-L-Epitope2-L-V$_2$-L-Epitope3-L; Epitope1-L-V$_1$-L-Epitope2-L-V$_2$-L-Epitope3; Epitope1-L-V$_1$-L$_1$-V$_2$-L-Epitope2-L; Epitope1-L-V$_1$-L$_1$-V$_2$-L-Epitope2-Epitope3; L-Epitope1-L-V$_1$-L$_1$-V$_2$-L-Epitope2-Epitope3, or Epitope1-L-V$_1$-L$_1$-V$_2$-L-Epitope2-L-Epitope3-Epitope4 wherein

V$_1$ is V$_L$ and V$_2$ is V$_H$ or V$_1$ is V$_H$ and V$_2$ is V$_L$;

L$_1$ is any linker suitable to link the V$_H$ chain to the V$_L$ chain;

L is a linker comprising glycine and serine residues, and each occurrence of L in the extracellular binding domain can be identical or different to other occurrence of L in the same extracellular binding domain, and, epitope 1, epitope 2 and epitope 3 are mAb-specific epitopes and can be identical or differents.

33. The polypeptide according to embodiment 31 or 32, wherein L$_1$ is a linker comprising Glycine and/or Serine.

34. The polypeptide according to embodiment 33, wherein L$_1$ is a linker comprising the amino acid sequence (Gly-Gly-Gly-Ser)$_n$ or (Gly-Gly-Gly-Gly-Ser)$_n$, where n is 1, 2, 3, 4 or 5.

35. The polypeptide according to embodiment 34, wherein L$_1$ is a linker comprising the amino acid sequence (Gly$_4$Ser)$_4$ or (Gly$_4$Ser)$_3$.

36. The polypeptide according to any one of embodiments 31 to 35 wherein L is a linker comprising Glycine and/or Serine.

37. The polypeptide according to embodiment 36, wherein L is a linker having an amino acid sequence selected from SGG, GGS, SGGS (SEQ ID NO. 200), SSGGS (SEQ ID NO. 201), GGGG (SEQ ID NO. 202), SGGGG (SEQ ID NO. 203), GGGGS (SEQ ID NO. 204), SGGGGS (SEQ ID NO. 205), GGGGGS (SEQ ID NO. 206), SGGGGGS (SEQ ID NO. 207), SGGGGG (SEQ ID NO. 208), GSGGGGS (SEQ ID NO. 209), GGGGGGS (SEQ ID NO. 210), SGGGGGGG (SEQ ID NO. 211), SGGGGGGGS (SEQ ID NO. 212), or SGGGGSGGGGS (SEQ ID NO. 213).

38. The polypeptide according to embodiment 37, wherein L is a SGGGG (SEQ ID NO. 203), GGGGS (SEQ ID NO. 204), or SGGGGS (SEQ ID NO. 205).

39. The polypeptide according to any one of embodiments 31 to 38 wherein Epitope 1, Epitope 2, Epitope 3 and Epitope 4 are independently selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, alemtuzumab or ustekinumab.

40. The polypeptide according to any one of embodiments 31 to 38 wherein Epitope 1, Epitope 2, Epitope 3 and Epitope 4 are independently selected from mAb-specific epitopes having an amino acid sequence of SEQ ID NO 113, SEQ ID NO 191, SEQ ID NO 192, SEQ ID NO 193, SEQ ID NO 194, SEQ ID NO 195, SEQ ID NO 195, SEQ ID NO 196, SEQ ID NO 197, SEQ ID NO 198 or SEQ ID NO 199.

41. The polypeptide according to any one of embodiments 31 to 40 wherein Epitope 1 is an mAb-specific epitope having an amino acid sequence of SEQ ID NO 113.

42. The polypeptide according to any one of embodiments 31 to 41 wherein Epitope 2 is an mAb-specific epitope having an amino acid sequence of SEQ ID NO 113.

43. The polypeptide according to any one of embodiments 31 to 42 wherein Epitope 3 is an mAb-specific epitope having an amino acid sequence of SEQ ID NO 113, SEQ ID NO 198 or SEQ ID NO 199.

44. The polypeptide according to any one of embodiments 31 to 43 wherein Epitope 4 is an mAb-specific epitope having an amino acid sequence of SEQ ID NO 113.

45. A polynucleotide encoding a chimeric antigen receptor according to any one of embodiments 1 to 44.

46. An expression vector comprising a nucleic acid of embodiment 39.

47. An engineered lymphoid immune cell expressing at the cell surface membrane an anti-CLL1 CAR according to any one of embodiments 1 to 44.

48. An engineered lymphoid immune cell according to embodiment 41 derived from inflammatory T-lymphocytes, cytotoxic T-lymphocytes, regulatory T-lymphocytes or helper T-lymphocytes.

49. An engineered cell according to embodiment 47 or 48 for use in therapy.

50. An engineered cell according to any one of embodiments 41 to 43 for use in therapy, wherein the patient is a human.

51. An engineered cell according to any one of embodiments 47 to 50 for use in therapy, wherein the condition is a pre-malignant or malignant cancer condition characterized by CLL1-expressing cells.

52. An engineered cell according to any one of embodiments 47 to 51 for use in therapy, wherein the condition is a condition which is characterized by an overabundance of CLL1-expressing cells.

53. An engineered cell according to any one of embodiments 51 to 52 for use in therapy, wherein the condition is a hematological cancer condition.

54. An engineered cell according to embodiment 53 for use in therapy, wherein the hematological cancer condition is leukemia.

55. An engineered cell according to embodiment 54 for use in therapy, wherein the leukemia is acute myelogenous leukemia (AML).

56. An engineered cell according to any one of embodiments 47 to 55, wherein expression of TCR is suppressed in said immune cell.

57. An engineered cell according to any one of embodiments 47 to 55, wherein expression of at least one MHC protein, preferably β2m or HLA, is repressed or suppressed in said immune cell.

58. An engineered cell according to any one of embodiments 47 to 57, wherein said cell is mutated to confer resistance to at least one immune suppressive or chemotherapy drug.
59. A method of impairing a hematologic cancer cell comprising contacting said cell with an engineered cell according to any one of embodiments 47 to 58 in an amount effective to cause impairment of said cancer cell.
60. A method of engineering an immune cell comprising:
   (a) Providing an immune cell,
   (b) Expressing at the surface of said cell at least one CLL1 single-chain specific chimeric antigen receptor according to any one of embodiments 1 to 44.
61. The method of engineering an immune cell of embodiment 60 comprising:
   (a) Providing an immune cell,
   (b) Introducing into said cell at least one polynucleotide encoding said CLL1 single-chain specific chimeric antigen receptor,
   (c) Expressing said polynucleotide into said cell.
62. The method of engineering an immune cell of embodiment 61 comprising:
   (a) Providing an immune cell,
   (b) Introducing into said cell at least one polynucleotide encoding said anti-CLL1 single-chain specific chimeric antigen receptor,
   (c) Introducing at least one other chimeric antigen receptor which is not specific for CLL1.
63. A method of treating a subject in need thereof comprising:
   (a) Providing an immune cell expressing at the surface an anti-CLL1 single-chain specific chimeric antigen receptor according to any one of embodiments 1 to 44;
   (b) Administrating said immune cells to said patient.
64. A method according to embodiment 63, wherein said immune cell is provided from a donor.
65. A method according to embodiment 63, wherein said immune cell is provided from the patient himself.

CLL1 Single-Chain Specific Chimeric Antigen Receptors

The present invention relates to CLL1 specific chimeric antigen receptor comprising an extracellular ligand-binding domain specifically directed against one portion of the CLL1 antigen, a transmembrane domain and a signaling transducing domain.

By chimeric antigen receptor (CAR) is intended molecules that combine an extracellular binding domain directed against a component present on a target cell, for example an antibody-based specificity for a desired antigen (e.g., tumor antigen) with an immune cell receptor component to generate a chimeric protein that will transduce an activating or inhibitory signal toward cellular immune activity.

The present invention more particularly relates to a CLL1 specific chimeric antigen receptor (anti-CLL1 CAR) comprising at least:
an extracellular ligand binding-domain anti-CLL1,
a transmembrane domain, and
a cytoplasmic signaling domain.

Preferably, the CLL1 specific chimeric antigen receptor according to the invention further comprises a co-stimulatory domain, and more preferably a CD28 or a 4-1BB co-stimulatory domain as described for instance by Jena, B., G. Dotti, et al. (2010). It can also comprise a transmembrane domain which can be a Cd8α transmembrane domain, as well as an optional hinge.

The signal transducing domain or "cytoplasmic signaling domain" of a CAR according to the present invention is responsible for intracellular signaling following the binding of extracellular ligand binding domain to the target resulting in the activation or inhibition of the immune cell and immune response. In other words, the signal transducing domain is responsible for the activation or inactivation of at least one of the normal effector functions of the immune cell in which the CAR is expressed. For example, the effector function of a T cell can be a cytolytic activity or helper activity including the secretion of cytokines. Thus, the term "cytoplasmic signaling domain" refers to the portion of a protein which transduces the effector signal function signal and directs the cell to perform a specialized function.

The cytoplasmic signaling domain, which is preferably from a human protein involved in signal transduction pathway(s), determines whether anti-CLL1 CAR is a positive CAR (PCAR) or a negative CAR (NCAR) depending on the nature of the signaling. Respectively, the CAR is a PCAR when the signaling domain, such as CD3zeta from human TCR receptor, has the effect of stimulating the cellular immune activity of the immune cell when the extracellular ligand binding-domain is bound to CLL1. Conversely, the anti-CLL1 CAR is a NCAR or inhibitory CAR (iCAR) when the signaling domain has the effect of reducing the cellular immune activity, such as signaling domains of human immunoinhibitory receptors CTLA-4 and PD-1 (Federov et al., Sci Transl Med. 2013 Dec. 11; 5 (215): 215ra172). Preferred examples of signal transducing domain for use in a anti-CLL1 CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the anti-CLL1 CAR can comprise the CD3zeta signaling domain which has amino acid sequence with at least 70%, preferably at least 80%, more preferably at least 90%, 95% 97% or 99% or 100% sequence identity with amino acid sequence selected from the group consisting of SEQ ID NO: 9.

A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible co-stimulatory ligand (ICOS- L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83. A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the co-stimulatory domain of the anti-CLL1 CAR of the present invention comprises a part of co-stimulatory signal molecule selected from the group consisting of fragment of 4-1BB (GenBank™: AAA53133.) and CD28 (NP_006130.1). In particular the signal transduction domain of the anti-CLL1 CAR of the present invention comprises amino acid sequence which comprises at least 70%, preferably at least 80%, more preferably at least 90%, 95% 97% or 99% sequence identity with amino acid sequence selected from the group consisting of SEQ ID NO: 8.

An anti-CLL1 CAR according to the present invention generally further comprises a transmembrane domain (TM). The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ζ, polypeptide constituting CD3 complex, IL2 receptor p55 (α chain), p75 ((β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain.

The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO.5, or hinge polypeptides which display preferably at least 80%, more preferably at least 90%, 95% 97% or 99% sequence identity with these polypeptides. According to one embodiment, the hinge can also be a human Ig (immunoglobulin) hinge, e.g., a PD-1 hinge, an IgG4 hinge.

According to a preferred embodiment, the anti-CLL1 CAR according to the invention comprises a transmembrane domain more particularly selected from Cd8α and 4-1BB, showing identity with the polypeptides of SEQ ID NO. 6 or 7.

An anti-CLL1 CAR according to the invention generally further comprises a transmembrane domain (TM) more particularly a TM selected from Cd8α and 4-1BB, and even more particularly showing identity with the polypeptides of SEQ ID NO. 6 or 7.

In a preferred embodiment, a anti-CLL1 CAR according to the invention further comprises a TM domain from Cd8α with SEQ ID NO. 6 or showing at least 90%, 91%, 92%, 93%, 94%, 95%, 96%, 97%, 98% or 99% sequence identity with SEQ ID NO. 6

Downregulation or mutation of target antigens is commonly observed in cancer cells, creating antigen-loss escape variants. Thus, to offset tumor escape and render immune cell more specific to target, the CLL1 specific anti-CLL1 CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the anti-CLL1 CAR. In another embodiment, the present invention relates to a population of anti-CLL1 CAR s comprising each one different extracellular ligand binding domains. In a particular, the present invention relates to a method of engineering immune cells comprising providing an immune cell and expressing at the surface of said cell a population of anti-CLL1 CAR each one comprising different extracellular ligand binding domains. In another particular embodiment, the present invention relates to a method of engineering an immune cell comprising providing an immune cell and introducing into said cell polynucleotides encoding polypeptides composing a population of anti-CLL1 CAR each one comprising different extracellular ligand binding domains. By population of anti-CLL1 CAR s, it is meant at least two, three, four, five, six or more anti-CLL1 CAR s each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of anti-CLL1 CAR s each one comprising different extracellular ligand binding domains.

CLL1 specific chimeric antigen receptors according to the invention can have different architectures, as they can be expressed, for instance, under a single-chain chimeric protein (scCAR) or under the form of several polypeptides (multi-chain) including at least one such chimeric protein. Such multi-chain CAR architectures are disclosed in WO2014/039523, especially in FIGS. 2 to 4, and from page 14 to 21, which are herein incorporated by reference.

In general, anti-CLL1 CAR comprises an extracellular single chain antibody (scFv Fc) fused to the intracellular signaling domain of T-cell antigen receptor complex zeta chain (scFv Fc:ζ), which has the ability, when expressed in T cells, to redirect antigen recognition based on the monoclonal antibody's specificity.

The present application discloses several anti-CLL1 single chain CAR directed against CLL1 antigen, which comprise as non-limiting example the amino acid sequences: SEQ ID NO: 35 to 112.

CLL1 CAR of the present invention can also be "multi-chain CARs" as previously mentioned, which means that the extracellular binding domain and the signaling domains are preferably located on different polypeptide chains, whereas co-stimulatory domains may be located on the same or a third polypeptide. Such multi-chain CARs can be derived from FcεRI (Ravetch et al, 1989), by replacing the high affinity IgE binding domain of FcεRI alpha chain by an extracellular ligand-binding domain such as scFv, whereas the N and/or C-termini tails of FcεRI beta and/or gamma chains are fused to signal transducing domains and co-stimulatory domains respectively. The extracellular ligand binding domain has the role of redirecting T-cell specificity towards cell targets, while the signal transducing domains activate or reduce the immune cell response. The fact that the different polypeptides derive from the alpha, beta and gamma polypeptides from FcεRI are transmembrane polypeptides sitting in juxtamembrane position provides a more flexible architecture to CARs, improving specificity towards the targeted molecule and reducing background activation of immune cells as described in WO2014/039523.

Extracellular Ligand-Binding Domain

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. It can be for instance binding domains derived from a ligand, a receptor, human or mice antibodies or antigen recognition domains derived from camels or cartilaginous fish.

In a preferred embodiment, said extracellular ligand-binding domain comprises a single chain antibody fragment (scFv) comprising the light ($V_L$) and the heavy ($V_H$) variable fragment of a target antigen specific monoclonal anti CLL1 antibody joined by a flexible linker. Said $V_L$ and $V_H$ are preferably selected from the antibodies referred to in the literature as SCO02-357, SCO2-378 and SC02-161 in WO2005/00894 (Applicant: Crucell Holland BV); M26, M31, G4, M22, M29, M2, M5, G12 in WO2013/169625 (Applicant: Cellerant Therapeutics); and 21.26, 1075.7 in WO2009/051974 (Applicant: Nuvelo Inc.), and more particularly as comprising CDRs from VH and VL domains of monoclonal anti-CLL1 antibodies selected from SEQ ID NO. 119 to 190 described below.

The CDR sequences of VH chain from monoclonal anti-CLL1 antibody may be chosen among GSISSSNWWS (SEQ ID NO 119), WIGEIYHSGSPDY (SEQ ID NO 120), KVSTGGFFDY (SEQ ID NO 121), and GSISSSNWWS (SEQ ID NO 122), WIGEIYHSGSPNY (SEQ ID NO 123), RSSSGGFFDY (SEQ ID NO 124), and GSISSSNWWS (SEQ ID NO 125), WIGEIYHSGSPNY (SEQ ID NO 126), RQTTAGSFDY (SEQ ID NO 127), and GYTFTSYFIH (SEQ ID NO 131), WIGFINPYNDGSKY (SEQ ID NO 132), TRDDGYYGYAMDY (SEQ ID NO 133), and GYTFTSYVMH (SEQ ID NO 137), WIGYINPYNDGTKY (SEQ ID NO 138), ARPIYFDNDY (SEQ ID NO 139), and QQNNYDPW (SEQ ID NO 143), WIGPINPYNDGTI (SEQ ID NO 144), ARTDDYDDYTMDY (SEQ ID NO 145), and GYTFTRYWMH (SEQ ID NO 149), WIGNIDPSDTETHY (SEQ ID NO 150), AIYYGNPSYYAMDY (SEQ ID NO 151), and GYIFTSYVMY (SEQ ID NO 155), WIGYINPY (SEQ ID NO 156), ARYYDYDYYFDY (SEQ ID NO 157), and GYTFTSYFMH (SEQ ID NO 161), WIGFINPYNDGTKY (SEQ ID NO 162), TRDDGYYDYAMDY (SEQ ID NO 163), and GFNIKDDYIH (SEQ ID NO 167), WIGWIDPEKGDTAYA (SEQ ID NO 168), TLTGRFDY (SEQ ID NO 169), and GYTFPSSNIH (SEQ ID NO 173), WIGVIYPGNGDTSY (SEQ ID NO 174), AIYFVYNWHFDV (SEQ ID NO 175), and GYTFTRYWMH (SEQ ID NO 179), MIHPSSGSTSYNEKVK (SEQ ID NO 180), RDGDYYYGTGDY (SEQ ID NO 181), and GYSITSAYYWN (SEQ ID NO 185), YISYDGRNNYNPSLKN (SEQ ID NO 186) and AKEGDYDVGNYYAMDY (SEQ ID NO 187).

Similarly, the CDR sequences of VL chain from monoclonal anti-CLL1 antibody may be chosen among: QSISSYLN (SEQ ID NO 128), LLIYAASSLQS (SEQ ID NO 129), QQSYSTPP (SEQ ID NO 130), and QELSGYLS (SEQ ID NO 134), RLIYAASTLDS (SEQ ID NO 135), LQYAIYPY (SEQ ID NO 136), and ESVDSYGNSFMH (SEQ ID NO 140), LLIYLASNLES (SEQ ID NO 141), QQNNYDPW (SEQ ID NO 142), HDISNYLN (SEQ ID NO 146), LLIYYTSRLHS (SEQ ID NO 147), QQGKTLLW (SEQ ID NO 148), and QNLLNSGNQKKYLN (SEQ ID NO 152), LLIYWASTRES (SEQ ID NO 153), QNDYSYPF (SEQ ID NO 154), and QDINKYIA (SEQ ID NO 158), LLIHYTSTLQP (SEQ ID NO 159), LQYDYLW (SEQ ID NO 160), and QEISVYLS (SEQ ID NO 164), RLIYAASTLDS (SEQ ID NO 165), LQYASYPY (SEQ ID NO 166), and QSLLYSSNQKNNLA (SEQ ID NO 170), LLIYWASTRES (SEQ ID NO 171), QQYYSYR (SEQ ID NO 172), and ESVDGYGDIFML (SEQ ID NO 176), LLIYFASNLES (SEQ ID NO 177), QQNNEDPY (SEQ ID NO 178), and RASSSINYMH (SEQ ID NO 182), PWIFATSNLAS (SEQ ID NO 183), QQWRSDRALT (SEQ ID NO 184), and RASSNVISSYVH (SEQ ID NO 188), LWIYSTSNLAS (SEQ ID NO 189) and QQYSGYPLT (SEQ ID NO 190).

The extracellular domain and the transmembrane domain are preferably linked together by a flexible linker comprising the sequence SEQ ID NO.10. In other words, said anti-CLL1 CARs preferentially comprise an extracellular ligand-biding domain comprising a polypeptide sequence displaying at least 90%, 95% 97% or 99% identity with an amino acid sequence selected from the group consisting of SEQ ID NO: 11 to SEQ ID NO: 34 (see Table 2).

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

The present invention discloses a CLL1 specific single-chain chimeric antigen receptor (anti-CLL1 scCAR) as described above, wherein said extra cellular ligand binding-domain comprises VH and VL chains which are humanized.

By the term "humanized antibody" as used herein, is meant the polypeptides include a humanized heavy chain variable region and a humanized light chain variable region. For example, the polypeptides may include the framework (FR) regions of the light and heavy chain variable regions of a human antibody, while retaining substantially the antigen-binding specificity of a parental monoclonal antibody. The humanized heavy chain variable region and/or the humanized light chain variable region are at least about 87% humanized, at least about 90% humanized, at least about 95% humanized, at least about 98% humanized, or at least about 100% humanized, excluding the complementary-determining regions (CDRs). The antigen-binding polypeptides molecules may be derived from monoclonal antibody donors (e.g., mouse monoclonal antibody donors) and may include CDRs from the monoclonal antibodies (e.g., mouse monoclonal CDRs).

By the term "monoclonal antibody" as used herein, is meant antibody produced by a laboratory-grown cell clone, either of a hybridoma or a virus-transformed lymphocyte that is more abundant and uniform than natural antibody and is able to bind specifically to a single site on CLL1 antigen. They are monospecific antibodies that are made by identical immune cells that are all clones of a unique parent cell, in contrast to polyclonal antibodies which are made from several different immune cells. Monoclonal antibodies have monovalent affinity, in that they bind to the same epitope. Current methodology applied for humanization is according to Lefranc M P et al (Lefranc, M P, Ehrenmann F, Ginestoux C, Giudicelli V, Duroux P "Use of IMGT® databases and tools for antibody engineering and humanization", Methods Mol Biol. 2012; 907: 3-37). In these four alignments are indicated.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.).

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a anti-CLL1 CAR of the invention can be replaced with other amino acid residues from the same side chain family and the altered anti-CLL1 CAR can be tested for the ability to bind CLL1 using the functional assays described herein.

An anti-CLL1 CAR of the invention optionally includes a suicide domain, which is intended to deplete the immune cells endowed with the CAR in the event these later would cause adverse effects in vivo. Such a suicide domain can be obtained, for instance, by including two copies of a CD20 mimotope, preferably of sequence CPYSNPSLCS (SEQ ID NO. 113), into the CAR polypeptide sequence. Said two copies of a CD20 mimotope can be linked to each other and also to the $V_L$ by a linker. They can also be inserted between the anti-CLL1 scFv and the hinge (such as CD8alpha), by using an optional linker. The CD20 mimotopes can be bound by anti-CD20 antibodies, such as Rituximab (McLaughlin P, et al. 1998). The anti-CLL1 CAR of the present invention may thus comprisea VH and a VL chains which are able to bind to CLL1 cell surface antigen, optionally humanized, a linker L, a suicide domain, a hinge or part of it, a transmembrane domain, a co-stimulatory domain and a stimulatory domain.

In a preferred embodiment, the present invention discloses an anti-CLL1 specific single-chain chimeric antigen receptor ("anti-CLL1 scCAR" or "scCAR") having one of the polypeptide structure selected from $V_1$ to V6, as illustrated in FIG. 2 and Tables 3-8, said structure comprising an extra cellular ligand binding-domain comprising VH and VL from a monoclonal anti-CLL1 antibody, a hinge, a transmembrane domain, a cytoplasmic domain including a signaling domain and a co-stimulatory domain.

In a more preferred embodiment, the present invention discloses a CLL1 specific scCAR as described above, wherein said structure V1, V3 or V5 comprises a FcγRIIIα, CD8 alpha or IgG1 hinge and a CD8 alpha transmembrane domain.

In another more preferred embodiment, said CLL1 specific scCAR comprises the co-stimulatory domain 4-1BB or the CD28, or more preferably the 4-1BB co-stimulatory domain.

The present invention discloses a CLL1 specific scCAR as described above, wherein said structure V1, V3 or V5 comprises a FcγRIIIα, CD8 alpha or IgG1 hinge and a 4-1BB transmembrane domain.

The present invention discloses a CLL1 specific scCAR as described above, wherein said structure V1, V3 or V5 comprises a FcγRIIIα, CD8 alpha or IgG1, a 4-1BB cytoplasmic domain and a CD8 alpha transmembrane domain.

According to a preferred embodiment, the anti-CLL1 scCAR of the invention has one of the polypeptide structure selected from V1 to V6, as illustrated in FIG. 2, said structure comprising an extra cellular ligand binding-domain comprising VH and VL from a monoclonal anti-CLL1 antibody, a hinge, a transmembrane domain, a cytoplasmic domain including a CD3 zeta signaling domain and a co-stimulatory domain, said CD3 zeta signaling domain preferably having a sequence SEQ ID NO.9.

According to another preferred embodiment, the anti-CLL1 scCAR of the invention has one of the polypeptide structure selected from V1 to V6, as illustrated in FIG. 2, said structure comprising an extra cellular ligand binding-domain comprising VH and VL from a monoclonal anti-CLL1 antibody, a hinge, a transmembrane domain, a cytoplasmic domain including a CD3 zeta signaling domain and a 4-1BB co-stimulatory domain, said 4-1BB co-stimulatory domain preferably having a sequence SEQ ID NO.8.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a FcγRIIIα hinge, a Cd8α transmembrane domain, preferably having SEQ ID NO.6, a cytoplasmic domain including a CD3 zeta signaling domain and a co-stimulatory domain.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a Cd8α hinge, a CD8α transmembrane domain, preferably having SEQ ID NO.6, a cytoplasmic domain including a CD3 zeta signaling domain and a co-stimulatory domain.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a IgG1 hinge, a CD8α transmembrane domain, preferably having SEQ ID NO.6, a cytoplasmic domain including a CD3 zeta signaling domain and a co-stimulatory domain.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a FcγRIIIα hinge, a 4-1BB transmembrane domain, preferably having SEQ ID NO.7, a cytoplasmic domain including a CD3 zeta signaling domain and a co-stimulatory domain.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a Cd8α hinge, a 4-1BB transmembrane domain, preferably having SEQ ID NO.7, a cytoplasmic domain including a CD3 zeta signaling domain and a co-stimulatory domain.

The present invention discloses anti-CLL1 scCAR having one of the polypeptide structure selected from V1 to V6, as illustrated in FIG. 2, said structure comprising an extra cellular ligand binding-domain comprising VH and VL from a monoclonal anti-CLL1 antibody, a IgG1 hinge, a 4-1BB transmembrane domain, preferably having SEQ ID NO.7, a cytoplasmic domain including a CD3 zeta signaling domain and a co-stimulatory domain.

In a particular aspect, the present invention discloses an anti-CLL1 specific scCAR having a V1 polypeptide structure, as illustrated in FIG. 2, said structure comprising an extra cellular ligand binding-domain comprising VH and VL from a monoclonal anti-CLL1 antibody, a FcγRIIIα hinge preferably with SEQ ID NO.3, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8.

More specifically, the present invention discloses an anti-CLL1 specific scCAR having a V1 polypeptide structure, as illustrated in FIG. 2, said structure comprising an extra cellular ligand binding-domain comprising VH and VL from a monoclonal anti-CLL1 antibody, a FcγRIIIα hinge preferably with SEQ ID NO.3, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11-13, 15, 17, 19, 21, 23, 25, 27, 29, 31 or 33 and said VL having at least 80% identity with SEQ ID NO.14, 16, 18, 20, 22, 24, 26, 28, 30, 32 or 34.

In another particular aspect, the present invention discloses an anti-CLL1 specific scCAR having a V3 polypeptide structure, as illustrated in FIG. 2, said structure comprising an extra cellular ligand binding-domain comprising VH and VL from a monoclonal anti-CLL1 antibody, a CD8α hinge preferably with SEQ ID NO.4, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8.

More specifically, the present invention discloses an anti-CLL1 specific scCAR having a V3 polypeptide structure, as illustrated in FIG. 2, said structure comprising an extra cellular ligand binding-domain comprising VH and VL from a monoclonal anti-CLL1 antibody, a Cd8α hinge preferably with SEQ ID NO.4, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11-13, 15, 17, 19, 21, 23, 25, 27, 29, 31 or 33 and said VL chain having at least 80% identity with SEQ ID NO.14, 16, 18, 20, 22, 24, 26, 28, 30, 32 or 34.

In still another particular aspect, the present invention discloses an anti-CLL1 specific scCAR having a V5 polypeptide structure, as illustrated in FIG. 2, said structure comprising an extra cellular ligand binding-domain comprising VH and VL from a monoclonal anti-CLL1 antibody, a IgG1 hinge preferably with SEQ ID NO.5, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8.

More specifically, the present invention discloses an anti-CLL1 specific scCAR having a V5 polypeptide structure, as illustrated in FIG. 2, said structure comprising an extra cellular ligand binding-domain comprising VH and VL from a monoclonal anti-CLL1 antibody, a IgG1 hinge preferably with SEQ ID NO.5, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11-13, 15, 17, 19, 21, 23, 25, 27, 29, 31 or 33 and said VL chain having at least 80% identity with SEQ ID NO.14, 16, 18, 20, 22, 24, 26, 28, 30, 32 or 34.

The present invention discloses an anti-CLL1 specific scCAR having a V1 polypeptide structure, as illustrated in FIG. 2, said polypeptide having at least 80% identity with SEQ ID NO. 35, 41, 47, 53, 59, 65, 71, 77, 83, 89, 95, 101 or 107.

In particular, said anti-CLL1 specific scCAR having a V1 polypeptide structure, as illustrated in FIG. 2, said structure comprising an extra cellular ligand binding-domain comprising VH and VL from a monoclonal anti-CLL1 antibody, a FcγRIIIα hinge preferably with SEQ ID NO.3, a CD8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11,13, 15, 17, 19, 21, 23, 25, 27, 29, 31 or 33 and said VL having at least 80% identity with SEQ ID NO.14, 16, 18, 20, 22, 24, 26, 28, 30, 32 or 34, and wherein said polypeptide has at least 80% identity with SEQ ID NO. 35, 41, 47, 53, 59, 65, 71, 77, 83, 89, 95, 101 or 107.

The present invention discloses an anti-CLL1 specific scCAR of structure V3, as illustrated in FIG. 2, said polypeptide having at least 80% identity with SEQ ID NO. 37, 43, 49, 55, 61, 67, 73, 79, 85, 91, 97, 103 or 109.

More specifically, the present invention discloses an anti-CLL1 specific scCAR having a V3 polypeptide structure, as illustrated in FIG. 2, said structure comprising an extra cellular ligand binding-domain comprising VH and VL from a monoclonal anti-CLL1 antibody, a Cd8α hinge preferably with SEQ ID NO.4, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11,13, 15, 17, 19, 21, 23, 25, 27, 29, 31 or 33 and said VL chain having at least 80% identity with SEQ ID NO.14, 16, 18, 20, 22, 24, 26, 28, 30, 32 or 34, and wherein said polypeptide has at least 80% identity with SEQ ID NO. 37, 43, 49, 55, 61, 67, 73, 79, 85, 91, 97, 103 or 109.

The present invention discloses an anti-CLL1 specific scCAR of structure V5, as illustrated in FIG. 2, said polypeptide having at least 80% identity with SEQ ID NO.39, 45, 51, 57, 63, 69, 75, 81, 87, 93, 99, 105 or 111.

More specifically, the present invention discloses an anti-CLL1 specific scCAR having a V5 polypeptide structure, as illustrated in FIG. 2, said structure comprising an extra cellular ligand binding-domain comprising VH and VL from a monoclonal anti-CLL1 antibody, a IgG1 hinge preferably with SEQ ID NO.5, a Cd8α transmembrane domain, preferably with SEQ ID NO.6, a cytoplasmic domain including a CD3 zeta signaling domain, preferably with SEQ ID NO.9, and a 4-1BB co-stimulatory domain, preferably with SEQ ID NO.8, wherein said VH chain having at least 80% identity with SEQ ID NO.11,13, 15, 17, 19, 21, 23, 25, 27, 29, 31 or 33 and said VL chain having at least 80% identity with SEQ ID NO.14, 16, 18, 20, 22, 24, 26, 28, 30, 32 or 34, and wherein said polypeptide having at least 80% identity with SEQ ID NO.39, 45, 51, 57, 63, 69, 75, 81, 87, 93, 99, 105 or 111.

The present invention more particularly discloses a CLL1 single-chain specific chimeric antigen receptor (scCAR) having a polypeptide structure V1, V3 or V5 as illustrated in FIG. 2, and described above said structure comprising an extra cellular ligand binding-domain VH from a monoclonal anti-CLL1 antibody comprising the following CDR sequences: GSISSSNWWS (SEQ ID NO 119), WIGEIYHSGSPDY (SEQ ID NO 120), KVSTGGFFDY (SEQ ID NO 121), and GSISSSNWWS (SEQ ID NO 122), WIGEIYHSGSPNY (SEQ ID NO 123), RSSSGGFFDY (SEQ ID NO 124), and GSISSSNWWS (SEQ ID NO 125), WIGEIYHSGSPNY (SEQ ID NO 126), RQTTAGSFDY (SEQ ID NO 127), and GYTFTSYFIH (SEQ ID NO 131), WIGFINPYNDGSKY (SEQ ID NO 132), TRDDGYYG-YAMDY (SEQ ID NO 133), and GYTFTSYVMH (SEQ ID NO 137), WIGYINPYNDGTKY (SEQ ID NO 138), ARPIYFDNDY (SEQ ID NO 139), and QQNNYDPW (SEQ ID NO 143), WIGPINPYNDGTI (SEQ ID NO 144), ARTDDYDDYTMDY (SEQ ID NO 145), and GYTFTRYWMH (SEQ ID NO 149), WIGNIDPSDTETHY (SEQ ID NO 150), AIYYGNPSYYAMDY (SEQ ID NO 151), and GYIFTSYVMY (SEQ ID NO 155), WIGYINPY (SEQ ID NO 156), ARYYDYDYYFDY (SEQ ID NO 157), and GYTFTSYFMH (SEQ ID NO 161), WIG-FINPYNDGTKY (SEQ ID NO 162), TRDDGYYDYAMDY (SEQ ID NO 163), and GFNIKD-DYIH (SEQ ID NO 167), WIGWIDPEKGDTAYA (SEQ ID NO 168), TLTGRFDY (SEQ ID NO 169), and GYTFPSSNIH (SEQ ID NO 173), WIGVIYPGNGDTSY (SEQ ID NO 174), AIYFVYNWHFDV (SEQ ID NO 175), and GYTFTRYWMH (SEQ ID NO 179), MIHPSSGST-SYNEKVK (SEQ ID NO 180), RDGDYYYGTGDY (SEQ ID NO 181), and GYSITSAYYWN (SEQ ID NO 185), YISYDGRNNYNPSLKN (SEQ ID NO 186), AKEG-DYDVGNYYAMDY (SEQ ID NO 187), and preferably an extra cellular ligand binding-domain VL from a monoclonal anti-CLL1 antibody comprising the following CDR sequences: QSISSYLN (SEQ ID NO 128), LLIYAASSLQS (SEQ ID NO 129), QQSYSTPP (SEQ ID NO 130), and QELSGYLS (SEQ ID NO 134), RLIYAASTLDS (SEQ ID NO 135), LQYAIYPY (SEQ ID NO 136), and ESVDSYG-NSFMH (SEQ ID NO 140), LLIYLASNLES (SEQ ID NO 141), QQNNYDPW (SEQ ID NO 142), HDISNYLN (SEQ ID NO 146), LLIYYTSRLHS (SEQ ID NO 147), QQGKTLLW (SEQ ID NO 148), and QNLLNSGNQK-KYLN (SEQ ID NO 152), LLIYWASTRES (SEQ ID NO 153), QNDYSYPF (SEQ ID NO 154), and QDINKYIA (SEQ ID NO 158), LLIHYTSTLQP (SEQ ID NO 159), LQYDYLW (SEQ ID NO 160), and QEISVYLS (SEQ ID NO 164), RLIYAASTLDS (SEQ ID NO 165), LQYASYPY (SEQ ID NO 166), and QSLLYSSNQKNNLA (SEQ ID NO 170), LLIYWASTRES (SEQ ID NO 171), QQYYSYR (SEQ ID NO 172), and ESVDGYGDIFML (SEQ ID NO 176), LLIYFASNLES (SEQ ID NO 177), QQNNEDPY (SEQ ID NO 178), and RASSSINYMH (SEQ ID NO 182), PWIFATSNLAS (SEQ ID NO 183), QQWRSDRALT (SEQ ID NO 184), and RASSNVISSYVH (SEQ ID NO 188), LWIYSTSNLAS (SEQ ID NO 189), QQYSGYPLT (SEQ ID NO 190), and wherein said structure generally comprising:
a hinge, a transmembrane domain and a cytoplasmic domain including a CD3 zeta signaling domain and a co-stimulatory domain from 4-1BB.

The present invention discloses an anti-CLL1 single-chain specific chimeric antigen receptor (anti-CLL1 scCAR) as above, wherein said extra cellular ligand binding-domain VH and VL is humanized.

The present invention discloses a CLL1 single-chain specific chimeric antigen receptor (scCAR) as described above, wherein said extra cellular ligand binding-domain VH from a monoclonal anti-CLL1 antibody comprise at least one of the following sequences:

The present invention discloses a CLL1 single-chain specific chimeric antigen receptor (scCAR) as described above, wherein said extra cellular ligand binding-domain VH from a monoclonal anti-CLL1 antibody comprise at least one of the following sequences:

QVQLQESGPGLVKPSETLSLTCVVSGGSIS-SSNWWSWVRQPPGKGLEWIG EIYHSGSPNYNPSLKSRVTISVDK-SKNQFSLKLSSVTAADTAVYYSSSGGF FDYWGQGTLVTVSS
(corresponding to SCO2-357; SEQ ID NO: 11),
QVQLQESGPGLVKPSETLSLTCVVSGGSIS-SSNWWSWVRQPPGKGLEWIG EIYHSGSPNYNPSLKSRVTISVDK-SKNQFSLKLSSVTAADTAVYYCARSSS GGFFDYWGQGTLVTVSS
(corresponding to SCO2-378; SEQ ID NO: 12),
QVQLQESGPGLVKPSETLSLTCVVSGGSIS-SSNWWSWVRQPPGKGLEWIG EIYHSGSPNYNPSLKSRVTISVDK-SKNQFSLKLSSVTAADTAVYYCARQTI AGSFDYWGQGTLVTVSS
(corresponding to SCO2-161; SEQ ID NO: 13),
EVQLQQSGPELVKPGASVKMSCKASGYTFTSY-FIHWVKQKPGQGLEWIG FINPYNDGSKY-NEKFKGKATLTSDKSSSTAYMELSSLTSED-SAVYYCTRD DGYYGYAMDYWGQGTSVTVSS
(corresponding to M26; SEQ ID NO: 15),
EVQLQQSGPELVKPGASVKMSCKASGYTFT-SYVMHWVKQKPGQGLEWI GYINPYNDGT-KYNEKFKGKATLTSDTSSSTAYMELNSLTSED-SAVYFCAR PIYFDNDYFDYWGQGTILKVSS
(corresponding to M31; SEQ ID NO: 17),
EVQLQQSGPELVKPGASMKISCK-ASGYSFTGYTMNWVKQSHEKNLEWIG PINPYNDGTIYNPNFKGKATLTVDKASSTAYMELLSLT-SDDPAVYYCART DDYDD-YTMDYWGQGTSVTVSS
(corresponding to G4; SEQ ID NO: 19),
QVQLQQPGAELVKPGASVKLSCK-ASGYTFTRYWMHWVKQRPGQGLEW IGNIDPSDT-ETHYNQQFKDKATLTVDKSSSTAYMQLSSLT-SEDSAVYYCA IYYG-NPSYYAMDYWGQGTSVTVSS
(corresponding to M22; SEQ ID NO: 21),
EVQLQQSGPELVKPGASVKMSCKASGYIFT-SYVMYWVKQKPGQGLEWI GYINPYNDGT-KYNEKFKGKATLTSDKSSSTAYMELSSLTSED-SAVYYCA RYYDYDYYFDYWGQGTTLTVSS
(corresponding to M29; SEQ ID NO: 23),
EVQLRQSGPELVKPGASVKMSCKASGYTFT-SYFMHWVKQKPGQGLEWI GFINPYNDGT-KYNEKFKGKATLTSDKSSSTAYMELNSLTSED-SAVYYCTR DDGYYDYAMDYWGQGTSVTVSS
(corresponding to M2; SEQ ID NO: 25),
EVQLQQSGAELVRPGASVKLSCTASGFNIKD-DYIHWVKQRPEQGLEWIG WIDPEKGD-TAYASKFQDKATITSDTSSNTAYLQLSSLTSED-TAVYYCTLT GRFDYWGQGTTLTVSS
(corresponding to M5; SEQ ID NO: 27),
QVQLQQPGAELVKPGASMKMSCK-ASGYTFPSSNIHWLKQTPGQGLEWIG VIYPGNGDTSYN-QKFKDKATLTTDKSSSTAYMQLSSLTSED-SAIYFCARV YNWHFDVWGAGTTVTVS S
(corresponding to G12; SEQ ID NO: 29),
QVQLQQPGAELVKPGTSVKLSCK-ASGYTFTRYWMHWVKQRPGQGLEWI GMIRPSSGSTSYNEKVKNKATLTVDRSST-TAYMQLSSLTSEDSAVYYCAR DGDYYYGTGDYWGQGTTLTVSS
(corresponding to 21.26; SEQ ID NO: 31),
DIQLQESGPGLVKPSQSLSLTCSVTGYSIT-SAYYWNWIRQFPGNKLEWMG YISYDGRN-NYNPSLKNRISITRDTSKNQFFLKLNSVTTED-TATYYCAKEG DYDVGNYYAMDYWGQGTSVTVSS
(corresponding to 1075.7; SEQ ID NO: 13), and VL from a monoclonal anti-CLL1 antibody comprise at least one of the following sequences:

DIQMTQSPSSLSASVGDRVTITCRASQSIS-SYLNWYQQKPGKAPKLLIYAA SSLQSGVPSRFSGSGSGTDFTLTISSLQPEDFA-TYYCQQSYSTPPTFGQGTK VEIK
(corresponding to SCO2-357, SCO2-378 and SCO2161; SEQ ID NO: 14),
DIQMTQSPSSLSASLGERVSLT-CRATQELSGYLSWLQQKPDGTIKRLIYAA STLDSGVPKRFSGNRSGSDYSLTISSLESED-FADYYCLQYAIYPYTFGGGT KLEIKR
(corresponding to M26; SEQ ID NO: 16),
TIVLTQSPASLAVSLGQRATISCRASESVDSYG-NSFMHWYQQKPGQPPKL LIYLASN-LESGVPARFSGSGSRTDFTLTIDPVEADD-AATYYCQQNNYDPW TFGGGTKLEIK
(corresponding to M31; SEQ ID NO: 18),
EIQMTQTPSSLSASLGDRVTISCRASHDIS-NYLNWYQQKPDGTLKLLIYYT SRLHSGVPSRFSGSGSGTDYSLTISNLEQEDI-ATYFCQQGKTLLWTFGGGT KLEIK
(corresponding to G4; SEQ ID NO: 20),
DIVMTQSPSSLTVTAGEKVTMSCK-SSQNLLNSGNQKKYLNWYQQKPGQP PKLLIY-WASTRESGVPDRFTGSGSGTDFTLTISSVQAED-LAVYFCQNDYS YPFTFGAGTKLELK
(corresponding to M22; SEQ ID NO: 22),
DIQMTQSPSSLSASLGGKVTITCKASQDIN-KYIAWYQHKPGKGPRLLIHYT STLQP-GIPSRFSGSGSGRDYSFSISNLEPEDIATYY-CLQYDYLWTFGGGTK LEIK
(corresponding to M29; SEQ ID NO: 24),
DIQMTQSPSSLSASLGERVSLT-CRASQEISVYLSWLQQKPDGTIKRLIYAA STLDSGVPERFSGSRSGSDYSLTISSLESED-FADYYCLQYASYPYTFGGGT KLEIKR
(corresponding to M2; SEQ ID NO: 26),
DIVMSQSPSSLAVSVGEKVTMSCKSSQSLLY-SSNQKNNLAWYQQKPGQS PKLLIYWAST-RESGVPDRFTGSGSGTDFTLTISSVQAED-LAVYYCQQYYS YRTFGGGTKLEIK
(corresponding to M5; SEQ ID NO: 28),
NIVLTQSPASLAVSLGQRATISCRAS-ESVDGYGDIFMLWYQQKPGQPPKL LIYFASN-LESGVPARFSGSGSRTDFTLTIDPVEADD-AATYYCQQNNEDPYT FGGGTKLEIKR
(corresponding to G12; SEQ ID NO: 30), QIVLSQSPAILSASPGEKVTMTCRASSS-
INYMHWYQQKPGSSPKPWIFATS
NLASGVPSRFSGSGSGTSYSLTISRVEAE-
DAATYYCQQWRSDRALTFGAG TKLEL
(corresponding to 21.26; SEQ ID NO: 32),
DIQLQESGPGLVKPSQSLSLTCSVTGYSIT-
SAYYWNWIRQFPGNKLEWMG YISYDGRN-
NYNPSLKNRISITRDTSKNQFFLKLNSVTIED-
TATYYCAKEGD
YDVGNYYAMDYWGQGTSVTVSS
(corresponding to 1075.7; SEQ ID NO: 34)

The present invention also discloses a CLL1 specific scCAR as previously defined, further comprising another extracellular ligand binding domain which is not specific for CLL1, such as CD33 antigen, CD44 antigen, CD47 antigen, CD123 antigen, CD96 antigen and T-cell immunoglobulin mucin-3 (TIM-3).

The present invention discloses a CLL1 specific scCAR as above, further comprising a signal peptide, preferably of SEQ ID NO 1 or SEQ ID NO 2, in order to help the CAR polypeptide to reach the immune cell's membrane.

The present invention discloses a CLL1 specific scCAR as above, wherein a linker of SEQ ID NO 10 is inserted between VH and VL.

Polynucleotides, Vectors:

The present invention also relates to polynucleotides and vectors allowing heterologous expression into cells of the anti-CLL1 CAR according to the invention, encoding the polypeptides sequences which have been previously detailed.

The polynucleotides may be included in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned else- where in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2 or at least 90%, 95% 97% or 99% sequence identity with SEQ ID NO: 1 and/or 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Delivery Methods

The present invention encompasses the different means to express the anti-CLL1 Chimeric Antigen Receptor (CAR) described herein in immune cells Methods for introducing a polynucleotide construct into cells are known in the art and include as non-limiting examples stable transformation methods wherein the polynucleotide construct encoding said CAR is integrated into the genome of the cell, transient transformation methods wherein the polynucleotide construct is not integrated into the genome of the cell and virus mediated methods.

Said polynucleotides may be introduced into a cell by for example, recombinant viral vectors (e.g. retroviruses, adenoviruses), liposome and the like. For example, transient transformation methods include for example microinjection, electroporation or particle bombardment, cell fusion. Said polynucleotides may be included in vectors, more particularly plasmids or virus, in view of being expressed in cells. Said plasmid vector can comprise a selection marker which provides for identification and/or selection of cells which received said vector.

Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)).

By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

In a more preferred embodiment of the invention, polynucleotides encoding polypeptides according to the present invention can be mRNA which is introduced directly into the cells, for example by electroporation. The inventors determined the optimal condition for mRNA electroporation in T-cell. The inventor used the cytoPulse technology which allows, by the use of pulsed electric fields, to transiently permeabilize living cells for delivery of material into the cells. The technology, based on the use of PulseAgile® (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow moving the polynucleotide into the cell.

The different methods described above involve introducing scCAR into a cell. As non-limiting example, said scCAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (LonzaLONZA®)) that may contain factors necessary for proliferation and viability, including serum (e.g., fetal bovine or human serum), interleukin-2 (IL-2), insulin, IFN-g, ll-4, ll-7, GM-CSF, -10, -2, ll-15, TGFp, and TNF- or any other additives for the growth of cells known to the skilled artisan. Other additives for the growth of cells include, but are not limited to, surfactant, plasmanate, and reducing agents such as N-acetylcysteine and 2-mercaptoethanoi. Media can include RPMI1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Engineered Immune Cells

A "Cell" according to the present invention generally refers to a cell of hematopoietic origin functionally involved in the initiation and/or execution of innate and/or adaptative immune response. Cell according to the present invention is preferably an isolated immune cell, and more preferably a T-cell obtained from a donor. Said immune cell according to the present invention can also be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used.

In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of primary T-cells, endowed with a CLL1 CAR as described above, that do not express functional TCR and that a reactive towards CLL1 positive cells, for their allogeneic transplantation into patients.

As a more preferred embodiment, the present invention provides T-cells or a population of T-cells endowed with a CLL1 scCAR and that a reactive towards CLL1 positive cells as described above, that do not express a functional TCR and are resistant to a selected drug, for their allogeneic transplantation into patients treated with said selected drug. The present invention encompasses the method of preparing engineered immune cells for immunotherapy comprising introducing ex-vivo into said immune cells the polynucleotides or vectors encoding the CLL1 CAR according to transformation methods as previously described in WO2014/130635WO2013176916, WO2013176915 and incorporated herein by reference.

In a preferred embodiment, said polynucleotides are introduced into the immune cells by means of retroviral vectors in view of being stably integrated into the cell genome.

Methods of Engineering Immune Cells Endowed with the CARs According to the Invention The present invention also aims to produce immune cells endowed with anti CLL1 CAR, which are less or non-alloreactive, which can be used in allogeneic treatments (i.e. with reduced risk of inducing Graft versus host reaction) and/or made resistant to various standard of care treatments).

As further described in this specification, said methods may further comprise the step of genetically modifying said immune cell by using at least one endonuclease.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp.

Preferably, the methods according to the present invention involve a rare cutting endonuclease. Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a TALE-nuclease, a Cas9 endonuclease from CRISPR system as described below (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of ortho-phenanthroline, a DNA cleaving molecule, and triplex-forming oligonucleotides (TFOs), known to bind specific DNA sequences (Kalish and Glazer 2005). Rare-cutting endonucleases can be used for inactivating genes at a locus or to integrate transgenes by homologous recombination (HR) i.e. by inducing DNA double-strand breaks (DSBs) at a locus and insertion of exogeneous DNA at this locus by gene repair mechanism (Perrin, Buckle et al. 1993; Rouet, Smih et al. 1994; Choulika, Perrin et al. 1995; Pingoud and Silva 2007).

By "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance 1-Tevl, CoiE7, NucA and Fok-1. In a particular embodiment, the TALE domain can be fused to a meganuclease like for instance 1-Crel and 1-0nul or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of 1-Tevl described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Bach, Scholze et al. 2009; Moscou and Bogdanove 2009; Christian, Cermak et al. 2010; Li, Huang et al. 2011). Engineered TAL-nucleases are available under the trade name TALEN™ (CELLECTIS®, 8 rue de Ia Croix Jarry, 75013 Paris, France) and can be ordered from manufacturers, such as Life Technologies (Carlsbad, Calif., USA).

Preferred TALE-nucleases recognizing and cleaving the target sequence are described in PCT/EP2014/075317. In particular, additional catalytic domain can be further introduced into the cell with said rare-cutting endonuclease to increase mutagenesis in order to enhance their capacity to inactivate targeted genes. More particularly, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), *E. coli*

ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX2 polypeptide. Said additional catalytic domain may be fused to a nuclease fusion protein or chimeric protein according to the invention optionally by a peptide linker.

By "Cas9 endonuclease". is meant any genome engineering tool developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the proto-spacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010). The use of Cas9 in immune cells, especially in T-Cells, has been previously described in WO2014191128.

Modifying T-Cell by Inactivating at Least One Gene Encoding a T-Cell Receptor (TCR) Component According to one aspect, T-cell endowed with anti-CLL1 CAR of the present invention can be made less alloreactive, for instance, by inactivating at least one gene expressing one or more component of T-cell receptor (TCR) as described in WO 2013/176915. This inactivation can be combined with that of another gene, such as of a gene encoding or regulating HLA or β2m protein expression. Accordingly, the risk of graft versus host syndrome and graft rejection is significantly reduced.

Methods of making cells less allogenic can comprise the step of inactivating at least one gene encoding a T-Cell Receptor (TCR) component, in particular TCRalpha and/or TCRbeta genes.

Methods disclosed in WO2013/176915 to prepare CAR expressing immune cell suitable for allogeneic transplantation, by inactivating one or more component of T-cell receptor (TCR), are all incorporated herein by reference.

The present invention encompasses an anti-CLL1 CAR expressing immune cell wherein at least one gene expressing one or more component of T-cell receptor (TCR) has been inactivated. Thus, the present invention provides an anti-CLL1 CAR expressing T cell wherein at least one gene expressing one or more component of T-cell receptor (TCR) is inactivated.

By inactivating a TCR gene it is intended that the gene of interest is not expressed in a functional protein form. In particular embodiments, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art. In a particular embodiment, the step of inactivating at least a gene encoding a component of the T-cell receptor (TCR) into the cells of each individual sample comprises introducing into the cell a rare-cutting endonuclease able to disrupt at least one gene encoding a component of the T-cell receptor (TCR). In a more particular embodiment, said cells of each individual sample are transformed with nucleic acid encoding a rare-cutting endonuclease capable of disrupting at least one gene encoding a component of the T-cell receptor (TCR), and said rare-cutting endonuclease is expressed into said cells.

In a preferred embodiment said method of further engineer the immune cells involves introducing into said T cells polynucleotides, in particular mRNAs, encoding specific rare-cutting endonuclease to selectively inactivate the genes mentioned above by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

According to the invention, anti-CLL1 CAR immune cells with one or more component of T-cell receptor (TCR) inactivated are intended to be used as a medicament.

Drug Resistant T-Cells

According to another aspect, anti-CLL1 CAR expressing immune cells of the invention can be further genetically engineered to make them resistant to immunosuppressive drugs or chemotherapy treatments, which are used as standard care for treating cancer associated with CLL1 positive malignant cell, especially AML.

Several cytotoxic agents (anti-cancer drug)s) such as anti-metabolites, alkylating agents, anthracyclines, DNA methyltransferase inhibitors, platinum compounds and spindle poisons have been developed to kill cancer cells. However, the introduction of these agents with novel therapies, such as immunotherapies, is problematic. For example, chemotherapy agents can be detrimental to the establishment of robust anti-tumor immunocompetent cells due to the agents' non-specific toxicity profiles. Small molecule-based therapies targeting cell proliferation pathways may also hamper the establishment of anti-tumor immunity. If chemotherapy regimens that are transiently effective can be combined with novel immunocompetent cell therapies then significant improvement in anti-neoplastic therapy might be achieved (for review (Dasgupta, McCarty et al. 2011).

To improve cancer therapy and selective engraftment of allogeneic immune cells, drug resistance is conferred to said allogeneic cells to protect them from the toxic side-effects of chemotherapy agents. The drug resistance of immune cells also permits their enrichment in or ex vivo, as T-cells which express the drug resistance gene will survive and multiply relative to drug sensitive cells.

Methods for engineering immunecells resistant to chemotherapeutic agents are disclosed in PCT/EP2014/075317 which is fully incorporated by reference herein.

In particular, the present invention relates to a method of engineering allogeneic cells suitable for immunotherapy wherein at least one gene encoding a T-cell receptor (TCR) component is inactivated and one gene is modified to confer drug resistance comprising:
  Providing an anti-CLL1 scCAR expressing T-cell; expressing T cell,
  Modifying said anti-CLL1 scCAR expressing T-cell by inactivating at least one gene encoding a T-cell receptor (TCR) component;
  Modifying said anti-CLL1 scCAR expressing T-cell, preferably humanized CLL1 scCAR, to confer drug resistance to said anti-CLL1 scCAR expressing T-cell;
  Expanding said engineered anti-CLL1 scCAR expressing T-cell in the presence of said drug.

Alternatively, the present invention relates to a method comprising:
  Providing an anti-CLL1 scCAR expressing T-cell; preferably humanized CLL1 scCAR;
  Modifying said anti-CLL1 scCAR expressing T-cell to confer drug resistance to said anti-CLL1 scCAR expressing T-cell;
  Modifying said anti-CLL1 scCAR expressing T-cell by inactivating at least one gene encoding a T-cell receptor (TCR) component;
  Expanding said engineered anti-CLL1 scCAR expressing T-cell in the presence of said drug.

In particular, the present invention also relates to a method of engineering allogeneic cells suitable for immunotherapy wherein at least one gene encoding a T-cell receptor (TCR) component is inactivated and one gene is modified to confer drug resistance comprising:
  Providing an anti-CLL1 scCAR expressing T-cell; preferably humanized CLL1 scCAR;
  Modifying said anti-CLL1 scCAR expressing T-cell by inactivating at least one gene encoding a T-cell receptor (TCR) component;
  Modifying said anti-CLL1 scCAR expressing T-cell to confer drug resistance to said anti-CLL1 scCAR expressing T-cell;
  Expanding said engineered anti-CLL1 scCAR expressing T-cell in the presence of said drug.

Alternatively, the present invention relates to a method comprising:
  Providing an anti-CLL1 scCAR expressing T-cell; preferably humanized CLL1 scCAR;
  Modifying said anti-CLL1 scCAR expressing T-cell to confer drug resistance to said anti-CLL1 scCAR expressing T-cell;
  Modifying said anti-CLL1 scCAR expressing T-cell by inactivating at least one gene encoding a T-cell receptor (TCR) component;
  Expanding said engineered anti-CLL1 scCAR expressing T-cell in the presence of said drug.

Expression of Drug Resistance Genes in Anti-CLL1 scCAR-Expressing Immune Cells

In a particular embodiment, said drug resistance can be conferred to the T-cell by the expression of at least one drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to a greater extent than the proliferation of a corresponding cell without the drug resistance gene. The expression of the drug resistance gene in a cell permits proliferation of the cells in the presence of the agent and does not affect its activity. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

In one embodiment, a drug resistance gene of the invention can confer resistance to a drug (or an agent), in particular an anti-cancer drug selected from aracytine, cytosine arabinoside, amsacrine, daunorubicine, idarubicine, novantrone, mitoxantrone, vepeside, etoposide (VP16), arsenic trioxyde, transretinoic acid, combination of arsenic trioxyde, transretinoic acid, mechlorethamine, procarbazine, chlorambucil, cytarabine, anthracyclines, 6-thioguanine, hydroxyurea, prednisone, and combination thereof.

Several drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank™: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer, Dicker et al. 1990); International application WO94/24277; US patent U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide set forth in GenBank™: AAH71996.1. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is an IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or S351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue. Correspondence of amino acid positions described herein is frequently expressed in terms of the positions of the amino acids of the form of wild-type human IMPDH2 polypeptide set forth in NP_000875.2.

Another drug resistance gene is the mutant form of calcineurin. Calcineurin (PP2B), an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagine residue, the leucine at position 354 can be replaced with an alanine residue; the lysine at position 360 can be replaced with an alanine or phenylalanine residue of a sequence corresponding to GenBank™: ACX34092.1. Correspondence of amino acid positions described herein is frequently expressed in terms of the positions of the amino acids of the form of wild-type human calcineurin heterodimer a polypeptide set forth in (GenBank™: ACX34092.1).

In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagine at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence corresponding to GenBank™: ACX34095.1. Correspondence of amino acid positions described herein is frequently expressed in terms of the positions of the amino acids of the form of wild-type human calcineurin heterodimer b polypeptide set forth in (GenBank™: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140, in the amino acid sequence such as disclosed in the database Uniprot under the reference P16455. In a preferred embodiment, said proline at position 140 is replaced with a lysine residue.

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents.

Overexpressing multidrug resistance protein 1 has been described to confer resistance to drugs such as Mitoxantrone (Charles S. Morrow, Christina Peklak-Scott, Bimjhana Bishwokarma, Timothy E. Kute, Pamela K. Smitherman, and Alan J. Townsend. Multidrug Resistance Protein 1 (MRP1, ABCC1) Mediates Resistance to Mitoxantrone via Glutathione-Dependent Drug Efflux *Mol Pharmacol* April 2006 69:1499-1505).

Thus, drug resistance can be conferred to cells by the expression of nucleic acid sequence that encodes MDR-1 (NP_000918).

Still another way of preparing drug resistant cells is to prepare cells with specific mutation (s) such as mutations at Arg486 and Glu571 in the Human Topoisomerase II gene, to confer resistance to amsacrine (S. PATEL, B. A. KELLER, and L. M. FISHER. 2000. MOLECULAR PHARMACOLOGY. Vol 57: p 784-791 (2000).

Still another way of preparing drug resistant cells is to prepare cells overexpressing microRNA-21 to confer resistance to Daunorubicine (Involvement of miR-21 in resistance to daunorubicin by regulating PTEN expression in the leukaemia K562 cell line Bai, Haitao et al. FEBS Letters, Volume 585, Issue 2, 402-408).

In a preferred embodiment, cells bearing such a drug resistance conferring mRNA or protein also comprise an inhibitory mRNA or a gene the expression of which is conditioned, allowing the selective destruction of said drug resistant cells in the presence of said drug or upon administration of said drug.

Drug resistance gene can also confer resistance to cytotoxic antibiotics, and can be ble gene or mcrA gene. Ectopic expression of ble gene or mcrA in an immune cell gives a selective advantage when exposed to the chemotherapeutic agent, respectively the bleomycine or the mitomycin C.

The most practical approach to gene therapy is the addition of a gene to engineer T-cell by using efficient gene delivery with vectors, preferably viral vector. Thus, in a particular embodiment, said drug resistance gene can be expressed in the cell by introducing a transgene preferably encoded by at least one vector into a cell.

In one embodiment, cells bearing a drug resistance gene or a modified gene conferring resistance to a drug also comprise an inducible suicide gene—the induction of which provokes cell death—allowing their selective destruction.

The random insertion of genes into the genome may lead to the inappropriate expression of the inserted gene or the gene near the insertion site. Specific gene therapy using homologous recombination of exogenous nucleic acid comprising endogenous sequences to target genes to specific sites within the genome can allow engineering secure T-cells. As described above, the genetic modification step of the method can comprise a step of introduction into cells of an exogeneous nucleic acid comprising at least a sequence encoding the drug resistance gene and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Endonucleolytic breaks are known to stimulate the rate of homologous recombination. Thus, in a particular embodiment, the method of the invention further comprises the step of expressing in the cell a rare-cutting endonuclease which is able to cleave a target sequence within an endogenous gene. Said endogenous gene can encode for examples DHFR, IMPDH2, calcineurin or AGT. Said rare-cutting endonuclease can be a TALE-nuclease, a Zinc finger nuclease, a CRISPR/Cas9 endonuclease, a MBBBD-nuclease or a meganuclease.

Inactivation of Drug Sensitizing Genes in Anti-CLL1 CAR-Expressing Immune Cells

In another particular embodiment, said drug resistance can be conferred to the cell of the invention (anti-CLL1 CAR expressing immune cell,) by the inactivation of a drug sensitizing gene.

The inventor sought to inactivate potential drug sensitizing gene to engineer T-cell for immunotherapy, in particular to engineer anti-CLL1 CAR expressing immune cell that can be used in combination with a therapeutic agent (anti-cancer drug).

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. In a particular embodiment, the step of inactivating at least one drug sensitizing gene comprises introducing into the cell a rare-cutting endonuclease able to disrupt at least one drug sensitizing gene. In a more particular embodiment, said cells are transformed with nucleic acid encoding a rare-cutting endonuclease capable of disrupting a drug sensitizing gene, and said rare-cutting endonuclease is expressed into said cells. Said rare-cutting endonuclease can be a meganuclease, a Zinc finger nuclease, CRISPR/Cas9 nuclease, A MBBBD-nuclease or a TALE-nuclease. In a preferred embodiment, said rare-cutting endonuclease is a TALE-nuclease.

In a preferred embodiment, drug sensitizing gene which can be inactivated to confer drug resistance to the T-cell is the human deoxycytidine kinase (dCK) gene. This enzyme is required for the phosphorylation of the deoxyribonucleosides deoxycytidine (dC), deoxyguanosine (dG) and deoxyadenosine (dA). Purine nucleotide analogs (PNAs) are metabolized by dCK into mono-, di- and tri-phosphate PNA. Their triphosphate forms and particularly clofarabine triphosphate compete with ATP for DNA synthesis, acts as proapoptotic agent and are potent inhibitors of ribonucleotide reductase (RNR) which is involved in trinucleotide production.

Preferably, the inactivation of dCK in T cells is mediated by TALE nuclease. To achieve this goal, several pairs of dCK TALE-nuclease have been designed, assembled at the polynucleotide level and validated by sequencing. Examples of TALE-nuclease pairs which can be used according to the invention are depicted in PCT/EP2014/075317.

This dCK inactivation in T cells confers resistance to purine nucleoside analogs (PNAs) such as clofarabine, fludarabine or decitabine (Dacogen).

In another preferred embodiment, the dCK inactivation in T cells is combined with an inactivation of TRAC genes rendering these double knock out (KO) T cells both resistant to drug such as clofarabine and less allogeneic. This double features is particularly useful for a therapeutic goal, allowing "off-the-shelf" allogeneic cells for immunotherapy in conjunction with chemotherapy to treat patients with cancer. This double KO inactivation dCK/TRAC can be performed simultaneously or sequentially. One example of TALE-nuclease dCK/TRAC pairs which gave success in the invention is described in PCT/EP2014/075317, in particular, the target sequences in the 2 loci (dCK and TRAC).

Another example of enzyme which can be inactivated is human hypoxanthine-guanine phosphoribosyl transferase (HPRT) gene (GenBank™: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Guanines analogs are metabolized by HPRT transferase that catalyzes addition of phosphoribosyl moiety and enables the formation of TGMP Guanine analogues including 6 mercapthopurine (6MP) and 6 thioguanine (6TG) are usually used as lymphodepleting drugs to treat leukemias. They are metabolized by HPRT (hypoxanthine phosphoribosyl transferase that catalyzes addition of phosphoribosyl moiety and enables formation TGMP. Their subsequent phosphorylations lead to the formation of their triphosphorylated forms that are eventually integrated into DNA. Once incorporated into DNA, thio GTP impairs fidelity of DNA replication via its thiolate groupment and generate random point mutation that are highly deleterious for cell integrity.

Thus, the present invention provides an anti-CLL1 scCAR expressing cell, in particular an anti-CLL1 scCAR expressing T cell wherein the scCAR has a polypeptide sequence according to SEQ ID NO.35 to 112 (optionally humanized) and wherein the dCK gene is inactivated.

In another embodiment, the inactivation of the CD3 normally expressed at the surface of the T-cell can confer resistance to anti-CD3 antibodies such as teplizumab.

Multiple Drug Resistance of Anti-CLL1 scCAR-Expressing Immune Cells

In another particular embodiment, the inventors sought to develop an "off-the shelf" immunotherapy strategy, using allogeneic T-cells, in particular allogenic anti-CLL1 scCAR expressing T-cell resistant to multiple drugs to mediate selection of engineered T-cells when the patient is treated with different drugs. The therapeutic efficiency can be significantly enhanced by genetically engineering multiple drug resistance allogeneic T-cells. Such a strategy can be particularly effective in treating tumors that respond to drug combinations that exhibit synergistic effects. Moreover multiple resistant engineered T-cells can expand and be selected using minimal dose of drug agents.

Thus, the method according to the present invention can comprise modifying T-cell to confer multiple drug resistance to said T-cell. Said multiple drug resistance can be conferred by either expressing more than one drug resistance gene or by inactivating more than one drug sensitizing gene. In another particular embodiment, the multiple drug resistance can be conferred to said T-cell by expressing at least one drug resistance gene and inactivating at least one drug sensitizing gene. In particular, the multiple drug resistance can be conferred to said T-cell by expressing at least one drug resistance gene such as mutant form of DHFR, mutant form of IMPDH2, mutant form of calcineurin, mutant form of MGMT, the ble gene, and the mcrA gene and inactivating at least one drug sensitizing gene such as HPRT gene. In a preferred embodiment, multiple drug resistance can be conferred by inactivating HPRT gene and expressing a mutant form of DHFR; or by inactivating HPRT gene and expressing a mutant form of IMPDH2; or by inactivating HPRT gene and expressing a mutant form of calcineurin; by inactivating HPRT gene and expressing a mutant form of MGMT; by inactivating HPRT gene and expressing the ble gene; by inactivating HPRT gene and expressing the mcrA gene.

In one embodiment, the present invention provides allogenic anti-CLL1 scCAR expressing T-cell expressing more than one drug resistance gene or wherein more than one drug sensitizing gene is inactivated.

Suicide Genes in Anti-CLL1 scCAR-Expressing Immune Cells

In some instances, since engineered T-cells can expand and persist for years after administration, it can be desirable to include a safety mechanism to allow selective deletion of administrated T-cells. Thus, in some embodiments, the method of the invention can comprises the transformation of said T-cells with a recombinant suicide gene. Said recombinant suicide gene is used to reduce the risk of direct toxicity and/or uncontrolled proliferation of said T-cells once administrated in a subject (Quintarelli C, Vera F, blood 2007; Tey S K, Dotti G., Rooney C M, boil blood marrow transplant 2007). Suicide genes enable selective deletion of transformed cells in vivo. In particular, the suicide gene has the ability to convert a non-toxic pro-drug into cytotoxic drug or to express the toxic gene expression product. In other words, "Suicide gene" is a nucleic acid coding for a product, wherein the product causes cell death by itself or in the presence of other compounds.

A representative example of such a suicide gene is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil. Suicide genes also include as non limiting examples caspase-9 or caspase-8 or cytosine deaminase. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deaminase.

One preferred suicide gene system employs a recombinant antigenic polypeptide comprising antigenic motif recognized by the anti-CD20 mAb Rituximab, especially QBen10, such as in the so-called RQR8 polypeptide described in WO2013153391, which is expressed independently from the anti-CLL1 CAR. Rituximab, an authorized antibody drug, can then be used for cell depletion when needed.

In one embodiment, the present invention provides allogenic anti-CLL1 scCAR expressing T-cell expressing more than one drug resistance gene or wherein more than one drug sensitizing gene is inactivated, and a suicide gene allowing said cells to be destroyed.

In particular, the present invention relates to an allogeneic T-cell, in particular an allogeneic anti-CLL1 scCAR expressing T-cell, and preferably an allogeneic anti-CLL1 scCAR expressing T-cell comprising a peptide having 80% to 100% identity with scfv from SC02-357, SC02-378, SCO2-161, M26, M31, G4, M22, M29, M2, M5, G12, 21.26 or 1075.7 antibodies, said allogeneic anti-CLL1 scCAR expressing T-cell comprising a peptide having 80% to 100% identity with scfv from SC02-357, SC02-378, SCO2-161, M26, M31, G4, M22, M29, M2, M5, G12, 21.26 and 1075.7 antibodies is more particularly resistant to a drug, and specifically suitable for immunotherapy.

The resistance of a drug can be conferred by inactivation of drug sensitizing genes or by expression of drug resistance genes. Some examples of drugs which suit to the invention are the purine nucleoside analogues (PNAs) such as clofarabine or fludarabine, or other drugs such as 6-Mercaptopurine (6MP) and 6 thio-guanine (6TG).

In one aspect, the present invention provides methods for engineering immune cells to make them resistant to purine nucleotide analogs (PNA), such a clorofarabine or fludarabine, so that they can be used in cancer immunotherapy treatments in patients pre-treated with these conventional chemotherapies.

The resistance to drugs can be conferred to the T-cells by inactivating one or more gene(s) responsible for the cell's sensitivity to the drug (drug sensitizing gene(s)), such as the dcK and/or HPRT genes.

According to another aspect, the resistance to drugs can be conferred to a T-cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell according to the invention.

For instance, CD52 and glucocorticoid receptors (GR), which are drug targets of Campath® (alemtuzumab) or rituximab and glucocorticoids treatments, can be inactivated to make the cells resistant to these treatments and give them a competitive advantage over patient's own T-cells not endowed with specific anti-CLL1 scCARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia.

Immune Checkpoints Engineered Cells

According to further aspect of the invention, the immune cells can be further manipulated to make them more active or limit exhaustion, by inactivating genes encoding proteins that act as "immune checkpoints" that act as regulators of T-cells activation, such as the following gene selected from CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, $IL_{10}RA$, IL10RB, HMOX2, IL6R, IL6ST, CSK, PAG1, SIT1, FOXP3, PRDM1 (orblimp1), BATF, GUCY1A2, GUCY1A3, GUCY1B2, GUCY1B3, preferably, said gene is PDCD1 or CTLA-4. Examples of genes, which expression could be reduced or suppressed are also indicated in Table 9.

The present invention also provides allogeneic T-cells expressing an anti-CLL1 scCAR, in particular an anti-CLL1, wherein at least one gene expressing one or more component of T-cell receptor (TCR) is inactivated and/or one gene selected from the genes CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, $IL_{10}RA$, $IL_{10}RB$, HMOX2, IL6R, IL6ST, CSK, PAG1, SIT1, FOXP3, PRDM1 (orblimp1), BATF, GUCY1A2, GUCY1A3, GUCY1B2, GUCY1B3, is inactivated as referred to in WO2014/184741.

In one embodiment said gene is a gene that acts as a regulator of T-cells activation coding the beta 2 microglobulin protein.

According to a further aspect of the invention, the anti-CLL1 scCAR-immune cells of the invention can be further manipulated to make them resistant to a drug, in particular to a drug used during chemotherapy against cancer, in particular a CLL1-expressing cell-mediated cancer such as AML. This can be achieved by introducing a gene conferring resistance to said drug. This same gene may be turned on and off by using a gene inducible inhibition/expression system as previously described (Garcia E L, Mills A A (2002) Getting around lethality with inducible Cre-mediated excision. Semin Cell Dev Biol 13:151-8, Lewandoski M (2001) Conditional control of gene expression in the mouse. Nat Rev Genet 2:743-55; Scharfenberger L, Hennerici T, Kirly G et al. (2014) Transgenic mouse technology in skin biology: Generation of complete or tissue-specific knockout mice. J Invest Dermatol 134:e16; Schwenk F, Kuhn R, Angrand P O et al. (1998) Temporally and spatially regulated somatic mutagenesis in mice. Nucleic Acids Res 26:1427-32

Thus, anti-CLL1 scCAR-expressing, drug resistant immune cell, wherein (i) at least one gene expressing one or more component of T-cell receptor (TCR) is inactivated (ii) at least one gene conferring resistance to a drug is incorporated or a gene conferring sensitivity to said drug is deleted or mutated to be inactivated (iii) optionally another gene selected from the gene disclosed in the following table 9 is inactivated—is an object of the present invention.

The present invention encompasses the isolated anti-CLL1 scCAR-immune cells or cell lines obtainable by the method of the invention, more particularly isolated cells comprising any of the proteins, polypeptides, allelic variants, altered or deleted genes or vectors described herein.

The immune cells of the present invention or cell lines can further comprise exogenous recombinant polynucleotides, in particular scCARs or suicide genes or they can comprise altered or deleted genes coding for checkpoint proteins or ligands thereof that contribute to their efficiency as a therapeutic product, ideally as an "off the shelf" product. In another aspect, the present invention concerns the method for treating or preventing cancer in the patient by administrating at least once an engineered immune cell obtainable by the above methods.

TABLE 9

List of genes encoding immune checkpoint proteins.

| | Pathway | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |

TABLE 9-continued

List of genes encoding immune checkpoint proteins.

| Pathway | | Genes that can be inactivated In the pathway |
|---|---|---|
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

CLL1+/luc+ Drug Resistant Daudi Cells for Testing the Cytotoxicity of Drug Resistant Allogenic scCAR T Cells The present invention encompasses also a method for manufacturing target cells which express both a surface receptor specific to the scCAR T cells and a resistance gene. These target cells are particularly useful for testing the cytotoxicity of scCAR T cells. These cells are readily resistant to clinically relevant dose of clofarabine and harbor luciferase activity. This combination of features enable traking them in vivo in a mice model or destroy them when required.

More particularly, they can be used to assess the cytotoxicity properties drug resistant T cells in mice in the presence of clofarabine or other PNAs. Clofarabine resistant Daudi cells mimick the physiological state of acute myeloma leukemia (AML) patients relapsing form induction therapy, that harbor drug resistant B cell malignancies. Thus, these cells are of great interest to evaluate the reliability and cytotoxicity of drug resistant scCAR T cells. Preferably, these target cells are CLL1+ Luciferase+ Daudi cells.

Insertion of at least one epitope in the extracellular domain of the anti-CLL1-single chain CAR An anti-CLL1 CAR of the invention may include at least the insertion of at least one epitope in the extracellular domain of said CAR. This is intended to tempatively deplete the immune cells endowed with the CAR in the event of in vivo adverse effects such as a cytokine storm. Moreover, such insertion of epitope or "epitope-tagging" may be useful to sort or purify the engineered immune cells in-vitro during their manufacturing process Said at least one epitope may be any antigenic peptide which is enough immunogenic to be bound by a specific antibody recognizing such peptide. For instance, this can be obtained, for instance, by inserting at least one, and preferably two copies of a CD20 mimotope, preferably of sequence CPYSNPSLCS (SEQ ID NO.113), into the CAR polypeptide sequence. For purpose of simplication hereafter, the order of the scFvs from the N terminal end to the C terminal end is presented as follows: the VH chain and then the VL chain. However, it can be envisioned in the scope of the present invention that this order is inversed: VL chain and then the VL chain.

Figure 3A:
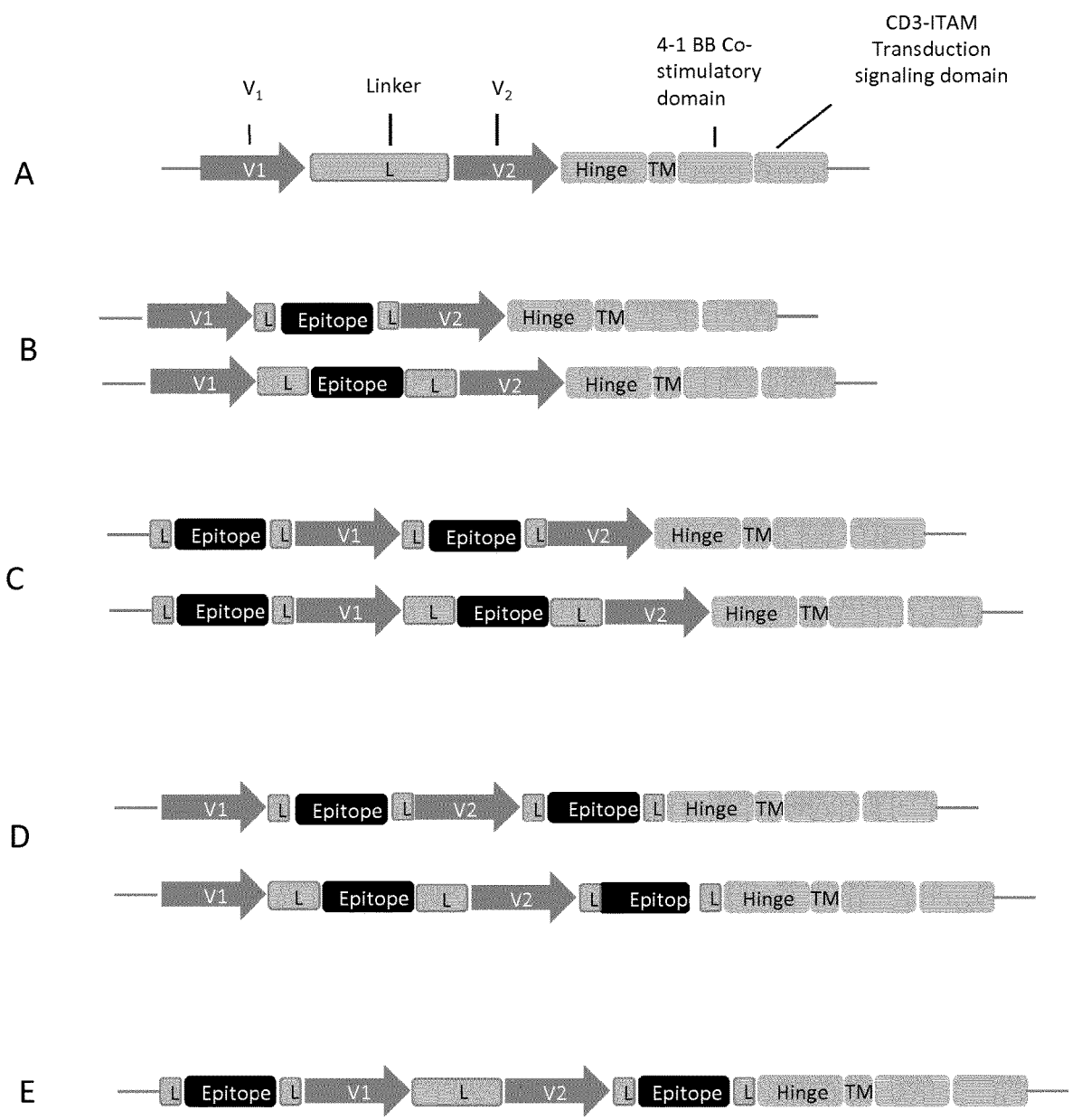
FIG. 3A and FIG. 3B: Schematic representation of exemplary CLL1 specific CARs according to the invention involving different mAb-epitope tagging for T cell depletion, especially CD20 mimotope(s), which are designed to mitigate possible side effects associated with CAR positive cells injection.
Figure 3B:
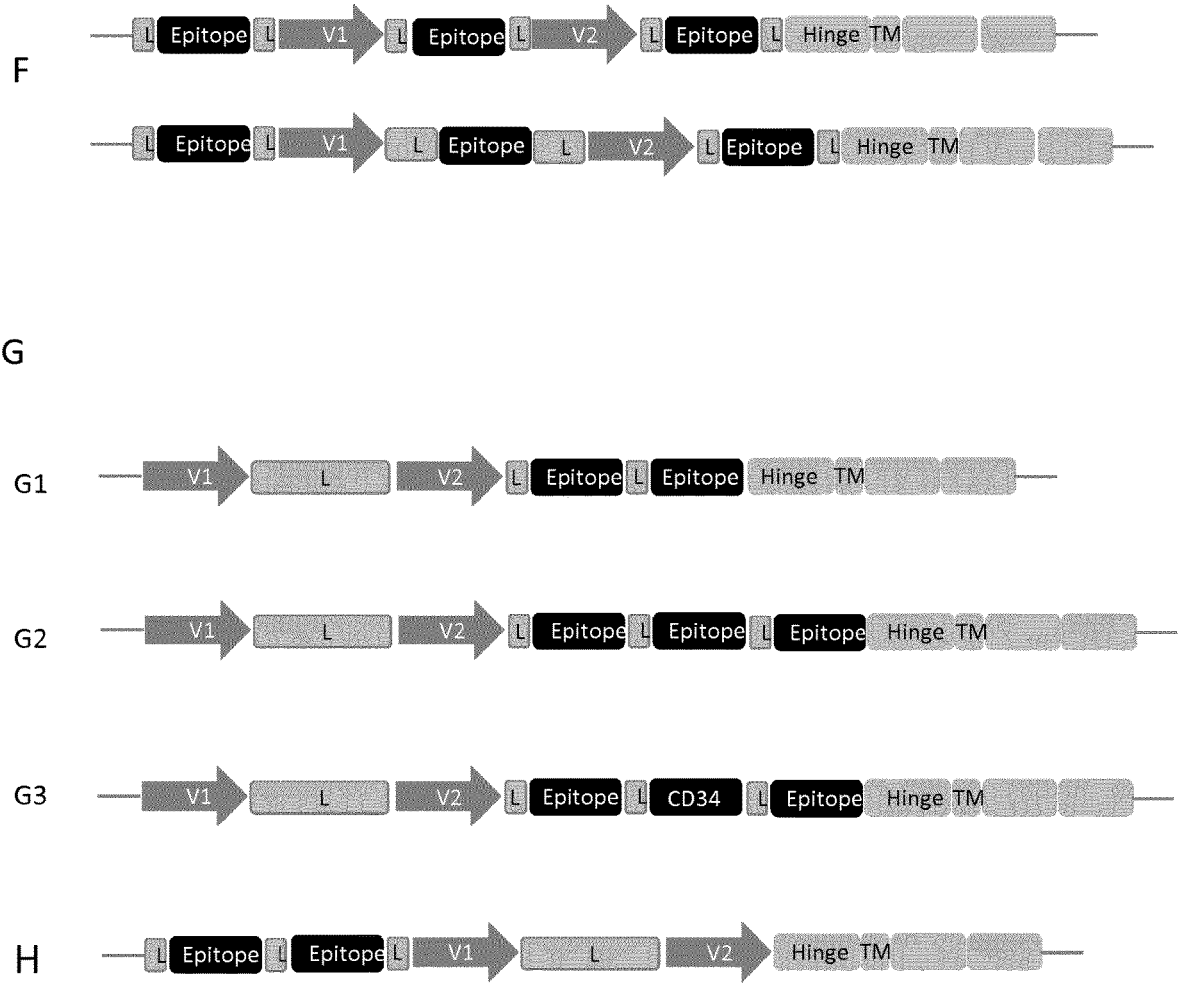

Different positions of the at least one CD20 mimotope within the anti-CLL1 CAR of the invention are schematized in FIG. 3. Said two copies of a CD20 mimotope can be linked to each other and also to the $V_L$ by a linker. They can also be inserted between the anti-CLL1 scFv and the hinge (such as CD8alpha), by using an optional linker. The CD20 mimotopes can be bound by anti-CD20 antibodies, such as Rituximab (McLaughlin P, et al. 1998).

Accordingly, the anti-CLL1 CAR of the present invention may comprise VH and a VL chains which are able to bind to CLL1 cell surface antigen, optionally humanized, a linker L, a suicide domain, a hinge or part of it, a transmembrane domain, a co-stimulatory domain and a stimulatory domain.

According to another embodiment, the epitope is a mimotope. As a macromolecule, often a peptide, which mimics the structure of an epitope, the mimotope has the advantage to be smaller than conventional epitope, and therefore may be beneficial for a non-conformational sequence and easier to reproduce in a long polypeptide such a CAR. Mimotopes are known for several pharmaceutically-approved mAb such as two 10 amino acid peptides for cetuximab (Riemer et al., 2005), or a 24 aa for palivizumab (Arbiza et al, 1992). As these mimotopes can be identified by phage display, it is possible to try several of them in order to obtain a sequence which does not perturb the scFv for the same mAb. Furthermore, their use can enhance a complement-dependent-cytotoxicity (CDC).

Several examples of such epitopes and mimotopes with their corresponding binding mAb are presented in the following Table 10.

TABLE 10

Mimotopes and epitope with their corresponding mAb

Rituximab

| Mimotope | SEQ ID NO 113 | CPYSNPSLC |

Palivizumab

| Epitope | SEQ ID NO 191 | NSELLSLINDMPITNDQKKLMSNN |

Cetuximab

| Mimotope 1 | SEQ ID NO 192 | CQFDLSTRRLKC |
| Mimotope 2 | SEQ ID NO 193 | CQYNLSSRALKC |
| Mimotope 3 | SEQ ID NO 194 | CVWQRWQKSYVC |
| Mimotope 4 | SEQ ID NO 195 | CMWDRFSRWYKC |

TABLE 10 -continued

Mimotopes and epitope with their corresponding mAb

Nivolumab

Epitope A  SEQ ID NO 196 SFVLNWYRMSPSNQTDKLAAFPEDR
Epitope B  SEQ ID NO 197 SGTYLCGAISLAPKAQIKE In a preferred embodiment, the epitope introduced within the chimeric scFv is the CD20 mimotope (SEQ ID NO.113) and the infused mAb presenting an affinity to this mimotope—for sorting and/or depletion purpose(s)—is rituximab.

In one embodiment, said at least one epitope is inserted between the VH and VL chains of the anti-CLL1.1 CAR, optionally linked to said VH and VL chains by one linker.

In some embodiment, the term "linker" as used in the context of a scFv refers to a peptide linker that consists of amino acids such as glycine and/or serine residues used alone or in combination, to link variable heavy and variable light chain regions together. In one embodiment, the flexible polypeptide linker is a Glycine/Serine linker and comprises the amino acid sequence (Gly-Gly-Gly-Ser)$_n$ or (Gly-Gly-Gly-Gly-Ser)$_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, (Gly$_4$Ser)$_4$ or (Gly$_4$Ser)$_3$. In another embodiment, the linkers include multiple repeats of (Gly$_x$Ser)$_n$, where x=1, 2, 3, 4 or 5 and n is 1, 2, 3, 4, 5, 6, 7, 8, 9 or 10, such as multiple repeat of (GlySer), (Gly$_2$Ser) or (Gly$_5$Ser). Also included within the scope of the invention are linkers described in WO2012/138475, incorporated herein by reference.

In a preferred embodiment, said CLL1 specific chimeric antigen receptor (anti-CLL1 CAR) has one of the polypeptide structure selected from V1, V3 or V5, as illustrated in FIG. 2, wherein one CD20 mimotope is inserted between the VH and VL chains of the anti-CLL1.1 CAR, optionally linked to said VH and VL chains by one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein one CD20 mimotope is inserted between the VH and VL chains of the anti-CLL1.1 CAR, optionally linked to said VH and VL chains by one linker.

In another embodiment, said at least one epitope is inserted at the N terminal end of the CAR—so upfront of the scFvs—, optionally linked to the VH chain and to the N terminal end of the CAR by one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein one epitope is inserted at the N terminal end of the CAR—so upfront of the scFvs—, optionally linked to the VH chain and to the N terminal end of the CAR by one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein one epitope is inserted at the N terminal end of the CAR—so upfront of the scFvs—, optionally linked to the VH chain and to the N terminal end of the CAR by one linker.

In another embodiment, said at least one epitope is inserted between the scFvs and the hinge of the CAR, optionally linked to the VL chain and to the hinge by one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein one epitope is inserted between the scFvs and the hinge of the CAR, optionally linked to the VL chain and to the hinge by one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein one epitope is inserted between the scFvs and the hinge of the CAR, optionally linked to the VL chain and to the hinge by one linker.

In a preferred embodiment, at least two epitopes are inserted in the extracellular domain of the anti-CLL1 CAR of the present invention.

In an embodiment, CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and two CD20 mimotopes, said extra-binding domain comprising VH and VL chains directed against CLL1 and a FcγRIIIα or Cd8α or IgG1 hinge;

wherein said 2 epitopes being inserted in tandem between the scFvs and said hinge, and optionally a linker (SEQ ID NO.10) being interspaced between the 2 epitopes and/or between the VH and the 2 epitopes.

In an embodiment, CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and two CD20 mimotopes, said extra-binding domain comprising VH and VL chains directed against CLL1 and a FcγRIIIα or Cd8α or IgG1 hinge;

wherein said 2 epitopes being inserted in tandem upfront the scFvs i.e. at the N terminal end of the CARand optionally, a linker (SEQ ID NO.10) being interspaced between the 2 epitopes and/or at the N terminal end of the CAR.

According to one embodiment, at least two epitopes are inserted in the extracellular domain in such a way that the VH is located between them, all these components being optionally interspaced by at least one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VH is located between them, all these components being optionally interspaced by at least one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VL is located between them, all these components being optionally interspaced by at least one linker.

According to another embodiment, two epitopes are inserted in the extracellular domain in such a way that the VL is located between them, all these components being optionally interspaced by at least one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VL is located between them, all these components being optionally interspaced by at least one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VL is located between them, all these components being optionally interspaced by at least one linker.

According to another embodiment, said CLL1 specific chimeric antigen receptor (anti-CLL1 CAR) comprises an extracellular binding domain wherein at least two epitopes are inserted in the extracellular domain in such a way that the VH and VL chains ar located between them, all these components being optionally interspaced by at least one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VH and VL chains ar located between them, all these components being optionally interspaced by at least one linker.

In a more preferred embodiment, said CLL1 specific chimeric antigen receptor (anti-CLL1 CAR) has one of the polypeptide structure of version V3 as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein two epitopes are inserted in the extracellular domain in such a way that the VH and VL chains ar located between them, all these components being optionally interspaced by at least one linker.

In another embodiment, three epitopes are inserted in the extracellular domain of the anti-CLL1 CAR of the present invention.

According to a particular embodiment, said CLL1 specific CAR of the invention contains an extracellular binding domain wherein three epitopes are inserted in the extracellular domain in such a way that the VH and VL chains ar located between them, all these components being optionally interspaced by at least one linker.

In a preferred embodiment, said CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and wherein three epitopes are inserted in the extracellular domain in such a way that the VH and VL chains ar located between them, all these components being optionally interspaced by at least one linker.

In a more preferred embodiment, said CLL1 specific chimeric antigen receptor (anti-CLL1 CAR) has one of the polypeptide structure of version V3 as illustrated in FIG. 2, said structure comprising at least an extracellular ligand binding-domain anti-CLL1, Cd8α transmembrane domain, 4-1BB co-stimulatory domain, CD3 zeta signaling domain, and wherein three epitopes are inserted in the extracellular domain in such a way that the VH and VL chains ar located between them, all these components being optionally interspaced by at least one linker.

In another embodiment, CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, and three CD20 epitopes, said extra-binding domain comprising VH and VL chains directed against CLL1 and a FcγRIIIα or Cd8α or IgG1 hinge;

wherein said 3 epitopes being inserted in tandem between the scFvs and said hinge, and optionally a linker (SEQ ID NO.10) being interspaced between the 3 epitopes and/or between the VH and the 3 epitopes.

In another embodiment, CLL1 specific chimeric antigen receptor (anti-CLL1 CAR) has one of the polypeptide structure selected from V1, V3 or V5, as illustrated in FIG. 2, said structure comprising at least an anti-CLL1 extra cellular ligand binding-domain, Cd8α transmembrane domain, 4-1BB co-stimulatory domain, CD3 zeta signaling domain, two CD20 epitopes, and one CD34 epitope;

said extra-binding domain comprising VH and VL chains directed against CLL1 and a FcγRIIIα or Cd8α or IgG1 hinge;

said 2 epitopes being inserted in tandem between the scFvs and said hinge, and said CD34 epitope being inserted between the said 2 CD20 epitopes, all components being interspaced between them by a linker (SEQ ID NO.10) and a linker between the epitope and and between the VH and the 3 epitopes.

In all the above embodiments relating to the epitope-containing anti-CLL1 CARs, the VH and VL chains which are used as extracellular binding domain are binding preferably to human membrane CLL1-1.

In a preferred embodiment, said above anti-CLL1 CARs comprising at least an extra cellular ligand binding-domain including VH and VL chains derived from anti-CLL1 monoclonal antibodies.

More specifically, the epitopes can be included into the CAR of the present invention such as follows:

In some embodiments, the extracellular binding domain comprises at least 1, 2, 3, 4, 5, 6, 7, 8, 9 or 10 mAb-specific epitopes.

In some embodiments, the extracellular binding domain comprises at least 1, 2 or 3 mAb-specific epitopes.

In some embodiments, when the extracellular binding domain comprises several mAb-specific epitopes, all the mAb-specific epitopes are identical.

In some embodiments, when the extracellular binding domain comprises several mAb-specific epitopes, the mAb-specific epitopes are not identical. For example, the extracellular binding domain can comprises three mAb-specific epitopes, two of them being identical and the third one being different.

In some embodiments, the extracellular binding domain comprises a VH, a VL, one or more mAb-specific epitopes, preferably 1, 2 or 3, more preferably 2 or 3 mAb-specific epitopes.

In some embodiments, the extracellular binding domain comprises the following sequence (Nterm is located on the left hand side):

$V_1$-$L_1$-$V_2$-$(L)_x$-Epitope1-$(L)_x$;
$V_1$-$L_1$-$V_2$-$(L)_x$-Epitope1-$(L)_x$-Epitope2-$(L)_x$;
$V_1$-$L_1$-$V_2$-$(L)_x$-Epitope1-$(L)_x$-Epitope2-$(L)_x$-Epitope3-$(L)_x$;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$;
$(L)_x$-Epitope1-$(L)_x$-Epitope2-$(L)_x$-$V_1$-$L_1$-$V_2$-$(L)_x$-Epitope3-$(L)_x$;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$;
$(L)_x$-Epitope1-$(L)_x$-$V_1$-$(L)_x$-Epitope2-$(L)_x$-$V_2$-$(L)_x$-Epitope3-$(L)_x$;
$V_1$-$L_1$-$V_2$-L-Epitope1;
$V_1$-$L_1$-$V_2$-L-Epitope1-L;
$V_1$-$L_1$-$V_2$-L-Epitope1-L-Epitope2;
$V_1$-$L_1$-$V_2$-L-Epitope1-L-Epitope2-L;
$V_1$-$L_1$-$V_2$-L-Epitope1-L-Epitope2-L-Epitope3;
$V_1$-$L_1$-$V_2$-L-Epitope1-L-Epitope2-L-Epitope3-L;
$V_1$-$L_1$-$V_2$-Epitope1;
$V_1$-$L_1$-$V_2$-Epitope1-L;
$V_1$-$L_1$-$V_2$-Epitope1-L-Epitope2;
$V_1$-$L_1$-$V_2$-Epitope1-L-Epitope2-L;
$V_1$-$L_1$-$V_2$-Epitope1-L-Epitope2-L-Epitope3;
$V_1$-$L_1$-$V_2$-Epitope1-L-Epitope2-L-Epitope3-L;
Epitope1-$V_1$-$L_1$-$V_2$;
Epitope1-L-$V_1$-$L_1$-$V_2$;
L-Epitope1-$V_1$-$L_1$-$V_2$;
L-Epitope1-L-$V_1$-$L_1$-$V_2$;
Epitope1-L-Epitope2-$V_1$-$L_1$-$V_2$;
Epitope1-L-Epitope2-L-$V_1$-$L_1$-$V_2$;
L-Epitope1-L-Epitope2-$V_1$-$L_1$-$V_2$;
L-Epitope1-L-Epitope2-L-$V_1$-$L_1$-$V_2$;
Epitope1-L-Epitope2-L-Epitope3-$V_1$-$L_1$-$V_2$;
Epitope1-L-Epitope2-L-Epitope3-L-$V_1$-$L_1$-$V_2$;
L-Epitope1-L-Epitope2-L-Epitope3-$V_1$-$L_1$-$V_2$;
L-Epitope1-L-Epitope2-L-Epitope3-L-$V_1$-$L_1$-$V_2$;
$V_1$-L-Epitope1-L-$V_2$;
L-Epitope1-L-$V_1$-L-Epitope2-L-$V_2$;
$V_1$-L-Epitope1-L-$V_2$-L-Epitope2-L;
$V_1$-L-Epitope1-L-$V_2$-L-Epitope2-L-Epitope3;
$V_1$-L-Epitope1-L-$V_2$-L-Epitope2-Epitope3;
$V_1$-L-Epitope1-L-$V_2$-L-Epitope2-L-Epitope3-Epitope4;
L-Epitope1-L-$V_1$-L-Epitope2-L-$V_2$-L-Epitope3-L;
Epitope1-L-$V_1$-L-Epitope2-L-$V_2$-L-Epitope3-L;
L-Epitope1-L-$V_1$-L-Epitope2-L-$V_2$-L-Epitope3;
L-Epitope1-L-$V_1$-$L_1$-$V_2$-L-Epitope2-L;
L-Epitope1-L-$V_1$-$L_1$-$V_2$-L-Epitope2-L-Epitope3;
L-Epitope1-L-$V_1$-$L_1$-$V_2$-L-Epitope2-Epitope3, or,
Epitope1-L-$V_1$-$L_1$-$V_2$-L-Epitope2-L-Epitope3-Epitope 4.
wherein, $V_1$ and $V_2$ are $V_H$ and $V_L$ of an ScFv (i.e., $V_1$ is $V_L$ and $V_2$ is $V_H$ or $V_1$ is $V_H$ and $V_2$ is $V_L$);

$L_1$ is any linker suitable to link the VH chain to the VL chain in an ScFv;

L is a linker, preferably comprising glycine and serine residues, and each occurrence of L in the extracellular binding domain can be identical or different to other occurrence of L in the same extracellular binding domain, and, x is 0 or 1 and each occurrence of x is independently from the others; and, epitope 1, epitope 2 and epitope 3 are mAb-specific epitopes and can be identical or different.

In some embodiments, the extracellular binding domain comprises the following sequence (Nterm is located on the left hand side):

$V_H$-$L_1$-$V_L$-L-Epitope1-L-Epitope2-L;
L-Epitope1-L-$V_H$-L-Epitope2-L-$V_L$-L-Epitope3-L;
$V_L$-$L^1$-$V_H$-L-Epitope1-L-Epitope2-L; or,
L-Epitope1-L-$V_L$-L-Epitope2-L-$V_H$-L-Epitope3-L.
wherein L, L1, epitope 1, epitope 2 and epitope 3 are as defined above.

In some embodiments, $L_1$ is a linker comprising Glycine and/or Serine. In some embodiment, $L_1$ is a linker comprising the amino acid sequence (Gly-Gly-Gly-Ser)$_n$ or (Gly-Gly-Gly-Gly-Ser)$_n$, where n is 1, 2, 3, 4 or 5. In some embodiments $L_1$ is (Gly$_4$Ser)$_4$ or (Gly4Ser)$_3$.

In some embodiment, L is a flexible linker, preferably comprising Glycine and/or Serine. In some embodiments, L has an amino acid sequence selected from SGG, GGS, SGGS (SEQ ID NO. 200), SSGGS (SEQ ID NO. 201), GGGG (SEQ ID NO. 202), SGGGG (SEQ ID NO. 203), GGGGS (SEQ ID NO. 204), SGGGGS (SEQ ID NO. 205), GGGGGS (SEQ ID NO. 206), SGGGGGS (SEQ ID NO. 207), SGGGGG (SEQ ID NO. 208), GSGGGGS (SEQ ID NO. 209), GGGGGGGS (SEQ ID NO. 210), SGGGGGGG (SEQ ID NO. 211), SGGGGGGGS (SEQ ID NO. 212), or SGGGGSGGGGS (SEQ ID NO. 213) preferably SGG, SGGS (SEQ ID NO. 200), SSGGS (SEQ ID NO. 201), GGGG (SEQ ID NO. 202), SGGGGS (SEQ ID NO. 205), SGGGGGS (SEQ ID NO. 207), SGGGGG (SEQ ID NO. 208), GSGGGGS (SEQ ID NO. 209), or SGGGGSGGGGS (SEQ ID NO. 213). In some embodiment, when the extracellular binding domain comprises several occurrences of L, all the Ls are identical. In some embodiments, when the extracellular binding domain comprises several occurrences of L, the Ls are not all identical. In some embodiments, L is SGGGGS (SEQ ID NO. 205). In some embodiments, the extracellular binding domain comprises several occurrences of L and all the Ls are SGGGGS (SEQ ID NO. 205).

In some embodiments, Epitope 1, Epitope 2 and Epitope 3 are identical or different and are selected from mAb-specific epitopes having an amino acid sequence of anyone of SEQ ID NO 33 to SEQ ID NO 42.

In some embodiments, Epitope 1, Epitope 2 and Epitope 3 are identical or different and are selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, alemtuzumab or ustekinumab.

In some embodiment, Epitope 1 is an mAb-specific epitope having an amino acid sequence of SEQ ID NO 33.

In some embodiments, Epitope 2 is an mAb-specific epitope having an amino acid sequence of SEQ ID NO 35.

In some embodiments, Epitope 3 is an mAb-specific epitope having an amino acid sequence of SEQ ID NO 36.

In some embodiments, Epitope 4 is an mAb-specific epitope having an amino acid sequence of SEQ ID NO 37.

In some embodiment, Epitope 4 is an mAb-specific epitope having an amino acid sequence of SEQ ID NO 38.

In some embodiment, Epitope 2 is an mAb-specific epitope having an amino acid sequence of SEQ ID NO 33 and Epitope 3 is an mAb-specific epitope having an amino acid sequence of SEQ ID NO 41 or 42.

In some embodiment, one of Epitope 1, Epitope 2, Epitope 3 and Epitope 4 is a CD34 epitope, preferably an epitope of SEQ ID 41 or 42. In some embodiment, one of Epitope1, Epitope 2, Epitope 3 and Epitope 4 is a CD34 epitope, preferably an epitope of SEQ ID 41 or 42 and the other mAb specific epitopes are CD20 mimotopes, preferably mimotope of SEQ ID NO 33.

Method for Depleting CAR-Expressing Immune Cells

The immune cells expressing the CLL1 sepcific CAR according to the present invention may comprise epitope(s) in their extracellular domain such as described above, so that they can be depleted in a patient in the event of adverse or too acute immune response (e.g. cytokine storm) by administering to said patient an antibody-preferably monoclonal-specific to said epitope (s).

By "in vivo depletion" is meant in the present invention the administration of a treatment to a mammalian organism aiming to stop the proliferation of CAR-expressing immune cells by inhibition or elimination.

One aspect of the invention is related to a method for in vivo depleting an engineered immune cell expressing a CAR comprising an m-Ab specific epitope as previously described, comprising contacting said engineered immune cell or said CAR-expressing immune cell with at least one epitope-specific mAbs. Another aspect of the invention relates to a method for in vivo depleting immune CAR-expressing immune cell which comprises the above chimeric scFv (formed by insertion of a mAb-specific epitope) by contacting said engineered immune cell with epitope-specific antibodies.

Preferably, said immune cells are T-cells and/or the antibodies are monoclonal.

According to one embodiment, the in vivo depletion of immune engineered cell is performed on engineered immune cell which has been previously sorted using the in vitro method of the present invention. In this case, this will be the same infused mAb used.

According to a preferred embodiment, the mAb-specific antigen is CD20 antigen and the epitope-specific mAb is rituximab.

In some embodiments, the invention relates to a method for in vivo depleting an engineered immune cell expressing a CAR comprising an mAb-specific epitope (CAR-expressing immune cell) as previously described, in a patient comprising contacting said CAR-expressing immune cell with at least one epitope-specific mAbs.

In some embodiment, said mAb-specific epitope is a CD20 epitope or mimotope, preferably SEQ ID NO 35 and the epitope-specific mAbs is rituximab.

In some embodiments, the step of contacting said engineered immune cell or said CAR-expressing immune cell with at least one epitope-specific mAb comprises infusing the patient with epitope-specific mAb, preferably rituximab.

In some embodiment, when immune cells expressing a CAR comprising an mAb-specific epitope (CAR-expressing immune cells) are depleted in a CDC assay using epitope specific mAb, the amount of viable CAR-expressing immune cells decreases, preferably by at least 10%, 20%, 30%, 40%, 50%, 60%, 70%, 80% or 90%. Preferably the CDC assay is the assay disclosed in Example 3, Example 4 or Example 7.4. In some embodiment, said mAb-specific epitope is a CD20 epitope or mimotope, preferably SEQ ID NO 35 and the epitope-specific mAbs is rituximab.

Besides the possibility of in-vivo depleting the immune cells according to the invention, the epitopes inserted into the extracellular domain of the CARs may be useful to the steps of sorting or purifying the immune cells expressing said CARs, as part of the method for producing them.

Isolated Cells

The resulting cells are engineered immune cell expressing at the cell surface membrane a CLL1 specific chimeric antigen receptor as previously described, in particular engineered immune cells derived from primary T-lymphocytes, optionally resistant to an anti-cancer drug, and bearing a deletion in a gene coding for an alpha TCR or a beta TCR.

The present invention discloses an engineered immune cell as above, wherein expression of TCR is suppressed.

The present invention discloses an engineered immune cell as above, wherein expression of at least one MHC protein, preferably β2m or HLA, is reduced or suppressed in said engineered immune cell. β2m stands for beta 2 microglobulin and HLA for human leukocyte antigen. The MHC protein is a MHC protein of Class I or of class II.

The present invention discloses an engineered immune cell as above, wherein said engineered immune cell is mutated to confer resistance to at least one immune suppressive drug, chemotherapy drug, or anti-cancer drug.

The present invention discloses an engineered immune cell as above for use in therapy.

The present invention discloses an engineered immune cell for use in therapy as above, wherein the patient is a human.

The present invention discloses an engineered immune cell for use in therapy as above, wherein the condition is a pre-malignant or malignant cancer condition characterized by CLL1-expressing cells.

The present invention discloses an engineered immune cell for use in therapy as above, wherein the condition is a condition which is characterized by an overabundance of CLL1-expressing cells.

The present invention discloses an engineered immune cell for use in therapy as above, wherein the malignant cancer condition is a hematological cancer condition.

The present invention discloses an engineered immune cell for use in therapy as above, wherein the hematological cancer condition is leukemia or malignant lymphoproliferative disorders.

The present invention discloses an engineered immune cell for use in therapy as above, wherein said leukemia is selected from the group consisting of acute myelogenous leukemia, chronic myelogenous leukemia, myelodysplastic syndrome, acute lymphoid leukemia, chronic lymphoid leukemia, and myelodysplastic syndrome.

The present invention discloses an engineered immune cell for use in therapy as above, wherein the leukemia is acute myelogenous leukemia (AML).

The present invention discloses an engineered immune cell for use in therapy as above, wherein said hematologic cancer is a malignant lymphoproliferative disorder.

The present invention discloses an engineered immune cell for use in therapy as above, wherein said malignant lymphoproliferative disorder is lymphoma.

The present invention discloses an engineered immune cell for use in therapy as above, wherein said lymphoma is selected from the group consisting of multiple myeloma, non-Hodgkin's lymphoma, Burkitt's lymphoma, and follicular lymphoma (small cell and large cell).

The present invention discloses a method of impairing a hematologic cancer cell comprising contacting said hematologic cancer cell with an engineered cell, which at least expresses anti-CLL1 CAR such as exposed above, in an amount effective to cause impairment of said cancer cell.

The present invention thus discloses a method of engineering an immune cell comprising:
(a) Providing an immune cell,
(b) Expressing at the surface of said cell at least one CLL1 single-chain specific chimeric antigen receptor such as previously exposed.

The present invention discloses a method of engineering an immune cell as above comprising:
(a) Providing an immune cell,
(b) Introducing into said cell at least one polynucleotide encoding said CLL1 single-chain specific chimeric antigen receptor,
(c) Expressing said polynucleotide into said cell.

The present invention discloses a method of engineering an immune cell as above comprising:
(a) Providing an immune cell,
(b) Introducing into said cell at least one polynucleotide encoding said CLL1 single-chain specific chimeric antigen receptor,
(c) Introducing at least one other chimeric antigen receptor which is not specific for CLL1.

The present invention discloses a method of treating a subject in need thereof comprising:
(a) Providing an immune cell expressing at the surface a CLL1 single-chain specific chimeric antigen receptor such as exposed above.
(b) Administrating said immune cells to said patient.

The present invention discloses a method of treating a subject in need thereof as above, wherein said immune cell is provided from a donor.

The present invention discloses a method of treating a subject in need thereof as above, wherein said immune cell is provided from the patient himself.

Therapeutic Applications

In another embodiment, isolated cell obtained by the different methods or cell line derived from said isolated cell as previously described can be used as a medicament.

In another embodiment, said medicament can be used for treating cancer, particularly for the treatment of leukemia in a patient in need thereof.

In another embodiment, said isolated cell according to the invention or cell line derived from said isolated cell can be used in the manufacture of a medicament for treatment of a cancer in a patient in need thereof.

In a particular embodiment, an anti-CLL1 CAR expressing T cell is provided as a medicament for the treatment of AML, of an AML subtype, of an AML-related complication, of an AML-related condition.

In another embodiment, said medicament can be used for treating a CLL1-expressing cell-mediated pathological condition or a condition characterized by the direct or indirect activity of a CLL1-expressing cell.

In another aspect, the present invention relies on methods for treating patients in need thereof, said method comprising at least one of the following steps:
(a) providing an immune-cell obtainable by any one of the methods previously described;
(b) Administrating said transformed immune cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed wherein a pre-malignant or malignant cancer condition characterized by CLL1-expressing cells, especially by an overabundance of CLL1-expressing cells. Such conditions are found in hematologic cancers, such as leukemia.

In one embodiment, the present invention provides a composition for its use in the treatment of a CLL1 expressing cells-mediated disease, in particular a CLL1 expressing cells—mediated hematologic cancer, said composition comprising said anti-CLL1 scCAR expressing T cell of the invention.

Any other CLL1-mediating or CLL1-involving malignant lymphoproliferative disorders disclosed herein may be improved with the anti-CLL1 CAR-expressing cells of the present invention.

In a preferred embodiment, the cancer that may be treated using the anti-CLL1 CAR-expressing cells of the present invention is leukemia, a disease associated to leukemia or a complication thereof.

Leukemias that can be treated using the anti-CLL1 CAR-expressing cells of the present invention can be acute myelogenous leukemia (AML). AML or AML subtypes that may be treated using the anti-CLL1 scCAR-expressing cells of the present invention may be in particular, acute myeloblastic leukemia, minimally differentiated acute myeloblastic leukemia, acute myeloblastic leukemia without maturation, acute myeloblastic leukemia with granulocytic maturation, promyelocytic or acute promyelocytic leukemia (APL), acute myelomonocytic leukemia, myelomonocytic together with bone marrow eosinophilia, acute monoblastic leukemia (M5a) or acute monocytic leukemia (M5b), acute erythroid leukemias, including erythroleukemia (M6a) and very rare pure erythroid leukemia (M6b), acute megakaryoblastic leukemia, acute basophilic leukemia, acute panmyelosis with myelofibrosis, whether involving CLL1-positive cells.

Subtypes of AML also include, hairy cell leukemia, philadelphia chromosome-positive acute lymphoblastic leukemia. AML may be classified as AML with specific genetic abnormalities. Classification is based on the ability of karyotype to predict response to induction therapy, relapse risk, survival.

Accordingly, AML that may be treated using the anti-CLL1 CAR-expressing cells of the present invention may be AML with a translocation between chromosomes 8 and 21, AML with a translocation or inversion in chromosome 16, AML with a translocation between chromosomes 9 and 11, APL (M3) with a translocation between chromosomes 15 and 17, AML with a translocation between chromosomes 6 and 9, AML with a translocation or inversion in chromosome 3, AML (megakaryoblastic) with a translocation between chromosomes 1 and 22.

The present invention is particularly useful for the treatment of AML associated with these particular cytogenetic markers.

The present invention also provides an anti-CLL1 CAR expressing T cell for the treatment of patients with specific cytogenetic subsets of AML, such as patients with t(15;17)(q22;q21) identified using all-trans retinoic acid (ATRA)16-19 and for the treatment of patients with t(8;21)(q22;q22) or inv(16)(p13q22)/t(16;16)(p13;q22) identified using repetitive doses of high-dose cytarabine.

Preferably, the present invention provides an anti-CLL1 CAR expressing T cell for the treatment of patients with aberrations, such as −5/del(5q), −7, abnormalities of 3q, or a complex karyotype, who have been shown to have inferior complete remission rates and survival.

The terms "therapeutic agent", "chemotherapeutic agent", or "drug" or "anti-cancer drug" as used herein refers to a medicament, preferably a compound or a derivative thereof that can interact with a cancer cell, thereby reducing the proliferative status of the cell and/or killing the cell. Examples of chemotherapeutic agents or "anti-cancer drug" include, but are not limited to, alkylating agents (e.g., busulfan, carboplatine, chlorambucil, cisplatine, cyclophosphamide, ifosfamide, melphalan, mechlorethamine, oxaliplatine, uramustine, temozolomide, fotemustine), metabolic antagonists (e.g., purine nucleoside antimetabolite such as clofarabine, fludarabine or T-deoxyadenosine, methotrexate (MTX), 5-fluorouracil or derivatives thereof, azathioprine, capecitabine, cytarabine, floxuridine, fluorouracile, gemcitabine, methotrexate, pemetrexed), antitumor antibiotics (e.g., mitomycin, adriamycin, bleomycine, daunorubicine, doxorubicine, epirubicine, hydroxyurea, idarubicine, mitomycin C, mitoxantrone), plant-derived antitumor agents (e.g., vincristine, vindesine, TAXOL™, vinblastine, vinorelbine, docetaxel, paclitaxel), topoisomerase inhibitor (irinotecan, topotecan, etoposide).

In a preferred embodiment, a therapeutic agent, a chemotherapy drug as used herein refers to a compound or a derivative thereof that may be used to treat cancer, in particular to treat a hematopoietic cancer cell and more particularly AML, thereby reducing the proliferative status of the cancer cell and/or killing the cancer cell. Examples of chemotherapeutic agents include, but are not limited to aracytine, Cytosine arabinoside, amsacrine, daunorubicine, idarubicine, novantrone, mitoxantrone, vepeside, etoposide (VP16), arsenic trioxyde, transretinoic acid, mechlorethamine, procarbazine, chlorambucil, and combination thereof.

In other embodiments of the present invention, cells of the invention are administered to a patient in conjunction with a drug (or an agent) selected from aracytine, cytosine arabinoside, amsacrine, daunorubicine, idarubicine, novantrone, mitoxantrone, vepeside, etoposide (VP16), arsenic trioxyde, transretinoic acid, cytarabine, anthracyclines, 6-thioguanine, hydroxyurea, prednisone, and combination thereof.

Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

In a more preferred embodiment an anti-CLL1 scCAR expressing T cell, is administered to a patient, in combination with at least one therapeutic agent selected from aracytine, Cytosine arabinoside, amsacrine, daunorubicine, idarubicine, novantrone, mitoxantrone, vepeside, etoposide (VP16), arsenic trioxyde, transretinoic acid and combination thereof.

As used herein, a cell which is "resistant or tolerant" to an agent means a cell which has been genetically modified so that the cell proliferates in the presence of an amount of an agent that inhibits or prevents proliferation of a cell without the modification.

Group of Patients

In a preferred embodiment, the invention provides a treatment for AML in patients over 60 years or in patients of less than 20 years.

In a more preferred embodiment, the present invention provides a pediatric treatment, in particular a pediatric treatment against AML, or AML-related diseases or complications.

In still another preferred embodiment, the present invention is used as a treatment in AML patients with low, poor or unfavorable status that is to say with a predicted survival of less than 5 years survival rate. In this group, patients suffering AML with the following cytogenetic characteristics: −5; 5q; −7; 7q-;11q23; non t(9;11); inv(3); t(3;3); t(6;9); t(9;22) is associated with poor-risk status (Byrd J. C. et al., Dec. 15, 2002; Blood: 100 (13) and is especially contemplated to be treated according to the present invention or with an object of the present invention.

In one embodiment, the anti-CLL1 CAR expressing T cell of present invention may be used as induction therapy, as post remission therapy of AML or as a consolidation therapy in patient with AML.

In one embodiment, the anti-CLL1 CAR expressing T cell of the present invention may be used in case of AML relapse, or in case of refractory or resistant AML, and more preferably, in combination with at least one other anti-cancer drug In another preferred embodiment, at least one anti-CLL1 CAR expressing cell of the invention is used for preventing cancer cells development occurring in particular after anti-cancer treatment, during bone marrow depletion or before bone marrow transplantation, after bone marrow destruction.

AML Complications

In one particular embodiment the invention provides a medicament that improves the health condition of a patient, in particular a patient undergoing a complication related to AML. More preferably, said engineered anti-CLL1 CAR expressing T cell of the invention is expressing at least one anti-CLL1 CAR of the invention and is used as a medicament for the treatment of a complication related to AML.

A complication or disease related to AML may include a preceding myelodysplasia phase, secondary leukemia, in particular secondary AML, high white blood cell count, and absence of Auer rods. Among others, leukostasis and involvement of the central nervous system (CNS), hyperleukocytosis, residual disease, are also considered as a complication or disease related to AML.

AML Associated Diseases

In one embodiment, the present invention also provides an anti-CLL1 CAR expressing T cell for the treatment of a pathological condition related to AML.

The present invention provides a therapy for AML related myeloid neoplasms, for acute myeloid leukemia and myelodysplastic syndrome, a treatment of relapsed or refractory acute myeloid leukemia, a treatment of relapsed or refractory acute promyelocytic leukemia in adults, a treatment for acute promyeloid leukaemia, a treatment of acute myeloid leukemia in adults over 60 years.

According to another aspect, the present invention provides a composition for the treatment of AML associated diseases, in particular hematologic malignancy related to AML.

Hematologic malignancy related to AML conditions include myelodysplasia syndromes (MDS, formerly known as "preleukemia") which are a diverse collection of hematological conditions united by ineffective production (or dysplasia) of myeloid blood cells and risk of transformation to AML.

Other pathological conditions or genetic syndromes associated with the risk of AML can be improved with the adequate use of the present invention, said genetic syndromes include Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome).

Other CLL1-Mediated Pathological Conditions

According to another aspect, the present invention provides a composition for the treatment of CLL1+cell-mediated diseases. These CLL1+cell mediated diseases include inflammation, such as rheumatoid arthritis.

In particular, the present invention can be used for the treatment of CLL1+cell mediated diseases such as inflammation and more particularly rheumatoid arthritis.

Compositions

The present invention also provides a composition comprising an engineered T cells according to the invention for its use or a method for treating a disease.

In one aspect, the disease is a hematologic cancer, in particular a stem cell cancer including but is not limited to leukemia (such as acute myelogenous leukemia (AML) or a complication thereof.

The present invention also provides a composition for its use or a method for inhibiting the proliferation or reducing a CLL1-expressing cell population or activity in a patient. An exemplary method includes contacting a population of cells comprising a CLL1-expressing cell with an anti-CLL1 CART cell, and in particular scCART, of the invention that binds to the CLL1-expressing cell.

In a more specific aspect, the present invention provides a composition for its use or a method for inhibiting the proliferation or reducing the population of cancer cells expressing CLL1 in a patient, the methods comprising contacting the CLL1-expressing cancer cell population with an anti-CLL1 CART cell, and in particular scCART, of the invention that binds to the CLL1-expressing cell, binding of an anti-CLL1 CAR cell, and in particular scCART, of the invention to the CLL1-expressing cancer cell resulting in the destruction of the CLL1-expressing cancer cells In certain aspects, the anti-CLL1 CART cell, and in particular scCART, of the invention reduces the quantity, number, amount or percentage of cells and/or cancer cells by at least 25%, at least 30%, at least 40%, at least 50%, at least 65%, at least 75%, at least 85%, at least 95%, or at least 99% (to undetectable level) in a subject with or animal model for myeloid leukemia or another cancer associated with CLL1-expressing cells, relative to a negative control.

The present invention also provides a composition for its use or a method for preventing, treating and/or managing a disorder or condition associated with CLL1-expressing cells (e.g., associated with a hematologic cancer), the methods comprising administering to a subject in need an anti-CLL1 CART cell, and in particular scCART, of the invention that binds to the CLL1-expressing cell. In one aspect, the subject is a human. Non-limiting examples of disorders associated with CLL1-expressing cells include inflammatory disorders (such as rheumatoid arthritis) and cancers (such as hematological cancers, in particular AML or AML complications).

The present invention also provides a composition for its use or a method for preventing, treating and/or managing a disease associated with CLL1-expressing cells, the method comprising administering to a subject in need an anti-CLL1 CART cell, and in particular scCART, of the invention that binds to the CLL1-expressing cell. In one aspect, the subject is a human. Non-limiting examples of diseases associated with CLL1-expressing cells include in particular Acute Myeloid Leukemia (AML).

The present invention provides a composition for its use or a method for treating or preventing relapse of cancer associated with CLL1-expressing cells, the method comprising administering to a subject in need thereof an anti-CLL1 CART cell, and in particular scCART, of the invention that binds to the CLL1-expressing cell. In another aspect, the methods comprise administering to the subject in need thereof an effective amount of an anti CLL1 CART cell, and in particular scCART, of the invention that binds to the CLL1-expressing cell in combination with an effective amount of another therapy.

In one aspect, CLL1 is considered to be a "cancer stem cell" marker in AML. Therefore, an anti-CLL1 CART cell, and in particular scCART, of the invention can prevent relapse of AML, or even treat AML that is mostly CLL1-negative but with a "stem" population of CLL1+ cells (a CLL1-expressing cells).

In one aspect, the invention provides compositions and methods for treating subjects that have undergone treatment for a disease or disorder associated with elevated expression levels of CD 19, and exhibits a disease or disorder associated with elevated levels of CLL1.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

Preferably, the treatment with the engineered immune cells according to the invention may be administered in combination (e.g., before, simultaneously or following) with one or more therapies against cancer selected from aracytine, cytosine arabinoside, amsacrine, daunorubicine, idarubicine, novantrone, mitoxantrone, vepeside, etoposide (VP16), arsenic trioxyde, transretinoic acid, combination of arsenic trioxyde, transretinoic acid, mechlorethamine, procarbazine, chlorambucil, and combination thereof.

According to a preferred embodiment of the invention, said treatment can be administered into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaly, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993).

In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH.

In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments of the present invention, anti-CLL1 scCAR expressing cells are administered to a patient in conjunction (e.g., before, simultaneously or following) with a drug selected from aracytine, cytosine arabinoside, amsacrine, daunorubicine, idarubicine, novantrone, mitoxantrone, vepeside, etoposide (VP16), arsenic trioxyde, transretinoic acid, combination of arsenic trioxyde, transretinoic acid, mechlorethamine, procarbazine, chlorambucil, and combination thereof. In these embodiments anti-CLL1 scCAR expressing cells may be resistant to the particular drug or combination of drugs that is (are) administered in conjunction with anti-CLL1 scCAR expressing cells.

In other embodiments of the present invention, anti-CLL1 scCAR expressing cells are administered to a patient in conjunction with a drug selected from cytarabine, anthracyclines, 6-thioguanine, hydroxyurea, prednisone, and combination thereof.

Other Definitions

Unless otherwise specified, "a," "an," "the," and "at least one" are used interchangeably and mean one or more than one. Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: A is adenine, T is thymine, C is cytosine, and G is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By "delivery vector" or "delivery vectors" is intended any delivery vector which can be used in the present invention to put into cell contact (i.e. "contacting") or deliver inside cells or subcellular compartments (i.e. "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO—S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means. For example, a functional variant of pTalpha can have 70%, 75%, 80%, 85%, 87.5%, 90%, 92.5%, 95%, 97.5%, 98%, 99% sequence similarity to the amino acid sequence of SEQ ID NO: 107 such as disclosed in WO2013176916. A polynucleotide encoding such a functional variant would be produced by reverse translating its amino acid sequence using the genetic code.

The term "subject" or "patient" as used herein includes all members of the animal kingdom including non-human primates and humans.

The term "relapsed" refers to a situation where a subject or a mammal, who has had a remission of cancer after therapy has a return of cancer cells.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic (or primary resistance), which means the disease has never been responsive to the drug or drugs, or it can be acquired, which means the disease ceases responding to a drug or drugs that the disease had previously responded to (secondary resistance). In certain embodiments, drug resistance is intrinsic. In certain embodiments, the drug resistance is acquired.

The term "hematologic malignancy" or "hematologic cancer" refers to a cancer of the body's blood-bone marrow and/or lymphatic tissue. Examples of hematological malignancies include, in particular, acute myeloid leukemia (AML), AML with trilineage myelodysplasia (AML/TMDS), mixed lineage leukemia (MLL), and other AM-related pathologies.

The term "leukemia" refers to malignant neoplasms of the blood-forming tissues, including, in particular to acute myeloid leukemia or acute myelogenous leukemia (AML).

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

General Methods
Primary T-Cell Cultures

T cells were purified from Buffy coat samples provided by EFS (Etablissement Francais du Sang, Paris, France) using Ficoll gradient density medium. The PBMC layer was recovered and T cells were purified using a commercially available T-cell enrichment kit. Purified T cells were activated in X-Vivo™-15 medium (LonzaLONZA®) supplemented with 20 ng/mL Human IL-2, 5% Human, and Dynabeads Human T activator CD3/CD28 at a bead:cell ratio 1:1 (Life Technologies).

scCAR mRNA Transfection

Transfections were done at Day 4 or Day 11 after T-cell purification and activation. 5 millions of cells were transfected with 15 µg of mRNA encoding the different scCAR constructs. scCAR mRNAs were produced using T7 mRNA polymerase transfections done using Cytopulse technology, by applying two 0.1 mS pulses at 3000V/cm followed by four 0.2 mS pulses at 325V/cm in 0.4 cm gap cuvettes in a final volume of 200 µl of "Cytoporation buffer T" (BTX Harvard Apparatus). Cells were immediately diluted in X-Vivo™-15 media and incubated at 37° C. with 5% $CO_2$. IL-2 was added 2 h after electroporation at 20 ng/mL.

Degranulation Assay (CD107a Mobilization)

T-cells were incubated in 96-well plates (40,000 cells/well), together with an equal amount of cells expressing various levels of the CLL1 protein. Co-cultures were maintained in a final volume of 100 µl of X-Vivo™-15 medium (LONZA®) for 6 hours at 37° C. with 5% $CO_2$. CD107a staining was done 20 during cell stimulation, by the addition of a fluorescent anti-CD107a antibody at the beginning of the co-culture, together with 1 µg/ml of anti-CD49d, 1 µg/ml of anti-CD28, and 1× Monensin solution. After the 6 h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

IFN Gamma Release Assay

T-cells were incubated in 96-well plates (40,000 cells/well), together with cell lines expressing various levels of the CLL1 protein. Co-cultures were maintained in a final volume of 100 μl of X-Vivo™-15 medium (LONZA®) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay. The IFN gamma release assays were carried by starting the cell co-cultures 24 h after mRNA transfection.

Cytotoxicity Assay

T-cells were incubated in 96-well plates (100,000 cells/well), together with 10,000 target cells (expressing CLL1) and 10,000 control (CLL1neg) cells in the same well. Target and control cells were labelled with fluorescent intracellular dyes (CFSE or Cell Trace Violet) before co-culturing them with scCAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or CLL1neg control cells) was determined and the % of specific cell lysis was calculated. Cytotoxicity assays were carried out 48 h after mRNA transfection.

T-Cell Transduction

Transduction of T-cells with recombinant lentiviral vectors expression the scCAR was carried out three days after T-cell purification/activation. scCAR detection at the surface of T-cells was done using a recombinant protein consisting on the fusion of the extracellular domain of the human CLL1 protein, together with a murine IgG1 Fc fragment. Binding of this protein to the scCAR molecule was detected with a fluorochrome-conjugated secondary antibody targeting the mouse Fc portion of the protein, and analyzed by flow cytometry.

Anti-Tumor Mouse Model

Immunodeficient NOG mice were intravenously (iv) injected with (CLL1 expressing_MOLM13-Luciferase cells as an AML xenograft mouse model. Optionally, mice received an anti-cancer treatment. Mice were then iv injected (either 2 or 7 days after injection of the tumor cell line) with different doses of scCAR+ T-cells to be tested, or with T-cells that were not transduced with the scCAR lentiviral vector. Bioluminescent signals were determined at the day of T-cell injection (D0), at D7, 14, 21, 28 and 40 after T-cell injection in order to follow tumoral progression on the different animals.

Example 1

Proliferation of TCRalpha Inactivated Cells Expressing a CLL1-scCAR

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10.

TABLE 10

TAL-nucleases targeting TCRalpha gene

| Target | Target sequence | Repeat sequence | Half TALE-nuclease |
|---|---|---|---|
| TRAC_T01 | TTGTCCCA CAGATATCC Agaaccc tgaccctg (SEQ ID NO: 114) | Repeat TRAC_T01-L (SEQ ID NO: 115) | TRAC_T01-L TALEN (SEQ ID NO: 117) |
| | CCGTGTAC CAGCTGAGA (SEQ ID NO: 116) | Repeat TRAC_T01-R (SEQ ID NO: 116) | TRAC_T01-R TALEN (SEQ ID NO: 118) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with antiCD3/CD28 coated beads were transfected with each of the 2 mRNAs encoding both half TRAC_T01 TALE-nucleases. 48 hours post-transfection, different groups of T cells from the same donor were respectively transduced with a lentiviral vector encoding one of the anti-CLL1 scCAR previously described (SEQ ID NO: 35 to 112). 2 days post-transduction, $CD3_{NEG}$ cells were purified using anti-CD3 magnetic beads and 5 days post-transduction cells were reactivated with soluble anti-CD28 (5 μg/ml).

Cell proliferation was followed for up to 30 days after reactivation by counting cell 2 times per week. Increased proliferation in TCR alpha inactivated cells expressing the CLL1 scCARs, especially when reactivated with anti-CD28, was observed compared to non-transduced cells.

To investigate whether the human T cells expressing the CLL1-scCAR display activated state, the expression of the activation marker CD25 are analyzed by FACS 7 days post transduction. The purified cells transduced with the lentiviral vector encoding CLL1 scCAR assayed for CD25 expression at their surface in order to assess their activation in comparison with the non-transduced cells. Increased CD25 expression is expected both in CD28 reactivation or no reactivation conditions.

Example 2

Construction of CLL1 scCAR Using Various Anti-CLL1 Antibody Fragments

Primary T-Cell Cultures

T cells were purified from Buffy coat samples provided by EFS (Etablissement Francais du Sang, Paris, France) using Ficoll gradient density medium (Ficoll Paque PLUS/GE Healthcare Life Sciences). The PBMC layer was recovered and T cells were purified using a commercially available T-cell enrichment kit (Stem Cell Technologies). Purified T cells were activated in X-Vivo™-15 medium (Lanza) supplemented with 20 ng/mL Human IL-2 (Miltenyi Biotech), 5% Human Serum (Sera Laboratories), and Dynabeads Human T activator CD3/CD28 at a bead:cell ratio 1:1 (Life Technologies). After activation cells were grown and maintained in X-Vivo™-15 medium (LONZA®) supplemented with 20 ng/mL Human IL-2 (Miltenyi Biotec) and 5% Human Serum (Sera Laboratories), scCAR mRNA Transfection Transfections were done at Day 4 or Day 11 after T-cell purification and activation. 5 millions of cells were transfected with 15 μg of mRNA encoding the different scCAR constructs. scCAR mRNAs were produced using the mMESSAGE mMACHINE® T7 Kit (Life Technologies) and purified using RNeasy® Mini Spin Columns (QIAGEN®). Transfections were done using Cytopulse technology, by applying two 0.1 mS pulses at 3000V/cm followed by four 0.2 mS pulses at 325V/cm in 0.4 cm gap 20 cuvettes in a final volume of 200 μl of "Cytoporation buffer T" (BTX Harvard Apparatus). Cells were immediately diluted in X-Vivo™-15 media (LONZA®) and incubated at 37° C. with 5% $CO_2$. IL-2 (from Miltenyi Biotec was added 2 h after electroporation at 20 ng/ml.

Degranulation Assay (CD107a Mobilization)

T-cells were incubated in 96-well plates (40,000 cells/well), together with an equal amount of cells expressing or not the CLL1 protein. Co-cultures were maintained in a final volume of 100 μl of X-Vivo™-15 medium (LONZA®) for 6 hours at 37° C. with 5% $CO_2$. CD107a staining was done during cell stimulation, by the addition of a fluorescent anti-CD107a antibody (APC conjugated, from Miltenyi Biotec) at the beginning of the co-culture, together with 1 μg/ml of anti-CD49d (BD Pharmingen), 1 μg/ml of anti-CD28 (Miltenyi Biotec), and 1× Monensin solution (eBioscience). After the 6 h incubation period, cells were stained with a fixable viability dye (eFiuor 780, from eBioscience) and fluorochrome-conjugated anti-CD8 (PE conjugated Miltenyi Biotec) and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

IFNGamma Release Assay

T-cells were incubated in 96-well plates (40,000 cells/well), together with cell lines expressing or not the CLL1 protein. Co-cultures were maintained in a final volume of 100 μl of X-Vivo™-15 medium (LONZA®) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay (Human IFN-gamma QUANTIKINE® ELISA Kit, from R&D Systems). The IFN gamma release assays were carried by starting the cell co-cultures 24 h after mRNA transfection.

Cytotoxicity Assay

T-cells were incubated in 96-well plates (100,000 cells/well), together with 10,000 target cells (expressing CLL1) and 10,000 control (CLL1neg) cells in the same well. Target and control cells were labelled with fluorescent intracellular dyes (CFSE or Cell Trace Violet, from Life Technologies) before co-culturing them with scCAR+ T-cells. The co-cultures were incubated for 4 hours at 37° C. with 5% $CO_2$. After this incubation period, cells were labelled with a fixable viability dye (eFluor 780, from eBioscience) and analyzed by flow cytometry. Viability of each cellular population (target cells or CLL1neg control cells) was determined and the % of specific cell lysis was calculated. Cytotoxicity assays were carried out 48 h after mRNA transfection.

Exemplary Anti-CLL1 Single Chain Chimeric Antigen Receptors

```
sc SC02-357-CAR-v1
                                              (SEQ ID NO. 1 + SEQ ID NO. 35)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKGLAVSTISSFFPPGYQIYIWAPLAGTCGVLLLSLVITLYCKRGRKKLLYI

FKQPFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDALHMQALPPR sc SC02-357-CAR-v2
                                              (SEQ ID NO. 1 + SEQ ID NO. 36)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKGLAVSTISSFFPPGYQIYIWAPLAGTCGVLLLSLVITLYCKRGRKKLL

YIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR
```

-continued sc SC02-357-CAR-v3
(SEQ ID NO. 1 + SEQ ID NO. 37)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKTTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR sc SC02-357-CAR-v4
(SEQ ID NO. 1 + SEQ ID NO. 38)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKTTTPAPRPPTPAPTIASQPLSLRPEACRPAAGGAVHTRGLDFACDIIS

FFLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHD

GLYQGLSTATKDTYDALHMQALPPR sc SC02-357-CAR-v5
(SEQ ID NO. 1 + SEQ ID NO. 39)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKEPKSPDKTHTCPPCPAPPVAGPSVFLFPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQWTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc SC02-357-CAR-v6
(SEQ ID NO. 1 + SEQ ID NO. 40)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKEPKSPDKTHTCPPCPAPPVAGPSVFLFPPKPKDTLMIARTPEVTCVV

VDVSHEDPEVKFNWYVDGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIISFFLALTSTALLFLLFFLTLRFSWKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKHDGLYQGLSTATKDTYDALHMQALPPR sc SC02-378 CAR-v1

(SEQ ID NO. 1 + SEQ ID NO. 41)

MALPVTALLLPLALLLHAARP QVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSS GGGGSGGGGSGG

GGS DIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIK GLAVSTISSFFPPGYQIYIWAPLAGTCGVLLLSLVITLYCKRGRKKLLYI

FKQPFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKHDGLYQGLSTATKDTYDALHMQALPPR sc SC02-378 CAR-v2

(SEQ ID NO. 1 + SEQ ID NO. 42)

MALPVTALLLPLALLLHAARP QVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSS GGGGSGGGGSGG

GGS DIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIK GLAVSTISSFFPPGYQIISFFLALTSTALLFLLFFLTLRFSVVKRGRKKLL

YIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKHDGLYQGLSTATKDTYDALHMQALPPR sc SC02-378 CAR-v3

(SEQ ID NO. 1 + SEQ ID NO. 43)

MALPVTALLLPLALLLHAARP QVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSS GGGGSGGGGSGG

GGS DIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIK TTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKHDG

LYQGLSTATKDTYDALHMQALPPR sc SC02-378 CAR-v4

(SEQ ID NO. 1 + SEQ ID NO. 44)

MALPVTALLLPLALLLHAARP QVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSS GGGGSGGGGSGG

GGS DIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIK TTTPAPRPPTPAPTIASQPLSLRPEACRPAAGGAVHTRGLDFACDIIS

FFLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKHD

GLYQGLSTATKDTYDALHMQALPPR sc SC02-378 CAR-v5

(SEQ ID NO. 1 + SEQ ID NO. 45)

MALPVTALLLPLALLLHAARP`QVQLQESGPGLVKPSETLSLTCVVSGGSISSSNWWSWVRQPPGKGLEWIGEIYHS`

`GSPNYNPSLKSRVTISVDKSKNQFSLKLSSVTAADTAVYYCARSSSGGFFDYWGQGTLVTVSS`GGGGSGGGGSGG

GGS`DIQMTQSPSSLSASVGDRVTITCRASQSISSYLNWYQQKPGKAPKLLIYAASSLQSGVPSRFSGSGSGTDFTLTIS`

`SLQPEDFATYYCQQSYSTPPTFGQGTKVEIK`EPKSPDKTHTCPPCPAPPVAGPSVFLPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHnQKSLSLSPGKIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc SC02-378 CAR-v6

(SEQ ID NO. 1 + SEQ ID NO. 46)

MALPVTALLLPLALLLHAARP`QVQLQESGPGLVKPSETLSLTCVVSGGSISSSNWWSWVRQPPGKGLEWIGEIYHS`

`GSPNYNPSLKSRVTISVDKSKNQFSLKLSSVTAADTAVYYCARSSSGGFFDYWGQGTLVTVSS`GGGGSGGGGSGG

GGS`DIQMTQSPSSLSASVGDRVTITCRASQSISSYLNWYQQKPGKAPKLLIYAASSLQSGVPSRFSGSGSGTDFTLTIS`

`SLQPEDFATYYCQQSYSTPPTFGQGTKVEIK`EPKSPDKTHTCPPCPAPPVAGPSVFLPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIISFFLALTSTALLFLLFFLTLRFSWKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc SC02-161 CAR-v1

(SEQ ID NO. 1 + SEQ ID NO. 47)

MALPVTALLLPLALLLHAARP`QVQLQESGPGLVKPSETLSLTCVVSGGSISSSNWWSWVRQPPGKGLEWIGEIYHS`

`GSPNYNPSLKSRVTISVDKSKNQFSLKLSSVTAADTAVYYCARSSSGGFFDYWGQGTLVTVSS`GGGGSGGGGSGG

GGS`DIQMTQSPSSLSASVGDRVTITCRASQSISSYLNWYQQKPGKAPKLLIYAASSLQSGVPSRFSGSGSGTDFTLTIS`

`SLQPEDFATYYCQQSYSTPPTFGQGTKVEIK`GLAVSTISSFFPPGYQIYIWAPLAGTCGVLLLSLVITLYCKRGRKKLLYI

FKQPFMRPVQTTQEEDGCSCRFPEEEEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGLSTATKDTYDALHMQALPPR sc SC02-161 CAR-v2

(SEQ ID NO. 1 + SEQ ID NO. 48)

MALPVTALLLPLALLLHAARP`QVQLQESGPGLVKPSETLSLTCVVSGGSISSSNWWSWVRQPPGKGLEWIGEIYHS`

`GSPNYNPSLKSRVTISVDKSKNQFSLKLSSVTAADTAVYYCARSSSGGFFDYWGQGTLVTVSS`GGGGSGGGGSGG

GGS`DIQMTQSPSSLSASVGDRVTITCRASQSISSYLNWYQQKPGKAPKLLIYAASSLQSGVPSRFSGSGSGTDFTLTIS`

`SLQPEDFATYYCQQSYSTPPTFGQGTKVEIK`GLAVSTISSFFPPGYQIISFFLALTSTALLFLLFFLTLRFSVVKRGRKKLL

YIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR sc SC02-161 CAR-v3 (SEQ ID NO. 1 + SEQ ID NO. 49)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKTTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR sc SC02-161 CAR-v4 (SEQ ID NO. 1 + SEQ ID NO. 50)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKTTTPAPRPPTPAPTIASQPLSLRPEACRPAAGGAVHTRGLDFACDIIS

FFLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHD

GLYQGLSTATKDTYDALHMQALPPR sc SC02-161 CAR-v5 (SEQ ID NO. 1 + SEQ ID NO. 51)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKEPKSPDKTHTCPPCPAPPVAGPSVFLFPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc SC02-161 CAR-v6 (SEQ ID NO. 1 + SEQ ID NO. 52)
MALPVTALLLPLALLLHAARPQVQLQESGPGLVKPSETLSLTCVVSGGSISSSNWWSWVRQPPGKGLEWIGEIYHS

GSPNYNPSLKSRVTISVDKSKNQFSLKLSSVTAADTAVYYCARSSSGGFFDYWGQGTLVTVSSGGGGSGGGGSGG

GGSDIQMTQSPSSLSASVGDRVTITCRASQSISSYLNWYQQKPGKAPKLLIYAASSLQSGVPSRFSGSGSGTDFTLTIS

SLQPEDFATYYCQQSYSTPPTFGQGTKVEIKEPKSPDKTHTCPPCPAPPVAGPSVFLFPPKPKDTLMIARTPEVTCVV

VDVSHEDPEVKFNWYVDGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIISFFLALTSTALLFLLFFLTLRFSWKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKHDGLYQGLSTATKDTYDALHMQALPPR sc M26 CAR-v1
(SEQ ID NO. 1 + SEQ ID NO. 53)
MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKRGLAVSTISSFFPPGYQIYIWAPLAGTCGVLLLSLVITLYCKRGRKKL

LYIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKHDGLYQGLSTATKDTYDALHMQALPPR sc M26 CAR-v2
(SEQ ID NO. 1 + SEQ ID NO. 54)
MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKRGLAVSTISSFFPPGYQIISFFLALTSTALLFLLFFLTLRFSVVKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKHDGLYQGLSTATKDTYDALHMQALPPR sc M26 CAR-v3
(SEQ ID NO. 1 + SEQ ID NO. 55)
MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKRTTTPAPRPPTPAPTIASQPLSLRPEACRPAAGGAVHTRGLDFACD

IYIWAPLAGTCGVLLLSLVITLYCKRGRKKLLYIFKQPFMRPVQTTQEEDGCSCRFPEEEEGGCELRVKFSRSADAPAY

QQGQNQLYNELNLGRREEYDVLDKRRGRDPEMGGKPRRKNPQEGLYNELQKDKMAEAYSEIGMKGERRRGKGH

DGLYQGLSTATKDTYDALHMQALPPR sc M26 CAR-v4
(SEQ ID NO. 1 + SEQ ID NO. 56)
MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKRTTTPAPRPPTPAPTIASQPLSLRPEACRPAAGGAVHTRGLDFACD

IISFFLALTSTALLFLLFFLTLRFSVVKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGERRRGKG

HDGLYQGLSTATKDTYDALHMQALPPR sc M26 CAR-v5

(SEQ ID NO. 1 + SEQ ID NO. 57)

MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKREPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLDSDGSFFLYSKLTVDK

SRWQQGNVFSKVMHEALHNHYTQKSLSLSPGKIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR sc M26 CAR-v6

(SEQ ID NO. 1 + SEQ ID NO. 58)

MALPVTALLLPLALLLHAARPEVQLQQSGPELVKPGASVKMSCKASGYTFTSYFIHWVKQKPGQGLEWIGFINPYN

DGSKYNEKFKGKATLTSDKSSSTAYMELSSLTSEDSAVYYCTRDDGYYGYAMDYWGQGTSVTVSSGGGGSGGGGS

GGGGSDIQMTQSPSSLSASLGERVSLTCRATQELSGYLSWLQQKPDGTIKRLIYAASTLDSGVPKRFSGNRSGSDYSL

TISSLESEDFADYYCLQYAIYPYTFGGGTKLEIKREPKSPDKTHTCPPCPAPPVAGPSVFLFPPKPKDTLMIARTPEVTC

VVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGKIISFFLALTSTALLFLLFFLTLRFSVVKRGRKKLLYIFKQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR sc M31 CAR-v1

(SEQ ID NO. 1 + SEQ ID NO. 59)

MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKGLAVSTISSFFPPGYQIYIWAPLAGTCGVLLLSLVITLYC

KRGRKKLLYIFKQPFMRPVQTTQEEDGCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGKGHDGLYQGLSTATKDTYDALHMQ

ALPPR sc M31 CAR-v2

(SEQ ID NO. 1 + SEQ ID NO. 60)

MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKGLAVSTISSFFPPGYQIISFFLALTSTALLFLLFFLTLRFSV

VKRGRKKLLYIFKQPFMRPVQTTQEEDGCSCRFPEEEEGGCELRVKFSRSADAPAYQQGQNQLYNELNLGRREEYD

VLDKRRGRDPEMGGKPRRKNPQEGLYNELQKDKMAEAYSEIGMKGERRRGKGHDGLYQGLSTATKDTYDALHM

QALPPR sc M31 CAR-v3
(SEQ ID NO. 1 + SEQ ID NO. 61)
MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKTTTPAPRPPTPAPTIASQPLSLRPEACRPAAGGAVHTR

GLDFACDIYIWAPLAGTCGVLLLSLVITLYCKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGLYNELQKDKMAEAYSEIGMKGE

RRRGKGHDGLYQGLSTATKDTYDALHMQALPPR sc M31 CAR-v4
(SEQ ID NO. 1 + SEQ ID NO. 62)
MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKTTTPAPRPPTPAPTIASQPLSLRPEACRPAAGGAVHTR

GLDFACDIISFFLALTSTALLFLLFFLTLRFSVVKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAYSEIGMKG

ERRRGKGHDGLYQGLSTATKDTYDALHMQALPPR sc M31 CAR-v5
(SEQ ID NO. 1 + SEQ ID NO. 63)
MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKEPKSPDKTHTCPPCPAPPVAGPSVFLFPPKPKDTLMIA

RTPEVTCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKIYIWAPLAGTCGVLLLSLVITLYCKRGRKKLLYIFKQP

FMRPVQTTQEEDGCSCRFPEEEEGGCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTATKDTYDALHMQALPPR sc M31 CAR-v6
(SEQ ID NO. 1 + SEQ ID NO. 64)
MALPVTALLLPLALLLHAARPEVQLQQSGPELVKPGASVKMSCKASGYTFTSYVMHWVKQKPGQGLEWIGYINPY

NDGTKYNEKFKGKATLTSDTSSSTAYMELNSLTSEDSAVYFCARPIYFDNDYFDYWGQGTTLKVSSGGGGSGGGGS

```
GGGGSTIVLTQSPASLAVSLGQRATISCRASESVDSYGNSFMHWYQQKPGQPPKLLIYLASNLESGVPARFSGSGSR

TDFTLTIDPVEADDAATYYCQQNNYDPWTFGGGTKLEIKEPKSPDKTHTCPPCPAPPVAGPSVFLFPPKPKDTLMIA

RTPEVTCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKIISFFLALTSTALLFLLFFLTRFSVVKRGRKKLLYIFKQ

PFMRPVQTTQEEDGCSCRFPEEEEGGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLSTATKDTYDALHMQALPPR
sc G4 CAR-v1
                                                    (SEQ ID NO. 1 + SEQ ID NO. 65)
MALPVTALLLPLALLLHAARPEVQLQQSGPELVKPGASVKMSCKASGYTFTSYFIHWVKQKPGQGLEWIGFINPYN

DGTIYNPNFKGKATLTVDKASSTAYMELLSLTSDDPAVYYCARTDDYDDYTMDYWGQGTSVTVSSGGGGSGGGG

SGGGGSEIQMTQTPSSLSASLGDRVTISCRASHDISNYLNWYQQKPDGTLKLLIYYTSRLHSGVPSRFSGSGSGTDYS

LTISNLEQEDIATYFCQQGKTLLWTFGGGTKLEIKGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDTYDALHMQALPPR
sc G4 CAR-v2
                                                    (SEQ ID NO. 1 + SEQ ID NO. 66)
MALPVTALLLPLALLLHAARPEVQLQQSGPELVKPGASVKMSCKASGYTFTSYFIHWVKQKPGQGLEWIGFINPYN

DGTIYNPNFKGKATLTVDKASSTAYMELLSLTSDDPAVYYCARTDDYDDYTMDYWGQGTSVTVSSGGGGSGGGG

SGGGGSEIQMTQTPSSLSASLGDRVTISCRASHDISNYLNWYQQKPDGTLKLLIYYTSRLHSGVPSRFSGSGSGTDYS

LTISNLEQEDIATYFCQQGKTLLWTFGGGTKLEIKGLAVSTISSFFPPGYQIISFFLALTSTALLFLLFFLTRFSVVKRGRK

KLLYIFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKDTYDALHMQALPPR
sc G4 CAR-v3
                                                    (SEQ ID NO. 1 + SEQ ID NO. 67)
MALPVTALLLPLALLLHAARPEVQLQQSGPELVKPGASVKMSCKASGYTFTSYFIHWVKQKPGQGLEWIGFINPYN

DGTIYNPNFKGKATLTVDKASSTAYMELLSLTSDDPAVYYCARTDDYDDYTMDYWGQGTSVTVSSGGGGSGGGG

SGGGGSEIQMTQTPSSLSASLGDRVTISCRASHDISNYLNWYQQKPDGTLKLLIYYTSRLHSGVPSRFSGSGSGTDYS

LTISNLEQEDIATYFCQQGKTLLWTFGGGTKLEIKTTTPAPRPPTPAPTIASQPLSLRPEACRPAAGGAVHTRGLDFA

CDIYIWAPLAGTCGVLLLSLVITLYCKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR
sc G4 CAR-v4
                                                    (SEQ ID NO. 1 + SEQ ID NO. 68)
MALPVTALLLPLALLLHAARPEVQLQQSGPELVKPGASVKMSCKASGYTFTSYFIHWVKQKPGQGLEWIGFINPYN

DGTIYNPNFKGKATLTVDKASSTAYMELLSLTSDDPAVYYCARTDDYDDYTMDYWGQGTSVTVSSGGGGSGGGG

SGGGGSEIQMTQTPSSLSASLGDRVTISCRASHDISNYLNWYQQKPDGTLKLLIYYTSRLHSGVPSRFSGSGSGTDYS
```

LTISNLEQEDIATYFCQQGKTLLWTFGGGTKLEIKTTTPAPRPPTPAPTIASQPLSLRPEACRPAAGGAVHTRGLDFA
CDIISFFLALTSTALLFLLFFLTLRFSVVKRGRKKLLYIFKQPFMRPVQTTQEEDGCSCRFPEEEEGGCELRVKFSRSADA
PAYQQGQNQLYNELNLGRREEYDVLDKRRGRDPEMGGKPRRKNPQEGLYNELQKDKMAEAYSEIGMKGERRRG
KGHDGLYQGLSTATKDTYDALHMQALPPR sc G4 CAR-v5
(SEQ ID NO. 1 + SEQ ID NO. 69)
MALPVTALLLPLALLLHAARPEVQLQQSGPELVKPGASVKMSCKASGYTFTSYFIHWVKQKPGQGLEWIGFINPYN
DGTIYNPNFKGKATLTVDKASSTAYMELLSLTSDDPAVYYCARTDDYDDYTMDYWGQGTSVTVSSGGGGSGGGG
SGGGGSEIQMTQTPSSLSASLGDRVTISCRASHDISNYLNWYQQKPDGTLKLLIYYTSRLHSGVPSRFSGSGSGTDYS
LTISNLEQEDIATYFCQQGKTLLWTFGGGTKLEIKEPKSPDKTHTCPPCPAPPVAGPSVFLFPPKPKDTLMIARTPEVT
CVVVDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGKIYIWAPLAGTCGVLLLSLVITLYCKRGRKKLLYIFKQPFMRPV
QTTQEEDGCSCRFPEEEEGGCELRVKFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYDALHMQALPPR sc G4 CAR-v6
(SEQ ID NO. 1 + SEQ ID NO. 70)
MALPVTALLLPLALLLHAARPEVQLQQSGPELVKPGASVKMSCKASGYTFTSYFIHWVKQKPGQGLEWIGFINPYN
DGTIYNPNFKGKATLTVDKASSTAYMELLSLTSDDPAVYYCARTDDYDDYTMDYWGQGTSVTVSSGGGGSGGGG
SGGGGSEIQMTQTPSSLSASLGDRVTISCRASHDISNYLNWYQQKPDGTLKLLIYYTSRLHSGVPSRFSGSGSGTDYS
LTISNLEQEDIATYFCQQGKTLLWTFGGGTKLEIKEPKSPDKTHTCPPCPAPPVAGPSVFLFPPKPKDTLMIARTPEVT
CVVVDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGKIISFFLALTSTALLFLLFFLTLRFSVVKRGRKKLLYIFKQPFMRP
VQTTQEEDGCSCRFPEEEEGGCELRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYDALHMQALPPR sc M22 CAR-v1
(SEQ ID NO. 1 + SEQ ID NO. 71)
MALPVTALLLPLALLLHAARPQVQLQQPGAELVKPGASVKLSCKASGYTFTRYWMHWVKQRPGQGLEWIGNIDP
SDTETHYNQQFKDKATLTVDKSSSTAYMQLSSLTSEDSAVYYCAIYYGNPSYYAMDYWGQGTSVTVSSGGGGSGG
GGSGGGGSDIVMTQSPSSLTVTAGEKVTMSCKSSQNLLNSGNQKKYLNWYQQKPGQPPKLLIYWASTRESGVPD
RFTGSGSGTDFTLTISSVQAEDLAVYFCQNDYSYPFTFGAGTKLELKGLAVSTISSFFPPGYQIYIWAPLAGTCGVLLLS
LVITLYCKRGRKKLLYIFKQPFMRPVQTTQEEDGCSCRFPEEEEGGCELRVKFSRSADAPAYQQGQNQLYNELNLGR
REEYDVLDKRRGRDPEMGGKPRRKNPQEGLYNELQKDKMAEAYSEIGMKGERRRGKGHDGLYQGLSTATKDTYD
ALHMQALPPR sc M22 CAR-v2
(SEQ ID NO. 1 + SEQ ID NO. 72)
MALPVTALLLPLALLLHAARP QVQLQQPGAELVKPGASVKLSCKASGYTFTRYWMHWVKQRPGQGLEWIGNIDP

SDTETHYNQQFKDKATLTVDKSSSTAYMQLSSLTSEDSAVYYCAIYYGNPSYYAMDYWGQGTSVTVSS GGGSGG

GGSGGGGS DIVMTQSPSSLTVTAGEKVTMSCKSSQNLLNSGNQKKYLNWYQQKPGQPPKLLIYWASTRESGVPD

RFTGSGSGTDFTLTISSVQAEDLAVYFCQNDYSYPFTFGAGTKLELK GLAVSTISSFFPPGYQIISFFLALTSTALLFLLFF

LTLRFSVVKRGRKKLLYIFKQPFMRPVQTTQEEDGCSCRFPEEEEGGCELRVKFSRSADAPAYQQGQNQLYNELNLG

RREEYDVLDKRRGRDPEMGGKPRRKNPQEGLYNELQKDKMAEAYSEIGMKGERRRGKGHDGLYQGLSTATKDTY

DALHMQALPPR sc M22 CAR-v3
(SEQ ID NO. 1 + SEQ ID NO. 73)
MALPVTALLLPLALLLHAARP QVQLQQPGAELVKPGASVKLSCKASGYTFTRYWMHWVKQRPGQGLEWIGNIDP

SDTETHYNQQFKDKATLTVDKSSSTAYMQLSSLTSEDSAVYYCAIYYGNPSYYAMDYWGQGTSVTVSS GGGSGG

GGSGGGGS DIVMTQSPSSLTVTAGEKVTMSCKSSQNLLNSGNQKKYLNWYQQKPGQPPKLLIYWASTRESGVPD

RFTGSGSGTDFTLTISSVQAEDLAVYFCQNDYSYPFTFGAGTKLELK TTTPAPRPPTPAPTIASQPLSLRPEACRPAAG

GAVHTRGLDFACDIYIWAPLAGTCGVLLLSLVITLYCKRGRKKLLYIFKQPFMRPVQTTQEEDGCSCRFPEEEEGGCEL

RVKFSRSADAPAYQQGQNQLYNELNLGRREEYDVLDKRRGRDPEMGGKPRRKNPQEGLYNELQKDKMAEAYSEI

GMKGERRRGKGHDGLYQGLSTATKDTYDALHMQALPPR sc M22 CAR-v4
(SEQ ID NO. 1 + SEQ ID NO. 74)
MALPVTALLLPLALLLHAARP QVQLQQPGAELVKPGASVKLSCKASGYTFTRYWMHWVKQRPGQGLEWIGNIDP

SDTETHYNQQFKDKATLTVDKSSSTAYMQLSSLTSEDSAVYYCAIYYGNPSYYAMDYWGQGTSVTVSS GGGSGG

GGSGGGGS DIVMTQSPSSLTVTAGEKVTMSCKSSQNLLNSGNQKKYLNWYQQKPGQPPKLLIYWASTRESGVPD

RFTGSGSGTDFTLTISSVQAEDLAVYFCQNDYSYPFTFGAGTKLELK TTTPAPRPPTPAPTIASQPLSLRPEACRPAAG

GAVHTRGLDFACDIISFFLALTSTALLFLLFFLTLRFSVVKRGRKKLLYIFKQPFMRPVQTTQEEDGCSCRFPEEEEGGC

ELRVKFSRSADAPAYQQGQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR sc M22 CAR-v5
(SEQ ID NO. 1 + SEQ ID NO. 75)
MALPVTALLLPLALLLHAARP QVQLQQPGAELVKPGASVKLSCKASGYTFTRYWMHWVKQRPGQGLEWIGNIDP

SDTETHYNQQFKDKATLTVDKSSSTAYMQLSSLTSEDSAVYYCAIYYGNPSYYAMDYWGQGTSVTVSS GGGSGG

GGSGGGGS DIVMTQSPSSLTVTAGEKVTMSCKSSQNLLNSGNQKKYLNWYQQKPGQPPKLLIYWASTRESGVPD

RFTGSGSGTDFTLTISSVQAEDLAVYFCQNDYSYPFTFGAGTKLELK EPKSPDKTHTCPPCPAPPVAGPSVFLFPPKPK

DTLMIARTPEVTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGKIYIWAPLAGTCGVLLLSLVITLYCKRGRKKL

LYIFKQPFMRPVQTTQEEDGCSCRFPEEEEGGCELRVKFSRSADAPAYQQGQNQLYNELNLGRREEYDVLDKRRGR

DPEMGGKPRRKNPQEGLYNELQKDKMAEAYSEIGMKGERRRGKHDGLYQGLSTATKDTYDALHMQALPPR sc M22 CAR-v6

(SEQ ID NO. 1 + SEQ ID NO. 76)

MALPVTALLLPLALLLHAARP QVQLQQPGAELVKPGASVKLSCKASGYTFTRYWMHWVKQRPGQGLEWIGNIDP

SDTETHYNQQFKDKATLTVDKSSSTAYMQLSSLTSEDSAVYYCAIYYGNPSYYAMDYWGQGTSVTVSS GGGGSGG

GGSGGGGS DIVMTQSPSSLTVTAGEKVTMSCKSSQNLLNSGNQKKYLNWYQQKPGQPPKLLIYWASTRESGVPD

RFTGSGSGTDFTLTISSVQAEDLAVYFCQNDYSYPFTFGAGTKLELK EPKSPDKTHTCPPCPAPPVAGPSVFLFPPKPK

DTLMIARTPEVTCVWDVSHEDPEVKFNWYVDGVEVHNAKTKPREEQYNSTYRWSVLTVLHQDWLNGKEYKCK

VSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGKIISFFLALTSTALLFLLFFLTLRFSVVKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKHDGLYQGLSTATKDTYDALHMQALPPR sc M29 CAR-v1

(SEQ ID NO. 1 + SEQ ID NO. 77)

MALPVTALLLPLALLLHAARP EVQLQQSGPELVKPGASVKMSCKASGYIFTSYVMYWVKQKPGQGLEWIGYINPY

NDGTKYNEKFKGKATLTSDKSSSTAYMELSSLTSEDSAVYYCARYYDYDYYFDYWGQGTTLTVSS GGGGSGGGGSG

GGGS DIQMTQSPSSLSASLGGKVTITCKASQDINKYIAWYQHKPGKGPRLLIHYTSTLQPGIPSRFSGSGSGRDYSFSI

SNLEPEDIATYYCLQYDYLWTFGGGTKLEIK GLAVSTISSFFPPGYQIYIWAPLAGTCGVLLLSLVITLYCKRGRKKLLYIF

KQPFMRPVQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKHDGLYQGLSTATKDTYDALHMQALPPR sc M29 CAR-v2

(SEQ ID NO. 1 + SEQ ID NO. 78)

MALPVTALLLPLALLLHAARP EVQLQQSGPELVKPGASVKMSCKASGYIFTSYVMYWVKQKPGQGLEWIGYINPY

NDGTKYNEKFKGKATLTSDKSSSTAYMELSSLTSEDSAVYYCARYYDYDYYFDYWGQGTTLTVSS GGGGSGGGGSG

GGGS DIQMTQSPSSLSASLGGKVTITCKASQDINKYIAWYQHKPGKGPRLLIHYTSTLQPGIPSRFSGSGSGRDYSFSI

SNLEPEDIATYYCLQYDYLWTFGGGTKLEIK GLAVSTISSFFPPGYQIISFFLALTSTALLFLLFFLTLRFSVVKRGRKKLLY

IFKQPFMRPVQTTQEEDGCSCRFPEEEEGGCELRVKFSRSADAPAYQQGQNQLYNELNLGRREEYDVLDKRRGRD

PEMGGKPRRKNPQEGLYNELQKDKMAEAYSEIGMKGERRRGKHDGLYQGLSTATKDTYDALHMQALPPR sc M29 CAR-v3

(SEQ ID NO. 1 + SEQ ID NO. 79)

MALPVTALLLPLALLLHAARP EVQLQQSGPELVKPGASVKMSCKASGYIFTSYVMYWVKQKPGQGLEWIGYINPY

NDGTKYNEKFKGKATLTSDKSSSTAYMELSSLTSEDSAVYYCARYYDYDYYFDYWGQGTTLTVSS GGGGSGGGGSG

GGGS DIQMTQSPSSLSASLGGKVTITCKASQDINKYIAWYQHKPGKGPRLLIHYTSTLQPGIPSRFSGSGSGRDYSFSI

SNLEPEDIATYYCLQYDYLWTFGGGTKLEIK TTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYSEIGMKGERRRGKGHDG

LYQGLSTATKDTYDALHMQALPPR sc M29 CAR-v4

(SEQ ID NO. 1 + SEQ ID NO. 80)

MALPVTALLLPLALLLHAARP`EVQLQQSGPELVKPGASVKMSCKASGYIFTSYVMYWVKQKPGQGLEWIGYINPY`

`NDGTKYNEKFKGKATLTSDKSSSTAYMELSSLTSEDSAVYYCARYYDYDYYFDYWGQGTTLTVSS`GGGGSGGGGSG

GGGS`DIQMTQSPSSLSASLGGKVTITCKASQDINKYIAWYQHKPGKGPRLLIHYTSTLQPGIPSRFSGSGSGRDYSFSI`

`SNLEPEDIATYYCLQYDYLWTFGGGTKLEIK`TTTPAPRPPTPAPTIASQPLSLRPEACRPAAGGAVHTRGLDFACDIIS

FFLALTSTALLFLLFFLTLRFSVVKRGRKKLLYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQKDKMAEAYSEIGMKGERRRGKGHD

GLYQGLSTATKDTYDALHMQALPPR sc M29 CAR-v5

(SEQ ID NO. 1 + SEQ ID NO. 81)

MALPVTALLLPLALLLHAARP`EVQLQQSGPELVKPGASVKMSCKASGYIFTSYVMYWVKQKPGQGLEWIGYINPY`

`NDGTKYNEKFKGKATLTSDKSSSTAYMELSSLTSEDSAVYYCARYYDYDYYFDYWGQGTTLTVSS`GGGGSGGGGSG

GGGS`DIQMTQSPSSLSASLGGKVTITCKASQDINKYIAWYQHKPGKGPRLLIHYTSTLQPGIPSRFSGSGSGRDYSFSI`

`SNLEPEDIATYYCLQYDYLWTFGGGTKLEIK`EPKSPDKTHTCPPCPAPPVAGPSVFLFPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIYIWAPLAGTCGVLLLSLVITLYCKRGRKKLLYIFKQPFMR

QEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc M29 CAR-v6

(SEQ ID NO. 1 + SEQ ID NO. 82)

MALPVTALLLPLALLLHAARP`EVQLQQSGPELVKPGASVKMSCKASGYIFTSYVMYWVKQKPGQGLEWIGYINPY`

`NDGTKYNEKFKGKATLTSDKSSSTAYMELSSLTSEDSAVYYCARYYDYDYYFDYWGQGTTLTVSS`GGGGSGGGGSG

GGGS`DIQMTQSPSSLSASLGGKVTITCKASQDINKYIAWYQHKPGKGPRLLIHYTSTLQPGIPSRFSGSGSGRDYSFSI`

`SNLEPEDIATYYCLQYDYLWTFGGGTKLEIK`EPKSPDKTHTCPPCPAPPVAGPSVFLFPPKPKDTLMIARTPEVTCVV

VDVSHEDPEVKFNWYVDGVEVHNAKTKPREEQYNSTYRWSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSDGSFFLYSKLTVDKSR

WQQGNVFSCSVMHEALHNHYTQKSLSLSPGKIISFFLALTSTALLFLLFFLTLRFSWKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR sc M2 CAR-v1

(SEQ ID NO. 1 + SEQ ID NO. 83)

MALPVTALLLPLALLLHAARP`EVQLQQSGPELVKPGASVKMSCKASGYIFTSYVMYWVKQKPGQGLEWIGYINPY`

`NDGTKYNEKFKGKATLTSDKSSSTAYMELNSLTSEDSAVYYCTRDDGYYDYAMDYWGQGTSVTVSS`GGGGSGGG

GSGGGGS`DIQMTQSPSSLSASLGERVSLTCRASQEISVYLSWLQQKPDGTIKRLIYAASTLDSGVPERFSGSRSGSDY`

SLTISSLESEDFADYYCLQYASYPYTFGGGTKLEIKRGLAVSTISSFFPPGYQIYIWAPLAGTCGVLLLSLVITLYCKRGRK

KLLYIFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKDTYDALHMQALPPR sc M2 CAR-v2

(SEQ ID NO. 1 + SEQ ID NO. 84)

MALPVTALLLPLALLLHAARPEVQLQQSGPELVKPGASVKMSCKASGYIFTSYVMYWVKQKPGQGLEWIGYINPY

NDGTKYNEKFKGKATLTSDKSSSTAYMELNSLTSEDSAVYYCTRDDGYYDYAMDYWGQGTSVTVSSGGGGSGGG

GSGGGGSDIQMTQSPSSLSASLGERVSLTCRASQEISVYLSWLQQKPDGTIKRLIYAASTLDSGVPERFSGSRSGSDY

SLTISSLESEDFADYYCLQYASYPYTFGGGTKLEIKRGLAVSTISSFFPPGYQIISFFLALTSTALLFLLFFLTLRFSVVKRGR

KKLLYIFKQPFMRPVQTTQEEDGCSCRFPEEEEGGCELRVKFSRSADAPAYQQGQNQLYNELNLGRREEYDVLDKR

RGRDPEMGGKPRRKNPQEGLYNELQKDKMAEAYSEIGMKGERRRGKGHDGLYQGLSTATKDTYDALHMQALPP

R sc M2 CAR-v3

(SEQ ID NO. 1 + SEQ ID NO. 85)

MALPVTALLLPLALLLHAARPEVQLQQSGPELVKPGASVKMSCKASGYIFTSYVMYWVKQKPGQGLEWIGYINPY

NDGTKYNEKFKGKATLTSDKSSSTAYMELNSLTSEDSAVYYCTRDDGYYDYAMDYWGQGTSVTVSSGGGGSGGG

GSGGGGSDIQMTQSPSSLSASLGERVSLTCRASQEISVYLSWLQQKPDGTIKRLIYAASTLDSGVPERFSGSRSGSDY

SLTISSLESEDFADYYCLQYASYPYTFGGGTKLEIKRTTTPAPRPPTPAPTIASQPLSLRPEACRPAAGGAVHTRGLDFA

CDIYIWAPLAGTCGVLLLSLVITLYCKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR sc M2 CAR-v4

(SEQ ID NO. 1 + SEQ ID NO. 86)

MALPVTALLLPLALLLHAARPEVQLQQSGPELVKPGASVKMSCKASGYIFTSYVMYWVKQKPGQGLEWIGYINPY

NDGTKYNEKFKGKATLTSDKSSSTAYMELNSLTSEDSAVYYCTRDDGYYDYAMDYWGQGTSVTVSSGGGGSGGG

GSGGGGSDIQMTQSPSSLSASLGERVSLTCRASQEISVYLSWLQQKPDGTIKRLIYAASTLDSGVPERFSGSRSGSDY

SLTISSLESEDFADYYCLQYASYPYTFGGGTKLEIKRTTTPAPRPPTPAPTIASQPLSLRPEACRPAAGGAVHTRGLDFA

CDIISFFLALTSTALLFLLFFLTLRFSVVKRGRKKLLYIFKQPFMRPVQTTQEEDGCSCRFPEEEEGGCELRVKFSRSADA

PAYQQGQNQLYNELNLGRREEYDVLDKRRGRDPEMGGKPRRKNPQEGLYNELQKDKMAEAYSEIGMKGERRRG

KGHDGLYQGLSTATKDTYDALHMQALPPR sc M2 CAR-v5

(SEQ ID NO. 1 + SEQ ID NO. 87)

MALPVTALLLPLALLLHAARPEVQLQQSGPELVKPGASVKMSCKASGYIFTSYVMYWVKQKPGQGLEWIGYINPY

NDGTKYNEKFKGKATLTSDKSSSTAYMELNSLTSEDSAVYYCTRDDGYYDYAMDYWGQGTSVTVSSGGGGSGGG

GSGGGGSDIQMTQSPSSLSASLGERVSLTCRASQEISVYLSWLQQKPDGTIKRLIYAASTLDSGVPERFSGSRSGSDY

SLTISSLESEDFADYYCLQYASYPYTFGGGTKLEIKREPKSPDKTHTCPPCPAPPVAGPSVFLFPPKPKDTLMIARTPEV

TCVVVDVSHEDPEVKFNWYVDGVEVHNAKTKPREEQYNSTYRWSVLTVLHQDWLNGKEYKCKVSNKALPAPIEK

TISKAKGQPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGKIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR sc M2 CAR-v6

(SEQ ID NO. 1 + SEQ ID NO. 88)

MALPVTALLLPLALLLHAARPEVQLQQSGPELVKPGASVKMSCKASGYIFTSYVMYWVKQKPGQGLEWIGYINPY

NDGTKYNEKFKGKATLTSDKSSSTAYMELNSLTSEDSAVYYCTRDDGYYDYAMDYWGQGTSVTVSSGGGGSGGG

GSGGGGSDIQMTQSPSSLSASLGERVSLTCRASQEISVYLSWLQQKPDGTIKRLIYAASTLDSGVPERFSGSRSGSDY

SLTISSLESEDFADYYCLQYASYPYTFGGGTKLEIKREPKSPDKTHTCPPCPAPPVAGPSVFLFPPKPKDTLMIARTPEV

TCVVVDVSHEDPEVKFNWYVDGVEVHNAKTKPREEQYNSTYRWSVLTVLHQDWLNGKEYKCKVSNKALPAPIEK

TISKAKGQPREPQVYTLPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGKIISFFUVLTSTALLFLLFFLTLRFSVVKRGRKKLLYIFKQPFMR

PVQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR sc M5 CAR-v1

(SEQ ID NO. 1 + SEQ ID NO. 89)

MALPVTALLLPLALLLHAARPEVQLQQSGAELVRPGASVKLSCTASGFNIKDDYIHWVKQRPEQGLEWIGWIDPEW

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDTYDALHMQALPPR sc M5 CAR-v2

(SEQ ID NO. 1 + SEQ ID NO. 90)

MALPVTALLLPLALLLHAARPEVQLQQSGAELVRPGASVKLSCTASGFNIKDDYIHWVKQRPEQGLEWIGWIDPEK

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKGLAVSTISSFFPPGYQIISFFLALTSTALLFLLFFLTLRFSVVKRGRK

KLLYIFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKDTYDALHMQALPPR sc M5 CAR-v3

(SEQ ID NO. 1 + SEQ ID NO. 91)

MALPVTALLLPLALLLHAARPEVQLQQSGAELVRPGASVKLSCTASGFNIKDDYIHWVKQRPEQGLEWIGWIDPEK

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKTTTPAPRPPTPAPTIASQPLSLRPEACRPAAGGAVHTRGLDFAC

DIYIWAPLAGTCGVLLLSLVITLYCKRGRKKLLYIFKQPFMRPVQTTQEEDGCSCRFPEEEEGGCELRVKFSRSADAPA

YQQGQNQLYNELNLGRREEYDVLDKRRGRDPEMGGKPRRKNPQEGLYNELQKDKMAEAYSEIGMKGERRRGKG

HDGLYQGLSTATKDTYDALHMQALPPR sc M5 CAR-v4

(SEQ ID NO. 1 + SEQ ID NO. 92)

MALPVTALLLPLALLLHAARPEVQLQQSGAELVRPGASVKLSCTASGFNIKDDYIHWVKQRPEQGLEWIGWIDPEK

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKTTTPAPRPPTPAPTIASQPLSLRPEACRPAAGGAVHTRGLDFAC

DIISFFLALTSTALLFLLFFLTLRFSWKRGRKKLLYIFKQPFMRPVQTTQEEDGCSCRFPEEEEGGCELRVKFSRSADAP

AYQQGQNQLYNELNLGRREEYDVLDKRRGRDPEMGGKPRRKNPQEGLYNELQKDKMAEAYSEIGMKGERRRGK

GHDGLYQGLSTATKDTYDALHMQALPPR sc M5 CAR-v5

(SEQ ID NO. 1 + SEQ ID NO. 93)

MALPVTALLLPLALLLHAARPEVQLQQSGAELVRPGASVKLSCTASGFNIKDDYIHWVKQRPEQGLEWIGWIDPEK

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIYIWAPLAGTCGVLLLSLVITLYCKRGRKKLLYIFKQPFMRPV

QTTQEEDGCSCRFPEEEEGGCELRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR sc M5 CAR-v6

(SEQ ID NO. 1 + SEQ ID NO. 94)

MALPVTALLLPLALLLHAARPEVQLQQSGAELVRPGASVKLSCTASGFNIKDDYIHWVKQRPEQGLEWIGWIDPEK

GDTAYASKFQDKATITSDTSSNTAYLQLSSLTSEDTAVYYCTLTGRFDYWGQGTTLTVSSGGGGSGGGGSGGGGSD

IVMSQSPSSLAVSVGEKVTMSCKSSQSLLYSSNQKNNLAWYQQKPGQSPKLLIYWASTRESGVPDRFTGSGSGTDF

TLTISSVQAEDLAVYYCQQYYSYRTFGGGTKLEIKEPKSPDKTHTCPPCPAPPVAGPSVFLFPPKPKDTLMIARTPEVT

CVVVDVSHEDPEVKFNWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPGKIISFFLALTSTALLFLLFFLTLRFSVVKRGRKKLLYIFKQPFMRP

VQTTQEEDGCSCRFPEEEEGGCELRVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDTYDALHMQALPPR

-continued sc G12 CAR-v1
(SEQ ID NO. 1 + SEQ ID NO. 95)
MALPVTALLLPLALLLHAARPQVQLQQPGAELVKPGASMKMSCKASGYTFPSSNIHWLKQTPGQGLEWIGVIYPG

NGDTSYNQKFKDKATLTTDKSSSTAYMQLSSLTSEDSAIYFCARVYNWHFDVWGAGTTVTVSSGGGGSGGGGSG

GGGSNIVLTQSPASLAVSLGQRATISCRASESVDGYGDIFMLWYQQKPGQPPKLUYFASNLESGVPARFSGSGSRT

DFTLTIDPVEADDAATYYCQQNNEDPYTFGGGTKLEIKRGLAVSTISSFFPPGYQIYIWAPLAGTCGVLLLSLVITLYCK

RGRKKLLYIFKQPFMRPVQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQGLSTATKDTYDALHMQA

LPPR sc G12 CAR-v2
(SEQ ID NO. 1 + SEQ ID NO. 96)
MALPVTALLLPLALLLHAARPQVQLQQPGAELVKPGASMKMSCKASGYTFPSSNIHWLKQTPGQGLEWIGVIYPG

NGDTSYNQKFKDKATLTTDKSSSTAYMQLSSLTSEDSAIYFCARVYNWHFDVWGAGTTVTVSSGGGGSGGGGSG

GGGSNIVLTQSPASLAVSLGQRATISCRASESVDGYGDIFMLWYQQKPGQPPKLUYFASNLESGVPARFSGSGSRT

DFTLTIDPVEADDAATYYCQQNNEDPYTFGGGTKLEIKRGLAVSTISSFFPPGYQIISFFLALTSTALLFLLFFLTLRFSVV

KRGRKKLLYIFKQPFMRPVQTTQEEDGCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGKGHDGLYQGLSTATKDTYDALHMQ

ALPPR sc G12 CAR-v3
(SEQ ID NO. 1 + SEQ ID NO. 97)
MALPVTALLLPLALLLHAARPQVQLQQPGAELVKPGASMKMSCKASGYTFPSSNIHWLKQTPGQGLEWIGVIYPG

NGDTSYNQKFKDKATLTTDKSSSTAYMQLSSLTSEDSAIYFCARVYNWHFDVWGAGTTVTVSSGGGGSGGGGSG

GGGSNIVLTQSPASLAVSLGQRATISCRASESVDGYGDIFMLWYQQKPGQPPKLUYFASNLESGVPARFSGSGSRT

DFTLTIDPVEADDAATYYCQQNNEDPYTFGGGTKLEIKRTTTPAPRPPTPAPTIASQPLSLRPEACRPAAGGAVHTR

GLDFACDIYIWAPLAGTCGVLLLSLVITLYCKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGLYNELQKDKMAEAYSEIGMKGE

RRRGKGHDGLYQGLSTATKDTYDALHMQALPPR sc G12 CAR-v4
(SEQ ID NO. 1 + SEQ ID NO. 98)
MALPVTALLLPLALLLHAARPQVQLQQPGAELVKPGASMKMSCKASGYTFPSSNIHWLKQTPGQGLEWIGVIYPG

NGDTSYNQKFKDKATLTTDKSSSTAYMQLSSLTSEDSAIYFCARVYNWHFDVWGAGTTVTVSSGGGGSGGGGSG

GGGSNIVLTQSPASLAVSLGQRATISCRASESVDGYGDIFMLWYQQKPGQPPKLUYFASNLESGVPARFSGSGSRT

DFTLTIDPVEADDAATYYCQQNNEDPYTFGGGTKLEIKRTTTPAPRPPTPAPTIASQPLSLRPEACRPAAGGAVHTR

GLDFACDIISFFLALTSTALLFLLFFLTLRFSVVKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAYSEIGMKG

ERRRGKGHDGLYQGLSTATKDTYDALHMQALPPR sc G12 CAR-v5

(SEQ ID NO. 1 + SEQ ID NO. 99)

MALPVTALLLPLALLLHAARP`QVQLQQPGAELVKPGASMKMSCKASGYTFPSSNIHWLKQTPGQGLEWIGVIYPG`

`NGDTSYNQKFKDKATLTTDKSSSTAYMQLSSLTSEDSAIYFCARVYNWHFDVWGAGTTVTVSS`GGGGSGGGGSG

GGGS`NIVLTQSPASLAVSLGQRATISCRASESVDGYGDIFMLWYQQKPGQPPKLUYFASNLESGVPARFSGSGSRT`

`DFTLTIDPVEADDAATYYCQQNNEDPYTFGGGTKLEIKR`EPKSPDKTHTCPPCPAPPVAGPSVFLFPPKPKDTLMIA

RTPEVTCWVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKIYIWAPLAGTCGVLLLSLVITLYCKRGRKKLLYIFKQP

FMRPVQTTQEEDGCSCRFPEEEEGGCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTATKDTYDALHMQALPPR sc G12 CAR-v6

(SEQ ID NO. 1 + SEQ ID NO. 100)

MALPVTALLLPLALLLHAARP`QVQLQQPGAELVKPGASMKMSCKASGYTFPSSNIHWLKQTPGQGLEWIGVIYPG`

`NGDTSYNQKFKDKATLTTDKSSSTAYMQLSSLTSEDSAIYFCARVYNWHFDVWGAGTTVTVSS`GGGGSGGGGSG

GGGS`NIVLTQSPASLAVSLGQRATISCRASESVDGYGDIFMLWYQQKPGQPPKLUYFASNLESGVPARFSGSGSRT`

`DFTLTIDPVEADDAATYYCQQNNEDPYTFGGGTKLEIKR`EPKSPDKTHTCPPCPAPPVAGPSVFLFPPKPKDTLMIA

RTPEVTCVVVDVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKIISFFLALTSTALLFLLFFLTLRFSVVKRGRKKLLYIFKQ

PFMRPVQTTQEEDGCSCRFPEEEEGGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLSTATKDTYDALHMQALPPR sc 21.26 CAR-v1

(SEQ ID NO. 1 + SEQ ID NO. 101)

MALPVTALLLPLALLLHAARP`QVQLQQPGAELVKPGTSVKLSCKASGYTFTRYWMHWVKQRPGQGLEWIGMIHP`

`SSGSTSYNEKVKNKATLTVDRSSTTAYMQLSSLTSEDSAVYYCARDGDYYYGTGDYWGQGTTLTVSS`GGGGSGGG

GSGGGGS`QIVLSQSPAILSASPGEKVTMTCRASSSINYMHWYQQKPGSSPKPWIFATSNLASGVPSRFSGSGSGTS`

`YSLTISRVEAEDAATYYCQQWRSDRALTFGAGTKLEL`GLAVSTISSFFPPGYQIYIWAPLAGTCGVLLLSLVITLYCKRG

RKKLLYIFKQPFMRPVQTTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKGHDGLYQGLSTATKDTYDALHMQALP

PR sc 21.26 CAR-v2

(SEQ ID NO. 1 + SEQ ID NO. 102)

MALPVTALLLPLALLLHAARP`QVQLQQPGAELVKPGTSVKLSCKASGYTFTRYWMHWVKQRPGQGLEWIGMIHP`

`SSGSTSYNEKVKNKATLTVDRSSTTAYMQLSSLTSEDSAVYYCARDGDYYYGTGDYWGQGTTLTVSS`GGGGSGGG

GSGGGGS`QIVLSQSPAILSASPGEKVTMTCRASSSINYMHWYQQKPGSSPKPWIFATSNLASGVPSRFSGSGSGTS`

`YSLTISRVEAEDAATYYCQQWRSDRALTFGAGTKLEL`GLAVSTISSFFPPGYQIISFFLALTSTALLFLLFFLTLRFSVVKR

GRKKLLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQAL

PPR sc 21.26 CAR-v3

(SEQ ID NO. 1 + SEQ ID NO. 103)

MALPVTALLLPLALLLHAARPQVQLQQPGAELVKPGTSVKLSCKASGYTFTRYWMHWVKQRPGQGLEWIGMIHP

SSGSTSYNEKVKNKATLTVDRSSTTAYMQLSSLTSEDSAVYYCARDGDYYYGTGDYWGQGTTLTVSSGGGGSGGG

GSGGGGSQIVLSQSPAILSASPGEKVTMTCRASSSINYMHWYQQKPGSSPKPWIFATSNLASGVPSRFSGSGSGTS

YSLTISRVEAEDAATYYCQQWRSDRALTFGAGTKLELTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR sc 21.26 CAR-v4

(SEQ ID NO. 1 + SEQ ID NO. 104)

MALPVTALLLPLALLLHAARPQVQLQQPGAELVKPGTSVKLSCKASGYTFTRYWMHWVKQRPGQGLEWIGMIHP

SSGSTSYNEKVKNKATLTVDRSSTTAYMQLSSLTSEDSAVYYCARDGDYYYGTGDYWGQGTTLTVSSGGGGSGGG

GSGGGGSQIVLSQSPAILSASPGEKVTMTCRASSSINYMHWYQQKPGSSPKPWIFATSNLASGVPSRFSGSGSGTS

YSLTISRVEAEDAATYYCQQWRSDRALTFGAGTKLELTTTPAPRPPTPAPTIASQPLSLRPEACRPAAGGAVHTRGL

DFACDIISFFLALTSTALLFLLFFLTLRFSWKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAEAYSEIGMKGER

RRGKGHDGLYQGLSTATKDTYDALHMQALPPR sc 21.26 CAR-v5

(SEQ ID NO. 1 + SEQ ID NO. 105)

MALPVTALLLPLALLLHAARPQVQLQQPGAELVKPGTSVKLSCKASGYTFTRYWMHWVKQRPGQGLEWIGMIHP

SSGSTSYNEKVKNKATLTVDRSSTTAYMQLSSLTSEDSAVYYCARDGDYYYGTGDYWGQGTTLTVSSGGGGSGGG

GSGGGGSQIVLSQSPAILSASPGEKVTMTCRASSSINYMHWYQQKPGSSPKPWIFATSNLASGVPSRFSGSGSGTS

YSLTISRVEAEDAATYYCQQWRSDRALTFGAGTKLELEPKSPDKTHTCPPCPAPPVAGPSVFLFPPKPKDTLMIARTP

EVTCVWDVSHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGKIYIWAPLAGTCGVLLLSLVITLYCKRGRKKLLYIFKQPFM

RPVQTTQEEDGCSCRFPEEEEGGCELRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKDTYDALHMQALPPR sc 21.26 CAR-v6

(SEQ ID NO. 1 + SEQ ID NO. 106)

MALPVTALLLPLALLLHAARPQVQLQQPGAELVKPGTSVKLSCKASGYTFTRYWMHWVKQRPGQGLEWIGMIHP

SSGSTSYNEKVKNKATLTVDRSSTTAYMQLSSLTSEDSAVYYCARDGDYYYGTGDYWGQGTTLTVSSGGGGSGGG

GSGGGGSQIVLSQSPAILSASPGEKVTMTCRASSSINYMHWYQQKPGSSPKPWIFATSNLASGVPSRFSGSGSGTS

YSLTISRVEAEDAATYYCQQWRSDRALTFGAGTKLELEPKSPDKTHTCPPCPAPPVAGPSVFLFPPKPKDTLMIARTP

EVTCVVVDVSHEDPEVKFNWYVDGVEVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGKIISFFLALTSTALLFLLFFLTLRFSVVKRGRKKLLYIFKQPF

MRPVQTTQEEDGCSCRFPEEEEGGCELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTATKDTYDALHMQALPPR sc 1075.7 CAR-v1
(SEQ ID NO. 1 + SEQ ID NO. 107)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELGLAVSTISSFFPPGYQIYIWAPLAGTCGVLLLSLVITLYCKR

GRKKLLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQAL

PPR sc 1075.7 CAR-v2
(SEQ ID NO. 1 + SEQ ID NO. 108)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELGLAVSTISSFFPPGYQIISFFLALTSTALLFLLFFLTLRFSVVK

RGRKKLLYIFKQPFMRPVQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQGLSTATKDTYDALHMQA

LPPR sc 1075.7 CAR-v3
(SEQ ID NO. 1 + SEQ ID NO. 109)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELTTTPAPRPPTPAPTIASQPLSLRPEACRPAAGGAVHTRGL

DFACDIYIWAPLAGTCGVLLLSLVITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR sc 1075.7 CAR-v4
(SEQ ID NO. 1 + SEQ ID NO. 110)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

```
GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELTTTPAPRPPTPAPTIASQPLSLRPEACRPAAGGAVHTRGL

DFACDIISFFLALTSTALLFLLFFLTLRFSWKRGRKKLLYIFKQPFMRPVQTTQEEDGCSCRFPEEEEGGCELRVKFSRS

ADAPAYQQGQNQLYNELNLGRREEYDVLDKRRGRDPEMGGKPRRKNPQEGLYNELQKDKMAEAYSEIGMKGER

RRGKGHDGLYQGLSTATKDTYDALHMQALPPR sc 1075.7 CAR-v5
                                                  (SEQ ID NO. 1 + SEQ ID NO. 111)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELEPKSPDKTHTCPPCPAPPVAGPSVFLFPPKPKDTLMIART

PEVTCVWDVSHEDPEVKFNWYVDGVEVHNAKTKPREEQYNSTYRWSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGKIYIWAPLAGTCGVLLLSLVITLYCKRGRKKLLYIFKQP

RPVQTTQEEDGCSCRFPEEEEGGCELRVKFSRSADAPAYQQGQNQLYNELNLGRREEYDVLDKRRGRDPEMGGKP

RRKNPQEGLYNELQKDKMAEAYSEIGMKGERRGKGHDGLYQGLSTATKDTYDALHMQALPPR sc 1075.7 CAR-v6
                                                  (SEQ ID NO. 1 + SEQ ID NO. 112)
MALPVTALLLPLALLLHAARPDIQLQESGPGLVKPSQSLSLTCSVTGYSITSAYYWNWIRQFPGNKLEWMGYISYDG

RNNYNPSLKNRISITRDTSKNQFFLKLNSVTTEDTATYYCAKEGDYDVGNYYAMDYWGQGTSVTVSSGGGGSGGG

GSGGGGSENVLTQSPAIMSASPGEKVTMTCRASSNVISSYVHWYQQRSGASPKLWIYSTSNLASGVPARFSGSGS

GTSYSLTISSVEAEDAATYYCQQYSGYPLTFGAGTKLELEPKSPDKTHTCPPCPAPPVAGPSVFLFPPKPKDTLMIART

PEVTCVVVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGKIISFFLALTSTALLFLLFFLTLRFSVVKRGRKKLLYIFKQPF

MRPVQTTQEEDGCSCRFPEEEEGGCELRVKFSRSADAPAYQQGQNQLYNELNLGRREEYDVLDKRRGRDPEMGG

KPRRKNPQEGLYNELQKDKMAEAYSEIGMKGERRGKGHDGLYQGLSTATKDTYDALHMQALPPR
```

REFERENCES

Arbiza J., Taylor G., López J. A., Furze J., Wyld S., Whyte P., Stott E. J., Wertz G., Sullender W., Trudel M., et al. (1992), Characterization of two antigenic sites recognized by neutralizing monoclonal antibodies directed against the fusion glycoprotein of human respiratory syncytial virus. *J Gen Virol.;* 73 (9):2225-34).

Arimondo, P. B., C. J. Thomas, et al. (2006). "Exploring the cellular activity of camptothecin-triple-helix-forming oligonucleotide conjugates." Mol Cell Biol 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." Rna 13(6): 803-10.

Bakker A B, Van den Oudenrijn S, Bakker A Q, Feller N, van Meijer M, Bia J A, Jongeneelen M A, Visser T J, Bijl N, Geuijen C A, Marissen W E, Radosevic K, Throsby M, Schuurhuis G J, Ossenkoppele G J, de Kruif J, Goudsmit J, Kruisbeek A M, (2004) "C-type lectin-like molecule-1: a novel myeloid cell surface marker associated with acute myeloid leukemia", Cancer Res. 64(22):8443-50).

Bardenheuer, W., K. Lehmberg, et al. (2005). "Resistance to cytarabine and gemcitabine and in vitro selection of transduced cells after retroviral expression of cytidine deaminase in human hematopoietic progenitor cells." Leukemia 19(12): 2281-8.

Betts, M. R., J. M. Brenchley, et al. (2003). "Sensitive and viable identification of antigen-specific CD8+ T cells by a flow cytometric assay for degranulation." J Immunol Methods 281(1-2): 65-78.

Bierer, B. E., G. Hollander, et al. (1993). "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Brewin, J., C. Mancao, et al. (2009). "Generation of EBV-specific cytotoxic T cells that are resistant to calcineurin inhibitors for the treatment of posttransplantation lymphoproliferative disease." *Blood* 114(23): 4792-803.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Dasgupta, A., D. McCarty, et al. (2011). "Engineered drug-resistant immunocompetent cells enhance tumor cell killing during a chemotherapy challenge." *Biochem Biophys Res Commun* 391(1): 170-5.

Deltcheva, E., K. Chylinski, et al. (2011). "CRISPR RNA maturation by trans-encoded small RNA and host factor RNase III." *Nature* 471(7340): 602-7.

Deng, D., C. Yan, et al. (2012). "Structural basis for sequence-specific recognition of DNA by TAL effectors." *Science* 335(6069): 720-3.

Donnelly, M. and G. Elliott (2001). "Nuclear localization and shuttling of herpes simplex virus tegument protein VP13/14." *J Virol* 75(6): 2566-74.

Doronina, V. A., C. Wu, et al. (2008). "Site-specific release of nascent chains from ribosomes at a sense codon." *Mol Cell Biol* 28(13): 4227-39.

Eisenschmidt, K., T. Lanio, et al. (2005). "Developing a programmed restriction endonuclease for highly specific DNA cleavage." *Nucleic Acids Res* 33(22): 7039-47.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Geissler, R., H. Scholze, et al. (2011). "Transcriptional activators of human genes with programmable DNA-specificity." *PLoS One* 6(5): e19509.

Hacke, K., J. A. Treger, et al. (2013). "Genetic modification of mouse bone marrow by lentiviral vector-mediated delivery of hypoxanthine-Guanine phosphoribosyltransferase short hairpin RNA confers chemoprotection against 6-thioguanine cytotoxicity." *Transplant Proc* 45(5): 2040-4.

Henderson, D. J., I. Naya, et al. (1991). "Comparison of the effects of FK-506, cyclosporin A and rapamycin on IL-2 production." *Immunology* 73(3): 316-21.

Huang, P., A. Xiao, et al. (2011). "Heritable gene targeting in zebrafish using customized TALENs." *Nat Biotechnol* 29(8): 699-700.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Jonnalagadda, M., C. E. Brown, et al. (2013). "Engineering human T cells for resistance to methotrexate and mycophenolate mofetil as an in vivo cell selection strategy." *PLoS One* 8(6): e65519.

Kalish, J. M. and P. M. Glazer (2005). "Targeted genome modification via triple helix formation." *Ann N Y Acad Sci* 1058: 151-61.

Kushman, M. E., S. L. Kabler, et al. (2007). "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1." Carcinogenesis 28(1): 207-14.

Larsen H Ø, Roug A S, Just T, Brown G D, Hokland P (2012), "Expression of the hMICL in acute myeloid leukemia-a highly reliable disease marker at diagnosis and during follow-up". Cytometry B Clin Cytom. 82(1): 3-8).

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knockout and gene replacement in eukaryotes." *Nucleic Acids Res* 39(14): 6315-25.

Liu, J., M. W. Albers, et al. (1992). "Inhibition of T cell signaling by immunophilin-ligand complexes correlates with loss of calcineurin phosphatase activity." *Biochemistry* 31(16): 3896-901.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Mali, P., L. Yang, et al. (2013). "RNA-guided human genome engineering via Cas9." *Science* 339(6121): 823-6.

McLaughlin P, et al. (1998) Rituximab chimeric anti-CD20 monoclonal antibody therapy for relapsed indolent lymphoma: half of patients respond to a four-dose treatment program. J Clin Oncol. 16(8):2825-33

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Nivens, M. C., T. Felder, et al. (2004). "Engineered resistance to camptothecin and antifolates by retroviral coexpression of tyrosyl DNA phosphodiesterase-I and thymidylate synthase." *Cancer Chemother Pharmacol* 53(2): 107-15.

Paques, F. and P. Duchateau (2007). "Meganucleases and DNA double-strand break-induced recombination: perspectives for gene therapy." *Curr Gene Ther* 7(1): 49-66.

Park, T. S., S. A. Rosenberg, et al. (2011). "Treating cancer with genetically engineered T cells." *Trends Biotechnol* 29(11): 550-7.

Peipp, M., D. Saul, et al. (2004). "Efficient eukaryotic expression of fluorescent scFv fusion proteins directed against CD antigens for FACS applications." *J Immunol Methods* 285(2): 265-80.

Perrin, A., M. Buckle, et al. (1993). "Asymmetrical recognition and activity of the I-SceI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Ravetch, J. V., Perussia, B., (1989). "Alternative membrane forms of Fc gamma RIII(CD16) on human natural killer cells and neutrophils. Cell type-specific expression of two genes that differ in single nucleotide substitutions". J. Exp. Med. 170, 481-497.

Riemer A. B., Kurz H., Klinger, M., Scheiner, O., Zielinski, C., and Jensen-Jarolim, E. (2005), Vaccination with cetuximab mimotopes and biological properties of induced anti-epidermal growth factor receptor antibodies, *J Natl Cancer Inst.;* 97(22):1663-70)

Rouet, P., F. Smih, et al. (1994). "Introduction of double-strand breaks into the genome of mouse cells by expression of a rare-cutting endonuclease." *Mol Cell Biol* 14(12): 8096-106.

Sander, J. D., L. Cade, et al. (2011). "Targeted gene disruption in somatic zebrafish cells using engineered TALENs." *Nat Biotechnol* 29(8): 697-8.

Sangiolo, D., M. Lesnikova, et al. (2007). "Lentiviral vector conferring resistance to mycophenolate mofetil and sensitivity to ganciclovir for in vivo T-cell selection." *Gene Ther* 14(21): 1549-54.

Schweitzer, B. I., A. P. Dicker, et al. (1990). "Dihydrofolate reductase as a therapeutic target." *Faseb J* 4(8): 2441-52.

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." *J Gene Med* 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." *Mol Ther* 3(1): 88-96.

Tesson, L., C. Usal, et al. (2011). "Knockout rats generated by embryo microinjection of TALENs." *Nat Biotechnol* 29(8): 695-6.

Van Rhenen A, van Dongen G A, Kelder A, Rombouts E J, Feller N, Moshaver B, Stigter-van Walsum M, Zweegman S, Ossenkoppele G J, Jan Schuurhuis G Blood. (2007) "The novel AML stem cell associated antigen CLL-1 aids in discrimination between normal and leukemic stem cells. *Blood,* 110(7):2659-66.

Weber, E., R. Gruetzner, et al. (2011). "Assembly of designer TAL effectors by Golden Gate cloning." *PLoS One* 6(5): e19722.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." *Mol Ther* 14(2): 236-44.

Zhang Hongyong, Luo Juntao, Li Yuanpei, Henderson Paul T, Wachsmann-Hogiu Sebastian, Lam Kit S., and Pan Chong-xian (2011) «Characterization of high-affinity peptides and their feasibility for use in nanotherapeutics targeting leukemia stem cells" *Nanomedicine;* 8(7): 1116-1124.

Zhang, F., L. Cong, et al. (2011). "Efficient construction of sequence-specific TAL effectors for modulating mammalian transcription." *Nat Biotechnol* 29(2): 149-53.

Zielske, S. P., J. S. Reese, et al. (2003). "In vivo selection of MGMT(P140K) lentivirus-transduced human NOD/SCID repopulating cells without pretransplant irradiation conditioning. "J Clin Invest 112(10)1561-70.

The invention claimed is:

1. An isolated Chimeric Antigen Receptor (CAR) comprising:
- an extracellular ligand binding domain that binds to C-type lectin molecule 1 (CCL1) comprising a heavy chain variable ($V_H$) region and a light chain variable ($V_L$) region wherein:
  - (i) the $V_H$ region comprises CDRs having the amino acid sequences set forth in SEQ ID NO: 131, SEQ ID NO: 132 and SEQ ID NO: 133, and the $V_L$ region comprises CDRs having the amino acid sequences set forth in SEQ ID NO: 134, SEQ ID NO: 135 and SEQ ID NO: 136; or
  - (ii) the $V_H$ region comprises CDRs having the amino acid sequences set forth in SEQ ID NO: 161, SEQ ID NO: 162 and SEQ ID NO: 163, and the $V_L$ region comprises CDRs having the amino acid sequences set forth in SEQ ID NO: 164, SEQ ID NO: 165 and SEQ ID NO: 166;
- a hinge region comprising an FcγRIIIα hinge having the amino acid sequence set forth in SEQ ID NO: 3, a CD8α hinge having the amino acid sequence set forth in SEQ ID NO: 4 or an IgG1 hinge having the amino acid sequence set forth in SEQ ID NO: 5;
- a CD8α transmembrane domain having the amino acid sequence set forth in SEQ ID NO: 6; and
- a cytoplasmic signaling domain comprising a CD3 zeta signaling domain having the amino acid sequence set forth in SEQ ID NO: 9, and a 4-1 BB co-stimulatory domain having the amino acid sequence set forth in SEQ ID NO: 8.

2. The CAR according to claim 1, further comprising at least one amino acid sequence of an epitope recognized by a therapeutic monoclonal antibody, wherein the epitope is located:
- (i) between the $V_H$ and $V_L$ regions of the CAR;
- (ii) at the N-terminus of the $V_H$ region of the CAR; or
- (iii) between the $V_L$ region and the hinge region of the CAR;

and wherein the amino acid sequence is selected from the group consisting of: SEQ ID NO: 113, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, and SEQ ID NO: 199.

3. The CAR of claim 1, wherein:
- the $V_H$ region comprises the amino acid sequence set forth in SEQ ID NO: 15, and wherein the $V_L$ region comprises the amino acid sequence set forth in SEQ ID NO: 16; or
- the $V_H$ region comprises the amino acid sequence set forth in SEQ ID NO: 25, and wherein the $V_L$ region comprises the amino acid sequence set forth in SEQ ID NO: 26.

4. The CAR according to claim 2, wherein the amino acid sequence of the epitope is the amino acid sequence set forth in SEQ ID NO: 113.

5. An isolated polynucleotide encoding a CAR according to claim 1.

6. An isolated, engineered lymphoid immune cell expressing the CAR according to claim 1, wherein the CAR is cell surface membrane expressed.

7. A method of treating cancer in a human patient having cancer, the method comprising:
administering to the patient an isolated, engineered cytotoxic T cell comprising the CAR according to claim 1, wherein the cancer comprises cells expressing C-type lectin like molecule 1 (CCL1), thereby treating the cancer in the patient.

8. The method of treating according to claim 7, wherein the cancer is a hematological cancer.

9. The CAR according to claim 1, wherein said CAR comprises the amino acid sequence set forth in SEQ ID NO: 55; or the amino acid sequence set forth in SEQ ID NO: 85.

10. A composition comprising the isolated, engineered lymphoid immune cell according to claim 6.

11. The CAR according to claim 2, wherein the CAR comprises the amino acid sequence(s) of one, two, three, or four of said epitopes.

12. The CAR according to claim 11, wherein the extracellular binding domain comprises one of the following sequences:

$V_1$-$L_1$-$V_2$-(L)$_x$-Epitope1-(L)$_x$-;
$V_1$-$L_1$-$V_2$-(L)$_x$-Epitope1-(L)$_x$-Epitope2-(L)$_x$-;
$V_1$-$L_1$-$V_2$-(L)$_x$-Epitope1-(L)$_x$-Epitope2-(L)$_x$-Epitope3-(L)$_x$-;
(L)$_x$-Epitope1-(L)$_x$-$V_1$-$L_1$-$V_2$-;
(L)$_x$-Epitope1-(L)$_x$-Epitope2-(L)$_x$-$V_1$-$L_1$-$V_2$-;
Epitope1-(L)$_x$-Epitope2-(L)$_x$-Epitope3-(L)$_x$-$V_1$-$L_1$-$V_2$-;
(L)$_x$-Epitope1-(L)$_x$-$V_1$-$L_1$-$V_2$-(L)$_x$-Epitope2-(L)$_x$;
(L)$_x$-Epitope1-(L)$_x$-$V_1$-$L_1$-$V_2$-(L)$_x$-Epitope2-(L)$_x$-Epitope3-(L)$_x$-;
(L)$_x$-Epitope1-(L)$_x$-$V_1$-$L_1$-$V_2$-(L)$_x$-Epitope2-(L)$_x$-Epitope3-(L)$_x$-Epitope4-(L)$_x$-;
(L)$_x$-Epitope1-(L)$_x$-Epitope2-(L)$_x$-$V_1$-$L_1$-$V_2$-(L)$_x$-Epitope3-(L)$_x$-;
(L)$_x$-Epitope1-(L)$_x$-Epitope2-(L)$_x$-$V_1$-$L_1$-$V_2$-(L)$_x$-Epitope3-(L)$_x$-Epitope4-(L)$_x$-;
$V_1$-(L)$_x$-Epitope1-(L)$_x$-$V_2$;
$V_1$-(L)$_x$-Epitope1-(L)$_x$-$V_2$-(L)$_x$-Epitope2-(L)$_x$;
$V_1$-(L)$_x$-Epitope1-(L)$_x$-$V_2$-(L)$_x$-Epitope2-(L)$_x$-Epitope3-(L)$_x$;
$V_1$-(L)$_x$-Epitope1-(L)$_x$-$V_2$-(L)$_x$-Epitope2-(L)$_x$-Epitope3-(L)$_x$-Epitope4-(L)$_x$;
(L)$_x$-Epitope1-(L)$_x$-$V_1$-(L)$_x$-Epitope2-(L)$_x$-$V_2$; and
(L)$_x$-Epitope1-(L)$_x$-$V_1$-(L)$_x$-Epitope2-(L)$_x$-$V_2$-(L)$_x$-Epitope3-(L)$_x$;
wherein,
$V_1$ is $V_L$ and $V_2$ is $V_H$ or $V_1$ is $V_H$ and $V_2$ is $V_L$;
$L_1$ is a linker suitable to link the $V_H$ chain to the $V_L$ chain;
L is a linker comprising glycine and serine residues, and each occurrence of L in the extracellular binding domain can be identical or different to other occurrences of L in the same extracellular binding domain; and
x is 0 or 1 and each occurrence of x is selected independently from the others; and
Epitope 1, Epitope 2, Epitope 3 and Epitope 4 are independently selected from monoclonal antibody-specific epitopes comprising an amino acid sequence selected from the group consisting of: SEQ ID NO: 113, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, and SEQ ID NO: 199.

13. An isolated, engineered lymphoid immune cell expressing the CAR according to claim 2, wherein the CAR is cell surface membrane expressed.

14. A method of treating cancer in a human patient having cancer, the method comprising:
administering to the patient an isolated, engineered cytotoxic T cell comprising the CAR according to claim 2, wherein the cancer comprises cells expressing C-type lectin like molecule 1 (CCL1), thereby treating the cancer in the patient.

15. A composition comprising the isolated, engineered lymphoid immune cell expressing the CAR according to claim 13.

16. The method of claim 7, wherein the cancer is acute myelogenous leukemia (AML).

17. The method of claim 14, wherein the cancer is acute myelogenous leukemia (AML).

18. The isolated, engineered lymphoid immune cell of claim 6, wherein the cell comprises an inactivating mutation in at least one gene encoding a T-Cell Receptor (TCR).

19. The isolated, engineered lymphoid immune cell of claim 6, wherein the cell comprises an inactivating mutation in a gene encoding a β2 microglobulin (β2m) or a gene encoding a human leukocyte antigen (HLA).

20. The isolated, engineered lymphoid immune cell of claim 6, wherein the cell comprises an inactivating mutation in a receptor of an immunosuppressive agent or a drug target to confer resistance to the immunosuppressive agent or drug.

21. The isolated, engineered lymphoid immune cell of claim 13, wherein the cell comprises an inactivating mutation in at least one gene encoding a T-Cell Receptor (TCR).

22. The isolated, engineered lymphoid immune cell of claim 13, wherein the cell comprises an inactivating mutation in a gene encoding a β2 microglobulin (β2m) or a gene encoding a human leukocyte antigen (HLA).

23. The isolated, engineered lymphoid immune cell of claim 13, wherein the cell comprises an inactivating mutation in a receptor of an immunosuppressive agent or a drug target to confer resistance to the immunosuppressive agent or drug.

24. A kit comprising the isolated, engineered lymphoid immune cell expressing the CAR according to claim 13, and a therapeutic monoclonal antibody selected from the group consisting of rituximab, palivizumab, cetuximab, and nivolumab.

* * * * *

SEQUENCE LISTING

```
<160> NUMBER OF SEQ ID NOS: 213

<210> SEQ ID NO 1
<211> LENGTH: 20
<212> TYPE: PRT
<213> ORGANISM: artificial sequence
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
            20
```

```
<210> SEQ ID NO 2
<211> LENGTH: 21
<212> TYPE: PRT
<213> ORGANISM: artificial sequence
<220> FEATURE:
<223> OTHER INFORMATION: signal peptide

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
<220> FEATURE:
<223> OTHER INFORMATION: CD8alpha hinge

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110
```

-continued

```
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

Ile Tyr Ile Trp Ala Pro Leu Ala Gly Thr Cys Gly Val Leu Leu Leu
1               5                   10                  15
Ser Leu Val Ile Thr Leu Tyr Cys
            20

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

Ile Ile Ser Phe Phe Leu Ala Leu Thr Ser Thr Ala Leu Leu Phe Leu
1               5                   10                  15
Leu Phe Phe Leu Thr Leu Arg Phe Ser Val Val
            20                  25

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Cys Glu Leu
        35                  40

<210> SEQ ID NO 9
<211> LENGTH: 112
```

```
<212> TYPE: PRT
<213> ORGANISM: homo sapiens
<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 115
<212> TYPE: PRT
<213> ORGANISM: artificial sequence
<220> FEATURE:
<223> OTHER INFORMATION: SC02-357 heavy chain variable region

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Ser
                85                  90                  95

Ser Ser Gly Gly Phe Phe Asp Tyr Trp Gly Gln Gly Thr Leu Val Thr
            100                 105                 110

Val Ser Ser
        115

<210> SEQ ID NO 12
<211> LENGTH: 118
```

```
<212> TYPE: PRT
<213> ORGANISM: artificial sequence
<220> FEATURE:
<223> OTHER INFORMATION: SC02-378 heavy chain variable region

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Ser Ser Gly Gly Phe Phe Asp Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: artificial sequence
<220> FEATURE:
<223> OTHER INFORMATION: SC02-161 heavy chain variable region

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Thr Thr Ala Gly Ser Phe Asp Tyr Trp Gly Gln Gly Thr
            100                 105                 110

Leu Val Thr Val Ser Ser
        115

<210> SEQ ID NO 14
<211> LENGTH: 107
<212> TYPE: PRT
<213> ORGANISM: artificial sequence
<220> FEATURE:
<223> OTHER INFORMATION: SC02-357 & SC02-378 & SC02-161 light chain
      variable region

<400> SEQUENCE: 14

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105
```

<210> SEQ ID NO 15
<211> LENGTH: 120
<212> TYPE: PRT
<213> ORGANISM: artificial sequence
<220> FEATURE:
<223> OTHER INFORMATION: M26 heavy chain variable region

<400> SEQUENCE: 15

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Phe Ile His Trp Val Lys Gln Lys Pro Gly Gln Gly Leu Glu Trp Ile
        35                  40                  45

Gly Phe Ile Asn Pro Tyr Asn Asp Gly Ser Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Asp Asp Gly Tyr Tyr Gly Tyr Ala Met Asp Tyr Trp Gly Gln
            100                 105                 110

Gly Thr Ser Val Thr Val Ser Ser
        115                 120
```

<210> SEQ ID NO 16
<211> LENGTH: 108
<212> TYPE: PRT
<213> ORGANISM: artificial sequence
<220> FEATURE:
<223> OTHER INFORMATION: M26 light chain variable region

<400> SEQUENCE: 16

```
Asp Ile Gln Met Thr Gln Ser Pro Ser Ser Leu Ser Ala Ser Leu Gly
1               5                   10                  15

Glu Arg Val Ser Leu Thr Cys Arg Ala Thr Gln Glu Leu Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Asn Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ile Tyr Pro Tyr
                85                  90                  95
```

```
Thr Phe Gly Gly Gly Thr Lys Leu Glu Ile Lys Arg
            100                 105
```

```
<210> SEQ ID NO 17
<211> LENGTH: 120
<212> TYPE: PRT
<213> ORGANISM: artificial sequence
<220> FEATURE:
<223> OTHER INFORMATION: M31 heavy chain variable region

<400> SEQUENCE: 17

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Thr Ser Ser Thr Ala Tyr
65                  70                  75                  80

Met Glu Leu Asn Ser Leu Thr Ser Glu Asp Ser Ala Val Tyr Phe Cys
                85                  90                  95

Ala Arg Pro Ile Tyr Phe Asp Asn Asp Tyr Phe Asp Tyr Trp Gly Gln
            100                 105                 110

Gly Thr Thr Leu Lys Val Ser Ser
        115                 120
```

```
<210> SEQ ID NO 18
<211> LENGTH: 111
<212> TYPE: PRT
<213> ORGANISM: artificial sequence
<220> FEATURE:
<223> OTHER INFORMATION: M31 light chain variable region

<400> SEQUENCE: 18

Thr Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
            100                 105                 110
```

```
<210> SEQ ID NO 19
<211> LENGTH: 120
<212> TYPE: PRT
<213> ORGANISM: artificial sequence
<220> FEATURE:
<223> OTHER INFORMATION: G4 heavy chain variable region

<400> SEQUENCE: 19
```

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Glu Lys Asn Leu Glu Trp Ile
        35                  40                  45

Gly Pro Ile Asn Pro Tyr Asn Asp Gly Thr Ile Tyr Asn Pro Asn Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Asp Asp Pro Ala Val Tyr Tyr Cys
                85                  90                  95

Ala Arg Thr Asp Asp Tyr Asp Asp Tyr Thr Met Asp Tyr Trp Gly Gln
                100                 105                 110

Gly Thr Ser Val Thr Val Ser Ser
            115                 120

<210> SEQ ID NO 20
<211> LENGTH: 107
<212> TYPE: PRT
<213> ORGANISM: artificial sequence
<220> FEATURE:
<223> OTHER INFORMATION: G4 light chain variable region

<400> SEQUENCE: 20

Glu Ile Gln Met Thr Gln Thr Pro Ser Ser Leu Ser Ala Ser Leu Gly
1               5                   10                  15

Asp Arg Val Thr Ile Ser Cys Arg Ala Ser His Asp Ile Ser Asn Tyr
            20                  25                  30

Leu Asn Trp Tyr Gln Gln Lys Pro Asp Gly Thr Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Leu Trp
                85                  90                  95

Thr Phe Gly Gly Gly Thr Lys Leu Glu Ile Lys
            100                 105

<210> SEQ ID NO 21
<211> LENGTH: 121
<212> TYPE: PRT
<213> ORGANISM: artificial sequence
<220> FEATURE:
<223> OTHER INFORMATION: M22  heavy chain variable region

<400> SEQUENCE: 21

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Thr Glu Thr His Tyr Asn Gln Gln Phe
    50                  55                  60

Lys Asp Lys Ala Thr Leu Thr Val Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Ile Tyr Tyr Gly Asn Pro Ser Tyr Ala Met Asp Tyr Trp Gly
            100                 105                 110

Gln Gly Thr Ser Val Thr Val Ser Ser
        115                 120

<210> SEQ ID NO 22
<211> LENGTH: 113
<212> TYPE: PRT
<213> ORGANISM: artificial sequence
<220> FEATURE:
<223> OTHER INFORMATION: M22 light chain variable region

<400> SEQUENCE: 22

Asp Ile Val Met Thr Gln Ser Pro Ser Ser Leu Thr Val Thr Ala Gly
1               5                   10                  15

Glu Lys Val Thr Met Ser Cys Lys Ser Ser Gln Asn Leu Leu Asn Ser
            20                  25                  30

Gly Asn Gln Lys Lys Tyr Leu Asn Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys Gln Asn
                85                  90                  95

Asp Tyr Ser Tyr Pro Phe Thr Phe Gly Ala Gly Thr Lys Leu Glu Leu
            100                 105                 110

Lys

<210> SEQ ID NO 23
<211> LENGTH: 119
<212> TYPE: PRT
<213> ORGANISM: artificial sequence
<220> FEATURE:
<223> OTHER INFORMATION: M29  heavy chain variable region

<400> SEQUENCE: 23

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr Ser Tyr
            20                  25                  30

Val Met Tyr Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Tyr Tyr Asp Tyr Asp Tyr Phe Asp Tyr Trp Gly Gln Gly
            100                 105                 110

Thr Thr Leu Thr Val Ser Ser
        115

<210> SEQ ID NO 24
```

<211> LENGTH: 106
<212> TYPE: PRT
<213> ORGANISM: artificial sequence
<220> FEATURE:
<223> OTHER INFORMATION: M29 light chain variable region

<400> SEQUENCE: 24

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Tyr Leu Trp Thr
                85                  90                  95

Phe Gly Gly Gly Thr Lys Leu Glu Ile Lys
            100                 105
```

<210> SEQ ID NO 25
<211> LENGTH: 120
<212> TYPE: PRT
<213> ORGANISM: artificial sequence
<220> FEATURE:
<223> OTHER INFORMATION: M2 heavy chain variable region

<400> SEQUENCE: 25

```
Glu Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Phe Met His Trp Val Lys Gln Lys Pro Gly Gln Gly Leu Glu Trp Ile
        35                  40                  45

Gly Phe Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Thr Arg Asp Asp Gly Tyr Tyr Asp Tyr Ala Met Asp Tyr Trp Gly Gln
            100                 105                 110

Gly Thr Ser Val Thr Val Ser Ser
        115                 120
```

<210> SEQ ID NO 26
<211> LENGTH: 108
<212> TYPE: PRT
<213> ORGANISM: artificial sequence
<220> FEATURE:
<223> OTHER INFORMATION: M2 light chain variable region

<400> SEQUENCE: 26

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Tyr
            20                  25                  30
```

```
Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Glu Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Tyr
                 85                  90                  95

Thr Phe Gly Gly Gly Thr Lys Leu Glu Ile Lys Arg
                100                 105
```

<210> SEQ ID NO 27
<211> LENGTH: 115
<212> TYPE: PRT
<213> ORGANISM: artificial sequence
<220> FEATURE:
<223> OTHER INFORMATION: M5 heavy chain variable region

<400> SEQUENCE: 27

```
Glu Val Gln Leu Gln Gln Ser Gly Ala Glu Leu Val Arg Pro Gly Ala
 1               5                   10                  15

Ser Val Lys Leu Ser Cys Thr Ala Ser Gly Phe Asn Ile Lys Asp Asp
                20                  25                  30

Tyr Ile His Trp Val Lys Gln Arg Pro Glu Gln Gly Leu Glu Trp Ile
            35                  40                  45

Gly Trp Ile Asp Pro Glu Lys Gly Asp Thr Ala Tyr Ala Ser Lys Phe
 50                  55                  60

Gln Asp Lys Ala Thr Ile Thr Ser Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Leu Thr Gly Arg Phe Asp Tyr Trp Gly Gln Gly Thr Thr Leu Thr
                100                 105                 110

Val Ser Ser
        115
```

<210> SEQ ID NO 28
<211> LENGTH: 112
<212> TYPE: PRT
<213> ORGANISM: artificial sequence
<220> FEATURE:
<223> OTHER INFORMATION: M5 light chain variable region

<400> SEQUENCE: 28

```
Asp Ile Val Met Ser Gln Ser Pro Ser Ser Leu Ala Val Ser Val Gly
 1               5                   10                  15

Glu Lys Val Thr Met Ser Cys Lys Ser Ser Gln Ser Leu Leu Tyr Ser
                20                  25                  30

Ser Asn Gln Lys Asn Asn Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Gln
                 85                  90                  95

Tyr Tyr Ser Tyr Arg Thr Phe Gly Gly Gly Thr Lys Leu Glu Ile Lys
                100                 105                 110
```

-continued

```
<210> SEQ ID NO 29
<211> LENGTH: 117
<212> TYPE: PRT
<213> ORGANISM: artificial sequence
<220> FEATURE:
<223> OTHER INFORMATION: G12 heavy chain variable region

<400> SEQUENCE: 29

Gln Val Gln Leu Gln Gln Pro Gly Ala Glu Leu Val Lys Pro Gly Ala
1               5                   10                  15

Ser Met Lys Met Ser Cys Lys Ala Ser Gly Tyr Thr Phe Pro Ser Ser
            20                  25                  30

Asn Ile His Trp Leu Lys Gln Thr Pro Gly Gln Gly Leu Glu Trp Ile
        35                  40                  45

Gly Val Ile Tyr Pro Gly Asn Gly Asp Thr Ser Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Ile Tyr Phe Cys
                85                  90                  95

Ala Arg Val Tyr Asn Trp His Phe Asp Val Trp Gly Ala Gly Thr Thr
            100                 105                 110

Val Thr Val Ser Ser
        115

<210> SEQ ID NO 30
<211> LENGTH: 112
<212> TYPE: PRT
<213> ORGANISM: artificial sequence
<220> FEATURE:
<223> OTHER INFORMATION: G12 light chain variable region

<400> SEQUENCE: 30

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Gly Tyr
            20                  25                  30

Gly Asp Ile Phe Met Leu Trp Tyr Gln Gln Lys Pro Gly Gln Pro Pro
        35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 31
<211> LENGTH: 120
<212> TYPE: PRT
<213> ORGANISM: artificial sequence
<220> FEATURE:
<223> OTHER INFORMATION: 21.26 heavy chain variable region

<400> SEQUENCE: 31

Gln Val Gln Leu Gln Gln Pro Gly Ala Glu Leu Val Lys Pro Gly Thr
1               5                   10                  15
```

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Met Ile His Pro Ser Ser Gly Ser Thr Ser Tyr Asn Glu Lys Val
    50                  55                  60

Lys Asn Lys Ala Thr Leu Thr Val Asp Arg Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Asp Tyr Tyr Gly Thr Gly Asp Tyr Trp Gly Gln
            100                 105                 110

Gly Thr Thr Leu Thr Val Ser Ser
        115                 120

<210> SEQ ID NO 32
<211> LENGTH: 106
<212> TYPE: PRT
<213> ORGANISM: artificial sequence
<220> FEATURE:
<223> OTHER INFORMATION: 21.26 light chain variable region

<400> SEQUENCE: 32

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Ile Asn Tyr Met
            20                  25                  30

His Trp Tyr Gln Gln Lys Pro Gly Ser Ser Pro Lys Pro Trp Ile Phe
        35                  40                  45

Ala Thr Ser Asn Leu Ala Ser Gly Val Pro Ser Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Arg Ser Asp Arg Ala Leu
                85                  90                  95

Thr Phe Gly Ala Gly Thr Lys Leu Glu Leu
            100                 105

<210> SEQ ID NO 33
<211> LENGTH: 123
<212> TYPE: PRT
<213> ORGANISM: artificial sequence
<220> FEATURE:
<223> OTHER INFORMATION: 1075.7 heavy chain variable region

<400> SEQUENCE: 33

Asp Ile Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Arg Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

```
Ala Lys Glu Gly Asp Tyr Asp Val Gly Asn Tyr Tyr Ala Met Asp Tyr
            100                 105                 110

Trp Gly Gln Gly Thr Ser Val Thr Val Ser Ser
        115                 120
```

<210> SEQ ID NO 34
<211> LENGTH: 107
<212> TYPE: PRT
<213> ORGANISM: artificial sequence
<220> FEATURE:
<223> OTHER INFORMATION: 1075.7 light chain variable region

<400> SEQUENCE: 34

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Asn Val Ile Ser Ser
            20                  25                  30

Tyr Val His Trp Tyr Gln Gln Arg Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu
            100                 105
```

<210> SEQ ID NO 35
<211> LENGTH: 455
<212> TYPE: PRT
<213> ORGANISM: artificial sequence
<220> FEATURE:
<223> OTHER INFORMATION: SC02-357 scCAR-v1 polypeptide

<400> SEQUENCE: 35

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
        130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
```

165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Gly Leu Ala Val Ser Thr Ile Ser Ser Phe Phe
            260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
    290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 36
<211> LENGTH: 458
<212> TYPE: PRT
<213> ORGANISM: artificial sequence
<220> FEATURE:
<223> OTHER INFORMATION: SC02-357 scCAR-v2 polypeptide

<400> SEQUENCE: 36

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn

```
                65                  70                  75                  80
Tyr Asn Pro Ser Leu Lys Ser Arg Val Thr Ile Ser Val Asp Lys Ser
                    85                  90                  95

Lys Asn Gln Phe Ser Leu Lys Leu Ser Ser Val Thr Ala Ala Asp Thr
                100                 105                 110

Ala Val Tyr Tyr Cys Ala Arg Ser Ser Gly Phe Phe Asp Tyr
                115                 120                 125

Trp Gly Gln Gly Thr Leu Val Thr Val Ser Ser Gly Gly Gly Ser
        130                 135                 140

Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                    165                 170                 175

Cys Arg Ala Ser Gln Ser Ile Ser Ser Tyr Leu Asn Trp Tyr Gln Gln
                180                 185                 190

Lys Pro Gly Lys Ala Pro Lys Leu Leu Ile Tyr Ala Ala Ser Ser Leu
                195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Gly Leu Ala Val Ser Thr Ile Ser Ser Phe Phe
                260                 265                 270

Pro Pro Gly Tyr Gln Ile Ile Ser Phe Phe Leu Ala Leu Thr Ser Thr
                275                 280                 285

Ala Leu Leu Phe Leu Leu Phe Phe Leu Thr Leu Arg Phe Ser Val Val
            290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
                340                 345                 350

Ser Ala Asp Ala Pro Ala Tyr Gln Gln Gly Gln Asn Gln Leu Tyr Asn
                355                 360                 365

Glu Leu Asn Leu Gly Arg Arg Glu Glu Tyr Asp Val Leu Asp Lys Arg
            370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Gly Lys Gly His
                420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
        450                 455

<210> SEQ ID NO 37
<211> LENGTH: 484
<212> TYPE: PRT
<213> ORGANISM: artificial sequence
```

<220> FEATURE:
<223> OTHER INFORMATION: SC02-357 scCAR-v3 polypeptide

<400> SEQUENCE: 37

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400
```

Arg Glu Glu Tyr Asp Val Leu Asp Lys Arg Arg Gly Arg Asp Pro Glu
            405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
        450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 38
<211> LENGTH: 487
<212> TYPE: PRT
<213> ORGANISM: artificial sequence
<220> FEATURE:
<223> OTHER INFORMATION: SC02-357 scCAR-v4 polypeptide

<400> SEQUENCE: 38

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

```
Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 39
<211> LENGTH: 670
<212> TYPE: PRT
<213> ORGANISM: artificial sequence
<220> FEATURE:
<223> OTHER INFORMATION: SC02-357 scCAR-v5 polypeptide

<400> SEQUENCE: 39

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly
50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Ser Gly Gly Phe Phe Asp Tyr
            115                 120                 125

Trp Gly Gln Gly Thr Leu Val Thr Val Ser Ser Gly Gly Gly Gly Ser
            130                 135                 140
```

-continued

```
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
            165                 170                 175
Cys Arg Ala Ser Gln Ser Ile Ser Ser Tyr Leu Asn Trp Tyr Gln Gln
        180                 185                 190
Lys Pro Gly Lys Ala Pro Lys Leu Leu Ile Tyr Ala Ala Ser Ser Leu
    195                 200                 205
Gln Ser Gly Val Pro Ser Arg Phe Ser Gly Ser Gly Ser Gly Thr Asp
210                 215                 220
Phe Thr Leu Thr Ile Ser Ser Leu Gln Pro Glu Asp Phe Ala Thr Tyr
225                 230                 235                 240
Tyr Cys Gln Gln Ser Tyr Ser Thr Pro Pro Thr Phe Gly Gln Gly Thr
            245                 250                 255
Lys Val Glu Ile Lys Glu Pro Lys Ser Pro Asp Lys Thr His Thr Cys
        260                 265                 270
Pro Pro Cys Pro Ala Pro Pro Val Ala Gly Pro Ser Val Phe Leu Phe
    275                 280                 285
Pro Pro Lys Pro Lys Asp Thr Leu Met Ile Ala Arg Thr Pro Glu Val
290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
            325                 330                 335
Arg Glu Glu Gln Tyr Asn Ser Thr Tyr Arg Val Val Ser Val Leu Thr
        340                 345                 350
Val Leu His Gln Asp Trp Leu Asn Gly Lys Glu Tyr Lys Cys Lys Val
    355                 360                 365
Ser Asn Lys Ala Leu Pro Ala Pro Ile Glu Lys Thr Ile Ser Lys Ala
370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
            405                 410                 415
Phe Tyr Pro Ser Asp Ile Ala Val Glu Trp Glu Ser Asn Gly Gln Pro
        420                 425                 430
Glu Asn Asn Tyr Lys Thr Thr Pro Pro Val Leu Asp Ser Asp Gly Ser
    435                 440                 445
Phe Phe Leu Tyr Ser Lys Leu Thr Val Asp Lys Ser Arg Trp Gln Gln
450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Tyr Ile Trp
            485                 490                 495
Ala Pro Leu Ala Gly Thr Cys Gly Val Leu Leu Leu Ser Leu Val Ile
        500                 505                 510
Thr Leu Tyr Cys Lys Arg Gly Arg Lys Lys Leu Leu Tyr Ile Phe Lys
    515                 520                 525
Gln Pro Phe Met Arg Pro Val Gln Thr Thr Gln Glu Glu Asp Gly Cys
530                 535                 540
Ser Cys Arg Phe Pro Glu Glu Glu Glu Gly Gly Cys Glu Leu Arg Val
545                 550                 555                 560
Lys Phe Ser Arg Ser Ala Asp Ala Pro Ala Tyr Gln Gln Gly Gln Asn
```

```
              565                 570                 575
Gln Leu Tyr Asn Glu Leu Asn Leu Gly Arg Arg Glu Tyr Asp Val
            580                 585                 590

Leu Asp Lys Arg Arg Gly Arg Asp Pro Glu Met Gly Gly Lys Pro Arg
            595                 600                 605

Arg Lys Asn Pro Gln Glu Gly Leu Tyr Asn Glu Leu Gln Lys Asp Lys
            610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
                660                 665                 670

<210> SEQ ID NO 40
<211> LENGTH: 673
<212> TYPE: PRT
<213> ORGANISM: artificial sequence
<220> FEATURE:
<223> OTHER INFORMATION: SC02-357 scCAR-v6 polypeptide

<400> SEQUENCE: 40

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly
        50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Glu Pro Lys Ser Pro Asp Lys Thr His Thr Cys
```

-continued

```
                260                 265                 270
Pro Pro Cys Pro Ala Pro Val Ala Gly Pro Ser Val Phe Leu Phe
            275                 280                 285
Pro Pro Lys Pro Lys Asp Thr Leu Met Ile Ala Arg Thr Pro Glu Val
        290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Ala Leu Pro Ala Pro Ile Glu Lys Thr Ile Ser Lys Ala
    370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
        435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Ile Ser Phe
                485                 490                 495
Phe Leu Ala Leu Thr Ser Thr Ala Leu Leu Phe Leu Leu Phe Phe Leu
            500                 505                 510
Thr Leu Arg Phe Ser Val Val Lys Arg Gly Arg Lys Lys Leu Leu Tyr
        515                 520                 525
Ile Phe Lys Gln Pro Phe Met Arg Pro Val Gln Thr Thr Gln Glu Glu
    530                 535                 540
Asp Gly Cys Ser Cys Arg Phe Pro Glu Glu Glu Glu Gly Gly Cys Glu
545                 550                 555                 560
Leu Arg Val Lys Phe Ser Arg Ser Ala Asp Ala Pro Ala Tyr Gln Gln
                565                 570                 575
Gly Gln Asn Gln Leu Tyr Asn Glu Leu Asn Leu Gly Arg Arg Glu Glu
            580                 585                 590
Tyr Asp Val Leu Asp Lys Arg Gly Arg Asp Pro Glu Met Gly Gly
        595                 600                 605
Lys Pro Arg Arg Lys Asn Pro Gln Glu Gly Leu Tyr Asn Glu Leu Gln
    610                 615                 620
Lys Asp Lys Met Ala Glu Ala Tyr Ser Glu Ile Gly Met Lys Gly Glu
625                 630                 635                 640
Arg Arg Arg Gly Lys Gly His Asp Gly Leu Tyr Gln Gly Leu Ser Thr
                645                 650                 655
Ala Thr Lys Asp Thr Tyr Asp Ala Leu His Met Gln Ala Leu Pro Pro
            660                 665                 670
Arg
```

<210> SEQ ID NO 41
<211> LENGTH: 455
<212> TYPE: PRT
<213> ORGANISM: artificial sequence
<220> FEATURE:
<223> OTHER INFORMATION: SC02-378 scCAR-v1 polypeptide

<400> SEQUENCE: 41

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Gly Leu Ala Val Ser Thr Ile Ser Ser Phe Phe
            260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
    290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365
```

Leu Gly Arg Arg Glu Glu Tyr Asp Val Leu Asp Lys Arg Arg Gly Arg
            370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 42
<211> LENGTH: 458
<212> TYPE: PRT
<213> ORGANISM: artificial sequence
<220> FEATURE:
<223> OTHER INFORMATION: SC02-378 scCAR-v2 polypeptide

<400> SEQUENCE: 42

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Gly Leu Ala Val Ser Thr Ile Ser Ser Phe Phe
            260                 265                 270

Pro Pro Gly Tyr Gln Ile Ile Ser Phe Phe Leu Ala Leu Thr Ser Thr
            275                 280                 285

Ala Leu Leu Phe Leu Leu Phe Phe Leu Thr Leu Arg Phe Ser Val Val
        290                 295                 300

Lys Arg Gly Arg Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
                340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
        370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
            450                 455

<210> SEQ ID NO 43
<211> LENGTH: 484
<212> TYPE: PRT
<213> ORGANISM: artificial sequence
<220> FEATURE:
<223> OTHER INFORMATION: SC02-378 scCAR-v3 polypeptide

<400> SEQUENCE: 43

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Phe Phe Asp Tyr
        115                 120                 125

Trp Gly Gln Gly Thr Leu Val Thr Val Ser Ser Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

-continued

```
Cys Arg Ala Ser Gln Ser Ile Ser Ser Tyr Leu Asn Trp Tyr Gln Gln
                180                 185                 190

Lys Pro Gly Lys Ala Pro Lys Leu Leu Ile Tyr Ala Ala Ser Ser Leu
            195                 200                 205

Gln Ser Gly Val Pro Ser Arg Phe Ser Gly Ser Gly Ser Gly Thr Asp
        210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 44
<211> LENGTH: 487
<212> TYPE: PRT
<213> ORGANISM: artificial sequence
<220> FEATURE:
<223> OTHER INFORMATION: SC02-378 scCAR-v4 polypeptide

<400> SEQUENCE: 44

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
```

-continued

```
            50                  55                  60
Lys Gly Leu Glu Trp Ile Gly Glu Ile Tyr His Ser Gly Ser Pro Asn
 65                  70                  75                  80

Tyr Asn Pro Ser Leu Lys Ser Arg Val Thr Ile Ser Val Asp Lys Ser
                 85                  90                  95

Lys Asn Gln Phe Ser Leu Lys Leu Ser Ser Val Thr Ala Ala Asp Thr
                100                 105                 110

Ala Val Tyr Tyr Cys Ala Arg Ser Ser Gly Gly Phe Phe Asp Tyr
            115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
                180                 185                 190

Lys Pro Gly Lys Ala Pro Lys Leu Leu Ile Tyr Ala Ala Ser Ser Leu
                195                 200                 205

Gln Ser Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
                275                 280                 285

Arg Pro Ala Ala Gly Gly Ala Val His Thr Arg Gly Leu Asp Phe Ala
                290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
                370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
                450                 455                 460

Tyr Gln Gly Leu Ser Thr Ala Thr Lys Asp Thr Tyr Asp Ala Leu His
465                 470                 475                 480
```

```
Met Gln Ala Leu Pro Pro Arg
                485

<210> SEQ ID NO 45
<211> LENGTH: 670
<212> TYPE: PRT
<213> ORGANISM: artificial sequence
<220> FEATURE:
<223> OTHER INFORMATION: SC02-378 scCAR-v5 polypeptide

<400> SEQUENCE: 45

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly
        50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ser Ser Gly Gly Phe Phe Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Glu Pro Lys Ser Pro Asp Lys Thr His Thr Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350
```

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
        370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
        515                 520                 525

Gln Pro Phe Met Arg Pro Val Gln Thr Thr Gln Glu Glu Asp Gly Cys
    530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
        595                 600                 605

Arg Lys Asn Pro Gln Glu Gly Leu Tyr Asn Glu Leu Gln Lys Asp Lys
    610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 46
<211> LENGTH: 673
<212> TYPE: PRT
<213> ORGANISM: artificial sequence
<220> FEATURE:
<223> OTHER INFORMATION: SC02-378 scCAR-v6 polypeptide

<400> SEQUENCE: 46

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

```
Ser Ile Ser Ser Ser Asn Trp Trp Ser Trp Val Arg Gln Pro Pro Gly
         50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                 85                  90                  95

Lys Asn Gln Phe Ser Leu Lys Leu Ser Ser Val Thr Ala Ala Asp Thr
                100                 105                 110

Ala Val Tyr Tyr Cys Ala Arg Ser Ser Gly Gly Phe Phe Asp Tyr
             115                 120                 125

Trp Gly Gln Gly Thr Leu Val Thr Val Ser Ser Gly Gly Gly Gly Ser
         130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
             180                 185                 190

Lys Pro Gly Lys Ala Pro Lys Leu Leu Ile Tyr Ala Ala Ser Ser Leu
         195                 200                 205

Gln Ser Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Glu Pro Lys Ser Pro Asp Lys Thr His Thr Cys
             260                 265                 270

Pro Pro Cys Pro Ala Pro Pro Val Ala Gly Pro Ser Val Phe Leu Phe
         275                 280                 285

Pro Pro Lys Pro Lys Asp Thr Leu Met Ile Ala Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
             340                 345                 350

Val Leu His Gln Asp Trp Leu Asn Gly Lys Glu Tyr Lys Cys Lys Val
         355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
             420                 425                 430

Glu Asn Asn Tyr Lys Thr Thr Pro Pro Val Leu Asp Ser Asp Gly Ser
         435                 440                 445

Phe Phe Leu Tyr Ser Lys Leu Thr Val Asp Lys Ser Arg Trp Gln Gln
450                 455                 460
```

-continued

```
Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Ile Ser Phe
                485                 490                 495

Phe Leu Ala Leu Thr Ser Thr Ala Leu Leu Phe Leu Leu Phe Phe Leu
            500                 505                 510

Thr Leu Arg Phe Ser Val Val Lys Arg Gly Arg Lys Lys Leu Leu Tyr
        515                 520                 525

Ile Phe Lys Gln Pro Phe Met Arg Pro Val Gln Thr Thr Gln Glu Glu
    530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 47
<211> LENGTH: 455
<212> TYPE: PRT
<213> ORGANISM: artificial sequence
<220> FEATURE:
<223> OTHER INFORMATION: SC02-161 scCAR-v1 polypeptide

<400> SEQUENCE: 47

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly
        50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Thr Thr Ala Gly Ser Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Gly Ser Asp Ile Gln Met Thr Gln
```

| | | | | 145 | | | | 150 | | | | 155 | | | | 160 |

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
                180                 185                 190

Lys Pro Gly Lys Ala Pro Lys Leu Leu Ile Tyr Ala Ala Ser Ser Leu
                195                 200                 205

Gln Ser Gly Val Pro Ser Arg Phe Ser Gly Ser Gly Ser Gly Thr Asp
            210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Gly Leu Ala Val Ser Thr Ile Ser Ser Phe Phe
                260                 265                 270

Pro Pro Gly Tyr Gln Ile Tyr Ile Trp Ala Pro Leu Ala Gly Thr Cys
                275                 280                 285

Gly Val Leu Leu Leu Ser Leu Val Ile Thr Leu Tyr Cys Lys Arg Gly
            290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp
                340                 345                 350

Ala Pro Ala Tyr Gln Gln Gly Gln Asn Gln Leu Tyr Asn Glu Leu Asn
                355                 360                 365

Leu Gly Arg Arg Glu Glu Tyr Asp Val Leu Asp Lys Arg Arg Gly Arg
            370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
                420                 425                 430

Tyr Gln Gly Leu Ser Thr Ala Thr Lys Asp Thr Tyr Asp Ala Leu His
            435                 440                 445

Met Gln Ala Leu Pro Pro Arg
    450                 455

<210> SEQ ID NO 48
<211> LENGTH: 458
<212> TYPE: PRT
<213> ORGANISM: artificial sequence
<220> FEATURE:
<223> OTHER INFORMATION: SC02-161 scCAR-v2 polypeptide

<400> SEQUENCE: 48

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly

```
                50              55              60
Lys Gly Leu Glu Trp Ile Gly Glu Ile Tyr His Ser Gly Ser Pro Asn
 65              70              75              80

Tyr Asn Pro Ser Leu Lys Ser Arg Val Thr Ile Ser Val Asp Lys Ser
                 85              90              95

Lys Asn Gln Phe Ser Leu Lys Leu Ser Ser Val Thr Ala Ala Asp Thr
            100             105             110

Ala Val Tyr Tyr Cys Ala Arg Gln Thr Thr Ala Gly Ser Phe Asp Tyr
        115             120             125

Trp Gly Gln Gly Thr Leu Val Thr Val Ser Ser Gly Gly Gly Gly Ser
    130             135             140

Gly Gly Gly Gly Ser Gly Gly Gly Ser Asp Ile Gln Met Thr Gln
145             150             155             160

Ser Pro Ser Ser Leu Ser Ala Ser Val Gly Asp Arg Val Thr Ile Thr
                165             170             175

Cys Arg Ala Ser Gln Ser Ile Ser Ser Tyr Leu Asn Trp Tyr Gln Gln
            180             185             190

Lys Pro Gly Lys Ala Pro Lys Leu Leu Ile Tyr Ala Ala Ser Ser Leu
        195             200             205

Gln Ser Gly Val Pro Ser Arg Phe Ser Gly Ser Gly Ser Gly Thr Asp
    210             215             220

Phe Thr Leu Thr Ile Ser Ser Leu Gln Pro Glu Asp Phe Ala Thr Tyr
225             230             235             240

Tyr Cys Gln Gln Ser Tyr Ser Thr Pro Pro Thr Phe Gly Gln Gly Thr
                245             250             255

Lys Val Glu Ile Lys Gly Leu Ala Val Ser Thr Ile Ser Ser Phe Phe
            260             265             270

Pro Pro Gly Tyr Gln Ile Ile Ser Phe Phe Leu Ala Leu Thr Ser Thr
        275             280             285

Ala Leu Leu Phe Leu Leu Phe Phe Leu Thr Leu Arg Phe Ser Val Val
    290             295             300

Lys Arg Gly Arg Lys Lys Leu Leu Tyr Ile Phe Lys Gln Pro Phe Met
305             310             315             320

Arg Pro Val Gln Thr Thr Gln Glu Glu Asp Gly Cys Ser Cys Arg Phe
                325             330             335

Pro Glu Glu Glu Glu Gly Gly Cys Glu Leu Arg Val Lys Phe Ser Arg
            340             345             350

Ser Ala Asp Ala Pro Ala Tyr Gln Gln Gly Gln Asn Gln Leu Tyr Asn
        355             360             365

Glu Leu Asn Leu Gly Arg Arg Glu Glu Tyr Asp Val Leu Asp Lys Arg
    370             375             380

Arg Gly Arg Asp Pro Glu Met Gly Gly Lys Pro Arg Arg Lys Asn Pro
385             390             395             400

Gln Glu Gly Leu Tyr Asn Glu Leu Gln Lys Asp Lys Met Ala Glu Ala
                405             410             415

Tyr Ser Glu Ile Gly Met Lys Gly Glu Arg Arg Gly Lys Gly His
            420             425             430

Asp Gly Leu Tyr Gln Gly Leu Ser Thr Ala Thr Lys Asp Thr Tyr Asp
        435             440             445

Ala Leu His Met Gln Ala Leu Pro Pro Arg
    450             455

<210> SEQ ID NO 49
```

<211> LENGTH: 484
<212> TYPE: PRT
<213> ORGANISM: artificial sequence
<220> FEATURE:
<223> OTHER INFORMATION: SC02-161 scCAR-v3 polypeptide

<400> SEQUENCE: 49

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Thr Thr Ala Gly Ser Phe Asp Tyr
        115                 120                 125

Trp Gly Gln Gly Thr Leu Val Thr Val Ser Ser Gly Gly Gly Gly Ser
130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
370                 375                 380
```

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
            405                 410                 415

Met Gly Gly Lys Pro Arg Arg Lys Asn Pro Gln Glu Gly Leu Tyr Asn
        420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 50
<211> LENGTH: 487
<212> TYPE: PRT
<213> ORGANISM: artificial sequence
<220> FEATURE:
<223> OTHER INFORMATION: SC02-161 scCAR-v4 polypeptide

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Thr Thr Ala Gly Ser Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
                245                 250                 255

```
Lys Val Glu Ile Lys Thr Thr Thr Pro Ala Pro Arg Pro Pro Thr Pro
                260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
        290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
        370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 51
<211> LENGTH: 670
<212> TYPE: PRT
<213> ORGANISM: artificial sequence
<220> FEATURE:
<223> OTHER INFORMATION: SC02-161 scCAR-v5 polypeptide

<400> SEQUENCE: 51

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Val Val Ser Gly Gly
        35                  40                  45

Ser Ile Ser Ser Ser Asn Trp Trp Ser Trp Val Arg Gln Pro Pro Gly
    50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Thr Thr Ala Gly Ser Phe Asp Tyr
        115                 120                 125
```

-continued

```
Trp Gly Gln Gly Thr Leu Val Thr Val Ser Ser Gly Gly Gly Ser
    130                 135                 140
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
                165                 170                 175
Cys Arg Ala Ser Gln Ser Ile Ser Ser Tyr Leu Asn Trp Tyr Gln Gln
                180                 185                 190
Lys Pro Gly Lys Ala Pro Lys Leu Leu Ile Tyr Ala Ala Ser Ser Leu
                195                 200                 205
Gln Ser Gly Val Pro Ser Arg Phe Ser Gly Ser Gly Ser Gly Thr Asp
    210                 215                 220
Phe Thr Leu Thr Ile Ser Ser Leu Gln Pro Glu Asp Phe Ala Thr Tyr
225                 230                 235                 240
Tyr Cys Gln Gln Ser Tyr Ser Thr Pro Pro Thr Phe Gly Gln Gly Thr
                245                 250                 255
Lys Val Glu Ile Lys Glu Pro Lys Ser Pro Asp Lys Thr His Thr Cys
                260                 265                 270
Pro Pro Cys Pro Ala Pro Pro Val Ala Gly Pro Ser Val Phe Leu Phe
    275                 280                 285
Pro Pro Lys Pro Lys Asp Thr Leu Met Ile Ala Arg Thr Pro Glu Val
290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
                340                 345                 350
Val Leu His Gln Asp Trp Leu Asn Gly Lys Glu Tyr Lys Cys Lys Val
            355                 360                 365
Ser Asn Lys Ala Leu Pro Ala Pro Ile Glu Lys Thr Ile Ser Lys Ala
    370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
                420                 425                 430
Glu Asn Asn Tyr Lys Thr Thr Pro Pro Val Leu Asp Ser Asp Gly Ser
            435                 440                 445
Phe Phe Leu Tyr Ser Lys Leu Thr Val Asp Lys Ser Arg Trp Gln Gln
    450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Tyr Ile Trp
                485                 490                 495
Ala Pro Leu Ala Gly Thr Cys Gly Val Leu Leu Leu Ser Leu Val Ile
                500                 505                 510
Thr Leu Tyr Cys Lys Arg Gly Arg Lys Lys Leu Leu Tyr Ile Phe Lys
            515                 520                 525
Gln Pro Phe Met Arg Pro Val Gln Thr Thr Gln Glu Glu Asp Gly Cys
    530                 535                 540
Ser Cys Arg Phe Pro Glu Glu Glu Glu Gly Gly Cys Glu Leu Arg Val
```

```
545                 550                 555                 560
Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
                580                 585                 590

Leu Asp Lys Arg Arg Gly Arg Asp Pro Glu Met Gly Gly Lys Pro Arg
                595                 600                 605

Arg Lys Asn Pro Gln Glu Gly Leu Tyr Asn Glu Leu Gln Lys Asp Lys
                610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
                660                 665                 670

<210> SEQ ID NO 52
<211> LENGTH: 673
<212> TYPE: PRT
<213> ORGANISM: artificial sequence
<220> FEATURE:
<223> OTHER INFORMATION: SC02-161 scCAR-v6 polypeptide

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Val Val Ser Gly Gly
            35                  40                  45

Ser Ile Ser Ser Ser Asn Trp Trp Ser Trp Val Arg Gln Pro Pro Gly
        50                  55                  60

Lys Gly Leu Glu Trp Ile Gly Glu Ile Tyr His Ser Gly Ser Pro Asn
65                  70                  75                  80

Tyr Asn Pro Ser Leu Lys Ser Arg Val Thr Ile Ser Val Asp Lys Ser
                85                  90                  95

Lys Asn Gln Phe Ser Leu Lys Leu Ser Ser Val Thr Ala Ala Asp Thr
                100                 105                 110

Ala Val Tyr Tyr Cys Ala Arg Gln Thr Thr Ala Gly Ser Phe Asp Tyr
            115                 120                 125

Trp Gly Gln Gly Thr Leu Val Thr Val Ser Ser Gly Gly Gly Gly Ser
        130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
                210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Pro Thr Phe Gly Gln Gly Thr
```

-continued

```
                245                 250                 255
Lys Val Glu Ile Lys Glu Pro Lys Ser Pro Asp Lys Thr His Thr Cys
                260                 265                 270
Pro Pro Cys Pro Ala Pro Pro Val Ala Gly Pro Ser Val Phe Leu Phe
                275                 280                 285
Pro Pro Lys Pro Lys Asp Thr Leu Met Ile Ala Arg Thr Pro Glu Val
290                 295                 300
Thr Cys Val Val Val Asp Val Ser His Glu Asp Pro Glu Val Lys Phe
305                 310                 315                 320
Asn Trp Tyr Val Asp Gly Val Glu Val His Asn Ala Lys Thr Lys Pro
                325                 330                 335
Arg Glu Glu Gln Tyr Asn Ser Thr Tyr Arg Val Val Ser Val Leu Thr
                340                 345                 350
Val Leu His Gln Asp Trp Leu Asn Gly Lys Glu Tyr Lys Cys Lys Val
                355                 360                 365
Ser Asn Lys Ala Leu Pro Ala Pro Ile Glu Lys Thr Ile Ser Lys Ala
            370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                405                 410                 415
Phe Tyr Pro Ser Asp Ile Ala Val Glu Trp Glu Ser Asn Gly Gln Pro
                420                 425                 430
Glu Asn Asn Tyr Lys Thr Thr Pro Pro Val Leu Asp Ser Asp Gly Ser
                435                 440                 445
Phe Phe Leu Tyr Ser Lys Leu Thr Val Asp Lys Ser Arg Trp Gln Gln
            450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Ile Ile Ser Phe
                485                 490                 495
Phe Leu Ala Leu Thr Ser Thr Ala Leu Leu Phe Leu Leu Phe Phe Leu
                500                 505                 510
Thr Leu Arg Phe Ser Val Val Lys Arg Gly Arg Lys Lys Leu Leu Tyr
            515                 520                 525
Ile Phe Lys Gln Pro Phe Met Arg Pro Val Gln Thr Thr Gln Glu Glu
            530                 535                 540
Asp Gly Cys Ser Cys Arg Phe Pro Glu Glu Glu Glu Gly Gly Cys Glu
545                 550                 555                 560
Leu Arg Val Lys Phe Ser Arg Ser Ala Asp Ala Pro Ala Tyr Gln Gln
                565                 570                 575
Gly Gln Asn Gln Leu Tyr Asn Glu Leu Asn Leu Gly Arg Arg Glu Glu
            580                 585                 590
Tyr Asp Val Leu Asp Lys Arg Arg Gly Arg Asp Pro Glu Met Gly Gly
            595                 600                 605
Lys Pro Arg Arg Lys Asn Pro Gln Glu Gly Leu Tyr Asn Glu Leu Gln
            610                 615                 620
Lys Asp Lys Met Ala Glu Ala Tyr Ser Glu Ile Gly Met Lys Gly Glu
625                 630                 635                 640
Arg Arg Arg Gly Lys Gly His Asp Gly Leu Tyr Gln Gly Leu Ser Thr
                645                 650                 655
Ala Thr Lys Asp Thr Tyr Asp Ala Leu His Met Gln Ala Leu Pro Pro
            660                 665                 670
```

Arg

<210> SEQ ID NO 53
<211> LENGTH: 458
<212> TYPE: PRT
<213> ORGANISM: artificial sequence
<220> FEATURE:
<223> OTHER INFORMATION: M26 scCAR-v1 polypeptide

<400> SEQUENCE: 53

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Ile His Trp Val Lys Gln Lys Pro Gly Gln
    50                  55                  60

Gly Leu Glu Trp Ile Gly Phe Ile Asn Pro Tyr Asn Asp Gly Ser Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Thr Arg Asp Asp Gly Tyr Tyr Gly Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
                245                 250                 255

Gly Thr Lys Leu Glu Ile Lys Arg Gly Leu Ala Val Ser Thr Ile Ser
            260                 265                 270

Ser Phe Phe Pro Pro Gly Tyr Gln Ile Tyr Ile Trp Ala Pro Leu Ala
        275                 280                 285

Gly Thr Cys Gly Val Leu Leu Leu Ser Leu Val Ile Thr Leu Tyr Cys
    290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350
```

```
Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
    450                 455

<210> SEQ ID NO 54
<211> LENGTH: 461
<212> TYPE: PRT
<213> ORGANISM: artificial sequence
<220> FEATURE:
<223> OTHER INFORMATION: M26 scCAR-v2 polypeptide

<400> SEQUENCE: 54

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Ile His Trp Val Lys Gln Lys Pro Gly Gln
    50                  55                  60

Gly Leu Glu Trp Ile Gly Phe Ile Asn Pro Tyr Asn Asp Gly Ser Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Thr Arg Asp Asp Gly Tyr Tyr Gly Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
                245                 250                 255
```

```
Gly Thr Lys Leu Glu Ile Lys Arg Gly Leu Ala Val Ser Thr Ile Ser
            260                 265                 270

Ser Phe Phe Pro Pro Gly Tyr Gln Ile Ile Ser Phe Phe Leu Ala Leu
        275                 280                 285

Thr Ser Thr Ala Leu Leu Phe Leu Leu Phe Phe Leu Thr Leu Arg Phe
    290                 295                 300

Ser Val Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 55
<211> LENGTH: 487
<212> TYPE: PRT
<213> ORGANISM: Artificial sequence
<220> FEATURE:
<223> OTHER INFORMATION: M26 scCAR-v3 polypeptide

<400> SEQUENCE: 55

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Ile His Trp Val Lys Gln Lys Pro Gly Gln
    50                  55                  60

Gly Leu Glu Trp Ile Gly Phe Ile Asn Pro Tyr Asn Asp Gly Ser Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Thr Arg Asp Asp Gly Tyr Tyr Gly Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160
```

-continued

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
                245                 250                 255

Gly Thr Lys Leu Glu Ile Lys Arg Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 56
<211> LENGTH: 490
<212> TYPE: PRT
<213> ORGANISM: Artificial sequence
<220> FEATURE:
<223> OTHER INFORMATION: M26 scCAR-v4 polypeptide

<400> SEQUENCE: 56

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

```
Val Lys Pro Gly Ala Ser Val Lys Met Ser Cys Lys Ala Ser Gly Tyr
             35                  40                  45

Thr Phe Thr Ser Tyr Phe Ile His Trp Val Lys Gln Lys Pro Gly Gln
 50                  55                  60

Gly Leu Glu Trp Ile Gly Phe Ile Asn Pro Tyr Asn Asp Gly Ser Lys
 65                  70                  75                  80

Tyr Asn Glu Lys Phe Lys Gly Lys Ala Thr Leu Thr Ser Asp Lys Ser
                 85                  90                  95

Ser Ser Thr Ala Tyr Met Glu Leu Ser Ser Leu Thr Ser Glu Asp Ser
                100                 105                 110

Ala Val Tyr Tyr Cys Thr Arg Asp Asp Gly Tyr Tyr Gly Tyr Ala Met
            115                 120                 125

Asp Tyr Trp Gly Gln Gly Thr Ser Val Thr Val Ser Ser Gly Gly Gly
130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
            245                 250                 255

Gly Thr Lys Leu Glu Ile Lys Arg Thr Thr Thr Pro Ala Pro Arg Pro
                260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
290                 295                 300

Asp Phe Ala Cys Asp Ile Ile Ser Phe Phe Leu Ala Leu Thr Ser Thr
305                 310                 315                 320

Ala Leu Leu Phe Leu Leu Phe Phe Leu Thr Leu Arg Phe Ser Val Val
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
```

```
                  450                 455                 460
Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 57
<211> LENGTH: 673
<212> TYPE: PRT
<213> ORGANISM: Artificial sequence
<220> FEATURE:
<223> OTHER INFORMATION: M26 scCAR-v5 polypeptide

<400> SEQUENCE: 57

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Met Ser Cys Lys Ala Ser Gly Tyr
            35                  40                  45

Thr Phe Thr Ser Tyr Phe Ile His Trp Val Lys Gln Lys Pro Gly Gln
        50                  55                  60

Gly Leu Glu Trp Ile Gly Phe Ile Asn Pro Tyr Asn Asp Gly Ser Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
                100                 105                 110

Ala Val Tyr Tyr Cys Thr Arg Asp Asp Gly Tyr Tyr Gly Tyr Ala Met
            115                 120                 125

Asp Tyr Trp Gly Gln Gly Thr Ser Val Thr Val Ser Ser Gly Gly Gly
        130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
                245                 250                 255

Gly Thr Lys Leu Glu Ile Lys Arg Glu Pro Lys Ser Pro Asp Lys Thr
            260                 265                 270

His Thr Cys Pro Pro Cys Pro Ala Pro Pro Val Ala Gly Pro Ser Val
        275                 280                 285

Phe Leu Phe Pro Pro Lys Pro Lys Asp Thr Leu Met Ile Ala Arg Thr
        290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
```

```
            325                 330                 335
Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
        515                 520                 525

Ile Phe Lys Gln Pro Phe Met Arg Pro Val Gln Thr Thr Gln Glu Glu
530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg
```

<210> SEQ ID NO 58
<211> LENGTH: 676
<212> TYPE: PRT
<213> ORGANISM: Artificial sequence
<220> FEATURE:
<223> OTHER INFORMATION: M26 scCAR-v6 polypeptide

<400> SEQUENCE: 58

```
Met Ala Leu Pro Val Thr Ala Leu Leu Leu Pro Leu Ala Leu Leu Leu
1               5                   10                  15
```

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Ile His Trp Val Lys Gln Lys Pro Gly Gln
    50                  55                  60

Gly Leu Glu Trp Ile Gly Phe Ile Asn Pro Tyr Asn Asp Gly Ser Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Thr Arg Asp Asp Gly Tyr Tyr Gly Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Thr Gln Glu Leu Ser Gly Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Lys Arg Phe Ser Gly Asn Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ile Tyr Pro Tyr Thr Phe Gly Gly
                245                 250                 255

Gly Thr Lys Leu Glu Ile Lys Arg Glu Pro Lys Ser Pro Asp Lys Thr
            260                 265                 270

His Thr Cys Pro Pro Cys Pro Ala Pro Val Ala Gly Pro Ser Val
        275                 280                 285

Phe Leu Phe Pro Pro Lys Pro Lys Asp Thr Leu Met Ile Ala Arg Thr
    290                 295                 300

Pro Glu Val Thr Cys Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
         435                 440                 445

Asp Gly Ser Phe Phe Leu Tyr Ser Lys Leu Thr Val Asp Lys Ser Arg
450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Ile
                485                 490                 495

Ile Ser Phe Phe Leu Ala Leu Thr Ser Thr Ala Leu Leu Phe Leu Leu
                500                 505                 510

Phe Phe Leu Thr Leu Arg Phe Ser Val Val Lys Arg Gly Arg Lys Lys
        515                 520                 525

Leu Leu Tyr Ile Phe Lys Gln Pro Phe Met Arg Pro Val Gln Thr Thr
        530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
                580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
        610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
                660                 665                 670

Leu Pro Pro Arg
        675

<210> SEQ ID NO 59
<211> LENGTH: 463
<212> TYPE: PRT
<213> ORGANISM: Artificial sequence
<220> FEATURE:
<223> OTHER INFORMATION: M31 scCAR-v1 polypeptide

<400> SEQUENCE: 59

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Thr Ser
                85                  90                  95

Ser Ser Thr Ala Tyr Met Glu Leu Asn Ser Leu Thr Ser Glu Asp Ser
                100                 105                 110

Ala Val Tyr Phe Ser Cys Cys Ala Arg Pro Ile Tyr Phe Asp Asn Asp
            115                 120                 125

Tyr Phe Asp Tyr Trp Gly Gln Gly Thr Thr Leu Lys Val Ser Ser Gly
        130                 135                 140

Gly Gly Gly Ser Gly Gly Gly Ser Gly Gly Gly Ser Thr Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Ser Tyr Gly Asn
            180                 185                 190

Ser Phe Met His Trp Tyr Gln Gln Lys Pro Gly Gln Pro Pro Lys Leu
        195                 200                 205

Leu Ile Tyr Leu Ala Ser Asn Leu Glu Ser Gly Val Pro Ala Arg Phe
    210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Gly Leu Ala
            260                 265                 270

Val Ser Thr Ile Ser Ser Phe Phe Pro Pro Gly Tyr Gln Ile Tyr Ile
        275                 280                 285

Trp Ala Pro Leu Ala Gly Thr Cys Gly Val Leu Leu Leu Ser Leu Val
    290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Gly Gly Cys Glu Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 60
<211> LENGTH: 466
<212> TYPE: PRT
<213> ORGANISM: Artificial sequence
<220> FEATURE:
<223> OTHER INFORMATION: M31 scCAR-v2 polypeptide

<400> SEQUENCE: 60

Met Ala Leu Pro Val Thr Ala Leu Leu Leu Pro Leu Ala Leu Leu Leu
1               5                   10                  15

-continued

```
His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Thr Ser
                85                  90                  95

Ser Ser Thr Ala Tyr Met Glu Leu Asn Ser Leu Thr Ser Glu Asp Ser
            100                 105                 110

Ala Val Tyr Phe Ser Cys Cys Ala Arg Pro Ile Tyr Phe Asp Asn Asp
        115                 120                 125

Tyr Phe Asp Tyr Trp Gly Gln Gly Thr Thr Leu Lys Val Ser Ser Gly
    130                 135                 140

Gly Gly Gly Ser Gly Gly Gly Ser Gly Gly Gly Ser Thr Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Ser Tyr Gly Asn
            180                 185                 190

Ser Phe Met His Trp Tyr Gln Gln Lys Pro Gly Gln Pro Pro Lys Leu
        195                 200                 205

Leu Ile Tyr Leu Ala Ser Asn Leu Glu Ser Gly Val Pro Ala Arg Phe
    210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Gly Leu Ala
            260                 265                 270

Val Ser Thr Ile Ser Ser Phe Phe Pro Pro Gly Tyr Gln Ile Ile Ser
        275                 280                 285

Phe Phe Leu Ala Leu Thr Ser Thr Ala Leu Leu Phe Leu Leu Phe Phe
    290                 295                 300

Leu Thr Leu Arg Phe Ser Val Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
```

```
                435                 440                 445
Thr Ala Thr Lys Asp Thr Tyr Asp Ala Leu His Met Gln Ala Leu Pro
    450                 455                 460

Pro Arg
465

<210> SEQ ID NO 61
<211> LENGTH: 492
<212> TYPE: PRT
<213> ORGANISM: Artificial sequence
<220> FEATURE:
<223> OTHER INFORMATION: M31 scCAR-v3 polypeptide

<400> SEQUENCE: 61

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Thr Ser
                85                  90                  95

Ser Ser Thr Ala Tyr Met Glu Leu Asn Ser Leu Thr Ser Glu Asp Ser
            100                 105                 110

Ala Val Tyr Phe Ser Cys Cys Ala Arg Pro Ile Tyr Phe Asp Asn Asp
        115                 120                 125

Tyr Phe Asp Tyr Trp Gly Gln Gly Thr Thr Leu Lys Val Ser Ser Gly
    130                 135                 140

Gly Gly Gly Ser Gly Gly Gly Gly Ser Gly Gly Gly Gly Ser Thr Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Ser Tyr Gly Asn
            180                 185                 190

Ser Phe Met His Trp Tyr Gln Gln Lys Pro Gly Gln Pro Pro Lys Leu
        195                 200                 205

Leu Ile Tyr Leu Ala Ser Asn Leu Glu Ser Gly Val Pro Ala Arg Phe
    210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
```

```
                    325                 330                 335
Tyr Cys Lys Arg Gly Arg Lys Leu Leu Tyr Ile Phe Lys Gln Pro
                340                 345                 350
Phe Met Arg Pro Val Gln Thr Thr Gln Glu Glu Asp Gly Cys Ser Cys
            355                 360                 365
Arg Phe Pro Glu Glu Glu Gly Gly Cys Glu Leu Arg Val Lys Phe
        370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Arg Arg Lys
                420                 425                 430
Asn Pro Gln Glu Gly Leu Tyr Asn Glu Leu Gln Lys Asp Lys Met Ala
                435                 440                 445
Glu Ala Tyr Ser Glu Ile Gly Met Lys Gly Glu Arg Arg Arg Gly Lys
            450                 455                 460
Gly His Asp Gly Leu Tyr Gln Gly Leu Ser Thr Ala Thr Lys Asp Thr
465                 470                 475                 480
Tyr Asp Ala Leu His Met Gln Ala Leu Pro Pro Arg
                485                 490
```

<210> SEQ ID NO 62
<211> LENGTH: 495
<212> TYPE: PRT
<213> ORGANISM: Artificial sequence
<220> FEATURE:
<223> OTHER INFORMATION: M31 scCAR-v4 polypeptide

<400> SEQUENCE: 62

```
Met Ala Leu Pro Val Thr Ala Leu Leu Leu Pro Leu Ala Leu Leu Leu
1               5                   10                  15
His Ala Ala Arg Pro Glu Val Gln Leu Gln Gln Ser Gly Pro Glu Leu
                20                  25                  30
Val Lys Pro Gly Ala Ser Val Lys Met Ser Cys Lys Ala Ser Gly Tyr
            35                  40                  45
Thr Phe Thr Ser Tyr Val Met His Trp Val Lys Gln Lys Pro Gly Gln
        50                  55                  60
Gly Leu Glu Trp Ile Gly Tyr Ile Asn Pro Tyr Asn Asp Gly Thr Lys
65                  70                  75                  80
Tyr Asn Glu Lys Phe Lys Gly Lys Ala Thr Leu Thr Ser Asp Thr Ser
                85                  90                  95
Ser Ser Thr Ala Tyr Met Glu Leu Asn Ser Leu Thr Ser Glu Asp Ser
                100                 105                 110
Ala Val Tyr Phe Ser Cys Cys Ala Arg Pro Ile Tyr Phe Asp Asn Asp
            115                 120                 125
Tyr Phe Asp Tyr Trp Gly Gln Gly Thr Thr Leu Lys Val Ser Ser Gly
        130                 135                 140
Gly Gly Gly Ser Gly Gly Gly Gly Ser Gly Gly Gly Gly Ser Thr Ile
145                 150                 155                 160
Val Leu Thr Gln Ser Pro Ala Ser Leu Ala Val Ser Leu Gly Gln Arg
                165                 170                 175
Ala Thr Ile Ser Cys Arg Ala Ser Glu Ser Val Asp Ser Tyr Gly Asn
                180                 185                 190
Ser Phe Met His Trp Tyr Gln Gln Lys Pro Gly Gln Pro Pro Lys Leu
```

```
            195                 200                 205
Leu Ile Tyr Leu Ala Ser Asn Leu Glu Ser Gly Val Pro Ala Arg Phe
        210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Ile Ser Phe Phe Leu
305                 310                 315                 320

Ala Leu Thr Ser Thr Ala Leu Leu Phe Leu Leu Phe Phe Leu Thr Leu
                325                 330                 335

Arg Phe Ser Val Val Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 63
<211> LENGTH: 678
<212> TYPE: PRT
<213> ORGANISM: Artificial sequence
<220> FEATURE:
<223> OTHER INFORMATION: M31 scCAR-v5 polypeptide

<400> SEQUENCE: 63

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
```

```
             65                  70                  75                  80

Tyr Asn Glu Lys Phe Lys Gly Lys Ala Thr Leu Thr Ser Asp Thr Ser
                    85                  90                  95

Ser Ser Thr Ala Tyr Met Glu Leu Asn Ser Leu Thr Ser Glu Asp Ser
                100                 105                 110

Ala Val Tyr Phe Ser Cys Cys Ala Arg Pro Ile Tyr Phe Asp Asn Asp
                115                 120                 125

Tyr Phe Asp Tyr Trp Gly Gln Gly Thr Thr Leu Lys Val Ser Ser Gly
            130                 135                 140

Gly Gly Gly Ser Gly Gly Gly Ser Gly Gly Gly Ser Thr Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Ser Tyr Gly Asn
                180                 185                 190

Ser Phe Met His Trp Tyr Gln Gln Lys Pro Gly Gln Pro Pro Lys Leu
            195                 200                 205

Leu Ile Tyr Leu Ala Ser Asn Leu Glu Ser Gly Val Pro Ala Arg Phe
            210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Glu Pro Lys
                260                 265                 270

Ser Pro Asp Lys Thr His Thr Cys Pro Pro Cys Pro Ala Pro Pro Val
                275                 280                 285

Ala Gly Pro Ser Val Phe Leu Phe Pro Pro Lys Pro Lys Asp Thr Leu
            290                 295                 300

Met Ile Ala Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
                340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Ala Leu Pro Ala Pro
            370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
            450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495
```

Ser Pro Gly Lys Ile Tyr Ile Trp Ala Pro Leu Ala Gly Thr Cys Gly
            500                 505                 510

Val Leu Leu Leu Ser Leu Val Ile Thr Leu Tyr Cys Lys Arg Gly Arg
        515                 520                 525

Lys Lys Leu Leu Tyr Ile Phe Lys Gln Pro Phe Met Arg Pro Val Gln
    530                 535                 540

Thr Thr Gln Glu Glu Asp Gly Cys Ser Cys Arg Phe Pro Glu Glu Glu
545                 550                 555                 560

Glu Gly Gly Cys Glu Leu Arg Val Lys Phe Ser Arg Ser Ala Asp Ala
                565                 570                 575

Pro Ala Tyr Gln Gln Gly Gln Asn Gln Leu Tyr Asn Glu Leu Asn Leu
            580                 585                 590

Gly Arg Arg Glu Glu Tyr Asp Val Leu Asp Lys Arg Arg Gly Arg Asp
        595                 600                 605

Pro Glu Met Gly Gly Lys Pro Arg Arg Lys Asn Pro Gln Glu Gly Leu
    610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
            660                 665                 670

Gln Ala Leu Pro Pro Arg
        675

<210> SEQ ID NO 64
<211> LENGTH: 681
<212> TYPE: PRT
<213> ORGANISM: Artificial sequence
<220> FEATURE:
<223> OTHER INFORMATION: M31 scCAR-v6 polypeptide

<400> SEQUENCE: 64

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Thr Ser
                85                  90                  95

Ser Ser Thr Ala Tyr Met Glu Leu Asn Ser Leu Thr Ser Glu Asp Ser
            100                 105                 110

Ala Val Tyr Phe Ser Cys Cys Ala Arg Pro Ile Tyr Phe Asp Asn Asp
        115                 120                 125

Tyr Phe Asp Tyr Trp Gly Gln Gly Thr Thr Leu Lys Val Ser Ser Gly
    130                 135                 140

Gly Gly Gly Ser Gly Gly Gly Gly Ser Gly Gly Gly Ser Thr Ile
145                 150                 155                 160

Val Leu Thr Gln Ser Pro Ala Ser Leu Ala Val Ser Leu Gly Gln Arg
                165                 170                 175

```
Ala Thr Ile Ser Cys Arg Ala Ser Glu Ser Val Asp Ser Tyr Gly Asn
            180                 185                 190

Ser Phe Met His Trp Tyr Gln Gln Lys Pro Gly Gln Pro Pro Lys Leu
        195                 200                 205

Leu Ile Tyr Leu Ala Ser Asn Leu Glu Ser Gly Val Pro Ala Arg Phe
    210                 215                 220

Ser Gly Ser Gly Ser Arg Thr Asp Phe Thr Leu Thr Ile Asp Pro Val
225                 230                 235                 240

Glu Ala Asp Asp Ala Ala Thr Tyr Tyr Cys Gln Gln Asn Asn Tyr Asp
                245                 250                 255

Pro Trp Thr Phe Gly Gly Gly Thr Lys Leu Glu Ile Lys Glu Pro Lys
            260                 265                 270

Ser Pro Asp Lys Thr His Thr Cys Pro Pro Cys Pro Ala Pro Pro Val
        275                 280                 285

Ala Gly Pro Ser Val Phe Leu Phe Pro Pro Lys Pro Lys Asp Thr Leu
    290                 295                 300

Met Ile Ala Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys Ile Ile Ser Phe Phe Leu Ala Leu Thr Ser Thr Ala
            500                 505                 510

Leu Leu Phe Leu Leu Phe Phe Leu Thr Leu Arg Phe Ser Val Val Lys
        515                 520                 525

Arg Gly Arg Lys Lys Leu Leu Tyr Ile Phe Lys Gln Pro Phe Met Arg
    530                 535                 540

Pro Val Gln Thr Thr Gln Glu Glu Asp Gly Cys Ser Cys Arg Phe Pro
545                 550                 555                 560

Glu Glu Glu Glu Gly Gly Cys Glu Leu Arg Val Lys Phe Ser Arg Ser
                565                 570                 575

Ala Asp Ala Pro Ala Tyr Gln Gln Gly Gln Asn Gln Leu Tyr Asn Glu
            580                 585                 590
```

```
Leu Asn Leu Gly Arg Arg Glu Glu Tyr Asp Val Leu Asp Lys Arg Arg
            595                 600                 605

Gly Arg Asp Pro Glu Met Gly Gly Lys Pro Arg Lys Asn Pro Gln
610                 615                 620

Glu Gly Leu Tyr Asn Glu Leu Gln Lys Asp Lys Met Ala Glu Ala Tyr
625                 630                 635                 640

Ser Glu Ile Gly Met Lys Gly Glu Arg Arg Arg Gly Lys Gly His Asp
                645                 650                 655

Gly Leu Tyr Gln Gly Leu Ser Thr Ala Thr Lys Asp Thr Tyr Asp Ala
                660                 665                 670

Leu His Met Gln Ala Leu Pro Pro Arg
                675                 680

<210> SEQ ID NO 65
<211> LENGTH: 459
<212> TYPE: PRT
<213> ORGANISM: Artificial sequence
<220> FEATURE:
<223> OTHER INFORMATION: G4 scCAR-v1 polypeptide

<400> SEQUENCE: 65

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Met Lys Ile Ser Cys Lys Ala Ser Gly Tyr
            35                  40                  45

Ser Phe Thr Gly Tyr Thr Met Asn Trp Val Lys Gln Ser His Glu Lys
    50                  55                  60

Asn Leu Glu Trp Ile Gly Pro Ile Asn Pro Tyr Asn Asp Gly Thr Ile
65                  70                  75                  80

Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
                100                 105                 110

Ala Val Tyr Tyr Ser Cys Cys Ala Arg Thr Asp Tyr Asp Asp Tyr
                115                 120                 125

Thr Met Asp Tyr Trp Gly Gln Gly Thr Ser Val Thr Val Ser Ser Gly
130                 135                 140

Gly Gly Gly Ser Gly Gly Gly Ser Gly Gly Gly Ser Glu Ile
145                 150                 155                 160

Gln Met Thr Gln Thr Pro Ser Ser Leu Ser Ala Ser Leu Gly Asp Arg
                165                 170                 175

Val Thr Ile Ser Cys Arg Ala Ser His Asp Ile Ser Asn Tyr Leu Asn
                180                 185                 190

Trp Tyr Gln Gln Lys Pro Asp Gly Thr Leu Lys Leu Leu Ile Tyr Tyr
            195                 200                 205

Thr Ser Arg Leu His Ser Gly Val Pro Ser Arg Phe Ser Gly Ser Gly
        210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Gly Lys Thr Leu Leu Trp Thr Phe
                245                 250                 255

Gly Gly Gly Thr Lys Leu Glu Ile Lys Gly Leu Ala Val Ser Thr Ile
                260                 265                 270
```

```
Ser Ser Phe Phe Pro Pro Gly Tyr Gln Ile Tyr Ile Trp Ala Pro Leu
            275                 280                 285

Ala Gly Thr Cys Gly Val Leu Leu Ser Leu Val Ile Thr Leu Tyr
    290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
                325                 330                 335

Phe Pro Glu Glu Glu Glu Gly Gly Cys Glu Leu Arg Val Lys Phe Ser
                340                 345                 350

Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
    370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
                420                 425                 430

His Asp Gly Leu Tyr Gln Gly Leu Ser Thr Ala Thr Lys Asp Thr Tyr
            435                 440                 445

Asp Ala Leu His Met Gln Ala Leu Pro Pro Arg
            450                 455

<210> SEQ ID NO 66
<211> LENGTH: 462
<212> TYPE: PRT
<213> ORGANISM: Artificial sequence
<220> FEATURE:
<223> OTHER INFORMATION: G4 scCAR-v2 polypeptide

<400> SEQUENCE: 66

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Met Lys Ile Ser Cys Lys Ala Ser Gly Tyr
            35                  40                  45

Ser Phe Thr Gly Tyr Thr Met Asn Trp Val Lys Gln Ser His Glu Lys
        50                  55                  60

Asn Leu Glu Trp Ile Gly Pro Ile Asn Pro Tyr Asn Asp Gly Thr Ile
65                  70                  75                  80

Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
            100                 105                 110

Ala Val Tyr Tyr Ser Cys Cys Ala Arg Thr Asp Tyr Asp Asp Tyr
            115                 120                 125

Thr Met Asp Tyr Trp Gly Gln Gly Thr Ser Val Thr Val Ser Ser Gly
            130                 135                 140

Gly Gly Gly Ser Gly Gly Gly Gly Ser Gly Gly Gly Gly Ser Glu Ile
145                 150                 155                 160

Gln Met Thr Gln Thr Pro Ser Ser Leu Ser Ala Ser Leu Gly Asp Arg
                165                 170                 175
```

Val Thr Ile Ser Cys Arg Ala Ser His Asp Ile Ser Asn Tyr Leu Asn
        180                 185                 190

Trp Tyr Gln Gln Lys Pro Asp Gly Thr Leu Lys Leu Leu Ile Tyr Tyr
            195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Gly Lys Thr Leu Leu Trp Thr Phe
                245                 250                 255

Gly Gly Gly Thr Lys Leu Glu Ile Lys Gly Leu Ala Val Ser Thr Ile
            260                 265                 270

Ser Ser Phe Phe Pro Pro Gly Tyr Gln Ile Ile Ser Phe Phe Leu Ala
    275                 280                 285

Leu Thr Ser Thr Ala Leu Leu Phe Leu Leu Phe Phe Leu Thr Leu Arg
    290                 295                 300

Phe Ser Val Val Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350

Lys Phe Ser Arg Ser Ala Asp Ala Pro Ala Tyr Gln Gln Gly Gln Asn
            355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
    435                 440                 445

Asp Thr Tyr Asp Ala Leu His Met Gln Ala Leu Pro Pro Arg
    450                 455                 460

<210> SEQ ID NO 67
<211> LENGTH: 488
<212> TYPE: PRT
<213> ORGANISM: Artificial sequence
<220> FEATURE:
<223> OTHER INFORMATION: G4 scCAR-v3 polypeptide

<400> SEQUENCE: 67

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Met Lys Ile Ser Cys Lys Ala Ser Gly Tyr
        35                  40                  45

Ser Phe Thr Gly Tyr Thr Met Asn Trp Val Lys Gln Ser His Glu Lys
    50                  55                  60

Asn Leu Glu Trp Ile Gly Pro Ile Asn Pro Tyr Asn Asp Gly Thr Ile
65                  70                  75                  80

```
Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
            100                 105                 110

Ala Val Tyr Tyr Ser Cys Cys Ala Arg Thr Asp Tyr Asp Tyr
        115                 120                 125

Thr Met Asp Tyr Trp Gly Gln Gly Thr Ser Val Thr Val Ser Ser Gly
    130                 135                 140

Gly Gly Gly Ser Gly Gly Gly Ser Gly Gly Gly Ser Glu Ile
145             150                 155                 160

Gln Met Thr Gln Thr Pro Ser Ser Leu Ser Ala Ser Leu Gly Asp Arg
                165                 170                 175

Val Thr Ile Ser Cys Arg Ala Ser His Asp Ile Ser Asn Tyr Leu Asn
            180                 185                 190

Trp Tyr Gln Gln Lys Pro Asp Gly Thr Leu Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225             230                 235                 240

Ile Ala Thr Tyr Phe Cys Gln Gln Gly Lys Thr Leu Leu Trp Thr Phe
                245                 250                 255

Gly Gly Gly Thr Lys Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305             310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385             390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465             470                 475                 480

His Met Gln Ala Leu Pro Pro Arg
                485
```

```
<210> SEQ ID NO 68
<211> LENGTH: 491
<212> TYPE: PRT
<213> ORGANISM: Artificial sequence
<220> FEATURE:
<223> OTHER INFORMATION: G4 scCAR-v4 polypeptide

<400> SEQUENCE: 68

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Met Lys Ile Ser Cys Lys Ala Ser Gly Tyr
        35                  40                  45

Ser Phe Thr Gly Tyr Thr Met Asn Trp Val Lys Gln Ser His Glu Lys
    50                  55                  60

Asn Leu Glu Trp Ile Gly Pro Ile Asn Pro Tyr Asn Asp Gly Thr Ile
65                  70                  75                  80

Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
            100                 105                 110

Ala Val Tyr Tyr Ser Cys Cys Ala Arg Thr Asp Asp Tyr Asp Asp Tyr
        115                 120                 125

Thr Met Asp Tyr Trp Gly Gln Gly Thr Ser Val Thr Val Ser Ser Gly
    130                 135                 140

Gly Gly Gly Ser Gly Gly Gly Ser Gly Gly Gly Ser Glu Ile
145                 150                 155                 160

Gln Met Thr Gln Thr Pro Ser Ser Leu Ser Ala Ser Leu Gly Asp Arg
                165                 170                 175

Val Thr Ile Ser Cys Arg Ala Ser His Asp Ile Ser Asn Tyr Leu Asn
            180                 185                 190

Trp Tyr Gln Gln Lys Pro Asp Gly Thr Leu Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Gly Lys Thr Leu Leu Trp Thr Phe
                245                 250                 255

Gly Gly Gly Thr Lys Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Ile Ser Phe Phe Leu Ala Leu Thr Ser
305                 310                 315                 320

Thr Ala Leu Leu Phe Leu Leu Phe Phe Leu Thr Leu Arg Phe Ser Val
                325                 330                 335

Val Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
```

```
                   370                 375                 380
Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 69
<211> LENGTH: 674
<212> TYPE: PRT
<213> ORGANISM: Artificial sequence
<220> FEATURE:
<223> OTHER INFORMATION: G4 scCAR-v5 polypeptide

<400> SEQUENCE: 69

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Met Lys Ile Ser Cys Lys Ala Ser Gly Tyr
            35                  40                  45

Ser Phe Thr Gly Tyr Thr Met Asn Trp Val Lys Gln Ser His Glu Lys
        50                  55                  60

Asn Leu Glu Trp Ile Gly Pro Ile Asn Pro Tyr Asn Asp Gly Thr Ile
65                  70                  75                  80

Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
            100                 105                 110

Ala Val Tyr Tyr Ser Cys Cys Ala Arg Thr Asp Asp Tyr Asp Asp Tyr
        115                 120                 125

Thr Met Asp Tyr Trp Gly Gln Gly Thr Ser Val Thr Val Ser Ser Gly
    130                 135                 140

Gly Gly Gly Ser Gly Gly Gly Ser Gly Gly Gly Ser Glu Ile
145                 150                 155                 160

Gln Met Thr Gln Thr Pro Ser Ser Leu Ser Ala Ser Leu Gly Asp Arg
                165                 170                 175

Val Thr Ile Ser Cys Arg Ala Ser His Asp Ile Ser Asn Tyr Leu Asn
            180                 185                 190

Trp Tyr Gln Gln Lys Pro Asp Gly Thr Leu Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Gly Lys Thr Leu Leu Trp Thr Phe
```

```
                245                 250                 255
Gly Gly Gly Thr Lys Leu Glu Ile Lys Glu Pro Lys Ser Pro Asp Lys
                260                 265                 270
Thr His Thr Cys Pro Pro Cys Pro Ala Pro Pro Val Ala Gly Pro Ser
            275                 280                 285
Val Phe Leu Phe Pro Pro Lys Pro Lys Asp Thr Leu Met Ile Ala Arg
    290                 295                 300
Thr Pro Glu Val Thr Cys Val Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
            340                 345                 350
Ser Val Leu Thr Val Leu His Gln Asp Trp Leu Asn Gly Lys Glu Tyr
        355                 360                 365
Lys Cys Lys Val Ser Asn Lys Ala Leu Pro Ala Pro Ile Glu Lys Thr
    370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495
Ile Tyr Ile Trp Ala Pro Leu Ala Gly Thr Cys Gly Val Leu Leu Leu
            500                 505                 510
Ser Leu Val Ile Thr Leu Tyr Cys Lys Arg Gly Arg Lys Lys Leu Leu
        515                 520                 525
Tyr Ile Phe Lys Gln Pro Phe Met Arg Pro Val Gln Thr Thr Gln Glu
    530                 535                 540
Glu Asp Gly Cys Ser Cys Arg Phe Pro Glu Glu Glu Glu Gly Gly Cys
545                 550                 555                 560
Glu Leu Arg Val Lys Phe Ser Arg Ser Ala Asp Ala Pro Ala Tyr Gln
                565                 570                 575
Gln Gly Gln Asn Gln Leu Tyr Asn Glu Leu Asn Leu Gly Arg Arg Glu
            580                 585                 590
Glu Tyr Asp Val Leu Asp Lys Arg Arg Gly Arg Asp Pro Glu Met Gly
        595                 600                 605
Gly Lys Pro Arg Arg Lys Asn Pro Gln Glu Gly Leu Tyr Asn Glu Leu
    610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                645                 650                 655
Thr Ala Thr Lys Asp Thr Tyr Asp Ala Leu His Met Gln Ala Leu Pro
            660                 665                 670
```

Pro Arg

<210> SEQ ID NO 70
<211> LENGTH: 677
<212> TYPE: PRT
<213> ORGANISM: Artificial sequence
<220> FEATURE:
<223> OTHER INFORMATION: G4 scCAR-v6 polypeptide

<400> SEQUENCE: 70

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Met Lys Ile Ser Cys Lys Ala Ser Gly Tyr
        35                  40                  45

Ser Phe Thr Gly Tyr Thr Met Asn Trp Val Lys Gln Ser His Glu Lys
    50                  55                  60

Asn Leu Glu Trp Ile Gly Pro Ile Asn Pro Tyr Asn Asp Gly Thr Ile
65                  70                  75                  80

Tyr Asn Pro Asn Phe Lys Gly Lys Ala Thr Leu Thr Val Asp Lys Ala
                85                  90                  95

Ser Ser Thr Ala Tyr Met Glu Leu Leu Ser Leu Thr Ser Asp Asp Pro
            100                 105                 110

Ala Val Tyr Tyr Ser Cys Cys Ala Arg Thr Asp Asp Tyr Asp Asp Tyr
        115                 120                 125

Thr Met Asp Tyr Trp Gly Gln Gly Thr Ser Val Thr Val Ser Ser Gly
    130                 135                 140

Gly Gly Gly Ser Gly Gly Gly Ser Gly Gly Gly Ser Glu Ile
145                 150                 155                 160

Gln Met Thr Gln Thr Pro Ser Ser Leu Ser Ala Ser Leu Gly Asp Arg
                165                 170                 175

Val Thr Ile Ser Cys Arg Ala Ser His Asp Ile Ser Asn Tyr Leu Asn
            180                 185                 190

Trp Tyr Gln Gln Lys Pro Asp Gly Thr Leu Lys Leu Leu Ile Tyr Tyr
        195                 200                 205

Thr Ser Arg Leu His Ser Gly Val Pro Ser Arg Phe Ser Gly Ser Gly
    210                 215                 220

Ser Gly Thr Asp Tyr Ser Leu Thr Ile Ser Asn Leu Glu Gln Glu Asp
225                 230                 235                 240

Ile Ala Thr Tyr Phe Cys Gln Gln Gly Lys Thr Leu Leu Trp Thr Phe
                245                 250                 255

Gly Gly Gly Thr Lys Leu Glu Ile Lys Glu Pro Lys Ser Pro Asp Lys
            260                 265                 270

Thr His Thr Cys Pro Pro Cys Pro Ala Pro Val Ala Gly Pro Ser
        275                 280                 285

Val Phe Leu Phe Pro Pro Lys Pro Lys Asp Thr Leu Met Ile Ala Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350
```

```
Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

Ile Ile Ser Phe Phe Leu Ala Leu Thr Ser Thr Ala Leu Leu Phe Leu
            500                 505                 510

Leu Phe Phe Leu Thr Leu Arg Phe Ser Val Val Lys Arg Gly Arg Lys
        515                 520                 525

Lys Leu Leu Tyr Ile Phe Lys Gln Pro Phe Met Arg Pro Val Gln Thr
        530                 535                 540

Thr Gln Glu Glu Asp Gly Cys Ser Cys Arg Phe Pro Glu Glu Glu Glu
545                 550                 555                 560

Gly Gly Cys Glu Leu Arg Val Lys Phe Ser Arg Ser Ala Asp Ala Pro
            565                 570                 575

Ala Tyr Gln Gln Gly Gln Asn Gln Leu Tyr Asn Glu Leu Asn Leu Gly
            580                 585                 590

Arg Arg Glu Glu Tyr Asp Val Leu Asp Lys Arg Arg Gly Arg Asp Pro
        595                 600                 605

Glu Met Gly Gly Lys Pro Arg Arg Lys Asn Pro Gln Glu Gly Leu Tyr
        610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
            645                 650                 655

Gly Leu Ser Thr Ala Thr Lys Asp Thr Tyr Asp Ala Leu His Met Gln
            660                 665                 670

Ala Leu Pro Pro Arg
            675

<210> SEQ ID NO 71
<211> LENGTH: 464
<212> TYPE: PRT
<213> ORGANISM: Artificial sequence
<220> FEATURE:
<223> OTHER INFORMATION: M22  scCAR-v1 polypeptide

<400> SEQUENCE: 71

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30
```

```
Val Lys Pro Gly Ala Ser Val Lys Leu Ser Cys Lys Ala Ser Gly Tyr
             35                  40                  45

Thr Phe Thr Arg Tyr Trp Met His Trp Val Lys Gln Arg Pro Gly Gln
 50                  55                  60

Gly Leu Glu Trp Ile Gly Asn Ile Asp Pro Ser Asp Thr Glu Thr His
 65                  70                  75                  80

Tyr Asn Gln Gln Phe Lys Asp Lys Ala Thr Leu Thr Val Asp Lys Ser
                 85                  90                  95

Ser Ser Thr Ala Tyr Met Gln Leu Ser Ser Leu Thr Ser Glu Asp Ser
                100                 105                 110

Ala Val Tyr Tyr Cys Ala Ile Tyr Tyr Gly Asn Pro Ser Tyr Tyr Ala
            115                 120                 125

Met Asp Tyr Trp Gly Gln Gly Thr Ser Val Thr Val Ser Ser Gly Gly
130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Asn Leu Leu Asn Ser Gly Asn Gln
            180                 185                 190

Lys Lys Tyr Leu Asn Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
        210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
                245                 250                 255

Tyr Pro Phe Thr Phe Gly Ala Gly Thr Lys Leu Glu Leu Lys Gly Leu
            260                 265                 270

Ala Val Ser Thr Ile Ser Ser Phe Phe Pro Pro Gly Tyr Gln Ile Tyr
            275                 280                 285

Ile Trp Ala Pro Leu Ala Gly Thr Cys Gly Val Leu Leu Leu Ser Leu
290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
        370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
```

```
                450                 455                 460

<210> SEQ ID NO 72
<211> LENGTH: 467
<212> TYPE: PRT
<213> ORGANISM: Artificial sequence
<220> FEATURE:
<223> OTHER INFORMATION: M22   scCAR-v2 polypeptide

<400> SEQUENCE: 72

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Asn Ile Asp Pro Ser Asp Thr Glu Thr His
65                  70                  75                  80

Tyr Asn Gln Gln Phe Lys Asp Lys Ala Thr Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Ile Tyr Tyr Gly Asn Pro Ser Tyr Tyr Ala
        115                 120                 125

Met Asp Tyr Trp Gly Gln Gly Thr Ser Val Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Asn Leu Leu Asn Ser Gly Asn Gln
            180                 185                 190

Lys Lys Tyr Leu Asn Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
                245                 250                 255

Tyr Pro Phe Thr Phe Gly Ala Gly Thr Lys Leu Glu Leu Lys Gly Leu
            260                 265                 270

Ala Val Ser Thr Ile Ser Ser Phe Phe Pro Pro Gly Tyr Gln Ile Ile
        275                 280                 285

Ser Phe Phe Leu Ala Leu Thr Ser Thr Ala Leu Leu Phe Leu Leu Phe
    290                 295                 300

Phe Leu Thr Leu Arg Phe Ser Val Val Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
```

```
                355                 360                 365
Gln Gln Gly Gln Asn Gln Leu Tyr Asn Glu Leu Asn Leu Gly Arg Arg
        370                 375                 380

Glu Glu Tyr Asp Val Leu Asp Lys Arg Arg Gly Arg Asp Pro Glu Met
385                 390                 395                 400

Gly Gly Lys Pro Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
                420                 425                 430

Gly Glu Arg Arg Arg Gly Lys Gly His Asp Gly Leu Tyr Gln Gly Leu
                435                 440                 445

Ser Thr Ala Thr Lys Asp Thr Tyr Asp Ala Leu His Met Gln Ala Leu
                450                 455                 460

Pro Pro Arg
465

<210> SEQ ID NO 73
<211> LENGTH: 493
<212> TYPE: PRT
<213> ORGANISM: Artificial sequence
<220> FEATURE:
<223> OTHER INFORMATION: M22  scCAR-v3 polypeptide

<400> SEQUENCE: 73

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Lys Pro Gly Ala Ser Val Lys Leu Ser Cys Lys Ala Ser Gly Tyr
            35                  40                  45

Thr Phe Thr Arg Tyr Trp Met His Trp Val Lys Gln Arg Pro Gly Gln
        50                  55                  60

Gly Leu Glu Trp Ile Gly Asn Ile Asp Pro Ser Asp Thr Glu Thr His
65                  70                  75                  80

Tyr Asn Gln Gln Phe Lys Asp Lys Ala Thr Leu Thr Val Asp Lys Ser
                85                  90                  95

Ser Ser Thr Ala Tyr Met Gln Leu Ser Ser Leu Thr Ser Glu Asp Ser
                100                 105                 110

Ala Val Tyr Tyr Cys Ala Ile Tyr Tyr Gly Asn Pro Ser Tyr Tyr Ala
            115                 120                 125

Met Asp Tyr Trp Gly Gln Gly Thr Ser Val Thr Val Ser Ser Gly Gly
        130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Asn Leu Leu Asn Ser Gly Asn Gln
            180                 185                 190

Lys Lys Tyr Leu Asn Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
        210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
```

```
            245                 250                 255
Tyr Pro Phe Thr Phe Gly Ala Gly Thr Lys Leu Glu Leu Lys Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 74
<211> LENGTH: 496
<212> TYPE: PRT
<213> ORGANISM: Artificial sequence
<220> FEATURE:
<223> OTHER INFORMATION: M22  scCAR-v4 polypeptide

<400> SEQUENCE: 74

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Asn Ile Asp Pro Ser Asp Thr Glu Thr His
65                  70                  75                  80

Tyr Asn Gln Gln Phe Lys Asp Lys Ala Thr Leu Thr Val Asp Lys Ser
            85                  90                  95

Ser Ser Thr Ala Tyr Met Gln Leu Ser Ser Leu Thr Ser Glu Asp Ser
            100                 105                 110

Ala Val Tyr Tyr Cys Ala Ile Tyr Tyr Gly Asn Pro Ser Tyr Tyr Ala
```

```
            115                 120                 125
Met Asp Tyr Trp Gly Gln Gly Thr Ser Val Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                    165                 170                 175

Thr Met Ser Cys Lys Ser Ser Gln Asn Leu Leu Asn Ser Gly Asn Gln
                180                 185                 190

Lys Lys Tyr Leu Asn Trp Tyr Gln Gln Lys Pro Gly Gln Pro Pro Lys
            195                 200                 205

Leu Leu Ile Tyr Trp Ala Ser Thr Arg Glu Ser Gly Val Pro Asp Arg
        210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
                    245                 250                 255

Tyr Pro Phe Thr Phe Gly Ala Gly Thr Lys Leu Glu Leu Lys Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Ile Ser Phe Phe
305                 310                 315                 320

Leu Ala Leu Thr Ser Thr Ala Leu Leu Phe Leu Leu Phe Phe Leu Thr
                    325                 330                 335

Leu Arg Phe Ser Val Val Lys Arg Gly Arg Lys Lys Leu Leu Tyr Ile
                340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Glu Gly Gly Cys Glu Leu
        370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                    405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
        450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                    485                 490                 495

<210> SEQ ID NO 75
<211> LENGTH: 679
<212> TYPE: PRT
<213> ORGANISM: Artificial sequence
<220> FEATURE:
<223> OTHER INFORMATION: M22  scCAR-v5 polypeptide
```

```
<400> SEQUENCE: 75

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Asn Ile Asp Pro Ser Asp Thr Glu Thr His
65                  70                  75                  80

Tyr Asn Gln Gln Phe Lys Asp Lys Ala Thr Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Ile Tyr Tyr Gly Asn Pro Ser Tyr Tyr Ala
        115                 120                 125

Met Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Asn Leu Leu Asn Ser Gly Asn Gln
            180                 185                 190

Lys Lys Tyr Leu Asn Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
                245                 250                 255

Tyr Pro Phe Thr Phe Gly Ala Gly Thr Lys Leu Glu Leu Lys Glu Pro
            260                 265                 270

Lys Ser Pro Asp Lys Thr His Thr Cys Pro Pro Cys Pro Ala Pro Pro
        275                 280                 285

Val Ala Gly Pro Ser Val Phe Leu Phe Pro Pro Lys Pro Lys Asp Thr
    290                 295                 300

Leu Met Ile Ala Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415
```

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
            485                 490                 495

Leu Ser Pro Gly Lys Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
            515                 520                 525

Arg Lys Lys Leu Leu Tyr Ile Phe Lys Gln Pro Phe Met Arg Pro Val
            530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
            565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
            595                 600                 605

Asp Pro Glu Met Gly Gly Lys Pro Arg Arg Lys Asn Pro Gln Glu Gly
            610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
            645                 650                 655

Tyr Gln Gly Leu Ser Thr Ala Thr Lys Asp Thr Tyr Asp Ala Leu His
            660                 665                 670

Met Gln Ala Leu Pro Pro Arg
            675

<210> SEQ ID NO 76
<211> LENGTH: 682
<212> TYPE: PRT
<213> ORGANISM: Artificial sequence
<220> FEATURE:
<223> OTHER INFORMATION: M22  scCAR-v6 polypeptide

<400> SEQUENCE: 76

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Leu Ser Cys Lys Ala Ser Gly Tyr
            35                  40                  45

Thr Phe Thr Arg Tyr Trp Met His Trp Val Lys Gln Arg Pro Gly Gln
            50                  55                  60

Gly Leu Glu Trp Ile Gly Asn Ile Asp Pro Ser Asp Thr Glu Thr His
65                  70                  75                  80

Tyr Asn Gln Gln Phe Lys Asp Lys Ala Thr Leu Thr Val Asp Lys Ser
            85                  90                  95

```
Ser Ser Thr Ala Tyr Met Gln Leu Ser Ser Leu Thr Ser Glu Asp Ser
                100                 105                 110

Ala Val Tyr Tyr Cys Ala Ile Tyr Tyr Gly Asn Pro Ser Tyr Tyr Ala
            115                 120                 125

Met Asp Tyr Trp Gly Gln Gly Thr Ser Val Thr Val Ser Ser Gly Gly
130                 135                 140

Gly Gly Ser Gly Gly Gly Ser Gly Gly Gly Ser Asp Ile Val
145                 150                 155                 160

Met Thr Gln Ser Pro Ser Ser Leu Thr Val Thr Ala Gly Glu Lys Val
                165                 170                 175

Thr Met Ser Cys Lys Ser Ser Gln Asn Leu Leu Asn Ser Gly Asn Gln
            180                 185                 190

Lys Lys Tyr Leu Asn Trp Tyr Gln Gln Lys Pro Gly Gln Pro Pro Lys
        195                 200                 205

Leu Leu Ile Tyr Trp Ala Ser Thr Arg Glu Ser Gly Val Pro Asp Arg
    210                 215                 220

Phe Thr Gly Ser Gly Ser Gly Thr Asp Phe Thr Leu Thr Ile Ser Ser
225                 230                 235                 240

Val Gln Ala Glu Asp Leu Ala Val Tyr Phe Cys Gln Asn Asp Tyr Ser
                245                 250                 255

Tyr Pro Phe Thr Phe Gly Ala Gly Thr Lys Leu Glu Leu Lys Glu Pro
            260                 265                 270

Lys Ser Pro Asp Lys Thr His Thr Cys Pro Pro Cys Pro Ala Pro Pro
        275                 280                 285

Val Ala Gly Pro Ser Val Phe Leu Phe Pro Pro Lys Pro Lys Asp Thr
    290                 295                 300

Leu Met Ile Ala Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
    450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys Ile Ile Ser Phe Phe Leu Ala Leu Thr Ser Thr
            500                 505                 510
```

```
Ala Leu Leu Phe Leu Leu Phe Phe Leu Thr Leu Arg Phe Ser Val Val
        515                 520                 525

Lys Arg Gly Arg Lys Leu Leu Tyr Ile Phe Lys Gln Pro Phe Met
530                 535                 540

Arg Pro Val Gln Thr Thr Gln Glu Glu Asp Gly Cys Ser Cys Arg Phe
545                 550                 555                 560

Pro Glu Glu Glu Gly Gly Cys Glu Leu Arg Val Lys Phe Ser Arg
                565                 570                 575

Ser Ala Asp Ala Pro Ala Tyr Gln Gln Gly Gln Asn Gln Leu Tyr Asn
            580                 585                 590

Glu Leu Asn Leu Gly Arg Arg Glu Glu Tyr Asp Val Leu Asp Lys Arg
        595                 600                 605

Arg Gly Arg Asp Pro Glu Met Gly Gly Lys Pro Arg Arg Lys Asn Pro
610                 615                 620

Gln Glu Gly Leu Tyr Asn Glu Leu Gln Lys Asp Lys Met Ala Glu Ala
625                 630                 635                 640

Tyr Ser Glu Ile Gly Met Lys Gly Glu Arg Arg Arg Gly Lys Gly His
                645                 650                 655

Asp Gly Leu Tyr Gln Gly Leu Ser Thr Ala Thr Lys Asp Thr Tyr Asp
                660                 665                 670

Ala Leu His Met Gln Ala Leu Pro Pro Arg
            675                 680

<210> SEQ ID NO 77
<211> LENGTH: 457
<212> TYPE: PRT
<213> ORGANISM: Artificial sequence
<220> FEATURE:
<223> OTHER INFORMATION: M29 scCAR-v1 polypeptide

<400> SEQUENCE: 77

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Ile Phe Thr Ser Tyr Val Met Tyr Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Ser Cys Cys Ala Arg Tyr Tyr Asp Tyr Asp Tyr Tyr
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Leu Gly Gly Lys Val
                165                 170                 175

Thr Ile Thr Cys Lys Ala Ser Gln Asp Ile Asn Lys Tyr Ile Ala Trp
            180                 185                 190
```

Tyr Gln His Lys Pro Gly Lys Gly Pro Arg Leu Leu Ile His Tyr Thr
                195                 200                 205

Ser Thr Leu Gln Pro Gly Ile Pro Ser Arg Phe Ser Gly Ser Gly Ser
    210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
                245                 250                 255

Gly Thr Lys Leu Glu Ile Lys Gly Leu Ala Val Ser Thr Ile Ser Ser
                260                 265                 270

Phe Phe Pro Pro Gly Tyr Gln Ile Tyr Ile Trp Ala Pro Leu Ala Gly
                275                 280                 285

Thr Cys Gly Val Leu Leu Leu Ser Leu Val Ile Thr Leu Tyr Cys Lys
        290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
                340                 345                 350

Ala Asp Ala Pro Ala Tyr Gln Gln Gly Gln Asn Gln Leu Tyr Asn Glu
                355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
                420                 425                 430

Gly Leu Tyr Gln Gly Leu Ser Thr Ala Thr Lys Asp Thr Tyr Asp Ala
                435                 440                 445

Leu His Met Gln Ala Leu Pro Pro Arg
    450                 455

<210> SEQ ID NO 78
<211> LENGTH: 460
<212> TYPE: PRT
<213> ORGANISM: Artificial sequence
<220> FEATURE:
<223> OTHER INFORMATION: M29 scCAR-v2 polypeptide

<400> SEQUENCE: 78

Met Ala Leu Pro Val Thr Ala Leu Leu Pro Leu Ala Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Met Ser Cys Lys Ala Ser Gly Tyr
            35                  40                  45

Ile Phe Thr Ser Tyr Val Met Tyr Trp Val Lys Gln Lys Pro Gly Gln
        50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

```
Ser Ser Thr Ala Tyr Met Glu Leu Ser Ser Leu Thr Ser Glu Asp Ser
            100                 105                 110

Ala Val Tyr Tyr Ser Cys Cys Ala Arg Tyr Tyr Asp Tyr Asp Tyr Tyr
        115                 120                 125

Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Leu Gly Gly Lys Val
                165                 170                 175

Thr Ile Thr Cys Lys Ala Ser Gln Asp Ile Asn Lys Tyr Ile Ala Trp
            180                 185                 190

Tyr Gln His Lys Pro Gly Lys Gly Pro Arg Leu Leu Ile His Tyr Thr
        195                 200                 205

Ser Thr Leu Gln Pro Gly Ile Pro Ser Arg Phe Ser Gly Ser Gly Ser
    210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Ile Ile Ser Phe Phe Leu Ala Leu Thr
        275                 280                 285

Ser Thr Ala Leu Leu Phe Leu Leu Phe Phe Leu Thr Leu Arg Phe Ser
    290                 295                 300

Val Val Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
    450                 455                 460

<210> SEQ ID NO 79
<211> LENGTH: 486
<212> TYPE: PRT
<213> ORGANISM: Artificial sequence
<220> FEATURE:
<223> OTHER INFORMATION: M29 scCAR-v3 polypeptide

<400> SEQUENCE: 79
```

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Ile Phe Thr Ser Tyr Val Met Tyr Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Ser Cys Cys Ala Arg Tyr Tyr Asp Tyr Asp Tyr Tyr
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Ser Asp Ile Gln Met
145                 150                 155                 160

Met Thr Gln Ser Pro Ser Ser Leu Ser Ala Ser Leu Gly Gly Lys Val
            165                 170                 175

Thr Ile Thr Cys Lys Ala Ser Gln Asp Ile Asn Lys Tyr Ile Ala Trp
        180                 185                 190

Tyr Gln His Lys Pro Gly Lys Gly Pro Arg Leu Leu Ile His Tyr Thr
    195                 200                 205

Ser Thr Leu Gln Pro Gly Ile Pro Ser Arg Phe Ser Gly Ser Gly Ser
210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
            245                 250                 255

Gly Thr Lys Leu Glu Ile Lys Thr Thr Thr Pro Ala Pro Arg Pro Pro
        260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
        340                 345                 350

Thr Thr Gln Glu Glu Asp Gly Cys Ser Cys Arg Phe Pro Glu Glu Glu
    355                 360                 365

Glu Gly Gly Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
```

```
                    420                 425                 430
Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 80
<211> LENGTH: 489
<212> TYPE: PRT
<213> ORGANISM: Artificial sequence
<220> FEATURE:
<223> OTHER INFORMATION: M29  scCAR-v4 polypeptide

<400> SEQUENCE: 80

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Ile Phe Thr Ser Tyr Val Met Tyr Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Ser Cys Cys Ala Arg Tyr Tyr Asp Tyr Asp Tyr Tyr
        115                 120                 125

Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Leu Gly Gly Lys Val
                165                 170                 175

Thr Ile Thr Cys Lys Ala Ser Gln Asp Ile Asn Lys Tyr Ile Ala Trp
            180                 185                 190

Tyr Gln His Lys Pro Gly Lys Gly Pro Arg Leu Leu Ile His Tyr Thr
        195                 200                 205

Ser Thr Leu Gln Pro Gly Ile Pro Ser Arg Phe Ser Gly Ser Gly Ser
    210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
```

```
                        290                 295                 300
Phe Ala Cys Asp Ile Ile Ser Phe Phe Leu Ala Leu Thr Ser Thr Ala
305                 310                 315                 320

Leu Leu Phe Leu Leu Phe Phe Leu Thr Leu Arg Phe Ser Val Val Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
                355                 360                 365

Glu Glu Glu Glu Gly Gly Cys Glu Leu Arg Val Lys Phe Ser Arg Ser
                370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
                450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 81
<211> LENGTH: 672
<212> TYPE: PRT
<213> ORGANISM: artificial sequence
<220> FEATURE:
<223> OTHER INFORMATION: M29  scCAR-v5 polypeptide

<400> SEQUENCE: 81

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Met Ser Cys Lys Ala Ser Gly Tyr
                35                  40                  45

Ile Phe Thr Ser Tyr Val Met Tyr Trp Val Lys Gln Lys Pro Gly Gln
            50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
                100                 105                 110

Ala Val Tyr Tyr Ser Cys Cys Ala Arg Tyr Tyr Asp Tyr Asp Tyr Tyr
                115                 120                 125

Phe Asp Tyr Trp Gly Gln Gly Thr Thr Leu Thr Val Ser Ser Gly Gly
                130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Leu Gly Gly Lys Val
```

```
                165                 170                 175
Thr Ile Thr Cys Lys Ala Ser Gln Asp Ile Asn Lys Tyr Ile Ala Trp
            180                 185                 190

Tyr Gln His Lys Pro Gly Lys Gly Pro Arg Leu Leu Ile His Tyr Thr
            195                 200                 205

Ser Thr Leu Gln Pro Gly Ile Pro Ser Arg Phe Ser Gly Ser Gly Ser
            210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
            245                 250                 255

Gly Thr Lys Leu Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
            275                 280                 285

Leu Phe Pro Pro Lys Pro Lys Asp Thr Leu Met Ile Ala Arg Thr Pro
            290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
            325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
            405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Ile Tyr
            485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
            515                 520                 525

Phe Lys Gln Pro Phe Met Arg Pro Val Gln Thr Thr Gln Glu Glu Asp
            530                 535                 540

Gly Cys Ser Cys Arg Phe Pro Glu Glu Glu Gly Gly Cys Glu Leu
545                 550                 555                 560

Arg Val Lys Phe Ser Arg Ser Ala Asp Ala Pro Ala Tyr Gln Gln Gly
            565                 570                 575

Gln Asn Gln Leu Tyr Asn Glu Leu Asn Leu Gly Arg Arg Glu Glu Tyr
            580                 585                 590
```

Asp Val Leu Asp Lys Arg Arg Gly Arg Asp Pro Glu Met Gly Gly Lys
         595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
            645                 650                 655

Thr Lys Asp Thr Tyr Asp Ala Leu His Met Gln Ala Leu Pro Pro Arg
            660                 665                 670

<210> SEQ ID NO 82
<211> LENGTH: 675
<212> TYPE: PRT
<213> ORGANISM: artificial sequence
<220> FEATURE:
<223> OTHER INFORMATION: M29 scCAR-v6 polypeptide

<400> SEQUENCE: 82

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Met Ser Cys Lys Ala Ser Gly Tyr
        35                  40                  45

Ile Phe Thr Ser Tyr Val Met Tyr Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Ser Cys Cys Ala Arg Tyr Tyr Asp Tyr Asp Tyr Tyr
        115                 120                 125

Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Leu Gly Gly Lys Val
                165                 170                 175

Thr Ile Thr Cys Lys Ala Ser Gln Asp Ile Asn Lys Tyr Ile Ala Trp
            180                 185                 190

Tyr Gln His Lys Pro Gly Lys Gly Pro Arg Leu Leu Ile His Tyr Thr
        195                 200                 205

Ser Thr Leu Gln Pro Gly Ile Pro Ser Arg Phe Ser Gly Ser Gly Ser
    210                 215                 220

Gly Arg Asp Tyr Ser Phe Ser Ile Ser Asn Leu Glu Pro Glu Asp Ile
225                 230                 235                 240

Ala Thr Tyr Tyr Cys Leu Gln Tyr Asp Tyr Leu Trp Thr Phe Gly Gly
                245                 250                 255

Gly Thr Lys Leu Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

```
Leu Phe Pro Pro Lys Pro Lys Asp Thr Leu Met Ile Ala Arg Thr Pro
            290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Ile Ile
                485                 490                 495

Ser Phe Phe Leu Ala Leu Thr Ser Thr Ala Leu Leu Phe Leu Leu Phe
            500                 505                 510

Phe Leu Thr Leu Arg Phe Ser Val Val Lys Arg Gly Arg Lys Lys Leu
        515                 520                 525

Leu Tyr Ile Phe Lys Gln Pro Phe Met Arg Pro Val Gln Thr Thr Gln
    530                 535                 540

Glu Glu Asp Gly Cys Ser Cys Arg Phe Pro Glu Glu Glu Glu Gly Gly
545                 550                 555                 560

Cys Glu Leu Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
        595                 600                 605

Gly Gly Lys Pro Arg Arg Lys Asn Pro Gln Glu Gly Leu Tyr Asn Glu
    610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
            660                 665                 670

Pro Pro Arg
    675

<210> SEQ ID NO 83
<211> LENGTH: 458
```

```
<212> TYPE: PRT
<213> ORGANISM: artificial sequence
<220> FEATURE:
<223> OTHER INFORMATION: M2 scCAR-v1 polypeptide

<400> SEQUENCE: 83
```

Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Met His Trp Val Lys Gln Lys Pro Gly Gln
    50                  55                  60

Gly Leu Glu Trp Ile Gly Phe Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Asn Ser Leu Thr Ser Glu Asp Ser
            100                 105                 110

Ala Val Tyr Tyr Cys Thr Arg Asp Asp Gly Tyr Tyr Ala Met
            115                 120                 125

Asp Tyr Trp Gly Gln Gly Thr Ser Val Thr Val Ser Ser Gly Gly Gly
130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
            165                 170                 175

Leu Thr Cys Arg Ala Ser Gln Glu Ile Ser Val Tyr Leu Ser Trp Leu
        180                 185                 190

Gln Gln Lys Pro Asp Gly Thr Ile Lys Arg Leu Ile Tyr Ala Ala Ser
    195                 200                 205

Thr Leu Asp Ser Gly Val Pro Glu Arg Phe Ser Gly Ser Arg Ser Gly
210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Gly Leu Ala Val Ser Thr Ile Ser
            260                 265                 270

Ser Phe Phe Pro Pro Gly Tyr Gln Ile Tyr Ile Trp Ala Pro Leu Ala
        275                 280                 285

Gly Thr Cys Gly Val Leu Leu Leu Ser Leu Val Ile Thr Leu Tyr Cys
    290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

```
Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
        450                 455

<210> SEQ ID NO 84
<211> LENGTH: 461
<212> TYPE: PRT
<213> ORGANISM: artificial sequence
<220> FEATURE:
<223> OTHER INFORMATION: M2 scCAR-v2 polypeptide

<400> SEQUENCE: 84

Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
                20                  25                  30

Val Lys Pro Gly Ala Ser Val Lys Met Ser Cys Lys Ala Ser Gly Tyr
            35                  40                  45

Thr Phe Thr Ser Tyr Phe Met His Trp Val Lys Gln Lys Pro Gly Gln
        50                  55                  60

Gly Leu Glu Trp Ile Gly Phe Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Asn Ser Leu Thr Ser Glu Asp Ser
            100                 105                 110

Ala Val Tyr Tyr Cys Thr Arg Asp Asp Gly Tyr Tyr Asp Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Ser Gln Glu Ile Ser Val Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Glu Arg Phe Ser Gly Ser Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Gly Leu Ala Val Ser Thr Ile Ser
            260                 265                 270

Ser Phe Phe Pro Pro Gly Tyr Gln Ile Ile Ser Phe Phe Leu Ala Leu
        275                 280                 285
```

```
Thr Ser Thr Ala Leu Leu Phe Leu Phe Phe Leu Thr Leu Arg Phe
    290             295             300

Ser Val Val Lys Arg Gly Arg Lys Lys Leu Leu Tyr Ile Phe Lys Gln
305             310             315             320

Pro Phe Met Arg Pro Val Gln Thr Thr Gln Glu Glu Asp Gly Cys Ser
            325             330             335

Cys Arg Phe Pro Glu Glu Glu Glu Gly Gly Cys Glu Leu Arg Val Lys
            340             345             350

Phe Ser Arg Ser Ala Asp Ala Pro Ala Tyr Gln Gln Gly Gln Asn Gln
            355             360             365

Leu Tyr Asn Glu Leu Asn Leu Gly Arg Arg Glu Glu Tyr Asp Val Leu
    370             375             380

Asp Lys Arg Arg Gly Arg Asp Pro Glu Met Gly Gly Lys Pro Arg Arg
385             390             395             400

Lys Asn Pro Gln Glu Gly Leu Tyr Asn Glu Leu Gln Lys Asp Lys Met
            405             410             415

Ala Glu Ala Tyr Ser Glu Ile Gly Met Lys Gly Glu Arg Arg Arg Gly
            420             425             430

Lys Gly His Asp Gly Leu Tyr Gln Gly Leu Ser Thr Ala Thr Lys Asp
            435             440             445

Thr Tyr Asp Ala Leu His Met Gln Ala Leu Pro Pro Arg
    450             455             460

<210> SEQ ID NO 85
<211> LENGTH: 487
<212> TYPE: PRT
<213> ORGANISM: artificial sequence
<220> FEATURE:
<223> OTHER INFORMATION: M2 scCAR-v3 polypeptide

<400> SEQUENCE: 85

Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
                20                  25                  30

Val Lys Pro Gly Ala Ser Val Lys Met Ser Cys Lys Ala Ser Gly Tyr
            35                  40                  45

Thr Phe Thr Ser Tyr Phe Met His Trp Val Lys Gln Lys Pro Gly Gln
        50                  55                  60

Gly Leu Glu Trp Ile Gly Phe Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Asn Ser Leu Thr Ser Glu Asp Ser
            100                 105                 110

Ala Val Tyr Tyr Cys Thr Arg Asp Asp Gly Tyr Tyr Asp Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Ser Gln Glu Ile Ser Val Tyr Leu Ser Trp Leu
            180                 185                 190
```

```
Gln Gln Lys Pro Asp Gly Thr Ile Lys Arg Leu Ile Tyr Ala Ala Ser
            195                 200                 205

Thr Leu Asp Ser Gly Val Pro Glu Arg Phe Ser Gly Ser Arg Ser Gly
        210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 86
<211> LENGTH: 490
<212> TYPE: PRT
<213> ORGANISM: artificial sequence
<220> FEATURE:
<223> OTHER INFORMATION: M2 scCAR-v4 polypeptide

<400> SEQUENCE: 86

```
Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Met His Trp Val Lys Gln Lys Pro Gly Gln
    50                  55                  60
```

```
Gly Leu Glu Trp Ile Gly Phe Ile Asn Pro Tyr Asn Asp Gly Thr Lys
 65                  70                  75                  80

Tyr Asn Glu Lys Phe Lys Gly Lys Ala Thr Leu Thr Ser Asp Lys Ser
                 85                  90                  95

Ser Ser Thr Ala Tyr Met Glu Leu Asn Ser Leu Thr Ser Glu Asp Ser
                100                 105                 110

Ala Val Tyr Tyr Cys Thr Arg Asp Asp Gly Tyr Tyr Asp Tyr Ala Met
            115                 120                 125

Asp Tyr Trp Gly Gln Gly Thr Ser Val Thr Val Ser Ser Gly Gly Gly
        130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Ser Gln Glu Ile Ser Val Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Glu Arg Phe Ser Gly Ser Arg Ser Gly
210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Thr Thr Pro Ala Pro Arg Pro
            260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
        290                 295                 300

Asp Phe Ala Cys Asp Ile Ile Ser Phe Phe Leu Ala Leu Thr Ser Thr
305                 310                 315                 320

Ala Leu Leu Phe Leu Leu Phe Phe Leu Thr Leu Arg Phe Ser Val Val
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
```

<210> SEQ ID NO 87
<211> LENGTH: 673
<212> TYPE: PRT
<213> ORGANISM: artificial sequence
<220> FEATURE:
<223> OTHER INFORMATION: M2 scCAR-v5 polypeptide

<400> SEQUENCE: 87

```
Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
            20                  25                  30

Val Lys Pro Gly Ala Ser Val Lys Met Ser Cys Lys Ala Ser Gly Tyr
        35                  40                  45

Thr Phe Thr Ser Tyr Phe Met His Trp Val Lys Gln Lys Pro Gly Gln
    50                  55                  60

Gly Leu Glu Trp Ile Gly Phe Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Asn Ser Leu Thr Ser Glu Asp Ser
            100                 105                 110

Ala Val Tyr Tyr Cys Thr Arg Asp Asp Gly Tyr Tyr Asp Tyr Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Ser Gln Glu Ile Ser Val Tyr Leu Ser Trp Leu
            180                 185                 190

Gln Gln Lys Pro Asp Gly Thr Ile Lys Arg Leu Ile Tyr Ala Ala Ser
        195                 200                 205

Thr Leu Asp Ser Gly Val Pro Glu Arg Phe Ser Gly Ser Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Glu Pro Lys Ser Pro Asp Lys Thr
            260                 265                 270

His Thr Cys Pro Pro Cys Pro Ala Pro Pro Val Ala Gly Pro Ser Val
        275                 280                 285

Phe Leu Phe Pro Pro Lys Pro Lys Asp Thr Leu Met Ile Ala Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
```

```
            355                 360                 365
Cys Lys Val Ser Asn Lys Ala Leu Pro Ala Pro Ile Glu Lys Thr Ile
            370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
        515                 520                 525

Ile Phe Lys Gln Pro Phe Met Arg Pro Val Gln Thr Thr Gln Glu Glu
    530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
    610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 88
<211> LENGTH: 676
<212> TYPE: PRT
<213> ORGANISM: artificial sequence
<220> FEATURE:
<223> OTHER INFORMATION: M2 scCAR-v6 polypeptide

<400> SEQUENCE: 88

Met Ala Leu Pro Val Thr Ala Leu Leu Leu Pro Leu Ala Leu Leu Leu
1               5                   10                  15

His Ala Ala Arg Pro Glu Val Gln Leu Arg Gln Ser Gly Pro Glu Leu
                20                  25                  30

Val Lys Pro Gly Ala Ser Val Lys Met Ser Cys Lys Ala Ser Gly Tyr
            35                  40                  45
```

```
Thr Phe Thr Ser Tyr Phe Met His Trp Val Lys Gln Lys Pro Gly Gln
 50                  55                  60

Gly Leu Glu Trp Ile Gly Phe Ile Asn Pro Tyr Asn Asp Gly Thr Lys
 65                  70                  75                  80

Tyr Asn Glu Lys Phe Lys Gly Lys Ala Thr Leu Thr Ser Asp Lys Ser
                 85                  90                  95

Ser Ser Thr Ala Tyr Met Glu Leu Asn Ser Leu Thr Ser Glu Asp Ser
                100                 105                 110

Ala Val Tyr Tyr Cys Thr Arg Asp Gly Tyr Tyr Asp Tyr Ala Met
                115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Leu Gly Glu Arg Val Ser
                165                 170                 175

Leu Thr Cys Arg Ala Ser Gln Glu Ile Ser Val Tyr Leu Ser Trp Leu
            180                 185                 190

Gln Gln Lys Pro Asp Gly Thr Ile Lys Arg Leu Ile Tyr Ala Ala Ser
            195                 200                 205

Thr Leu Asp Ser Gly Val Pro Glu Arg Phe Ser Gly Ser Arg Ser Gly
    210                 215                 220

Ser Asp Tyr Ser Leu Thr Ile Ser Ser Leu Glu Ser Glu Asp Phe Ala
225                 230                 235                 240

Asp Tyr Tyr Cys Leu Gln Tyr Ala Ser Tyr Pro Tyr Thr Phe Gly Gly
                245                 250                 255

Gly Thr Lys Leu Glu Ile Lys Arg Glu Pro Lys Ser Pro Asp Lys Thr
            260                 265                 270

His Thr Cys Pro Pro Cys Pro Ala Pro Pro Val Ala Gly Pro Ser Val
            275                 280                 285

Phe Leu Phe Pro Pro Lys Pro Lys Asp Thr Leu Met Ile Ala Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
    355                 360                 365

Cys Lys Val Ser Asn Lys Ala Leu Pro Ala Pro Ile Glu Lys Thr Ile
370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
    435                 440                 445

Asp Gly Ser Phe Phe Leu Tyr Ser Lys Leu Thr Val Asp Lys Ser Arg
    450                 455                 460
```

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Ile
            485                 490                 495

Ile Ser Phe Phe Leu Ala Leu Thr Ser Thr Ala Leu Leu Phe Leu Leu
            500                 505                 510

Phe Phe Leu Thr Leu Arg Phe Ser Val Val Lys Arg Gly Arg Lys Lys
            515                 520                 525

Leu Leu Tyr Ile Phe Lys Gln Pro Phe Met Arg Pro Val Gln Thr Thr
            530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
            565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
            595                 600                 605

Met Gly Gly Lys Pro Arg Arg Lys Asn Pro Gln Glu Gly Leu Tyr Asn
610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
            645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 89
<211> LENGTH: 457
<212> TYPE: PRT
<213> ORGANISM: artificial sequence
<220> FEATURE:
<223> OTHER INFORMATION: M5scCAR-v1 polypeptide

<400> SEQUENCE: 89

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
            35                  40                  45

Asn Ile Lys Asp Asp Tyr Ile His Trp Val Lys Gln Arg Pro Glu Gln
50                  55                  60

Gly Leu Glu Trp Ile Gly Trp Ile Asp Pro Glu Lys Gly Asp Thr Ala
65                  70                  75                  80

Tyr Ala Ser Lys Phe Gln Asp Lys Ala Thr Ile Thr Ser Asp Thr Ser
            85                  90                  95

Ser Asn Thr Ala Tyr Leu Gln Leu Ser Ser Leu Thr Ser Glu Asp Thr
            100                 105                 110

Ala Val Tyr Tyr Cys Thr Leu Thr Gly Arg Phe Asp Tyr Trp Gly Gln
            115                 120                 125

Gly Thr Thr Leu Thr Val Ser Ser Gly Gly Gly Ser Gly Gly Gly Gly
            130                 135                 140

```
Gly Ser Gly Gly Gly Gly Ser Asp Ile Val Met Ser Gln Ser Pro Ser
145                 150                 155                 160

Ser Leu Ala Val Ser Val Gly Glu Lys Val Thr Met Ser Cys Lys Ser
            165                 170                 175

Ser Gln Ser Leu Leu Tyr Ser Ser Asn Gln Lys Asn Asn Leu Ala Trp
            180                 185                 190

Tyr Gln Gln Lys Pro Gly Gln Ser Pro Lys Leu Leu Ile Tyr Trp Ala
            195                 200                 205

Ser Thr Arg Glu Ser Gly Val Pro Asp Arg Phe Thr Gly Ser Gly Ser
            210                 215                 220

Gly Thr Asp Phe Thr Leu Thr Ile Ser Ser Val Gln Ala Glu Asp Leu
225                 230                 235                 240

Ala Val Tyr Tyr Cys Gln Gln Tyr Tyr Ser Tyr Arg Thr Phe Gly Gly
            245                 250                 255

Gly Thr Lys Leu Glu Ile Lys Gly Leu Ala Val Ser Thr Ile Ser Ser
            260                 265                 270

Phe Phe Pro Pro Gly Tyr Gln Ile Tyr Ile Trp Ala Pro Leu Ala Gly
            275                 280                 285

Thr Cys Gly Val Leu Leu Leu Ser Leu Val Ile Thr Leu Tyr Cys Lys
290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
                340                 345                 350

Ala Asp Ala Pro Ala Tyr Gln Gln Gly Gln Asn Gln Leu Tyr Asn Glu
            355                 360                 365

Leu Asn Leu Gly Arg Arg Glu Glu Tyr Asp Val Leu Asp Lys Arg Arg
            370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
                420                 425                 430

Gly Leu Tyr Gln Gly Leu Ser Thr Ala Thr Lys Asp Thr Tyr Asp Ala
            435                 440                 445

Leu His Met Gln Ala Leu Pro Pro Arg
    450                 455

<210> SEQ ID NO 90
<211> LENGTH: 460
<212> TYPE: PRT
<213> ORGANISM: artificial sequence
<220> FEATURE:
<223> OTHER INFORMATION: M5 scCAR-v2 polypeptide

<400> SEQUENCE: 90

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
        35                  40                  45
```

```
Asn Ile Lys Asp Asp Tyr Ile His Trp Val Lys Gln Arg Pro Glu Gln
 50                  55                  60

Gly Leu Glu Trp Ile Gly Trp Ile Asp Pro Glu Lys Gly Asp Thr Ala
 65                  70                  75                  80

Tyr Ala Ser Lys Phe Gln Asp Lys Ala Thr Ile Thr Ser Asp Thr Ser
                 85                  90                  95

Ser Asn Thr Ala Tyr Leu Gln Leu Ser Ser Leu Thr Ser Glu Asp Thr
                100                 105                 110

Ala Val Tyr Tyr Cys Thr Leu Thr Gly Arg Phe Asp Tyr Trp Gly Gln
            115                 120                 125

Gly Thr Thr Leu Thr Val Ser Ser Gly Gly Gly Ser Gly Gly Gly
130                 135                 140

Gly Ser Gly Gly Gly Gly Ser Asp Ile Val Met Ser Gln Ser Pro Ser
145                 150                 155                 160

Ser Leu Ala Val Ser Val Gly Glu Lys Val Thr Met Ser Cys Lys Ser
                165                 170                 175

Ser Gln Ser Leu Leu Tyr Ser Ser Asn Gln Lys Asn Asn Leu Ala Trp
            180                 185                 190

Tyr Gln Gln Lys Pro Gly Gln Ser Pro Lys Leu Leu Ile Tyr Trp Ala
            195                 200                 205

Ser Thr Arg Glu Ser Gly Val Pro Asp Arg Phe Thr Gly Ser Gly Ser
210                 215                 220

Gly Thr Asp Phe Thr Leu Thr Ile Ser Ser Val Gln Ala Glu Asp Leu
225                 230                 235                 240

Ala Val Tyr Tyr Cys Gln Gln Tyr Tyr Ser Tyr Arg Thr Phe Gly Gly
            245                 250                 255

Gly Thr Lys Leu Glu Ile Lys Gly Leu Ala Val Ser Thr Ile Ser Ser
            260                 265                 270

Phe Phe Pro Pro Gly Tyr Gln Ile Ile Ser Phe Phe Leu Ala Leu Thr
            275                 280                 285

Ser Thr Ala Leu Leu Phe Leu Leu Phe Phe Leu Thr Leu Arg Phe Ser
            290                 295                 300

Val Val Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
                340                 345                 350

Ser Arg Ser Ala Asp Ala Pro Ala Tyr Gln Gln Gly Gln Asn Gln Leu
            355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
            435                 440                 445

Tyr Asp Ala Leu His Met Gln Ala Leu Pro Pro Arg
450                 455                 460
```

<210> SEQ ID NO 91
<211> LENGTH: 486
<212> TYPE: PRT
<213> ORGANISM: artificial sequence
<220> FEATURE:
<223> OTHER INFORMATION: M5 scCAR-v3 polypeptide

<400> SEQUENCE: 91

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
        35                  40                  45

Asn Ile Lys Asp Asp Tyr Ile His Trp Val Lys Gln Arg Pro Glu Gln
50                  55                  60

Gly Leu Glu Trp Ile Gly Trp Ile Asp Pro Glu Lys Gly Asp Thr Ala
65                  70                  75                  80

Tyr Ala Ser Lys Phe Gln Asp Lys Ala Thr Ile Thr Ser Asp Thr Ser
                85                  90                  95

Ser Asn Thr Ala Tyr Leu Gln Leu Ser Ser Leu Thr Ser Glu Asp Thr
            100                 105                 110

Ala Val Tyr Tyr Cys Thr Leu Thr Gly Arg Phe Asp Tyr Trp Gly Gln
        115                 120                 125

Gly Thr Thr Leu Thr Val Ser Ser Gly Gly Gly Gly Ser Gly Gly Gly
130                 135                 140

Gly Ser Gly Gly Gly Gly Ser Asp Ile Val Met Ser Gln Ser Pro Ser
145                 150                 155                 160

Ser Leu Ala Val Ser Val Gly Glu Lys Val Thr Met Ser Cys Lys Ser
                165                 170                 175

Ser Gln Ser Leu Leu Tyr Ser Ser Asn Gln Lys Asn Asn Leu Ala Trp
            180                 185                 190

Tyr Gln Gln Lys Pro Gly Gln Ser Pro Lys Leu Leu Ile Tyr Trp Ala
        195                 200                 205

Ser Thr Arg Glu Ser Gly Val Pro Asp Arg Phe Thr Gly Ser Gly Ser
210                 215                 220

Gly Thr Asp Phe Thr Leu Thr Ile Ser Ser Val Gln Ala Glu Asp Leu
225                 230                 235                 240

Ala Val Tyr Tyr Cys Gln Gln Tyr Tyr Ser Tyr Arg Thr Phe Gly Gly
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
```

```
             370                 375                 380
Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 92
<211> LENGTH: 489
<212> TYPE: PRT
<213> ORGANISM: artificial sequence
<220> FEATURE:
<223> OTHER INFORMATION: M5 scCAR-v4 polypeptide

<400> SEQUENCE: 92

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Arg Pro Gly Ala Ser Val Lys Leu Ser Cys Thr Ala Ser Gly Phe
            35                  40                  45

Asn Ile Lys Asp Asp Tyr Ile His Trp Val Lys Gln Arg Pro Glu Gln
        50                  55                  60

Gly Leu Glu Trp Ile Gly Trp Ile Asp Pro Glu Lys Gly Asp Thr Ala
65                  70                  75                  80

Tyr Ala Ser Lys Phe Gln Asp Lys Ala Thr Ile Thr Ser Asp Thr Ser
                85                  90                  95

Ser Asn Thr Ala Tyr Leu Gln Leu Ser Ser Leu Thr Ser Glu Asp Thr
                100                 105                 110

Ala Val Tyr Tyr Cys Thr Leu Thr Gly Arg Phe Asp Tyr Trp Gly Gln
            115                 120                 125

Gly Thr Thr Leu Thr Val Ser Ser Gly Gly Gly Gly Ser Gly Gly Gly
        130                 135                 140

Gly Ser Gly Gly Gly Gly Ser Asp Ile Val Met Ser Gln Ser Pro Ser
145                 150                 155                 160

Ser Leu Ala Val Ser Val Gly Glu Lys Val Thr Met Ser Cys Lys Ser
                165                 170                 175

Ser Gln Ser Leu Leu Tyr Ser Ser Asn Gln Lys Asn Asn Leu Ala Trp
            180                 185                 190

Tyr Gln Gln Lys Pro Gly Gln Ser Pro Lys Leu Leu Ile Tyr Trp Ala
        195                 200                 205

Ser Thr Arg Glu Ser Gly Val Pro Asp Arg Phe Thr Gly Ser Gly Ser
    210                 215                 220

Gly Thr Asp Phe Thr Leu Thr Ile Ser Ser Val Gln Ala Glu Asp Leu
225                 230                 235                 240

Ala Val Tyr Tyr Cys Gln Gln Tyr Tyr Ser Tyr Arg Thr Phe Gly Gly
```

245                 250                 255
Gly Thr Lys Leu Glu Ile Lys Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Ile Ser Phe Phe Leu Ala Leu Thr Ser Thr Ala
305                 310                 315                 320

Leu Leu Phe Leu Leu Phe Phe Leu Thr Leu Arg Phe Ser Val Val Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
        370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 93
<211> LENGTH: 672
<212> TYPE: PRT
<213> ORGANISM: artificial sequence
<220> FEATURE:
<223> OTHER INFORMATION: M5 scCAR-v5 polypeptide

<400> SEQUENCE: 93

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Arg Pro Gly Ala Ser Val Lys Leu Ser Cys Thr Ala Ser Gly Phe
            35                  40                  45

Asn Ile Lys Asp Asp Tyr Ile His Trp Val Lys Gln Arg Pro Glu Gln
        50                  55                  60

Gly Leu Glu Trp Ile Gly Trp Ile Asp Pro Glu Lys Gly Asp Thr Ala
65                  70                  75                  80

Tyr Ala Ser Lys Phe Gln Asp Lys Ala Thr Ile Thr Ser Asp Thr Ser
                85                  90                  95

Ser Asn Thr Ala Tyr Leu Gln Leu Ser Ser Leu Thr Ser Glu Asp Thr
            100                 105                 110

Ala Val Tyr Tyr Cys Thr Leu Thr Gly Arg Phe Asp Tyr Trp Gly Gln

-continued

```
                115                 120                 125
Gly Thr Thr Leu Thr Val Ser Ser Gly Gly Gly Ser Gly Gly
        130                 135                 140
Gly Ser Gly Gly Gly Ser Asp Ile Val Met Ser Gln Ser Pro Ser
145                 150                 155                 160
Ser Leu Ala Val Ser Val Gly Glu Lys Val Thr Met Ser Cys Lys Ser
                165                 170                 175
Ser Gln Ser Leu Leu Tyr Ser Ser Asn Gln Lys Asn Asn Leu Ala Trp
        180                 185                 190
Tyr Gln Gln Lys Pro Gly Gln Ser Pro Lys Leu Leu Ile Tyr Trp Ala
        195                 200                 205
Ser Thr Arg Glu Ser Gly Val Pro Asp Arg Phe Thr Gly Ser Gly Ser
    210                 215                 220
Gly Thr Asp Phe Thr Leu Thr Ile Ser Ser Val Gln Ala Glu Asp Leu
225                 230                 235                 240
Ala Val Tyr Tyr Cys Gln Gln Tyr Tyr Ser Tyr Arg Thr Phe Gly Gly
                245                 250                 255
Gly Thr Lys Leu Glu Ile Lys Glu Pro Lys Ser Pro Asp Lys Thr His
        260                 265                 270
Thr Cys Pro Pro Cys Pro Ala Pro Pro Val Ala Gly Pro Ser Val Phe
        275                 280                 285
Leu Phe Pro Pro Lys Pro Lys Asp Thr Leu Met Ile Ala Arg Thr Pro
    290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
        340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
    370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
        420                 425                 430
Gln Pro Glu Asn Asn Tyr Lys Thr Thr Pro Pro Val Leu Asp Ser Asp
        435                 440                 445
Gly Ser Phe Phe Leu Tyr Ser Lys Leu Thr Val Asp Lys Ser Arg Trp
    450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys Ile Tyr
                485                 490                 495
Ile Trp Ala Pro Leu Ala Gly Thr Cys Gly Val Leu Leu Leu Ser Leu
        500                 505                 510
Val Ile Thr Leu Tyr Cys Lys Arg Gly Arg Lys Lys Leu Leu Tyr Ile
        515                 520                 525
Phe Lys Gln Pro Phe Met Arg Pro Val Gln Thr Thr Gln Glu Glu Asp
    530                 535                 540
```

```
Gly Cys Ser Cys Arg Phe Pro Glu Glu Glu Gly Cys Glu Leu
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
                580                 585                 590

Asp Val Leu Asp Lys Arg Gly Arg Asp Pro Glu Met Gly Gly Lys
            595                 600                 605

Pro Arg Arg Lys Asn Pro Gln Glu Gly Leu Tyr Asn Glu Leu Gln Lys
            610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
                660                 665                 670

<210> SEQ ID NO 94
<211> LENGTH: 675
<212> TYPE: PRT
<213> ORGANISM: artificial sequence
<220> FEATURE:
<223> OTHER INFORMATION: M5 scCAR-v6 polypeptide

<400> SEQUENCE: 94

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Arg Pro Gly Ala Ser Val Lys Leu Ser Cys Thr Ala Ser Gly Phe
            35                  40                  45

Asn Ile Lys Asp Asp Tyr Ile His Trp Val Lys Gln Arg Pro Glu Gln
        50                  55                  60

Gly Leu Glu Trp Ile Gly Trp Ile Asp Pro Glu Lys Gly Asp Thr Ala
65                  70                  75                  80

Tyr Ala Ser Lys Phe Gln Asp Lys Ala Thr Ile Thr Ser Asp Thr Ser
                85                  90                  95

Ser Asn Thr Ala Tyr Leu Gln Leu Ser Ser Leu Thr Ser Glu Asp Thr
            100                 105                 110

Ala Val Tyr Tyr Cys Thr Leu Thr Gly Arg Phe Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Ile Val Met Ser Gln Ser Pro Ser
145                 150                 155                 160

Ser Leu Ala Val Ser Val Gly Glu Lys Val Thr Met Ser Cys Lys Ser
                165                 170                 175

Ser Gln Ser Leu Leu Tyr Ser Ser Asn Gln Lys Asn Asn Leu Ala Trp
            180                 185                 190

Tyr Gln Gln Lys Pro Gly Gln Ser Pro Lys Leu Leu Ile Tyr Trp Ala
        195                 200                 205

Ser Thr Arg Glu Ser Gly Val Pro Asp Arg Phe Thr Gly Ser Gly Ser
    210                 215                 220

Gly Thr Asp Phe Thr Leu Thr Ile Ser Ser Val Gln Ala Glu Asp Leu
225                 230                 235                 240
```

-continued

Ala Val Tyr Tyr Cys Gln Gln Tyr Tyr Ser Tyr Arg Thr Phe Gly Gly
                245                 250                 255

Gly Thr Lys Leu Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Ile Ile
                485                 490                 495

Ser Phe Phe Leu Ala Leu Thr Ser Thr Ala Leu Leu Phe Leu Leu Phe
            500                 505                 510

Phe Leu Thr Leu Arg Phe Ser Val Val Lys Arg Gly Arg Lys Lys Leu
        515                 520                 525

Leu Tyr Ile Phe Lys Gln Pro Phe Met Arg Pro Val Gln Thr Thr Gln
530                 535                 540

Glu Glu Asp Gly Cys Ser Cys Arg Phe Pro Glu Glu Glu Glu Gly Gly
545                 550                 555                 560

Cys Glu Leu Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
        595                 600                 605

Gly Gly Lys Pro Arg Arg Lys Asn Pro Gln Glu Gly Leu Tyr Asn Glu
610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
        660                 665                 670

Pro Pro Arg
        675

<210> SEQ ID NO 95
<211> LENGTH: 461
<212> TYPE: PRT
<213> ORGANISM: artificial sequence
<220> FEATURE:
<223> OTHER INFORMATION: G12 scCAR-v1 polypeptide

<400> SEQUENCE: 95

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Met Lys Met Ser Cys Lys Ala Ser Gly Tyr
        35                  40                  45

Thr Phe Pro Ser Ser Asn Ile His Trp Leu Lys Gln Thr Pro Gly Gln
    50                  55                  60

Gly Leu Glu Trp Ile Gly Val Ile Tyr Pro Gly Asn Gly Asp Thr Ser
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Gly Ser Asn Ile Val Leu Thr
145                 150                 155                 160

Gln Ser Pro Ala Ser Leu Ala Val Ser Leu Gly Gln Arg Ala Thr Ile
                165                 170                 175

Ser Cys Arg Ala Ser Glu Ser Val Asp Gly Tyr Gly Asp Ile Phe Met
            180                 185                 190

Leu Trp Tyr Gln Gln Lys Pro Gly Gln Pro Pro Lys Leu Leu Ile Tyr
        195                 200                 205

Phe Ala Ser Asn Leu Glu Ser Gly Val Pro Ala Arg Phe Ser Gly Ser
    210                 215                 220

Gly Ser Arg Thr Asp Phe Thr Leu Thr Ile Asp Pro Val Glu Ala Asp
225                 230                 235                 240

Asp Ala Ala Thr Tyr Tyr Cys Gln Gln Asn Asn Glu Asp Pro Tyr Thr
                245                 250                 255

Phe Gly Gly Gly Thr Lys Leu Glu Ile Lys Arg Gly Leu Ala Val Ser
            260                 265                 270

Thr Ile Ser Ser Phe Phe Pro Pro Gly Tyr Gln Ile Tyr Ile Trp Ala
        275                 280                 285

Pro Leu Ala Gly Thr Cys Gly Val Leu Leu Leu Ser Leu Val Ile Thr
    290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

-continued

```
Cys Arg Phe Pro Glu Glu Glu Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 96
<211> LENGTH: 464
<212> TYPE: PRT
<213> ORGANISM: artificial sequence
<220> FEATURE:
<223> OTHER INFORMATION: G12 scCAR-v2 polypeptide

<400> SEQUENCE: 96

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Met Lys Met Ser Cys Lys Ala Ser Gly Tyr
        35                  40                  45

Thr Phe Pro Ser Ser Asn Ile His Trp Leu Lys Gln Thr Pro Gly Gln
    50                  55                  60

Gly Leu Glu Trp Ile Gly Val Ile Tyr Pro Gly Asn Gly Asp Thr Ser
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Ser Asn Ile Val Leu Thr
145                 150                 155                 160

Gln Ser Pro Ala Ser Leu Ala Val Ser Leu Gly Gln Arg Ala Thr Ile
                165                 170                 175

Ser Cys Arg Ala Ser Glu Ser Val Asp Gly Tyr Gly Asp Ile Phe Met
            180                 185                 190

Leu Trp Tyr Gln Gln Lys Pro Gly Gln Pro Pro Lys Leu Leu Ile Tyr
        195                 200                 205

Phe Ala Ser Asn Leu Glu Ser Gly Val Pro Ala Arg Phe Ser Gly Ser
    210                 215                 220

Gly Ser Arg Thr Asp Phe Thr Leu Thr Ile Asp Pro Val Glu Ala Asp
225                 230                 235                 240
```

```
Asp Ala Ala Thr Tyr Tyr Cys Gln Gln Asn Asn Glu Asp Pro Tyr Thr
            245                 250                 255

Phe Gly Gly Gly Thr Lys Leu Glu Ile Lys Arg Gly Leu Ala Val Ser
        260                 265                 270

Thr Ile Ser Ser Phe Phe Pro Pro Gly Tyr Gln Ile Ile Ser Phe Phe
        275                 280                 285

Leu Ala Leu Thr Ser Thr Ala Leu Leu Phe Leu Leu Phe Phe Leu Thr
        290                 295                 300

Leu Arg Phe Ser Val Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
                355                 360                 365

Gln Asn Gln Leu Tyr Asn Glu Leu Asn Leu Gly Arg Arg Glu Glu Tyr
        370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
                435                 440                 445

Thr Lys Asp Thr Tyr Asp Ala Leu His Met Gln Ala Leu Pro Pro Arg
        450                 455                 460
```

<210> SEQ ID NO 97
<211> LENGTH: 490
<212> TYPE: PRT
<213> ORGANISM: artificial sequence
<220> FEATURE:
<223> OTHER INFORMATION: G12 scCAR-v3 polypeptide

<400> SEQUENCE: 97

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Met Lys Met Ser Cys Lys Ala Ser Gly Tyr
        35                  40                  45

Thr Phe Pro Ser Ser Asn Ile His Trp Leu Lys Gln Thr Pro Gly Gln
    50                  55                  60

Gly Leu Glu Trp Ile Gly Val Ile Tyr Pro Gly Asn Gly Asp Thr Ser
65              70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140
```

Ser Gly Gly Gly Gly Ser Gly Gly Gly Ser Asn Ile Val Leu Thr
145                 150                 155                 160

Gln Ser Pro Ala Ser Leu Ala Val Ser Leu Gly Gln Arg Ala Thr Ile
            165                 170                 175

Ser Cys Arg Ala Ser Glu Ser Val Asp Gly Tyr Gly Asp Ile Phe Met
        180                 185                 190

Leu Trp Tyr Gln Gln Lys Pro Gly Gln Pro Pro Lys Leu Leu Ile Tyr
    195                 200                 205

Phe Ala Ser Asn Leu Glu Ser Gly Val Pro Ala Arg Phe Ser Gly Ser
210                 215                 220

Gly Ser Arg Thr Asp Phe Thr Leu Thr Ile Asp Pro Val Glu Ala Asp
225                 230                 235                 240

Asp Ala Ala Thr Tyr Tyr Cys Gln Gln Asn Asn Glu Asp Pro Tyr Thr
                245                 250                 255

Phe Gly Gly Gly Thr Lys Leu Glu Ile Lys Arg Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 98
<211> LENGTH: 493
<212> TYPE: PRT
<213> ORGANISM: artificial sequence
<220> FEATURE:
<223> OTHER INFORMATION: G12 scCAR-v4 polypeptide

<400> SEQUENCE: 98

Met Ala Leu Pro Val Thr Ala Leu Leu Leu Pro Leu Ala Leu Leu Leu
1               5                   10                  15

-continued

His Ala Ala Arg Pro Gln Val Gln Leu Gln Pro Gly Ala Glu Leu
            20                  25                  30

Val Lys Pro Gly Ala Ser Met Lys Met Ser Cys Lys Ala Ser Gly Tyr
        35                  40                  45

Thr Phe Pro Ser Ser Asn Ile His Trp Leu Lys Gln Thr Pro Gly Gln
    50                  55                  60

Gly Leu Glu Trp Ile Gly Val Ile Tyr Pro Gly Asn Gly Asp Thr Ser
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Ser Asn Ile Val Leu Thr
145                 150                 155                 160

Gln Ser Pro Ala Ser Leu Ala Val Ser Leu Gly Gln Arg Ala Thr Ile
            165                 170                 175

Ser Cys Arg Ala Ser Glu Ser Val Asp Gly Tyr Gly Asp Ile Phe Met
        180                 185                 190

Leu Trp Tyr Gln Gln Lys Pro Gly Gln Pro Pro Lys Leu Leu Ile Tyr
    195                 200                 205

Phe Ala Ser Asn Leu Glu Ser Gly Val Pro Ala Arg Phe Ser Gly Ser
210                 215                 220

Gly Ser Arg Thr Asp Phe Thr Leu Thr Ile Asp Pro Val Glu Ala Asp
225                 230                 235                 240

Asp Ala Ala Thr Tyr Tyr Cys Gln Gln Asn Asn Glu Asp Pro Tyr Thr
            245                 250                 255

Phe Gly Gly Gly Thr Lys Leu Glu Ile Lys Arg Thr Thr Thr Pro Ala
        260                 265                 270

Pro Arg Pro Pro Thr Pro Ala Pro Thr Ile Ala Ser Gln Pro Leu Ser
    275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Ile Ser Phe Phe Leu Ala Leu
305                 310                 315                 320

Thr Ser Thr Ala Leu Leu Phe Leu Leu Phe Phe Leu Thr Leu Arg Phe
            325                 330                 335

Ser Val Val Lys Arg Gly Arg Lys Lys Leu Leu Tyr Ile Phe Lys Gln
        340                 345                 350

Pro Phe Met Arg Pro Val Gln Thr Thr Gln Glu Glu Asp Gly Cys Ser
    355                 360                 365

Cys Arg Phe Pro Glu Glu Glu Glu Gly Gly Cys Glu Leu Arg Val Lys
370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
        420                 425                 430

Lys Asn Pro Gln Glu Gly Leu Tyr Asn Glu Leu Gln Lys Asp Lys Met

```
            435                 440                 445
Ala Glu Ala Tyr Ser Glu Ile Gly Met Lys Gly Glu Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                    485                 490

<210> SEQ ID NO 99
<211> LENGTH: 676
<212> TYPE: PRT
<213> ORGANISM: artificial sequence
<220> FEATURE:
<223> OTHER INFORMATION: G12 scCAR-v5 polypeptide

<400> SEQUENCE: 99

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Lys Pro Gly Ala Ser Met Lys Met Ser Cys Lys Ala Ser Gly Tyr
            35                  40                  45

Thr Phe Pro Ser Ser Asn Ile His Trp Leu Lys Gln Thr Pro Gly Gln
        50                  55                  60

Gly Leu Glu Trp Ile Gly Val Ile Tyr Pro Gly Asn Gly Asp Thr Ser
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Gly Ser Asn Ile Val Leu Thr
145                 150                 155                 160

Gln Ser Pro Ala Ser Leu Ala Val Ser Leu Gly Gln Arg Ala Thr Ile
                165                 170                 175

Ser Cys Arg Ala Ser Glu Ser Val Asp Gly Tyr Gly Asp Ile Phe Met
            180                 185                 190

Leu Trp Tyr Gln Gln Lys Pro Gly Gln Pro Pro Lys Leu Leu Ile Tyr
        195                 200                 205

Phe Ala Ser Asn Leu Glu Ser Gly Val Pro Ala Arg Phe Ser Gly Ser
    210                 215                 220

Gly Ser Arg Thr Asp Phe Thr Leu Thr Ile Asp Pro Val Glu Ala Asp
225                 230                 235                 240

Asp Ala Ala Thr Tyr Tyr Cys Gln Gln Asn Asn Glu Asp Pro Tyr Thr
                245                 250                 255

Phe Gly Gly Gly Thr Lys Leu Glu Ile Lys Arg Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
```

```
                305                 310                 315                 320
Asp Pro Glu Val Lys Phe Asn Trp Tyr Val Asp Gly Val Glu Val His
                    325                 330                 335
Asn Ala Lys Thr Lys Pro Arg Glu Glu Gln Tyr Asn Ser Thr Tyr Arg
                340                 345                 350
Val Val Ser Val Leu Thr Val Leu His Gln Asp Trp Leu Asn Gly Lys
            355                 360                 365
Glu Tyr Lys Cys Lys Val Ser Asn Lys Ala Leu Pro Ala Pro Ile Glu
        370                 375                 380
Lys Thr Ile Ser Lys Ala Lys Gly Gln Pro Arg Glu Pro Gln Val Tyr
385                 390                 395                 400
Thr Leu Pro Pro Ser Arg Asp Glu Leu Thr Lys Asn Gln Val Ser Leu
                405                 410                 415
Thr Cys Leu Val Lys Gly Phe Tyr Pro Ser Asp Ile Ala Val Glu Trp
            420                 425                 430
Glu Ser Asn Gly Gln Pro Glu Asn Asn Tyr Lys Thr Thr Pro Pro Val
        435                 440                 445
Leu Asp Ser Asp Gly Ser Phe Phe Leu Tyr Ser Lys Leu Thr Val Asp
    450                 455                 460
Lys Ser Arg Trp Gln Gln Gly Asn Val Phe Ser Cys Ser Val Met His
465                 470                 475                 480
Glu Ala Leu His Asn His Tyr Thr Gln Lys Ser Leu Ser Leu Ser Pro
                485                 490                 495
Gly Lys Ile Tyr Ile Trp Ala Pro Leu Ala Gly Thr Cys Gly Val Leu
            500                 505                 510
Leu Leu Ser Leu Val Ile Thr Leu Tyr Cys Lys Arg Gly Arg Lys Lys
        515                 520                 525
Leu Leu Tyr Ile Phe Lys Gln Pro Phe Met Arg Pro Val Gln Thr Thr
        530                 535                 540
Gln Glu Glu Asp Gly Cys Ser Cys Arg Phe Pro Glu Glu Glu Glu Gly
545                 550                 555                 560
Gly Cys Glu Leu Arg Val Lys Phe Ser Arg Ser Ala Asp Ala Pro Ala
                565                 570                 575
Tyr Gln Gln Gly Gln Asn Gln Leu Tyr Asn Glu Leu Asn Leu Gly Arg
                580                 585                 590
Arg Glu Glu Tyr Asp Val Leu Asp Lys Arg Arg Gly Arg Asp Pro Glu
            595                 600                 605
Met Gly Gly Lys Pro Arg Arg Lys Asn Pro Gln Glu Gly Leu Tyr Asn
        610                 615                 620
Glu Leu Gln Lys Asp Lys Met Ala Glu Ala Tyr Ser Glu Ile Gly Met
625                 630                 635                 640
Lys Gly Glu Arg Arg Arg Gly Lys Gly His Asp Gly Leu Tyr Gln Gly
                645                 650                 655
Leu Ser Thr Ala Thr Lys Asp Thr Tyr Asp Ala Leu His Met Gln Ala
            660                 665                 670
Leu Pro Pro Arg
        675

<210> SEQ ID NO 100
<211> LENGTH: 679
<212> TYPE: PRT
<213> ORGANISM: artificial sequence
<220> FEATURE:
<223> OTHER INFORMATION: G12 scCAR-v6 polypeptide
```

<400> SEQUENCE: 100

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Met Lys Met Ser Cys Lys Ala Ser Gly Tyr
        35                  40                  45

Thr Phe Pro Ser Ser Asn Ile His Trp Leu Lys Gln Thr Pro Gly Gln
    50                  55                  60

Gly Leu Glu Trp Ile Gly Val Ile Tyr Pro Gly Asn Gly Asp Thr Ser
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Ile Tyr Phe Ser Cys Cys Ala Arg Val Tyr Asn Trp His Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Gly Ser Asn Ile Val Leu Thr
145                 150                 155                 160

Gln Ser Pro Ala Ser Leu Ala Val Ser Leu Gly Gln Arg Ala Thr Ile
                165                 170                 175

Ser Cys Arg Ala Ser Glu Ser Val Asp Gly Tyr Gly Asp Ile Phe Met
            180                 185                 190

Leu Trp Tyr Gln Gln Lys Pro Gly Gln Pro Pro Lys Leu Leu Ile Tyr
        195                 200                 205

Phe Ala Ser Asn Leu Glu Ser Gly Val Pro Ala Arg Phe Ser Gly Ser
    210                 215                 220

Gly Ser Arg Thr Asp Phe Thr Leu Thr Ile Asp Pro Val Glu Ala Asp
225                 230                 235                 240

Asp Ala Ala Thr Tyr Tyr Cys Gln Gln Asn Asn Glu Asp Pro Tyr Thr
                245                 250                 255

Phe Gly Gly Gly Thr Lys Leu Glu Ile Lys Arg Glu Pro Lys Ser Pro
            260                 265                 270

Asp Lys Thr His Thr Cys Pro Pro Cys Pro Ala Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415
```

Thr Cys Leu Val Lys Gly Phe Tyr Pro Ser Asp Ile Ala Val Glu Trp
                420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
        450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Ile Ser Phe Phe Leu Ala Leu Thr Ser Thr Ala Leu Leu
            500                 505                 510

Phe Leu Leu Phe Phe Leu Thr Leu Arg Phe Ser Val Val Lys Arg Gly
        515                 520                 525

Arg Lys Lys Leu Leu Tyr Ile Phe Lys Gln Pro Phe Met Arg Pro Val
    530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
        595                 600                 605

Asp Pro Glu Met Gly Gly Lys Pro Arg Arg Lys Asn Pro Gln Glu Gly
    610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
        675

<210> SEQ ID NO 101
<211> LENGTH: 456
<212> TYPE: PRT
<213> ORGANISM: artificial sequence
<220> FEATURE:
<223> OTHER INFORMATION: 21.26 scCAR-v1 polypeptide

<400> SEQUENCE: 101

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Lys Pro Gly Thr Ser Val Lys Leu Ser Cys Lys Ala Ser Gly Tyr
            35                  40                  45

Thr Phe Thr Arg Tyr Trp Met His Trp Val Lys Gln Arg Pro Gly Gln
        50                  55                  60

Gly Leu Glu Trp Ile Gly Met Ile His Pro Ser Ser Gly Ser Thr Ser
65                  70                  75                  80

Tyr Asn Glu Lys Val Lys Asn Lys Ala Thr Leu Thr Val Asp Arg Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Asp Gly Asp Tyr Tyr Gly Thr Gly
    115                 120                 125

Asp Tyr Trp Gly Gln Gly Thr Thr Leu Thr Val Ser Ser Gly Gly Gly
130                 135                 140

Gly Ser Gly Gly Gly Gly Ser Gly Gly Gly Gly Ser Gln Ile Val Leu
145                 150                 155                 160

Ser Gln Ser Pro Ala Ile Leu Ser Ala Ser Pro Gly Glu Lys Val Thr
                165                 170                 175

Met Thr Cys Arg Ala Ser Ser Ser Ile Asn Tyr Met His Trp Tyr Gln
            180                 185                 190

Gln Lys Pro Gly Ser Ser Pro Lys Pro Trp Ile Phe Ala Thr Ser Asn
        195                 200                 205

Leu Ala Ser Gly Val Pro Ser Arg Phe Ser Gly Ser Gly Ser Gly Thr
    210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
                245                 250                 255

Gly Thr Lys Leu Glu Leu Gly Leu Ala Val Ser Thr Ile Ser Ser Phe
            260                 265                 270

Phe Pro Pro Gly Tyr Gln Ile Tyr Ile Trp Ala Pro Leu Ala Gly Thr
        275                 280                 285

Cys Gly Val Leu Leu Leu Ser Leu Val Ile Thr Leu Tyr Cys Lys Arg
    290                 295                 300

Gly Arg Lys Lys Leu Leu Tyr Ile Phe Lys Gln Pro Phe Met Arg Pro
305                 310                 315                 320

Val Gln Thr Thr Gln Glu Glu Asp Gly Cys Ser Cys Arg Phe Pro Glu
                325                 330                 335

Glu Glu Glu Gly Gly Cys Glu Leu Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455

<210> SEQ ID NO 102
<211> LENGTH: 459
<212> TYPE: PRT
<213> ORGANISM: artificial sequence
<220> FEATURE:
<223> OTHER INFORMATION: 21.26 scCAR-v2 polypeptide

<400> SEQUENCE: 102

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Thr Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Met Ile His Pro Ser Ser Gly Ser Thr Ser
65                  70                  75                  80

Tyr Asn Glu Lys Val Lys Asn Lys Ala Thr Leu Thr Val Asp Arg Ser
            85                  90                  95

Ser Thr Thr Ala Tyr Met Gln Leu Ser Ser Leu Thr Ser Glu Asp Ser
            100                 105                 110

Ala Val Tyr Tyr Cys Ala Arg Asp Gly Asp Tyr Tyr Gly Thr Gly
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Ser Gln Ser Pro Ala Ile Leu Ser Ala Ser Pro Gly Glu Lys Val Thr
            165                 170                 175

Met Thr Cys Arg Ala Ser Ser Ile Asn Tyr Met His Trp Tyr Gln
            180                 185                 190

Gln Lys Pro Gly Ser Ser Pro Lys Pro Trp Ile Phe Ala Thr Ser Asn
            195                 200                 205

Leu Ala Ser Gly Val Pro Ser Arg Phe Ser Gly Ser Gly Ser Gly Thr
    210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
            245                 250                 255

Gly Thr Lys Leu Glu Leu Gly Leu Ala Val Ser Thr Ile Ser Ser Phe
        260                 265                 270

Phe Pro Pro Gly Tyr Gln Ile Ile Ser Phe Phe Leu Ala Leu Thr Ser
    275                 280                 285

Thr Ala Leu Leu Phe Leu Leu Phe Phe Leu Thr Leu Arg Phe Ser Val
    290                 295                 300

Val Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
            325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
            370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
            405                 410                 415
```

```
Ala Tyr Ser Glu Ile Gly Met Lys Gly Glu Arg Arg Gly Lys Gly
            420                 425                 430

His Asp Gly Leu Tyr Gln Gly Leu Ser Thr Ala Thr Lys Asp Thr Tyr
            435                 440                 445

Asp Ala Leu His Met Gln Ala Leu Pro Pro Arg
            450                 455

<210> SEQ ID NO 103
<211> LENGTH: 485
<212> TYPE: PRT
<213> ORGANISM: artificial sequence
<220> FEATURE:
<223> OTHER INFORMATION: 21.26 scCAR-v3 polypeptide

<400> SEQUENCE: 103

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Thr Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Met Ile His Pro Ser Ser Gly Ser Thr Ser
65                  70                  75                  80

Tyr Asn Glu Lys Val Lys Asn Lys Ala Thr Leu Thr Val Asp Arg Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Asp Gly Asp Tyr Tyr Gly Thr Gly
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Ser Gln Ser Pro Ala Ile Leu Ser Ala Ser Pro Gly Glu Lys Val Thr
                165                 170                 175

Met Thr Cys Arg Ala Ser Ser Ser Ile Asn Tyr Met His Trp Tyr Gln
            180                 185                 190

Gln Lys Pro Gly Ser Ser Pro Lys Pro Trp Ile Phe Ala Thr Ser Asn
        195                 200                 205

Leu Ala Ser Gly Val Pro Ser Arg Phe Ser Gly Ser Gly Ser Gly Thr
    210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
                245                 250                 255

Gly Thr Lys Leu Glu Leu Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320
```

```
Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 104
<211> LENGTH: 488
<212> TYPE: PRT
<213> ORGANISM: artificial sequence
<220> FEATURE:
<223> OTHER INFORMATION: 21.26 scCAR-v4 polypeptide

<400> SEQUENCE: 104

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Thr Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

Gly Leu Glu Trp Ile Gly Met Ile His Pro Ser Ser Gly Ser Thr Ser
65                  70                  75                  80

Tyr Asn Glu Lys Val Lys Asn Lys Ala Thr Leu Thr Val Asp Arg Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Asp Gly Asp Tyr Tyr Gly Thr Gly
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Ser Gln Ser Pro Ala Ile Leu Ser Ala Ser Pro Gly Glu Lys Val Thr
                165                 170                 175

Met Thr Cys Arg Ala Ser Ser Ser Ile Asn Tyr Met His Trp Tyr Gln
            180                 185                 190
```

Gln Lys Pro Gly Ser Ser Pro Lys Pro Trp Ile Phe Ala Thr Ser Asn
            195                 200                 205

Leu Ala Ser Gly Val Pro Ser Arg Phe Ser Gly Ser Gly Ser Gly Thr
    210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
                245                 250                 255

Gly Thr Lys Leu Glu Leu Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
290                 295                 300

Ala Cys Asp Ile Ile Ser Phe Phe Leu Ala Leu Thr Ser Thr Ala Leu
305                 310                 315                 320

Leu Phe Leu Leu Phe Phe Leu Thr Leu Arg Phe Ser Val Val Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 105
<211> LENGTH: 671
<212> TYPE: PRT
<213> ORGANISM: artificial sequence
<220> FEATURE:
<223> OTHER INFORMATION: 21.26 scCAR-v5 polypeptide

<400> SEQUENCE: 105

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Thr Ser Val Lys Leu Ser Cys Lys Ala Ser Gly Tyr
        35                  40                  45

Thr Phe Thr Arg Tyr Trp Met His Trp Val Lys Gln Arg Pro Gly Gln
    50                  55                  60

```
Gly Leu Glu Trp Ile Gly Met Ile His Pro Ser Ser Gly Ser Thr Ser
 65                  70                  75                  80

Tyr Asn Glu Lys Val Lys Asn Lys Ala Thr Leu Thr Val Asp Arg Ser
                 85                  90                  95

Ser Thr Thr Ala Tyr Met Gln Leu Ser Ser Leu Thr Ser Glu Asp Ser
            100                 105                 110

Ala Val Tyr Tyr Cys Ala Arg Asp Gly Asp Tyr Tyr Gly Thr Gly
            115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Gln Ile Val Leu
145                 150                 155                 160

Ser Gln Ser Pro Ala Ile Leu Ser Ala Ser Pro Gly Glu Lys Val Thr
                165                 170                 175

Met Thr Cys Arg Ala Ser Ser Ser Ile Asn Tyr Met His Trp Tyr Gln
            180                 185                 190

Gln Lys Pro Gly Ser Ser Pro Lys Pro Trp Ile Phe Ala Thr Ser Asn
            195                 200                 205

Leu Ala Ser Gly Val Pro Ser Arg Phe Ser Gly Ser Gly Ser Gly Thr
    210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
                245                 250                 255

Gly Thr Lys Leu Glu Leu Glu Pro Lys Ser Pro Asp Lys Thr His Thr
                260                 265                 270

Cys Pro Pro Cys Pro Ala Pro Pro Val Ala Gly Pro Ser Val Phe Leu
            275                 280                 285

Phe Pro Pro Lys Pro Lys Asp Thr Leu Met Ile Ala Arg Thr Pro Glu
            290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Ile Tyr Ile
```

```
                485                 490                 495
Trp Ala Pro Leu Ala Gly Thr Cys Gly Val Leu Leu Ser Leu Val
            500                 505                 510
Ile Thr Leu Tyr Cys Lys Arg Gly Arg Lys Lys Leu Leu Tyr Ile Phe
            515                 520                 525
Lys Gln Pro Phe Met Arg Pro Val Gln Thr Thr Gln Glu Glu Asp Gly
    530                 535                 540
Cys Ser Cys Arg Phe Pro Glu Glu Glu Glu Gly Gly Cys Glu Leu Arg
545                 550                 555                 560
Val Lys Phe Ser Arg Ser Ala Asp Ala Pro Ala Tyr Gln Gln Gly Gln
                565                 570                 575
Asn Gln Leu Tyr Asn Glu Leu Asn Leu Gly Arg Arg Glu Glu Tyr Asp
            580                 585                 590
Val Leu Asp Lys Arg Arg Gly Arg Asp Pro Glu Met Gly Gly Lys Pro
            595                 600                 605
Arg Arg Lys Asn Pro Gln Glu Gly Leu Tyr Asn Glu Leu Gln Lys Asp
    610                 615                 620
Lys Met Ala Glu Ala Tyr Ser Glu Ile Gly Met Lys Gly Glu Arg Arg
625                 630                 635                 640
Arg Gly Lys Gly His Asp Gly Leu Tyr Gln Gly Leu Ser Thr Ala Thr
                645                 650                 655
Lys Asp Thr Tyr Asp Ala Leu His Met Gln Ala Leu Pro Pro Arg
            660                 665                 670
```

<210> SEQ ID NO 106
<211> LENGTH: 674
<212> TYPE: PRT
<213> ORGANISM: artificial sequence
<220> FEATURE:
<223> OTHER INFORMATION: 21.26 scCAR-v6 polypeptide

<400> SEQUENCE: 106

```
Met Ala Leu Pro Val Thr Ala Leu Leu Leu Pro Leu Ala Leu Leu Leu
1               5                   10                  15
His Ala Ala Arg Pro Gln Val Gln Leu Gln Gln Pro Gly Ala Glu Leu
            20                  25                  30
Val Lys Pro Gly Thr Ser Val Lys Leu Ser Cys Lys Ala Ser Gly Tyr
        35                  40                  45
Thr Phe Thr Arg Tyr Trp Met His Trp Val Lys Gln Arg Pro Gly Gln
    50                  55                  60
Gly Leu Glu Trp Ile Gly Met Ile His Pro Ser Ser Gly Ser Thr Ser
65                  70                  75                  80
Tyr Asn Glu Lys Val Lys Asn Lys Ala Thr Leu Thr Val Asp Arg Ser
                85                  90                  95
Ser Thr Thr Ala Tyr Met Gln Leu Ser Ser Leu Thr Ser Glu Asp Ser
            100                 105                 110
Ala Val Tyr Tyr Cys Ala Arg Asp Gly Asp Tyr Tyr Gly Thr Gly
        115                 120                 125
Asp Tyr Trp Gly Gln Gly Thr Thr Leu Thr Val Ser Ser Gly Gly Gly
    130                 135                 140
Gly Ser Gly Gly Gly Gly Ser Gly Gly Gly Gly Ser Gln Ile Val Leu
145                 150                 155                 160
Ser Gln Ser Pro Ala Ile Leu Ser Ala Ser Pro Gly Glu Lys Val Thr
                165                 170                 175
Met Thr Cys Arg Ala Ser Ser Ser Ile Asn Tyr Met His Trp Tyr Gln
```

```
            180                 185                 190
Gln Lys Pro Gly Ser Ser Pro Lys Pro Trp Ile Phe Ala Thr Ser Asn
            195                 200                 205

Leu Ala Ser Gly Val Pro Ser Arg Phe Ser Gly Ser Gly Ser Gly Thr
            210                 215                 220

Ser Tyr Ser Leu Thr Ile Ser Arg Val Glu Ala Glu Asp Ala Ala Thr
225                 230                 235                 240

Tyr Tyr Cys Gln Gln Trp Arg Ser Asp Arg Ala Leu Thr Phe Gly Ala
            245                 250                 255

Gly Thr Lys Leu Glu Leu Glu Pro Lys Ser Pro Asp Lys Thr His Thr
            260                 265                 270

Cys Pro Pro Cys Pro Ala Pro Pro Val Ala Gly Pro Ser Val Phe Leu
            275                 280                 285

Phe Pro Pro Lys Pro Lys Asp Thr Leu Met Ile Ala Arg Thr Pro Glu
            290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
            325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
            370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Ile Ile Ser
            485                 490                 495

Phe Phe Leu Ala Leu Thr Ser Thr Ala Leu Leu Phe Leu Leu Phe Phe
            500                 505                 510

Leu Thr Leu Arg Phe Ser Val Val Lys Arg Gly Arg Lys Lys Leu Leu
            515                 520                 525

Tyr Ile Phe Lys Gln Pro Phe Met Arg Pro Val Gln Thr Thr Gln Glu
            530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Gln
            565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
            595                 600                 605
```

```
Gly Lys Pro Arg Arg Lys Asn Pro Gln Glu Gly Leu Tyr Asn Glu Leu
        610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
            660                 665                 670

Pro Arg

<210> SEQ ID NO 107
<211> LENGTH: 460
<212> TYPE: PRT
<213> ORGANISM: artificial sequence
<220> FEATURE:
<223> OTHER INFORMATION: 1075.7 scCAR-v1 polypeptide

<400> SEQUENCE: 107

Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
            20                  25                  30

Val Lys Pro Ser Gln Ser Leu Ser Leu Thr Cys Ser Val Thr Gly Tyr
        35                  40                  45

Ser Ile Thr Ser Ala Tyr Tyr Trp Asn Trp Ile Arg Gln Phe Pro Gly
    50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
            100                 105                 110

Ala Thr Tyr Tyr Cys Ala Lys Glu Gly Asp Tyr Asp Val Gly Asn Tyr
        115                 120                 125

Tyr Ala Met Asp Tyr Trp Gly Gln Gly Thr Ser Val Thr Val Ser Ser
    130                 135                 140

Gly Gly Gly Gly Ser Gly Gly Gly Ser Gly Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
            180                 185                 190

Val His Trp Tyr Gln Gln Arg Ser Gly Ala Ser Pro Lys Leu Trp Ile
        195                 200                 205

Tyr Ser Thr Ser Asn Leu Ala Ser Gly Val Pro Ala Arg Phe Ser Gly
    210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Gly Leu Ala Val Ser Thr
            260                 265                 270

Ile Ser Ser Phe Phe Pro Pro Gly Tyr Gln Ile Tyr Ile Trp Ala Pro
        275                 280                 285
```

-continued

```
Leu Ala Gly Thr Cys Gly Val Leu Leu Ser Leu Val Ile Thr Leu
        290                 295                 300

Tyr Cys Lys Arg Gly Arg Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
                340                 345                 350

Ser Arg Ser Ala Asp Ala Pro Ala Tyr Gln Gln Gly Gln Asn Gln Leu
                355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
                420                 425                 430

Gly His Asp Gly Leu Tyr Gln Gly Leu Ser Thr Ala Thr Lys Asp Thr
                435                 440                 445

Tyr Asp Ala Leu His Met Gln Ala Leu Pro Pro Arg
450                 455                 460

<210> SEQ ID NO 108
<211> LENGTH: 463
<212> TYPE: PRT
<213> ORGANISM: artificial sequence
<220> FEATURE:
<223> OTHER INFORMATION: 1075.7 scCAR-v2 polypeptide

<400> SEQUENCE: 108

Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
                20                  25                  30

Val Lys Pro Ser Gln Ser Leu Ser Leu Thr Cys Ser Val Thr Gly Tyr
            35                  40                  45

Ser Ile Thr Ser Ala Tyr Tyr Trp Asn Trp Ile Arg Gln Phe Pro Gly
        50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
            100                 105                 110

Ala Thr Tyr Tyr Cys Ala Lys Glu Gly Asp Tyr Asp Val Gly Asn Tyr
        115                 120                 125

Tyr Ala Met Asp Tyr Trp Gly Gln Gly Thr Ser Val Thr Val Ser Ser
    130                 135                 140

Gly Gly Gly Gly Ser Gly Gly Gly Ser Gly Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
            180                 185                 190
```

Val His Trp Tyr Gln Gln Arg Ser Gly Ala Ser Pro Lys Leu Trp Ile
    195                 200                 205

Tyr Ser Thr Ser Asn Leu Ala Ser Gly Val Pro Ala Arg Phe Ser Gly
    210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Gly Leu Ala Val Ser Thr
                260                 265                 270

Ile Ser Ser Phe Phe Pro Pro Gly Tyr Gln Ile Ile Ser Phe Phe Leu
                275                 280                 285

Ala Leu Thr Ser Thr Ala Leu Leu Phe Leu Leu Phe Phe Leu Thr Leu
            290                 295                 300

Arg Phe Ser Val Val Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Gly Gly Cys Glu Leu Arg
                340                 345                 350

Val Lys Phe Ser Arg Ser Ala Asp Ala Pro Ala Tyr Gln Gln Gly Gln
            355                 360                 365

Asn Gln Leu Tyr Asn Glu Leu Asn Leu Gly Arg Arg Glu Glu Tyr Asp
        370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 109
<211> LENGTH: 489
<212> TYPE: PRT
<213> ORGANISM: artificial sequence
<220> FEATURE:
<223> OTHER INFORMATION: 1075.7 scCAR-v3 polypeptide

<400> SEQUENCE: 109

Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
            20                  25                  30

Val Lys Pro Ser Gln Ser Leu Ser Leu Thr Cys Ser Val Thr Gly Tyr
        35                  40                  45

Ser Ile Thr Ser Ala Tyr Tyr Trp Asn Trp Ile Arg Gln Phe Pro Gly
    50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
                100                 105                 110

Ala Thr Tyr Tyr Cys Ala Lys Glu Gly Asp Tyr Asp Val Gly Asn Tyr
        115                 120                 125

Tyr Ala Met Asp Tyr Trp Gly Gln Gly Thr Ser Val Thr Val Ser Ser
    130                 135                 140

Gly Gly Gly Gly Ser Gly Gly Gly Ser Gly Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
        180                 185                 190

Val His Trp Tyr Gln Gln Arg Ser Gly Ala Ser Pro Lys Leu Trp Ile
    195                 200                 205

Tyr Ser Thr Ser Asn Leu Ala Ser Gly Val Pro Ala Arg Phe Ser Gly
        210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Thr Thr Thr Pro Ala Pro
        260                 265                 270

Arg Pro Pro Thr Pro Ala Pro Thr Ile Ala Ser Gln Pro Leu Ser Leu
    275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
        340                 345                 350

Pro Val Gln Thr Thr Gln Glu Glu Asp Gly Cys Ser Cys Arg Phe Pro
    355                 360                 365

Glu Glu Glu Glu Gly Gly Cys Glu Leu Arg Val Lys Phe Ser Arg Ser
        370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
        420                 425                 430

Glu Gly Leu Tyr Asn Glu Leu Gln Lys Asp Lys Met Ala Glu Ala Tyr
    435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 110
<211> LENGTH: 492
<212> TYPE: PRT

<213> ORGANISM: artificial sequence
<220> FEATURE:
<223> OTHER INFORMATION: 1075.7 scCAR-v4 polypeptide

<400> SEQUENCE: 110

Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
            20                  25                  30

Val Lys Pro Ser Gln Ser Leu Ser Leu Thr Cys Ser Val Thr Gly Tyr
        35                  40                  45

Ser Ile Thr Ser Ala Tyr Tyr Trp Asn Trp Ile Arg Gln Phe Pro Gly
    50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
            100                 105                 110

Ala Thr Tyr Tyr Cys Ala Lys Glu Gly Asp Tyr Asp Val Gly Asn Tyr
        115                 120                 125

Tyr Ala Met Asp Tyr Trp Gly Gln Gly Thr Ser Val Thr Val Ser Ser
    130                 135                 140

Gly Gly Gly Gly Ser Gly Gly Gly Ser Gly Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
            180                 185                 190

Val His Trp Tyr Gln Gln Arg Ser Gly Ala Ser Pro Lys Leu Trp Ile
        195                 200                 205

Tyr Ser Thr Ser Asn Leu Ala Ser Gly Val Pro Ala Arg Phe Ser Gly
    210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Ile Ser Phe Phe Leu Ala Leu Thr
305                 310                 315                 320

Ser Thr Ala Leu Leu Phe Leu Leu Phe Phe Leu Thr Leu Arg Phe Ser
                325                 330                 335

Val Val Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu

```
                385                 390                 395                 400
Tyr Asn Glu Leu Asn Leu Gly Arg Arg Glu Glu Tyr Asp Val Leu Asp
                    405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 111
<211> LENGTH: 675
<212> TYPE: PRT
<213> ORGANISM: artificial sequence
<220> FEATURE:
<223> OTHER INFORMATION: 1075.7 scCAR-v5 polypeptide

<400> SEQUENCE: 111

Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
                20                  25                  30

Val Lys Pro Ser Gln Ser Leu Ser Leu Thr Cys Ser Val Thr Gly Tyr
            35                  40                  45

Ser Ile Thr Ser Ala Tyr Tyr Trp Asn Trp Ile Arg Gln Phe Pro Gly
        50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
                100                 105                 110

Ala Thr Tyr Tyr Cys Ala Lys Glu Gly Asp Tyr Asp Val Gly Asn Tyr
            115                 120                 125

Tyr Ala Met Asp Tyr Trp Gly Gln Gly Thr Ser Val Thr Val Ser Ser
        130                 135                 140

Gly Gly Gly Gly Ser Gly Gly Gly Ser Gly Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
                180                 185                 190

Val His Trp Tyr Gln Gln Arg Ser Gly Ala Ser Pro Lys Leu Trp Ile
            195                 200                 205

Tyr Ser Thr Ser Asn Leu Ala Ser Gly Val Pro Ala Arg Phe Ser Gly
        210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Glu Pro Lys Ser Pro Asp
```

```
            260                 265                 270
Lys Thr His Thr Cys Pro Pro Cys Pro Ala Pro Pro Val Ala Gly Pro
            275                 280                 285

Ser Val Phe Leu Phe Pro Pro Lys Pro Lys Asp Thr Leu Met Ile Ala
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Ile Tyr Ile Trp Ala Pro Leu Ala Gly Thr Cys Gly Val Leu Leu
            500                 505                 510

Leu Ser Leu Val Ile Thr Leu Tyr Cys Lys Arg Gly Arg Lys Lys Leu
            515                 520                 525

Leu Tyr Ile Phe Lys Gln Pro Phe Met Arg Pro Val Gln Thr Thr Gln
            530                 535                 540

Glu Glu Asp Gly Cys Ser Cys Arg Phe Pro Glu Glu Glu Glu Gly Gly
545                 550                 555                 560

Cys Glu Leu Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
            595                 600                 605

Gly Gly Lys Pro Arg Arg Lys Asn Pro Gln Glu Gly Leu Tyr Asn Glu
            610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
            660                 665                 670

Pro Pro Arg
            675
```

<210> SEQ ID NO 112
<211> LENGTH: 678
<212> TYPE: PRT
<213> ORGANISM: artificial sequence
<220> FEATURE:
<223> OTHER INFORMATION: 1075.7 scCAR-v6 polypeptide

<400> SEQUENCE: 112

```
Met Ala Leu Pro Val Thr Ala Leu Leu Leu Pro Leu Ala Leu Leu Leu
1               5                   10                  15

His Ala Ala Arg Pro Asp Ile Gln Leu Gln Glu Ser Gly Pro Gly Leu
            20                  25                  30

Val Lys Pro Ser Gln Ser Leu Ser Leu Thr Cys Ser Val Thr Gly Tyr
        35                  40                  45

Ser Ile Thr Ser Ala Tyr Tyr Trp Asn Trp Ile Arg Gln Phe Pro Gly
    50                  55                  60

Asn Lys Leu Glu Trp Met Gly Tyr Ile Ser Tyr Asp Gly Arg Asn Asn
65                  70                  75                  80

Tyr Asn Pro Ser Leu Lys Asn Arg Ile Ser Ile Thr Arg Asp Thr Ser
                85                  90                  95

Lys Asn Gln Phe Phe Leu Lys Leu Asn Ser Val Thr Thr Glu Asp Thr
            100                 105                 110

Ala Thr Tyr Tyr Cys Ala Lys Glu Gly Asp Tyr Asp Val Gly Asn Tyr
        115                 120                 125

Tyr Ala Met Asp Tyr Trp Gly Gln Gly Thr Ser Val Thr Val Ser Ser
    130                 135                 140

Gly Gly Gly Gly Ser Gly Gly Gly Ser Gly Gly Gly Ser Glu
145                 150                 155                 160

Asn Val Leu Thr Gln Ser Pro Ala Ile Met Ser Ala Ser Pro Gly Glu
                165                 170                 175

Lys Val Thr Met Thr Cys Arg Ala Ser Ser Asn Val Ile Ser Ser Tyr
            180                 185                 190

Val His Trp Tyr Gln Gln Arg Ser Gly Ala Ser Pro Lys Leu Trp Ile
        195                 200                 205

Tyr Ser Thr Ser Asn Leu Ala Ser Gly Val Pro Ala Arg Phe Ser Gly
    210                 215                 220

Ser Gly Ser Gly Thr Ser Tyr Ser Leu Thr Ile Ser Ser Val Glu Ala
225                 230                 235                 240

Glu Asp Ala Ala Thr Tyr Tyr Cys Gln Gln Tyr Ser Gly Tyr Pro Leu
                245                 250                 255

Thr Phe Gly Ala Gly Thr Lys Leu Glu Leu Glu Pro Lys Ser Pro Asp
            260                 265                 270

Lys Thr His Thr Cys Pro Pro Cys Pro Ala Pro Pro Val Ala Gly Pro
        275                 280                 285

Ser Val Phe Leu Phe Pro Pro Lys Pro Lys Asp Thr Leu Met Ile Ala
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365
```

```
Tyr Lys Cys Lys Val Ser Asn Lys Ala Leu Pro Ala Pro Ile Glu Lys
        370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys Ile Ile Ser Phe Phe Leu Ala Leu Thr Ser Thr Ala Leu Leu Phe
                500                 505                 510

Leu Leu Phe Phe Leu Thr Leu Arg Phe Ser Val Val Lys Arg Gly Arg
        515                 520                 525

Lys Lys Leu Leu Tyr Ile Phe Lys Gln Pro Phe Met Arg Pro Val Gln
        530                 535                 540

Thr Thr Gln Glu Glu Asp Gly Cys Ser Cys Arg Phe Pro Glu Glu Glu
545                 550                 555                 560

Glu Gly Gly Cys Glu Leu Arg Val Lys Phe Ser Arg Ser Ala Asp Ala
                565                 570                 575

Pro Ala Tyr Gln Gln Gly Gln Asn Gln Leu Tyr Asn Glu Leu Asn Leu
                580                 585                 590

Gly Arg Arg Glu Glu Tyr Asp Val Leu Asp Lys Arg Arg Gly Arg Asp
        595                 600                 605

Pro Glu Met Gly Gly Lys Pro Arg Arg Lys Asn Pro Gln Glu Gly Leu
        610                 615                 620

Tyr Asn Glu Leu Gln Lys Asp Lys Met Ala Glu Ala Tyr Ser Glu Ile
625                 630                 635                 640

Gly Met Lys Gly Glu Arg Arg Arg Gly Lys Gly His Asp Gly Leu Tyr
                645                 650                 655

Gln Gly Leu Ser Thr Ala Thr Lys Asp Thr Tyr Asp Ala Leu His Met
                660                 665                 670

Gln Ala Leu Pro Pro Arg
        675

<210> SEQ ID NO 113
<211> LENGTH: 10
<212> TYPE: PRT
<213> ORGANISM: artificial sequence
<220> FEATURE:
<223> OTHER INFORMATION: CD20 mimotope

<400> SEQUENCE: 113

Cys Pro Tyr Ser Asn Pro Ser Leu Cys Ser
1               5                   10

<210> SEQ ID NO 114
<211> LENGTH: 49
<212> TYPE: DNA
<213> ORGANISM: artificial sequence
```

<220> FEATURE:
<223> OTHER INFORMATION: Target TALEN TRAC_T01

<400> SEQUENCE: 114
ttgtcccaca gatatccaga accctgaccc tgccgtgtac cagctgaga         49

<210> SEQ ID NO 115
<211> LENGTH: 530
<212> TYPE: PRT
<213> ORGANISM: artificial sequence
<220> FEATURE:
<223> OTHER INFORMATION: TAL binding domain   TRAC_T01-L

<400> SEQUENCE: 115

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335
```

Gln Ala His Gly Leu Thr Pro Glu Gln Val Ala Ile Ala Ser Asn
                340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 116
<211> LENGTH: 530
<212> TYPE: PRT
<213> ORGANISM: artificial sequence
<220> FEATURE:
<223> OTHER INFORMATION: TAL binding domain TRAC_T01-R

<400> SEQUENCE: 116

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

```
Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530

<210> SEQ ID NO 117
<211> LENGTH: 2814
<212> TYPE: DNA
<213> ORGANISM: artificial sequence
<220> FEATURE:
```

<223> OTHER INFORMATION: polynucleotide encoding TRAC_T01-L TALEN

<400> SEQUENCE: 117

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccc agcaggtggt ggccatcgcc agcaatggcg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc cccagcagg tggtggccat cgccagcaat     720
ggcggtggca agcaggcgct ggagacggtc agcggctgt gccggtgct gtgccaggcc     780
cacggcttga ccccggagca ggtggtggcc atcgccagcc acgatggcgg caagcaggcg     840
ctggagacgg tccagcggct gttgccggtg ctgtgccagg cccacggctt gaccccggag     900
caggtggtgg ccatcgccag ccacgatggc ggcaagcagg cgctggagac ggtccagcgg     960
ctgttgccgg tgctgtgcca ggcccacggc ttgaccccgg agcaggtggt ggccatcgcc    1020
agccacgatg gcggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccggagcagg tggtggccat cgccagccac gatggcggca agcaggcgct ggagacggtc    1260
cagcggctgt gccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gacccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt gccggtgct gtgccaggcc    1800
cacggcttga ccccccagca ggtggtggcc atcgccagca atggcggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgaccccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctga tgcagtgaa aagggattg ggggatccta tcagccgttc ccagctggtg    2220
aagtccgagc tggaggagaa gaaatccgag ttgaggcaca agctgaagta cgtgccccac    2280
```

```
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca accccaacga gtggtggaag    2580 gtgtaccccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gacccctggag    2760 gaggtgagga ggaagttcaa caacggcgag atcaacttcg cggccgactg ataa           2814
```

<210> SEQ ID NO 118
<211> LENGTH: 2832
<212> TYPE: DNA
<213> ORGANISM: artificial sequence
<220> FEATURE:
<223> OTHER INFORMATION: polynucleotide encoding TRAC_T01-R TALEN

<400> SEQUENCE: 118

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt gccggtgct gtgccaggcc    900 cacggcttga ccccccagca ggtggtggcc atcgccagca ataatggtgg caagcaggcg    960
ctggagacgt ccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
```

```
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccccctcc agcgtgaccg agttcaagtt cctgttcgtg    2640
tccggccact tcaagggcaa ctacaaggcc cagctgacca ggctgaacca tcatcaccaac    2700 tgcaacggcg ccgtgctgtc cgtggaggag ctcctgatcg cggcgagat gatcaaggcc    2760 ggcaccctga ccctggagga ggtgaggagg aagttcaaca acggcgagat caacttcgcg    2820
gccgactgat aa                                                        2832

<210> SEQ ID NO 119
<211> LENGTH: 10
<212> TYPE: PRT
<213> ORGANISM: artificial sequence
<220> FEATURE:
<223> OTHER INFORMATION: CDR1 of SC02-357 heavy chain variable region

<400> SEQUENCE: 119

Gly Ser Ile Ser Ser Ser Asn Trp Trp Ser
1               5                   10

<210> SEQ ID NO 120
<211> LENGTH: 13
<212> TYPE: PRT
<213> ORGANISM: artificial sequence
<220> FEATURE:
<223> OTHER INFORMATION: CDR2 of SC02-357 heavy chain variable region

<400> SEQUENCE: 120

Trp Ile Gly Glu Ile Tyr His Ser Gly Ser Pro Asp Tyr
1               5                   10

<210> SEQ ID NO 121
<211> LENGTH: 10
<212> TYPE: PRT
<213> ORGANISM: artificial sequence
<220> FEATURE:
<223> OTHER INFORMATION: CDR3 of SC02-357 heavy chain variable region
```

```
<400> SEQUENCE: 121

Lys Val Ser Thr Gly Gly Phe Phe Asp Tyr
1               5                   10

<210> SEQ ID NO 122
<211> LENGTH: 10
<212> TYPE: PRT
<213> ORGANISM: artificial sequence
<220> FEATURE:
<223> OTHER INFORMATION: CDR1 of SC02-378 heavy chain variable region

<400> SEQUENCE: 122

Gly Ser Ile Ser Ser Ser Asn Trp Trp Ser
1               5                   10

<210> SEQ ID NO 123
<211> LENGTH: 13
<212> TYPE: PRT
<213> ORGANISM: artificial sequence
<220> FEATURE:
<223> OTHER INFORMATION: CDR2 of SC02-378 heavy chain variable region

<400> SEQUENCE: 123

Trp Ile Gly Glu Ile Tyr His Ser Gly Ser Pro Asn Tyr
1               5                   10

<210> SEQ ID NO 124
<211> LENGTH: 10
<212> TYPE: PRT
<213> ORGANISM: artificial sequence
<220> FEATURE:
<223> OTHER INFORMATION: CDR3 of SC02-378 heavy chain variable region

<400> SEQUENCE: 124

Arg Ser Ser Ser Gly Gly Phe Phe Asp Tyr
1               5                   10

<210> SEQ ID NO 125
<211> LENGTH: 10
<212> TYPE: PRT
<213> ORGANISM: artificial sequence
<220> FEATURE:
<223> OTHER INFORMATION: CDR1 of SC02-161 heavy chain variable region

<400> SEQUENCE: 125

Gly Ser Ile Ser Ser Ser Asn Trp Trp Ser
1               5                   10

<210> SEQ ID NO 126
<211> LENGTH: 13
<212> TYPE: PRT
<213> ORGANISM: artificial sequence
<220> FEATURE:
<223> OTHER INFORMATION: CDR2 of SC02-161 heavy chain variable region

<400> SEQUENCE: 126

Trp Ile Gly Glu Ile Tyr His Ser Gly Ser Pro Asn Tyr
1               5                   10

<210> SEQ ID NO 127
<211> LENGTH: 10
<212> TYPE: PRT
<213> ORGANISM: artificial sequence
<220> FEATURE:
<223> OTHER INFORMATION: CDR3 of SC02-161 heavy chain variable region
```

```
<400> SEQUENCE: 127

Arg Gln Thr Thr Ala Gly Ser Phe Asp Tyr
1               5                   10

<210> SEQ ID NO 128
<211> LENGTH: 8
<212> TYPE: PRT
<213> ORGANISM: artificial sequence
<220> FEATURE:
<223> OTHER INFORMATION: CDR1 of SC02-357 & SC02-378 & SC02-161 light
      chain variable region

<400> SEQUENCE: 128

Gln Ser Ile Ser Ser Tyr Leu Asn
1               5

<210> SEQ ID NO 129
<211> LENGTH: 11
<212> TYPE: PRT
<213> ORGANISM: artificial sequence
<220> FEATURE:
<223> OTHER INFORMATION: CDR2 of SC02-357 & SC02-378 & SC02-161 light
      chain variable region

<400> SEQUENCE: 129

Leu Leu Ile Tyr Ala Ala Ser Ser Leu Gln Ser
1               5                   10

<210> SEQ ID NO 130
<211> LENGTH: 8
<212> TYPE: PRT
<213> ORGANISM: artificial sequence
<220> FEATURE:
<223> OTHER INFORMATION: CDR3 of SC02-357 & SC02-378 & SC02-161 light
      chain variable region

<400> SEQUENCE: 130

Gln Gln Ser Tyr Ser Thr Pro Pro
1               5

<210> SEQ ID NO 131
<211> LENGTH: 10
<212> TYPE: PRT
<213> ORGANISM: artificial sequence
<220> FEATURE:
<223> OTHER INFORMATION: CDR1 of M26 heavy chain variable region

<400> SEQUENCE: 131

Gly Tyr Thr Phe Thr Ser Tyr Phe Ile His
1               5                   10

<210> SEQ ID NO 132
<211> LENGTH: 14
<212> TYPE: PRT
<213> ORGANISM: artificial sequence
<220> FEATURE:
<223> OTHER INFORMATION: CDR2 of M26 heavy chain variable region

<400> SEQUENCE: 132

Trp Ile Gly Phe Ile Asn Pro Tyr Asn Asp Gly Ser Lys Tyr
1               5                   10

<210> SEQ ID NO 133
<211> LENGTH: 13
<212> TYPE: PRT
<213> ORGANISM: artificial sequence
<220> FEATURE:
```

```
<223> OTHER INFORMATION: CDR3 of M26 heavy chain variable region

<400> SEQUENCE: 133

Thr Arg Asp Asp Gly Tyr Tyr Gly Tyr Ala Met Asp Tyr
1               5                   10

<210> SEQ ID NO 134
<211> LENGTH: 8
<212> TYPE: PRT
<213> ORGANISM: artificial sequence
<220> FEATURE:
<223> OTHER INFORMATION: CDR1 of M26 light chain variable region

<400> SEQUENCE: 134

Gln Glu Leu Ser Gly Tyr Leu Ser
1               5

<210> SEQ ID NO 135
<211> LENGTH: 11
<212> TYPE: PRT
<213> ORGANISM: artificial sequence
<220> FEATURE:
<223> OTHER INFORMATION: CDR2 of M26 light chain variable region

<400> SEQUENCE: 135

Arg Leu Ile Tyr Ala Ala Ser Thr Leu Asp Ser
1               5                   10

<210> SEQ ID NO 136
<211> LENGTH: 8
<212> TYPE: PRT
<213> ORGANISM: artificial sequence
<220> FEATURE:
<223> OTHER INFORMATION: CDR3 of M26 light chain variable region

<400> SEQUENCE: 136

Leu Gln Tyr Ala Ile Tyr Pro Tyr
1               5

<210> SEQ ID NO 137
<211> LENGTH: 10
<212> TYPE: PRT
<213> ORGANISM: artificial sequence
<220> FEATURE:
<223> OTHER INFORMATION: CDR1 of M31 heavy chain variable region

<400> SEQUENCE: 137

Gly Tyr Thr Phe Thr Ser Tyr Val Met His
1               5                   10

<210> SEQ ID NO 138
<211> LENGTH: 14
<212> TYPE: PRT
<213> ORGANISM: artificial sequence
<220> FEATURE:
<223> OTHER INFORMATION: CDR2 of M31 heavy chain variable region

<400> SEQUENCE: 138

Trp Ile Gly Tyr Ile Asn Pro Tyr Asn Asp Gly Thr Lys Tyr
1               5                   10

<210> SEQ ID NO 139
<211> LENGTH: 10
<212> TYPE: PRT
<213> ORGANISM: artificial sequence
<220> FEATURE:
<223> OTHER INFORMATION: CDR3 of M31 heavy chain variable region
```

<400> SEQUENCE: 139

Ala Arg Pro Ile Tyr Phe Asp Asn Asp Tyr
1               5                   10

<210> SEQ ID NO 140
<211> LENGTH: 12
<212> TYPE: PRT
<213> ORGANISM: artificial sequence
<220> FEATURE:
<223> OTHER INFORMATION: CDR1 of M31 light chain variable region

<400> SEQUENCE: 140

Glu Ser Val Asp Ser Tyr Gly Asn Ser Phe Met His
1               5                   10

<210> SEQ ID NO 141
<211> LENGTH: 11
<212> TYPE: PRT
<213> ORGANISM: artificial sequence
<220> FEATURE:
<223> OTHER INFORMATION: CDR2 of M31 light chain variable region

<400> SEQUENCE: 141

Leu Leu Ile Tyr Leu Ala Ser Asn Leu Glu Ser
1               5                   10

<210> SEQ ID NO 142
<211> LENGTH: 8
<212> TYPE: PRT
<213> ORGANISM: artificial sequence
<220> FEATURE:
<223> OTHER INFORMATION: CDR3 of M31 light chain variable region

<400> SEQUENCE: 142

Gln Gln Asn Asn Tyr Asp Pro Trp
1               5

<210> SEQ ID NO 143
<211> LENGTH: 8
<212> TYPE: PRT
<213> ORGANISM: artificial sequence
<220> FEATURE:
<223> OTHER INFORMATION: CDR1 of G4 heavy chain variable region

<400> SEQUENCE: 143

Gln Gln Asn Asn Tyr Asp Pro Trp
1               5

<210> SEQ ID NO 144
<211> LENGTH: 14
<212> TYPE: PRT
<213> ORGANISM: artificial sequence
<220> FEATURE:
<223> OTHER INFORMATION: CDR2 of G4 heavy chain variable region

<400> SEQUENCE: 144

Trp Ile Gly Pro Ile Asn Pro Tyr Asn Asp Gly Thr Ile Tyr
1               5                   10

<210> SEQ ID NO 145
<211> LENGTH: 13
<212> TYPE: PRT
<213> ORGANISM: artificial sequence
<220> FEATURE:
<223> OTHER INFORMATION: CDR3 of G4 heavy chain variable region

```
<400> SEQUENCE: 145

Ala Arg Thr Asp Asp Tyr Asp Asp Tyr Thr Met Asp Tyr
1               5                   10

<210> SEQ ID NO 146
<211> LENGTH: 8
<212> TYPE: PRT
<213> ORGANISM: artificial sequence
<220> FEATURE:
<223> OTHER INFORMATION: CDR1 of G4 light chain variable region

<400> SEQUENCE: 146

His Asp Ile Ser Asn Tyr Leu Asn
1               5

<210> SEQ ID NO 147
<211> LENGTH: 11
<212> TYPE: PRT
<213> ORGANISM: artificial sequence
<220> FEATURE:
<223> OTHER INFORMATION: CDR2 of G4 light chain variable region

<400> SEQUENCE: 147

Leu Leu Ile Tyr Tyr Thr Ser Arg Leu His Ser
1               5                   10

<210> SEQ ID NO 148
<211> LENGTH: 8
<212> TYPE: PRT
<213> ORGANISM: artificial sequence
<220> FEATURE:
<223> OTHER INFORMATION: CDR3 of G4 light chain variable region

<400> SEQUENCE: 148

Gln Gln Gly Lys Thr Leu Leu Trp
1               5

<210> SEQ ID NO 149
<211> LENGTH: 10
<212> TYPE: PRT
<213> ORGANISM: artificial sequence
<220> FEATURE:
<223> OTHER INFORMATION: CDR1 of M22 heavy chain variable region

<400> SEQUENCE: 149

Gly Tyr Thr Phe Thr Arg Tyr Trp Met His
1               5                   10

<210> SEQ ID NO 150
<211> LENGTH: 14
<212> TYPE: PRT
<213> ORGANISM: artificial sequence
<220> FEATURE:
<223> OTHER INFORMATION: CDR2 of M22 heavy chain variable region

<400> SEQUENCE: 150

Trp Ile Gly Asn Ile Asp Pro Ser Asp Thr Glu Thr His Tyr
1               5                   10

<210> SEQ ID NO 151
<211> LENGTH: 14
<212> TYPE: PRT
<213> ORGANISM: artificial sequence
<220> FEATURE:
<223> OTHER INFORMATION: CDR3 of M22 heavy chain variable region

<400> SEQUENCE: 151
```

Ala Ile Tyr Tyr Gly Asn Pro Ser Tyr Tyr Ala Met Asp Tyr
1               5                   10

<210> SEQ ID NO 152
<211> LENGTH: 14
<212> TYPE: PRT
<213> ORGANISM: artificial sequence
<220> FEATURE:
<223> OTHER INFORMATION: CDR1 of M22 light chain variable region

<400> SEQUENCE: 152

Gln Asn Leu Leu Asn Ser Gly Asn Gln Lys Tyr Leu Asn
1               5                   10

<210> SEQ ID NO 153
<211> LENGTH: 11
<212> TYPE: PRT
<213> ORGANISM: artificial sequence
<220> FEATURE:
<223> OTHER INFORMATION: CDR2 of M22 light chain variable region

<400> SEQUENCE: 153

Leu Leu Ile Tyr Trp Ala Ser Thr Arg Glu Ser
1               5                   10

<210> SEQ ID NO 154
<211> LENGTH: 8
<212> TYPE: PRT
<213> ORGANISM: artificial sequence
<220> FEATURE:
<223> OTHER INFORMATION: CDR3 of M22 light chain variable region

<400> SEQUENCE: 154

Gln Asn Asp Tyr Ser Tyr Pro Phe
1               5

<210> SEQ ID NO 155
<211> LENGTH: 10
<212> TYPE: PRT
<213> ORGANISM: artificial sequence
<220> FEATURE:
<223> OTHER INFORMATION: CDR1 of M29 heavy chain variable region

<400> SEQUENCE: 155

Gly Tyr Ile Phe Thr Ser Tyr Val Met Tyr
1               5                   10

<210> SEQ ID NO 156
<211> LENGTH: 8
<212> TYPE: PRT
<213> ORGANISM: artificial sequence
<220> FEATURE:
<223> OTHER INFORMATION: CDR2 of M29 heavy chain variable region

<400> SEQUENCE: 156

Trp Ile Gly Tyr Ile Asn Pro Tyr
1               5

<210> SEQ ID NO 157
<211> LENGTH: 12
<212> TYPE: PRT
<213> ORGANISM: artificial sequence
<220> FEATURE:
<223> OTHER INFORMATION: CDR3 of M29 heavy chain variable region

<400> SEQUENCE: 157

Ala Arg Tyr Tyr Asp Tyr Asp Tyr Tyr Phe Asp Tyr
1               5                   10

<210> SEQ ID NO 158
<211> LENGTH: 8
<212> TYPE: PRT
<213> ORGANISM: artificial sequence
<220> FEATURE:
<223> OTHER INFORMATION: CDR1 of M29 light chain variable region

<400> SEQUENCE: 158

Gln Asp Ile Asn Lys Tyr Ile Ala
1               5

<210> SEQ ID NO 159
<211> LENGTH: 11
<212> TYPE: PRT
<213> ORGANISM: artificial sequence
<220> FEATURE:
<223> OTHER INFORMATION: CDR2 of M29 light chain variable region

<400> SEQUENCE: 159

Leu Leu Ile His Tyr Thr Ser Thr Leu Gln Pro
1               5                   10

<210> SEQ ID NO 160
<211> LENGTH: 7
<212> TYPE: PRT
<213> ORGANISM: artificial sequence
<220> FEATURE:
<223> OTHER INFORMATION: CDR3 of M29 light chain variable region

<400> SEQUENCE: 160

Leu Gln Tyr Asp Tyr Leu Trp
1               5

<210> SEQ ID NO 161
<211> LENGTH: 10
<212> TYPE: PRT
<213> ORGANISM: artificial sequence
<220> FEATURE:
<223> OTHER INFORMATION: CDR1 of M2 heavy chain variable region

<400> SEQUENCE: 161

Gly Tyr Thr Phe Thr Ser Tyr Phe Met His
1               5                   10

<210> SEQ ID NO 162
<211> LENGTH: 14
<212> TYPE: PRT
<213> ORGANISM: artificial sequence
<220> FEATURE:
<223> OTHER INFORMATION: CDR2 of M2 heavy chain variable region

<400> SEQUENCE: 162

Trp Ile Gly Phe Ile Asn Pro Tyr Asn Asp Gly Thr Lys Tyr
1               5                   10

<210> SEQ ID NO 163
<211> LENGTH: 13
<212> TYPE: PRT
<213> ORGANISM: artificial sequence
<220> FEATURE:
<223> OTHER INFORMATION: CDR3 of M2 heavy chain variable region

<400> SEQUENCE: 163

Thr Arg Asp Asp Gly Tyr Tyr Asp Tyr Ala Met Asp Tyr

```
1               5                    10
```

<210> SEQ ID NO 164
<211> LENGTH: 8
<212> TYPE: PRT
<213> ORGANISM: artificial sequence
<220> FEATURE:
<223> OTHER INFORMATION: CDR1 of M2 light chain variable region

<400> SEQUENCE: 164

```
Gln Glu Ile Ser Val Tyr Leu Ser
1               5
```

<210> SEQ ID NO 165
<211> LENGTH: 11
<212> TYPE: PRT
<213> ORGANISM: artificial sequence
<220> FEATURE:
<223> OTHER INFORMATION: CDR2 of M2 light chain variable region

<400> SEQUENCE: 165

```
Arg Leu Ile Tyr Ala Ala Ser Thr Leu Asp Ser
1               5                   10
```

<210> SEQ ID NO 166
<211> LENGTH: 8
<212> TYPE: PRT
<213> ORGANISM: artificial sequence
<220> FEATURE:
<223> OTHER INFORMATION: CDR3 of M2 light chain variable region

<400> SEQUENCE: 166

```
Leu Gln Tyr Ala Ser Tyr Pro Tyr
1               5
```

<210> SEQ ID NO 167
<211> LENGTH: 10
<212> TYPE: PRT
<213> ORGANISM: artificial sequence
<220> FEATURE:
<223> OTHER INFORMATION: CDR1 of M5 heavy chain variable region

<400> SEQUENCE: 167

```
Gly Phe Asn Ile Lys Asp Asp Tyr Ile His
1               5                   10
```

<210> SEQ ID NO 168
<211> LENGTH: 16
<212> TYPE: PRT
<213> ORGANISM: artificial sequence
<220> FEATURE:
<223> OTHER INFORMATION: CDR2 of M5 heavy chain variable region

<400> SEQUENCE: 168

```
Trp Ile Gly Trp Ile Asp Pro Glu Lys Gly Asp Thr Ala Tyr Ala Ser
1               5                   10                  15
```

<210> SEQ ID NO 169
<211> LENGTH: 8
<212> TYPE: PRT
<213> ORGANISM: artificial sequence
<220> FEATURE:
<223> OTHER INFORMATION: CDR3 of M5 heavy chain variable region

<400> SEQUENCE: 169

```
Thr Leu Thr Gly Arg Phe Asp Tyr
1               5
```

<210> SEQ ID NO 170
<211> LENGTH: 14
<212> TYPE: PRT
<213> ORGANISM: artificial sequence
<220> FEATURE:
<223> OTHER INFORMATION: CDR1 of M5 light chain variable region

<400> SEQUENCE: 170

Gln Ser Leu Leu Tyr Ser Ser Asn Gln Lys Asn Asn Leu Ala
1               5                   10

<210> SEQ ID NO 171
<211> LENGTH: 11
<212> TYPE: PRT
<213> ORGANISM: artificial sequence
<220> FEATURE:
<223> OTHER INFORMATION: CDR2 of M5 light chain variable region

<400> SEQUENCE: 171

Leu Leu Ile Tyr Trp Ala Ser Thr Arg Glu Ser
1               5                   10

<210> SEQ ID NO 172
<211> LENGTH: 7
<212> TYPE: PRT
<213> ORGANISM: artificial sequence
<220> FEATURE:
<223> OTHER INFORMATION: CDR3 of M5 light chain variable region

<400> SEQUENCE: 172

Gln Gln Tyr Tyr Ser Tyr Arg
1               5

<210> SEQ ID NO 173
<211> LENGTH: 10
<212> TYPE: PRT
<213> ORGANISM: artificial sequence
<220> FEATURE:
<223> OTHER INFORMATION: CDR1 of G12 heavy chain variable region

<400> SEQUENCE: 173

Gly Tyr Thr Phe Pro Ser Ser Asn Ile His
1               5                   10

<210> SEQ ID NO 174
<211> LENGTH: 14
<212> TYPE: PRT
<213> ORGANISM: artificial sequence
<220> FEATURE:
<223> OTHER INFORMATION: CDR2 of G12 heavy chain variable region

<400> SEQUENCE: 174

Trp Ile Gly Val Ile Tyr Pro Gly Asn Gly Asp Thr Ser Tyr
1               5                   10

<210> SEQ ID NO 175
<211> LENGTH: 12
<212> TYPE: PRT
<213> ORGANISM: artificial sequence
<220> FEATURE:
<223> OTHER INFORMATION: CDR3 of G12 heavy chain variable region

<400> SEQUENCE: 175

Ala Ile Tyr Phe Val Tyr Asn Trp His Phe Asp Val
1               5                   10

<210> SEQ ID NO 176
<211> LENGTH: 12
<212> TYPE: PRT
<213> ORGANISM: artificial sequence
<220> FEATURE:
<223> OTHER INFORMATION: CDR1 of G12 light chain variable region

<400> SEQUENCE: 176

Glu Ser Val Asp Gly Tyr Gly Asp Ile Phe Met Leu
1               5                   10

<210> SEQ ID NO 177
<211> LENGTH: 11
<212> TYPE: PRT
<213> ORGANISM: artificial sequence
<220> FEATURE:
<223> OTHER INFORMATION: CDR2 of G12 light chain variable region

<400> SEQUENCE: 177

Leu Leu Ile Tyr Phe Ala Ser Asn Leu Glu Ser
1               5                   10

<210> SEQ ID NO 178
<211> LENGTH: 8
<212> TYPE: PRT
<213> ORGANISM: artificial sequence
<220> FEATURE:
<223> OTHER INFORMATION: CDR3 of G12 light chain variable region

<400> SEQUENCE: 178

Gln Gln Asn Asn Glu Asp Pro Tyr
1               5

<210> SEQ ID NO 179
<211> LENGTH: 10
<212> TYPE: PRT
<213> ORGANISM: artificial sequence
<220> FEATURE:
<223> OTHER INFORMATION: CDR1 of 21.26 heavy chain variable region

<400> SEQUENCE: 179

Gly Tyr Thr Phe Thr Arg Tyr Trp Met His
1               5                   10

<210> SEQ ID NO 180
<211> LENGTH: 16
<212> TYPE: PRT
<213> ORGANISM: artificial sequence
<220> FEATURE:
<223> OTHER INFORMATION: CDR2 of 21.26 heavy chain variable region

<400> SEQUENCE: 180

Met Ile His Pro Ser Ser Gly Ser Thr Ser Tyr Asn Glu Lys Val Lys
1               5                   10                  15

<210> SEQ ID NO 181
<211> LENGTH: 12
<212> TYPE: PRT
<213> ORGANISM: artificial sequence
<220> FEATURE:
<223> OTHER INFORMATION: CDR3 of 21.26 heavy chain variable region

<400> SEQUENCE: 181

Arg Asp Gly Asp Tyr Tyr Tyr Gly Thr Gly Asp Tyr
1               5                   10

-continued

```
<210> SEQ ID NO 182
<211> LENGTH: 10
<212> TYPE: PRT
<213> ORGANISM: artificial sequence
<220> FEATURE:
<223> OTHER INFORMATION: CDR1 of 21.26 light chain variable region

<400> SEQUENCE: 182

Arg Ala Ser Ser Ser Ile Asn Tyr Met His
1               5                   10

<210> SEQ ID NO 183
<211> LENGTH: 11
<212> TYPE: PRT
<213> ORGANISM: artificial sequence
<220> FEATURE:
<223> OTHER INFORMATION: CDR2 of 21.26 light chain variable region

<400> SEQUENCE: 183

Pro Trp Ile Phe Ala Thr Ser Asn Leu Ala Ser
1               5                   10

<210> SEQ ID NO 184
<211> LENGTH: 10
<212> TYPE: PRT
<213> ORGANISM: artificial sequence
<220> FEATURE:
<223> OTHER INFORMATION: CDR3 of 21.26 light chain variable region

<400> SEQUENCE: 184

Gln Gln Trp Arg Ser Asp Arg Ala Leu Thr
1               5                   10

<210> SEQ ID NO 185
<211> LENGTH: 11
<212> TYPE: PRT
<213> ORGANISM: artificial sequence
<220> FEATURE:
<223> OTHER INFORMATION: CDR1 of 1075.7 heavy chain variable region

<400> SEQUENCE: 185

Gly Tyr Ser Ile Thr Ser Ala Tyr Tyr Trp Asn
1               5                   10

<210> SEQ ID NO 186
<211> LENGTH: 16
<212> TYPE: PRT
<213> ORGANISM: artificial sequence
<220> FEATURE:
<223> OTHER INFORMATION: CDR2 of 1075.7 heavy chain variable region

<400> SEQUENCE: 186

Tyr Ile Ser Tyr Asp Gly Arg Asn Asn Tyr Asn Pro Ser Leu Lys Asn
1               5                   10                  15

<210> SEQ ID NO 187
<211> LENGTH: 16
<212> TYPE: PRT
<213> ORGANISM: artificial sequence
<220> FEATURE:
<223> OTHER INFORMATION: CDR3 of 1075.7 heavy chain variable region

<400> SEQUENCE: 187

Ala Lys Glu Gly Asp Tyr Asp Val Gly Asn Tyr Tyr Ala Met Asp Tyr
1               5                   10                  15

<210> SEQ ID NO 188
```

```
<211> LENGTH: 12
<212> TYPE: PRT
<213> ORGANISM: artificial sequence
<220> FEATURE:
<223> OTHER INFORMATION: CDR1 of 1075.7 light chain variable region

<400> SEQUENCE: 188

Arg Ala Ser Ser Asn Val Ile Ser Ser Tyr Val His
1               5                   10

<210> SEQ ID NO 189
<211> LENGTH: 11
<212> TYPE: PRT
<213> ORGANISM: artificial sequence
<220> FEATURE:
<223> OTHER INFORMATION: CDR2 of 1075.7 light chain variable region

<400> SEQUENCE: 189

Leu Trp Ile Tyr Ser Thr Ser Asn Leu Ala Ser
1               5                   10

<210> SEQ ID NO 190
<211> LENGTH: 9
<212> TYPE: PRT
<213> ORGANISM: artificial sequence
<220> FEATURE:
<223> OTHER INFORMATION: CDR3 of 1075.7 light chain variable region

<400> SEQUENCE: 190

Gln Gln Tyr Ser Gly Tyr Pro Leu Thr
1               5

<210> SEQ ID NO 191
<211> LENGTH: 24
<212> TYPE: PRT
<213> ORGANISM: artificial sequence
<220> FEATURE:
<223> OTHER INFORMATION: Epitope for palivizumab

<400> SEQUENCE: 191

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 192
<211> LENGTH: 12
<212> TYPE: PRT
<213> ORGANISM: artificial sequence
<220> FEATURE:
<223> OTHER INFORMATION: Mimotope 1 for cetuximab

<400> SEQUENCE: 192

Cys Gln Phe Asp Leu Ser Thr Arg Arg Leu Lys Cys
1               5                   10

<210> SEQ ID NO 193
<211> LENGTH: 12
<212> TYPE: PRT
<213> ORGANISM: artificial sequence
<220> FEATURE:
<223> OTHER INFORMATION: Mimotope 2 for cetuximab

<400> SEQUENCE: 193

Cys Gln Tyr Asn Leu Ser Ser Arg Ala Leu Lys Cys
1               5                   10
```

-continued

<210> SEQ ID NO 194
<211> LENGTH: 12
<212> TYPE: PRT
<213> ORGANISM: artificial sequence
<220> FEATURE:
<223> OTHER INFORMATION: Mimotope 3 for cetuximab

<400> SEQUENCE: 194

Cys Val Trp Gln Arg Trp Gln Lys Ser Tyr Val Cys
1               5                   10

<210> SEQ ID NO 195
<211> LENGTH: 12
<212> TYPE: PRT
<213> ORGANISM: artificial sequence
<220> FEATURE:
<223> OTHER INFORMATION: Mimotope 4 for cetuximab

<400> SEQUENCE: 195

Cys Met Trp Asp Arg Phe Ser Arg Trp Tyr Lys Cys
1               5                   10

<210> SEQ ID NO 196
<211> LENGTH: 25
<212> TYPE: PRT
<213> ORGANISM: artificial sequence
<220> FEATURE:
<223> OTHER INFORMATION: Epitope 1 for nivolumab

<400> SEQUENCE: 196

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 197
<211> LENGTH: 19
<212> TYPE: PRT
<213> ORGANISM: artificial sequence
<220> FEATURE:
<223> OTHER INFORMATION: Epitope 2 for nivolumab

<400> SEQUENCE: 197

Ser Gly Thr Tyr Leu Cys Gly Ala Ile Ser Leu Ala Pro Lys Ala Gln
1               5                   10                  15

Ile Lys Glu

<210> SEQ ID NO 198
<211> LENGTH: 14
<212> TYPE: PRT
<213> ORGANISM: artificial sequence
<220> FEATURE:
<223> OTHER INFORMATION: Epitope 1 for CD34

<400> SEQUENCE: 198

Thr Phe Ser Asn Val Ser Thr Asn Val Ser Tyr Gln Glu Thr
1               5                   10

<210> SEQ ID NO 199
<211> LENGTH: 14
<212> TYPE: PRT
<213> ORGANISM: artificial sequence
<220> FEATURE:
<223> OTHER INFORMATION: Epitope 2 for CD34

<400> SEQUENCE: 199

Asn Thr Asn Ser Ser Val Gln Ser Gln Thr Ser Val Ile Ser
1               5                   10

<210> SEQ ID NO 200
<211> LENGTH: 4
<212> TYPE: PRT
<213> ORGANISM: artificial sequence
<220> FEATURE:
<223> OTHER INFORMATION: linker

<400> SEQUENCE: 200

Ser Gly Gly Ser
1

<210> SEQ ID NO 201
<211> LENGTH: 5
<212> TYPE: PRT
<213> ORGANISM: artificial sequence
<220> FEATURE:
<223> OTHER INFORMATION: linker

<400> SEQUENCE: 201

Ser Ser Gly Gly Ser
1               5

<210> SEQ ID NO 202
<211> LENGTH: 4
<212> TYPE: PRT
<213> ORGANISM: artificial sequence
<220> FEATURE:
<223> OTHER INFORMATION: linker

<400> SEQUENCE: 202

Gly Gly Gly Gly
1

<210> SEQ ID NO 203
<211> LENGTH: 5
<212> TYPE: PRT
<213> ORGANISM: artificial sequence
<220> FEATURE:
<223> OTHER INFORMATION: linker

<400> SEQUENCE: 203

Ser Gly Gly Gly Gly
1               5

<210> SEQ ID NO 204
<211> LENGTH: 5
<212> TYPE: PRT
<213> ORGANISM: artificial sequence
<220> FEATURE:
<223> OTHER INFORMATION: linker

<400> SEQUENCE: 204

Gly Gly Gly Gly Ser
1               5

<210> SEQ ID NO 205
<211> LENGTH: 6
<212> TYPE: PRT
<213> ORGANISM: artificial sequence
<220> FEATURE:
<223> OTHER INFORMATION: linker

<400> SEQUENCE: 205

Ser Gly Gly Gly Gly Ser
1               5

<210> SEQ ID NO 206
<211> LENGTH: 6
<212> TYPE: PRT
<213> ORGANISM: artificial sequence
<220> FEATURE:
<223> OTHER INFORMATION: linker

<400> SEQUENCE: 206

Gly Gly Gly Gly Gly Ser
1               5

<210> SEQ ID NO 207
<211> LENGTH: 7
<212> TYPE: PRT
<213> ORGANISM: artificial sequence
<220> FEATURE:
<223> OTHER INFORMATION: linker

<400> SEQUENCE: 207

Ser Gly Gly Gly Gly Gly Ser
1               5

<210> SEQ ID NO 208
<211> LENGTH: 6
<212> TYPE: PRT
<213> ORGANISM: artificial sequence
<220> FEATURE:
<223> OTHER INFORMATION: linker

<400> SEQUENCE: 208

Ser Gly Gly Gly Gly Gly
1               5

<210> SEQ ID NO 209
<211> LENGTH: 7
<212> TYPE: PRT
<213> ORGANISM: artificial sequence
<220> FEATURE:
<223> OTHER INFORMATION: linker

<400> SEQUENCE: 209

Gly Ser Gly Gly Gly Gly Ser
1               5

<210> SEQ ID NO 210
<211> LENGTH: 8
<212> TYPE: PRT
<213> ORGANISM: artificial sequence
<220> FEATURE:
<223> OTHER INFORMATION: linker

<400> SEQUENCE: 210

Gly Gly Gly Gly Gly Gly Gly Ser
1               5

<210> SEQ ID NO 211
<211> LENGTH: 8
<212> TYPE: PRT
<213> ORGANISM: artificial sequence
<220> FEATURE:
<223> OTHER INFORMATION: linker

<400> SEQUENCE: 211

Ser Gly Gly Gly Gly Gly Gly Gly

```
<210> SEQ ID NO 212
<211> LENGTH: 9
<212> TYPE: PRT
<213> ORGANISM: artificial sequence
<220> FEATURE:
<223> OTHER INFORMATION: linker

<400> SEQUENCE: 212

Ser Gly Gly Gly Gly Gly Gly Gly Ser
1               5

<210> SEQ ID NO 213
<211> LENGTH: 11
<212> TYPE: PRT
<213> ORGANISM: artificial sequence
<220> FEATURE:
<223> OTHER INFORMATION: linker

<400> SEQUENCE: 213

Ser Gly Gly Gly Gly Ser Gly Gly Gly Gly Ser
1               5                   10
```